United States Patent
Salzwedel et al.

(10) Patent No.: US 7,537,765 B2
(45) Date of Patent: May 26, 2009

(54) INHIBITION OF HIV-1 REPLICATION BY DISRUPTION OF THE PROCESSING OF THE VIRAL CAPSID-SPACER PEPTIDE 1 PROTEIN

(75) Inventors: Karl Salzwedel, Olney, MD (US); Feng Li, Gaithersburg, MD (US); Carl T. Wild, Gaithersburg, MD (US); Graham P. Allaway, Darnestown, MD (US); Eric O. Freed, Frederick, MD (US)

(73) Assignees: Panacos Pharmaceuticals, Inc., Gaithersburg, MD (US); The United States of America as represented by the Department of Health and Human Services, Washington, DC (US)

( * ) Notice: Subject to any disclaimer, the term of this patent is extended or adjusted under 35 U.S.C. 154(b) by 311 days.

(21) Appl. No.: 10/851,637

(22) Filed: May 24, 2004

(65) Prior Publication Data

US 2005/0015039 A1 Jan. 20, 2005

Related U.S. Application Data

(63) Continuation-in-part of application No. 10/766,528, filed on Jan. 29, 2004.

(60) Provisional application No. 60/496,660, filed on Aug. 21, 2003, provisional application No. 60/443,180, filed on Jan. 29, 2003.

(51) Int. Cl.
*A61K 39/00* (2006.01)
*A61K 39/12* (2006.01)
*A61K 39/21* (2006.01)
*A61K 38/00* (2006.01)

(52) U.S. Cl. ............... 424/184.1; 530/300; 424/186.1; 424/187.1; 424/188.1

(58) Field of Classification Search .............. 424/9.1; 530/300

See application file for complete search history.

(56) References Cited

U.S. PATENT DOCUMENTS

| 4,683,195 | A | 7/1987 | Mullis et al. |
|---|---|---|---|
| 4,683,202 | A | 7/1987 | Mullis |
| 5,468,888 | A | 11/1995 | Bouboutou et al. |
| 5,679,828 | A | 10/1997 | Lee et al. |
| 6,172,110 | B1 | 1/2001 | Lee et al. |
| 2004/0131629 | A1 | 7/2004 | Allaway et al. |
| 2005/0009743 | A1 | 1/2005 | Sundquist et al. |
| 2005/0015039 | A1 | 1/2005 | Salzwedel et al. |

FOREIGN PATENT DOCUMENTS

| JP | 1-143832 | 6/1989 |
|---|---|---|
| WO | WO 96/39033 | 12/1996 |
| WO | WO 02/26761 A1 | 4/2002 |

OTHER PUBLICATIONS

Krausslich et al. The Spacer Peptide between Human Immunodeficiency Virus Capsid and Nucleocapsid Proteins Is Essential for Ordered Assembly and Viral Infectivity. Journal of Virology, Jun. 1995, vol. 69, No. 6, p. 3407-3419.*

Accola, M.A., et al., "Efficient Particle Production by Minimal Gag Constructs Which Retain the Carboxy-Terminal Domain of Human Immunodeficiency Virus Type 1 Capsid-p2 and a Late Assembly Domain," *J. Virol.* 74:5395-5402, American Society for Microbiology (2000).

Adamson, C.S., et al., "In Vitro Resistance to the Human Immunodeficiency Virus Type 1 Maturation Inhibitor PA-457 (Bevirimat)," *J. Virol.*, published online, doi:10.1128/JVI.01369-06, 47 pages, American Society for Microbiology (Sep. 2006).

Altschul, S.F., et al., "Basic Local Alignment Search Tool," *J. Mol. Biol.* 215:403-410, Academic Press Limited (1990).

Brutlag, D.L., et al., "Improved sensitivity of biological sequence database searches," *Comput. Appl. Biosci.* 6:237-245, Oxford University Press (1990).

Cleland, J.L., et al., "The Development of Stable Protein Formulations: A Close Look at Protein Aggregation, Deamidation, and Oxidation," *Crit. Rev. Ther. Drug Carrier Syst.* 10:307-377, CRC Press, Inc. (1993).

Dalgeish, A.G., et al., "The CD4 (T4) antigen is an essential component of the receptor for the AIDS retrovirus," *Nature* 312:763-767, Macmillan Journals Ltd. (1984).

Demirov, D.G., et al., "The Late Domain of Human Immunodeficiency Virus Type 1 p6 Promotes Virus Release in a Cell Type-Dependent Manner," *J. Virol.* 76:105-117, American Society for Microbiology (Jan. 2002).

Devereux, J., et al., "A comprehensive set of sequence analysis programs for the VAX," *Nucl. Acids Res.* 12:387-395, IRL Press Limited (1984).

(Continued)

*Primary Examiner*—Bruce Campell
*Assistant Examiner*—Louise Humphrey
(74) *Attorney, Agent, or Firm*—Sterne, Kessler, Goldstein & Fox P.L.L.C.

(57) ABSTRACT

Inhibition of HIV-1 replication by disrupting the processing of the viral Gag capsid (CA) protein (p24) from the CA-spacer peptide 1 (SP1) protein precursor (p25) is disclosed. Amino acid sequences containing a mutation in the Gag p25 protein, with the mutation resulting in a decrease in the inhibition of processing of p25 to p24 by dimethylsuccinyl betulinic acid or dimethylsuccinyl betulin, polynucleotides encoding such mutated sequences and antibodies that selectively bind such mutated sequences are also included. Methods of inhibiting, inhibitory compounds and methods of discovering inhibitory compounds that target proteolytic processing of the HIV Gag protein are included. In one embodiment, such compounds inhibit the interaction of the HIV protease enzyme with Gag by binding to Gag rather than to the protease enzyme. In another embodiment, viruses or recombinant proteins that contain mutations in the region of the Gag proteolytic cleavage site can be used in screening assays to identify compounds that target proteolytic processing.

40 Claims, 31 Drawing Sheets

OTHER PUBLICATIONS

Erickson-Viitanen, S., et al., "Cleavage of HIV-1 *gag* Polyprotein Synthesized In Vitro: Sequential Cleavage by the Viral Protease," *AIDS Res. Hum. Retroviruses* 5:577-591, Mary Ann Liebert, Inc. (1989).

Fujioka, T., and Kashiwada, Y., "Anti-AIDS Agents, 11. Betulinic Acid and Platanic Acid as Anti-HIV Principles from *Syzigium claviflorum*, and the Anti-HIV Activity of Structurally Related Triterpenoids," *J. Nat. Prod.* 57:243-247, American Society of Pharmacognosy and the Lloyd Library and Museum (1994).

Garrus, J.E., et al., "Tsg101 and the Vacuolar Protein Sorting Pathway Are Essential for HIV-1 Budding," *Cell* 107:55-65, Cell Press (2001).

Haan, K., "HIV gags on PA-457," *BioCentury, The Bernstein Report on BioBusiness*: p. A12 of 22, Biocentury Publications, Inc. (Oct. 27, 2003 issue).

Hopp, T.P., et al., "A Short Polypeptide Marker Sequence Useful for Recombinant Protein Identification and Purification," *Biotechnology* 6:1204-1210, Nature Publishing Co. (1988).

Kanamoto, T., et al., "Anti-Human Immunodeficiency Virus Activity of YK-FH312 (a Betulinic Acid Derivative), a Novel Compound Blocking Viral Maturation," *Antimicrob. Agents Chemother.* 45:1225-1230, American Society for Microbiology (2001).

Kashiwada, Y., et al., "Betulinic Acid and Dihydrobetulinic Acid Derivatives as Potent Anti-HIV Agents," *J. Med. Chem.* 39:1016-1017, American Chemical Society (1996).

Kashiwada, Y., et al., "Anti-AIDS Agents. 30. Anti-HIV Activity of Oleanolic Acid, Pomolic Acid, and Structurally Related Triterpenoids," *J. Nat. Prod.* 61:1090-1095, American Chemical Society and American Society of Pharmacognosy (1998).

Kashiwada, Y., et al., "Anti-AIDS Agents 38. Anti-HIV Activity of 3-*O*-Acyl Ursolic Acid Derivatives," *J. Nat. Prod.* 63:1619-1622, American Chemical Society and American Society of Pharmacognosy (2000).

Kashiwada, Y., et al., "Synthesis and Anti-HIV Activity of 3-Alkylamido-3-deoxy-betulinic Acid Derivatives," *Chem. Pharm. Bull.* 48:1387-1390, Pharmaceutical Society of Japan (2000).

Kashiwada, Y., et al., "3,28-Di-*O*-(dimethylsuccinyl)-betulin Isomers as Anti-HIV Agents," *Bioorg. Med. Chem. Lett.* 11:183-185, Pergamon Press (2001).

Kohl, N.E., et al., "Active human immunodeficiency virus protease is required for viral infectivity," *Proc. Natl. Acad. Sci. USA* 85:4686-4690, National Academy of Sciences (1988).

Lee, H., et al., "Toxicity of Nucleoside Analogues Used to Treat AIDS and the Selectivity of the Mitochondrial DNA Polymerase," *Biochemistry* 42:14711-14719, American Chemical Society (Dec. 2003).

Li, F., et al., "PA-457: A potent HIV inhibitor that disrupts core condensation by targeting a late step in Gag processing," *Proc. Natl. Acad. Sci.* 100:13555-13560, National Academy of Sciences (Nov. 2003).

Li, F., et al., "Determinants of activity of the HIV-1 maturation inhibitor PA-457," *Virology*, published online, doi:10.1016/j.virol. 2006.07.023, 8 pages, Academic Press (Dec. 2006).

Liang, C., et al., "Deletion Mutagenesis within the Dimerization Initiation Site of Human Immunodeficiency Virus Type 1 Results in Delayed Processing of the p2 Peptide from Precursor Proteins," *J. Virol.* 73:6147-6151, American Society for Microbiology (1999).

Liang, C., et al., "Characterization of a Putative α-Helix across the Capsid-SP1 Boundary That Is Critical for the Multimerization of Human Immunodeficiency Virus Type 1 Gag," *J. Virol.* 76:11729-11737, American Society for Microbiology (Nov. 2002).

Martinez-Picado, J., et al., HIV-1 Drug Resistance Assays in Clinical Management, *AIDS Clin. Care* 10:81-88, Medical Publishing Group (1998).

Morellet, N., et al., "Helical structure determined by NMR of the HIV-1 (345-392) Gag sequence, surrounding p2: Implications for particle assembly and RNA packaging," *Protein Sci.* 14:375-386, Cold Spring Harbor Laboratory Press (Feb. 2005).

Pettit, S.C., et al., "The p2 Domain of Human Immunodeficiency Virus Type 1 Gag Regulates Sequential Proteolytic Processing and Is Required To Produce Fully Infectious Virions," *J. Virol.* 68:8017-8027, American Society for Microbiology (1994).

Pettit, S.C., et al., "Replacement of the P1 Amino Acid of Human Immunodeficiency Virus Type 1 Gag Processing Sites Can Inhibit or Enhance the Rate of Cleavage by the Viral Protease," *J. Virol.* 76:10226-10233, American Society for Microbiology (Oct. 2002).

Pinckard, R.N., et al., "Factors Influencing the Immune Response. I. Effects of the Physical State of the Antigen and of Lymphoreticular Cell Proliferation on the Response to Intravenous Injection of Bovine Serum Albumin in Rabbits," *Clin. Exp. Immunol.* 2:331-341, Blackwell Scientific Publications (1967).

Pokrovskii, A.G., et al., "Synthesis of derivatives of plant triterpenes and study of their antiviral and immunostimulating activiy," *Khimiya v Interesakh Ustoichivogo Razvitiya* 9:485-491, Siberian Branch of the Russian Academy of Sciences (2001).

Robbins, D.C., et al., "Antibodies to Covalent Aggregates of Insulin in Blood of Insulin-Using Diabetic Patients," *Diabetes* 36:838-841, American Diabetes Association (1987).

Sakalian, M., et al., "The Mason-Pfizer Monkey Virus Internal Scaffold Domain Enables In Vitro Assembly of Human Immunodeficiency Virus Type 1 Gag," *J. Virol.* 76:10811-10820, American Society for Microbiology (Nov. 2002).

Sakalian, M., et al., "3-*O*-(3', 3'-Dimethysuccinyl) Betulinic Acid Inhibits Maturation of the Human Immunodeficiency virus Type 1 Gag Precursor Assembled In Vitro," *J. Virol.* 80:5716-5722, American Society for Microbiology (Jun. 2006).

Sandefur, S., et al., "The I Domain Is Required for Efficient Plasma Membrane Binding of Human Immunodeficiency Virus Type 1 Pr55$^{Gag}$," *J. Virol.* 72:2723-2732, American Society for Microbiology (1998).

Schinazi, R.F., et al., "Mutations in retroviral genes associated with drug resistance," in *International Antiviral News* 496:95-107, International Medical Press (1996).

Sidhu, M.K., et al., "Distinction Between HIV-1 and HIV-2 Nucleotide Sequences by PCR and Restriction Enzyme Analysis," *Biotechniques* 18:20-24, Eaton Publishing Co. (1995).

Smith, T.F., and Waterman, M.S., "Comparison of Biosequences," *Adv. Appl. Mathematics* 2:482-489, Academic Press, Inc. (1981).

von Schwedler, U.K., et al., "Functional Surfaces of the Human Immunodeficiency Virus Type 1 Capsid Protein," *J. Virol.* 77:5439-5450, American Society for Microbiology (May 2003).

Wiegers, K., et al., "Sequential Steps in Human Immunodeficiency Virus Particle Maturation Revealed by Alterations of Individual Gag Polyprotein Cleavage Sites," *J. Virol.* 72:2846-2854, American Society for Microbiology (1998).

Wild, C.T., et al., "In vitro and in vivo pre-clinical analyses of PA-457, a novel betulinic acid derivative that potently inhibits HIV-1 replication," *AIDS 2002 Barcelona, XIV International AIDS Conference*, Abstract MoPeA3030, International AIDS Conference (Jul. 2002).

Zhou, J., et al., "Small-Molecule Inhibition of Human Immunodeficiency Virus Type 1 Replication by Specific Targeting of the Final Step of Virion Maturation," *J. Virol.* 78:922-929, American Society for Microbiology (Jan. 2004).

Zhou, J., et al., "The sequence of the CA-SP1 junction accounts for the differential sensitivity of HIV-1 and SIV to the small molecule maturation inhibitor 3-*O*-{3',3'-dimethlsuccinyl}-betulinic acid," *Retrovirology* 1:15, published on-line, doi:10.1186/1742-4690-1-15, 25 pages, BioMed Central (Jun. 2004).

Zhou, J., et al., "The Specificity of the Small-Molecule Maturation Inhibitor 3-O-{3',3'-Dimtheylsuccinyl}-Betulinic Acid for HIV-1 is Determined by the Sequence of the CA-SP1 Junction of GAG," poster 26, presented at the Fifth HIV DRP Symposium: Antiviral Drug Resistance, Chantilly, VA (Nov. 2004).

Zhou, J., et al., "Inhibition of HIV-1 Maturation via Drug Association with the Viral Gag Protein in Immature HIV-1 Particles," *J. Biol. Chem.* 280:42149-42155, American Society for Biochemistry and Molecular Biology (Dec. 2005).

Zhou, J., et al., "HIV-1 Resistance to the Small Molecule Maturation Inhibitor 3-*O*-{3',3'-dimethlsuccinyl}-betulinic acid is Conferred by a Variety of Single Amino Acid Substitutions at the CA-SP1 Cleavage Site in Gag," *J. Virol.*, published online, doi:10.1128/JVI.01626-06, 17 pages, American Society for Microbiology (Oct. 2006).

Zhu, Y.-M., et al., "Synthesis and Anti-HIV Activity of Oleanolic Acid Derivatives," *Bioorg. Med. Chem. Lett.* 11:3115-3118, Elsevier Science Ltd. (2001).

NCBI Entrez, GenBank Report, Accession No. M17451, Starcich, B.R., et al., National Center for Biotechnology Information (1993).

NCBI Entrez, GenBank Report, Accession No. M19921, Adachi, A., et al., National Center for Biotechnology Information (1993).

Database Caplus, Accession No. 2001:541179, English language abstract for Pokrovskii, A.G., et al., (Document NPL31), published by The American Chemical Society on STN.

Dialog File 351, Accession No. 7938971, Derwent WPI English language abstract for JP 1-143832 (Document FP1), 1989.

U.S. Appl. No. 11/597,431, Salzwedel et al., international filing date of May 24, 2005 (Not Published).

Holz-Smith, S.L., et al., "Role of human immunodeficiency virus (HIV) type 1 envelope in the anti-HIV activity of the betulinic acid derivative IC9564," *Antimicrob. Agents Chemother.* 45:60-66, American Society for Microbiology (2001).

Lee, K.-H., and Morris-Natschke, S.L., "Recent advances in the discovery and development of plant-derived natuaral products and their anaalogs as anti-HIV agents," *Pure Appl. Chem.* 71:1045-1051, IUPAC (1999).

Sun, I.C., "Anti-AIDS Agents. 34. Synthesis and Structure-Activity Relationships of Betulin Derivatives as Anti-HIV Agents," *J. Med. Chem.* 41:4648-4657, American Chemical Society (1998).

Fields, B.N., *Fields Virology*, 3$^{rd}$ Ed., Lippincott Williams & Wilkins, Philadelphia, PA, pp. 1882-1886 (1995).

Lee, K.-H. and Morris-Natschke, S.L., "Recent adveances in the discovery and development of plant-derived natural products and their analogs as anti-HIV agents," *Pure Appl. Chem.* 71:1045-1051, Blackwell Scientific Publications (1999).

\* cited by examiner

FIGURE 4

|                              | CA  |     | SP1 |
|------------------------------|-----|-----|-----|

Gag protein amino acid sequence no.: 357   363   370

Gag sequence #1:   G/S-H-K-A-R-V/I-L-|-A-E-A-M-S-Q-V   (SEQ ID NO: 1)

Gag sequence #2: G-H-K-A-R-V-L-|-V-E-A-M-S-Q-V   (SEQ ID NO: 2) [NL4-3]

Gag sequence #3: S-H-K-A-R-I-L-|-A-E-V-M-S-Q-V   (SEQ ID NO: 3) [RF]

FIGURE 5
(SEQ ID NO: 4) DSB-RESISTANT NL4-3

ATGGGTGCGAGAGCGTCGGTATTAAGCGGGGGAGAATTAGATAAATGGGAAAA
AATTCGGTTAAGGCCAGGGGGAAAGAAACAATATAAACTAAAACATATAGTAT
GGGCAAGCAGGGAGCTAGAACGATTCGCAGTTAATCCTGGCCTTTTAGAGACA
TCAGAAGGCTGTAGACAAATACTGGGACAGCTACAACCATCCCTTCAGACAGG
ATCAGAAGAACTTAGATCATTATATAATACAATAGCAGTCCTCTATTGTGTGC
ATCAAAGGATAGATGTAAAAGACACCAAGGAAGCCTTAGATAAGATAGAGGAA
GAGCAAAACAAAAGTAAGAAAAGGCACAGCAAGCAGCAGCTGACACAGGAAA
CAACAGCCAGGTCAGCCAAAATTACCCTATAGTGCAGAACCTCCAGGGGCAAA
TGGTACATCAGGCCATATCACCTAGAACTTTAAATGCATGGGTAAAAGTAGTA
GAAGAGAAGGCTTTCAGCCCAGAAGTAATACCCATGTTTTCAGCATTATCAGA
AGGAGCCACCCCACAAGATTTAAATACCATGCTAAACACAGTGGGGGGACATC
AAGCAGCCATGCAAATGTTAAAGAGACCATCAATGAGGAAGCTGCAGAATGG
GATAGATTGCATCCAGTGCATGCAGGGCCTATTGCACCAGGCCAGATGAGAGA
ACCAAGGGGAAGTGACATAGCAGGAACTACTAGTACCCTTCAGGAACAAATAG
GATGGATGACACATAATCCACCTATCCCAGTAGGAGAAATCTATAAAAGATGG
ATAATCCTGGGATTAAATAAAATAGTAAGAATGTATAGCCCTACCAGCATTCT
GGACATAAGACAAGGACCAAAGGAACCCTTTAGAGACTATGTAGACCGATTCT
ATAAAACTCTAAGAGCCGAGCAAGCTTCACAAGAGGTAAAAAATTGGATGACA
GAAACCTTGTTGGTCCAAAATGCGAACCCAGATTGTAAGACTATTTTAAAAGC
ATTGGGACCAGGAGCGACACTAGAAGAAATGATGACAGCATGTCAGGGAGTGG
GGGGACCCGGCCATAAAGCAAGAGTTTTGGTTGAAGCAATGAGCCAAGTAACA
AATCCAGCTACCATAATGATACAGAAAGGCAATTTTAGGAACCAAAGAAAGAC
TGTTAAGTGTTTCAATTGTGGCAAAGAAGGGCACATAGCCAAAAATTGCAGGG
CCCCTAGGAAAAAGGGCTGTTGGAAATGTGGAAAGGAAGGACACCAAATGAAA
GATTGTACTGAGAGACAGGCTAATTTTTTAGGGAAGATCTGGCCTTCCCACAA
GGGAAGGCCAGGGAATTTTCTTCAGAGCAGACCAGAGCCNACAGCCCCACCAG
AAGAGAGCTTCAGGTTTGGGGAAGAGACAACAACTCCCTCTCAGAAGCAGGAG
CCGATAGACAAGGAACTGTATCCTTTAGCTTCCCTCAGATCACTCTTTGGCAG
CGACCCCTCGTCACAATAAAGATAGGGGGGCAATTAAAGGAAGCTCTATTAGA
TACAGGAGCAGATGATACAGTATTAGAAGAAATGAATTTGCCAGGAAGATGGA
AACCAAAAATGATAGGGGGAATTGGAGGTTTTATCAAAGTAAGACAGTATGAT
CAGATACTCATAGAAATCTGCGGACATAAAGCTATAGGTACAGTATTAGTAGG
ACCTACACCTGTCAACATAATTGGAAGAAATCTGTTGACTCAGATTGGCTGCA
CTTTAAATTTTCCCATTAGTCCTATTGAGACTGTACCAGTAAAATTAAAGCCA
GGAATGGATGGCCCAAAAGTT

FIGURE 6
(SEQ ID NO: 5) WILD-TYPE NL4-3

ATGGGTGCGAGAGCGTCGGTATTAAGCGGGGGAGAATTAGATAAATGGGAAAA
AATTCGGTTAAGGCCAGGGGGAAAGAAACAATATAAACTAAAACATATAGTAT
GGGCAAGCAGGGAGCTAGAACGATTCGCAGTTAATCCTGGCCTTTTAGAGACA
TCAGAAGGCTGTAGACAAATACTGGGACAGCTACAACCATCCCTTCAGACAGG
ATCAGAAGAACTTAGATCATTATATAATACAATAGCAGTCCTCTATTGTGTGC
ATCAAAGGATAGATGTAAAAGACACCAAGGAAGCCTTAGATAAGATAGAGGAA
GAGCAAAACAAAAGTAAGAAAAAGGCACAGCAAGCAGCAGCTGACACAGGAAA
CAACAGCCAGGTCAGCCAAAATTACCCTATAGTGCAGAACCTCCAGGGGCAAA
TGGTACATCAGGCCATATCACCTAGAACTTTAAATGCATGGGTAAAAGTAGTA
GAAGAGAAGGCTTTCAGCCCAGAAGTAATACCCATGTTTTCAGCATTATCAGA
AGGAGCCACCCCACAAGATTTAAATACCATGCTAAACACAGTGGGGGGACATC
AAGCAGCCATGCAAATGTTAAAAGAGACCATCAATGAGGAAGCTGCAGAATGG
GATAGATTGCATCCAGTGCAGGCAGGGCCTATTGCACCAGGCCAGATGAGAGA
ACCAAGGGGAAGTGACATAGCAGGAACTACTAGTACCCTTCAGGAACAAATAG
GATGGATGACACATAATCCACCTATCCCAGTAGGAGAAATCTATAAAAGATGG
ATAATCCTGGGATTAAATAAAATAGTAAGAATGTATAGCCCTACCAGCATTCT
GGACATAAGACAAGGACCAAAGGAACCCTTTAGAGACTATGTAGACCGATTCT
ATAAAACTCTAAGAGCCGAGCAAGCTTCACAAGAGGTAAAAAATTGGATGACA
GAAACCTTGTTGGTCCAAAATGCGAACCCAGATTGTAAGACTATTTTAAAAGC
ATTGGGACCAGGAGCGACACTAGAAGAAATGATGACAGCATGTCAGGGAGTGG
GGGGACCCGGCCATAAAGCAAGAGTTTTGGCTGAAGCAATGAGCCAAGTAACA
AATCCAGCTACCATAATGATACAGAAAGGCAATTTTAGGAACCAAAGAAAGAC
TGTTAAGTGTTTCAATTGTGGCAAAGAAGGGCACATAGCCAAAAATTGCAGGG
CCCCTAGGAAAAAGGGCTGTTGGAAATGTGGAAAGGAAGGACACCAAATGAAA
GATTGTACTGAGAGACAGGCTAATTTTTTAGGGAAGATCTGGCCTTCCCACAA
GGGAAGGCCAGGGAATTTTCTTCAGAGCAGACCAGAGCCAACAGCCCCACCAG
AAGAGAGCTTCAGGTTTGGGGAAGAGACAACAACTCCCTCTCAGAAGCAGGAG
CCGATAGACAAGGAACTGTATCCTTTAGCTTCCCTCAGATCACTCTTTGGCAG
CGACCCCTCGTCACAATAAAGATAGGGGGGCAATTAAAGGAAGCTCTATTAGA
TACAGGAGCAGATGATACAGTATTAGAAGAAATGAATTTGCCAGGAAGATGGA
AACCAAAAATGATAGGGGGAATTGGAGGTTTTATCAAAGTAAGACAGTATGAT
CAGATACTCATAGAAATCTGCGGACATAAAGCTATAGGTACAGTATTAGTAGG
ACCTACACCTGTCAACATAATTGGAAGAAATCTGTTGACTCAGATTGGCTGCA
CTTTAAATTTTCCCATTAGTCCTATTGAGACTGTACCAGTAAAATTAAAGCCA
GGAATGGATGGCCCAAAG

FIGURE 7
(SEQ ID NO: 6) DSB-RESISTANT RF

ATGGGTGCGAGAGCGTCAGTATTAAGCGGCGGAAAATTAGACAAATGGGAAAA
AATTCGGTTAAGGCCAGGGGGAAAGAAAAGATATAAGTTAAAACATATAATAT
GGGCAAGCAGGGAGCTAGAACGATTTGCTGTCAATCCTGGCCTTTTAGAGACA
GCAGAGGGCTGTAGACAAATACTGGGACAGCTACAACCAGCCCTTCAGACAGG
ATCAGAAGAACTTAAATCATTATATAATGCAGTAGCAACCCTCTATTGTGTAC
ATCAAAATATAGAGGTAAGAGACACCAAGGAAGCTTTAGACAAGATAGAGGAA
GAGCAAAACAAAAGTAAGAAAAAGCACAGCAAGCAGCAGCTGACACAGGAAA
CGGCAGCCAGGTCAGCCAAAATTACCCTATAGTGCAGAACCTTCAGGGGCAAA
TGGTACATCAAGCCATATCACCTAGAACTTTAAATGCATGGGTAAAAGTAGTA
GAAGAGAAGGCTTTTAGCCCAGAAGTAATACCCATGTTTTCAGCATTATCAGA
AGGAGCCACCCCACAAGATTTAAACACCATGCTAAACACAGTGGGGGGACATC
AAGCAGCCATGCAAATGTTAAAAGAGACTATCAATGAGGAAGCTGCAGAATGG
GATAGATTGCATCCAGTGCAAGCAGGGCCTATTGCACCAGGCCAGATGAGAGA
ACCAAGGGGAAGTGACATAGCAGGAACCACTAGTACCCTTCAGGAACAAATAG
GATGGATGACAAATAATCCACCTATCCCAGTAGGAGAAATCTATAAAAGGTGG
ATAATTCTGGGATTAAATAAAATAGTAAGAATGTATAGCCCCATCAGCATTCT
GGACATAAGACAAGGACCTAAGGAACCCTTTAGAGACTATGTAGACCGGTTCT
ATAAAACTCTAAGAGCCGAGCAAGCTTCACAGGATGTAAAAAATTGGATGACA
GAAACCTTGCTGGTCCAAAATGCGAACCCAGATTGTAAAACTATTTTAAAAGC
ATTGGGACCAGCAGCTACACTAGAAGAAATGATGACAGCATGTCAGGGAGTAG
GGGGACCCAGCCATAAAGCAAGAATTTTGGCTGAAGTAATGAGCCAAGTAACA
AATTCAGCTACCATAATGCTGCAGAAAGGTAATTTTAGGGACCAAAGAAAAAT
TGTTAAGTGTTTCAACTGTGGCAAAGTAGGGCACATAGCCAAAAATTGCAGGG
CCCCTAGGAAAAAGGGCTGTTGGAAATGTGGAAAGGAAGGACACCAAATGAAA
GATTGCACTAGTGAGGGACGACAGGCTAATTTTTTAGGGAAAATCTGGCCTTC
CCACAAGGGAAGGCCAGGGAACTTTCTTCAGAGCAGACCAGAGCCAACAGCCC
CACCAGAAGAGAGCTTCAGGTTTGGGGAAGAGACAACTCCCTCTCAGAAGCAG
GAGAAGATAGACAAGGAACTGTATCCTTTAGCTTCCCTCAAATCACTCTTTGG
CAACGACCCATCGTCACAGTAAAGATAGGGGGGCAATTAAAGGAAGCTCTATT
AGATACAGGAGCAGATGATACAGTATTAGAAGAAATGAATTTGCCAGGAAAAT
GGAAACCAAAAATGATAGGGGGAATTGGAGGTTTTATCAAAGTAAGGCAGTAT
GATCAAATACTCATAGAAATCTGTGGACATAAAGCTATAGGTACAGTATTAGT
AGGACCTACACCTGTCAACATAATTGGAAGAAATCTGTTGACTCAGATTGGTT
GCACTTTAAATTTTCCCATTAGTCCTATTGAAACTATACCAGTAAAATTAAAG
CCAGGAATGGATGGCCCAAAAGTTAAACAATGGCCATTGACAGAGGAAAAAAT
AAAAGCATTGATAGAAATTTGTACAGAAATGGAAAAGGAAGGAAAAATTTCAA
AAATTGGGCCTGAAAATCCATACAATACTCCAGTATTTGCCATAAAGAAAAAN
GACAGTACTAAATGGAGAAAA

FIGURE 8

(SEQ ID NO: 7) WILD-TYPE RF

ATGGGTGCGAGAGCGTCAGTATTAAGCGGCGGAAAATTAGACAAATGGGAAAA
AATTCGGTTAAGGCCAGGGGGAAAGAAAAGATATAAGTTAAAACATATAATAT
GGGCAAGCAGGGAGCTAGAACGATTTGCTGTCAATCCTGGCCTTTTAGAGACA
GCAGAGGGCTGTAGACAAATACTGGGACAGCTACAACCAGCCCTTCAGACAGG
ATCAGAAGAACTTAAATCATTATATAATGCAGTAGCAACCCTCTATTGTGTAC
ATCAAAATATAGAGGTAAGAGACACCAAGGAAGCTTTAGACAAGATAGAGGAA
GAGCAAAACAAAAGTAAGAAAAAGCACAGCAAGCAGCAGCTGACACAGGAAA
CGGCAGCCAGGTCAGCCAAAATTACCCTATAGTGCAGAACCTTCAGGGGCAAA
TGGTACATCAAGCCATATCACCTAGAACTTTAAATGCATGGGTAAAAGTAGTA
GAAGAGAAGGCTTTTAGCCCAGAAGTAATACCCATGTTTTCAGCATTATCAGA
AGGAGCCACCCCACAAGATTTAAACACCATGCTAAACACAGTGGGGGGACATC
AAGCAGCCATGCAAATGTTAAAAGAGACTATCAATGAGGAAGCTGCAGAATGG
GATAGATTGCATCCAGTGCAAGCAGGGCCTATTGCACCAGGCCAGATGAGAGA
ACCAAGGGGAAGTGACATAGCAGGAACCACTAGTACCCTTCAGGAACAAATAG
GATGGATGACAAATAATCCACCTATCCCAGTAGGAGAAATCTATAAAAGGTGG
ATAATTCTGGGATTAAATAAAATAGTAAGAATGTATAGCCCCATCAGCATTCT
GGACATAAGACAAGGACCTAAGGAACCCTTTAGAGACTATGTAGACCGGTTCT
ATAAAACTCTAAGAGCCGAGCAAGCTTCACAGGATGTAAAAAATTGGATGACA
GAAACCTTGCTGGTCCAAAATGCGAACCCAGATTGTAAAACTATTTTAAAGC
ATTGGGACCAGCAGCTACACTAGAAGAAATGATGACAGCATGTCAGGGAGTAG
GGGGACCCAGCCATAAAGCAAGAATTTTGGCTGAAGCAATGAGCCAAGTAACA
AATTCAGCTACCATAATGCTGCAGAAAGGTAATTTTAGGGACCAAAGAAAAAT
TGTTAAGTGTTTCAACTGTGGCAAAGTAGGGCACATAGCCAAAAATTGCAGGG
CCCCTAGGAAAAAGGGCTGTTGGAAATGTGGAAAGGAAGGACACCAAATGAAA
GATTGCACTACTGAGGGACGACAGGCTAATTTTTTAGGGAAAATCTGGCCTTC
CCACAAGGGAAGGCCAGGGAACTTTCTTCAGAGCAGACCAGAGCCAACAGCCC
CACCAGAAGAGAGCTTCAGGTTTGGGGAAGAGACAACTCCCTCTCAGAAGCAG
GAGAAGATAGACAAGGAACTGTATCCTTTAGCTTCCCTCAAATCACTCTTTGG
CAACGACCCATCGTCACAGTAAAGATAGGGGGCAATTAAAGGAAGCTCTATT
AGATACAGGAGCAGATGATACAGTATTAGAAGAAATGAATTTGCCAGGAAAAT
GGAAACCAAAAATGATAGGGGGAATTGGAGGTTTTATCAAAGTAAGGCAGTAT
GATCAAATACTCATAGAAATCTGTGGACATAAAGCTATAGGTACAGTATTAGT
AGGACCTACACCTGTCAACATAATTGGAAGAAATCTGTTGACTCAGATTGGTT
GCACTTTAAATTTTCCCATTAGTCCTATTGAAACTATACCAGTAAAATTAAAG
CCAGGAATGGATGGCCCAAAAGTTAAACAATGGCCATTGACAGAGGAAAAAAT
AAAAGCATTGATAGAAATTTGTACAGAAATGGAAAAGGAAGGAAAAATT

FIGURE 9

GGCCATAAAGCAAGAGTTTTGGITGAAGCAATGAGCCAAGTA (SEQ ID NO: 8)

AGCCATAAAGCAAGAATTTTG-GCTGAAGTAATGAGCCAAGTA (SEQ ID NO: 9)

GGCCATAAAGCAAGAGTTTTGGCTGAAGCAATGAGCCAAGTA (SEQ ID NO: 10) NL4-3

AGCCATAAAGCAAGAATTTTGGCTGAAGCAATGAGCCAAGTA (SEQ ID NO: 12) RF

Figure 10

Figure 10A
Amino acid sequences in the region of the CA-SP1 cleavage site for a variety of lentiviruses

|  | CA<br>357      363 | SP1<br>364      370 |  |
|---|---|---|---|
| HIV-1 NL4-3 | GHKARVL | AEAMSQVTNPATIM | |
| HIV-1 RF | SHKARIL | AEAMSQVTNSATIM | |
| SIV mac239 | GQKARLM | AEALKEALAPVPIPFAA | |
| SIV.DD | GQKARLM | AEAMSQVLAPVPIPFAA | |
| SIV.DE | GQKARVL | AEALKEALAPVPIPFAA | |
| SIV.DM | GQKARVL chimera) | AEAMSQVLAPVPIPFAA | (DSB-sensitive |
| SIV.DJ | GQKARVM | AEAMSQVLAPVPIPFAA | |
| FIV | GYKMQLL | AEALTKVQ | |
| EIAV | KQKMMLL | AKALQ | |
| BIV | KSKMQFL | VAAMKEMGIQSPIPAVLPHTPEAYA | |

Figure 10B

<u>Amino Acid Sequences (-50 amino acids upstream of CA-SP1 cleavage site in CA and all of SP1)</u>

<u>HIV-1 RF</u>

CA               SP1
KNWMTETFLVQNANPDCKTILKALGPAATLEEMMTACQGVGGPSHKARIL  AEAMSQVTNSATIM

<u>HIV-1 NL4-3</u>

CA               SP1
KNWMTETLLVQNANPDCKTILKALGPGATLEEMMTACQGVGGPGHKARVL  AEAMSQVTNPATIM

Figure 10C. GAG gene of SIV DM (DSB-sensitive SIV chimera)

Amino Acid Sequence (-50 amino acids upstream of CA-SP1 cleavage site in CA and all of SP1)

CA                                      SP1

KNWMTQTLLIQNANPDCKLVLKGLGVNPTLEEMLTACQGVGGPGQKARVL
       AEAMSQVLAPVPIPFAA

Nucleotide Sequence SEQ ID NO: 90. encoding SEQ ID NO: 91 atgggcgtgagaaactccgtcttgtcagggaagaaagcagatgaattagaaaaattagg
ctacgacccaacggaaagaaaaagtacatgttgaagcatgtagtatgggcagcaaatgaa
ttagatagatttggattagcagaaagcctgttggagaacaaagaaggatgtcaaaaaata
ctttcggtcttagctccattagtgccaacaggctcagaaatttaaaaagcctttataat
actgtctgcgtcatctggtgcattcacgcagaagagaaagtgaaacacactgaggaagca
aaacagatagtgcagagacacctagtggtggaaacaggaacaacagaaactatgccaaaa
acaagtagaccaacagcaccatctagcggcagaggaggaaattacccagtacaacaaata
ggtggtaactatgtccacctgccattaagcccgagaacattaaatgcctgggtaaaattg
atagaggaaaagaaatttggagcagaagtagtgccaggatttcaggcactgtcagaaggt
tgcaccccctatgacattaatcagatgttaaattgtgtgggagaccatcaagcggctatg
cagattatcagagatattataaacgaggaggctgcagattgggacttgcagcacccacaa
ccagctccacaacaaggacaacttagggagccgtcaggatcagatattgcaggaacaact
agttcagtagatgaacaaatccagtggatgtacagacaacagaacccataccagtaggc
aacatttacaggagatggatccaactgggggttgcaaaaatgtgtcagaatgtataaccca
acaaacattctagatgtaaaacaagggccaaaagagccatttcagagctatgtagacagg
ttctacaaaagtttaagagcagaacagacagatgcagcagtaaagaattggatgactcaa
acactgctgattcaaaatgctaacccagattgcaagctagtgctgaaggggctgggtgtg
aatccaccctagaagaaatgctgacggcttgtcaaggagtagggggccg**ggacagaag
gctagagtattg**-
gcagaagccatgagtcaggtcctcgcaccagtgccaatcccttttgca
gcagcccaacagaggggaccaagaaagccaattaagtgttggaattgtgggaagaggga
cactctgcaaggcaatgcagagccccaagaagacagggatgctggaaatgtggaaaatg
gaccatgttatggccaaatgcccagacagacaggcgggttttttaggccttggtccatgg
ggaaagaagccccgcaatttccccatggctcaagtgcatcaggggctgatgccaactgct
cccccagaggacccagctgtggatctgctaaagaactacatgcagttgggcaagcagcag
agagaaaagcagagagaaagcagagagaagccttacaaggaggtgacagaggatttgctg
cacctcaattctctctttggaggagaccag Figure 10D. GAG gene of SIV Chimera with Q358 changed to H358

Amino Acid Sequence
```
                CA                                        SP1
KNWMTQTLLIQNANPDCKLVLKGLGVNPTLEEMLTACQGVGGPGHKARVL
        AEAMSQVLAPVPIPFAA
```

Nucleotide Sequence SEQ ID NO: 92. encoding amino acids SEQ ID NO: 93

```
atgggcgtgagaaactccgtcttgtcagggaagaaagcagatgaattagaaaaaattagg
ctacgacccaacggaaagaaaaagtacatgttgaagcatgtagtatgggcagcaaatgaa
ttagatagatttggattagcagaaagcctgttggagaacaaagaaggatgtcaaaaaata
ctttcggtcttagctccattagtgccaacaggctcagaaaatttaaaaagcctttataat
actgtctgcgtcatctggtgcattcacgcagaagagaaagtgaaacacactgaggaagca
aaacagatagtgcagagacacctagtggtggaaacaggaacaacagaaactatgccaaaa
acaagtagaccaacagcaccatctagcggcagaggaggaaattacccagtacaacaata
ggtggtaactatgtccacctgccattaagcccgagaacattaaatgcctgggtaaaattg
atagaggaaaagaaatttggagcagaagtagtgccaggatttcaggcactgtcagaaggt
tgcaccccctatgacattaatcagatgttaaattgtgtgggagaccatcaagcggctatg
cagattatcagagatattataaacgaggaggctgcagattgggacttgcagcacccacaa
ccagctccacaacaaggacaacttagggagccgtcaggatcagatattgcaggacaact
agttcagtagatgaacaaatccagtggatgtacagacaacagaacccataccagtaggc
aacatttacaggagatggatccaactgggggttgcaaaaatgtgtcagaatgtataaccca
acaaacattctagatgtaaaacaagggccaaaagagccatttcagagctatgtagacagg
ttctacaaaagtttaagagcagaacagacagatgcagcagtaaagaattggatgactcaa
acactgctgattcaaaatgctaacccagattgcaagctagtgctgaaggggctgggtgtg
aatcccaccctagaagaaatgctgacggcttgtcaaggagtagggggccg**ggacataag
gctagagtattg-
gcagaagccatgagtcaggtc**ctcgcaccagtgccaatccctttgca
gcagcccaacagaggggaccaagaaagccaattaagtgttggaattgtgggaagaggga
cactctgcaaggcaatgcagagccccaagaagacagggatgctggaaatgtggaaaatg
gaccatgttatggccaaatgcccagacagacaggcgggtttttaggccttggtccatgg
ggaaagaagccccgcaatttccccatggctcaagtgcatcaggggctgatgccaactgct
ccccagaggacccagctgtggatctgctaaagaactacatgcagttgggcaagcagcag
agagaaaagcagagagaaagcagagagaagccttacaaggaggtgacagaggatttgctg
cacctcaattctctctttggaggagaccag
```

Figure 10E: GAG gene in Chimeric Lentiviruses (FIV, EIAV, BIV) in 10F-H

The GAG gene of Chimeric Lentiviruses contains the following HIV-1 NL4-3 virus CA-SP1 region (bold).

```
HIV1 NL4-3:      5'GGCCATAAAGCAAGAGTTTTG-GCTGAAGCAATGAGCCAAGTA 3'(nt)
CA-SP1 region       G  H  K  A  R  V  L  A  E  A  M  S  Q  V      (aa)
```

---

Figure 10F. Nucleotide sequence of GAG gene of Chimeric Feline Immunodeficiency Virus (FIV) containing the HIV CA-SP1 region:

ATGGGGAATGGACAGGGGCGAGATTGGAAAATGGCCATTAAGAGATGTAGTAATGTTGCT 60
GTAGGAGTAGGGGGGAAGAGTAAAAAATTTGGAGAAGGGAATTTCAGATGGGCCATTAGA 120
ATGGCTAATGTATCTACAGGACGAGAACCTGGTGATATACCAGAGACTTTAGATCAACTA 180
AGGTTGGTTATTTGCGATTTACAAGAAAGAAGAGAAAAATTTGGATCTAGCAAAGAAATT 240
GATATGGCAATTGTGACATTAAAAGTCTTTGCGGTAGCAGGACTTTTAAATATGACGGTG 300
TCTACTGCTGCTGCAGCTGAAAATATGTATTCTCAAATGGGATTAGACACTAGGCCATCT 360
ATGAAAGAAGCAGGTGGAAAAGAGGAAGGCCCTCCACAGGCATATCCTATTCAAACAGTA 420
AATGGAGTACCACAATATGTAGCACTTGACCCAAAAATGGTGTCCATTTTTATGGAAAAG 480
GCAAGAGAAGGACTAGGAGGTGAGGAAGTTCAACTATGGTTTACTGCCTTCTCTGCAAAT 540
TTAACACCTACTGACATGGCCACATTAATAATGGCCGCACCAGGGTGCGCTGCAGATAAA 600
GAAATATTGGATGAAAGCTTAAAGCAACTGACAGCAGAATATGATCGCACACATCCCCCT 660
GATGCTCCCAGACCATTACCCTATTTTACTGCAGCAGAAATTATGGGTATAGGATTAACT 720
CAAGAACAACAAGCAGAAGCAAGATTTGCACCAGCTAGGATGCAGTGTAGAGCATGGTAT 780
CTCGAGGCATTAGGAAAATTGGCTGCCATAAAAGCTAAGTCTCCTCGAGCTGTGCAGTTA 840
AGACAAGGAGCTAAGGAAGATTATTCATCCTTTATAGACAGATTGTTTGCCCAAATAGAT 900
CAAGAACAAAATACAGCTGAAGTTAAGTTATATTTAAAACAGTCATTGAGCATAGCTAAT 960
GCTAATGCAGACTGTAAAAAGGCAATGAGCCACCTTAAGCCAGAAAGTACCCTAGAAGAA 1020
AAGTTGAGAGCTTGTCAAGAAATAGGCTCACCAGGCCATAAAGCAAGAGTTTTGGCTGAA 1080
GCAATGAGCCAAGTACAAGTAGTGCAATCAAAAGGATCAGGACCAGTGTGTTTTAATTGT 1140
AAAAAACCAGGACATCTAGCAAGACAATGTAGAGAAGTGAAAAAATGTAATAAATGTGGA 1200
AAACCTGGTCATGTAGCTGCCAAATGTTGGCAAGGAAATAGAAAGAATTCGGGAAACTGG 1260
AAGGCGGGGCGAGCTGCAGCCCCAGTGAATCAAATGCAGCAAGCAGTAATGCCATCTGCA 1320
CCTCCAATGGAGGAGAAACTATTGGATTTATAA 1353

10G. Nucleotide Sequence of GAG gene of Chimeric Equine Infectious Anemia Virus (EIAV) containing the HIV1 CA-SP1 region

```
ATGGGAGACCCTTTGACATGGAGCAAGGCGCTCAAGAAGTTAGAGAAGGTGACGGTACAA    60
GGGTCTCAGAAATTAACTACTGGTAACTGTAATTGGGCGCTAAGTCTAGTAGACTTATTT   120
CATGATACCAACTTTGTAAAAGAAAAGGACTGGCAGCTGAGGGATGTCATTCCATTGCTG   180
GAAGATGTAACTCAGACGCTGTCAGGACAAGAAAGAGAGGCCTTTGAAAGAACATGGTGG   360
GCAATTTCTGCTGTAAAGATGGGCCTCCAGATTAATAATGTAGTAGATGGAAAGGCATCA   420
TTCCAGCTCCTAAGAGCGAAATATGAAAAGAAGACTGCTAATAAAAAGCAGTCTGAGCCC   480
TCTGAAGAATATCCAATCATGATAGATGGGGCTGGAAACAGAAATTTTAGACCTCTAACA   540
CCTAGAGGATATACTACTTGGGTGAATACCATACAGACAAATGGTCTATTAAATGAAGCT   600
AGTCAAAACTTATTTGGGATATTATCAGTAGACTGTACTTCTGAAGAAATGAATGCATTT   660
TTGGATGTGGTACCTGGCCAGGCAGGACAAAAGCAGATATTACTTGATGCAATTGATAAG   720
ATAGCAGATGATTGGGATAATAGACATCCATTACCGAATGCTCCACTGGTGGCACCACCA   780
CAAGGGCCTATTCCCATGACAGCAAGGTTTATTAGAGGTTTAGGAGTACCTAGAGAAAGA   840
CAGATGGAGCCTGCTTTTGATCAGTTTAGGCAGACATATAGACAATGGATAATAGAAGCC   900
ATGTCAGAAGGCATCAAAGTGATGATTGGAAAACCTAAAGCTCAAAATATTAGGCAAGGA   960
GCTAAGGAACCTTACCCAGAATTTGTAGACAGACTATTATCCCAAATAAAAAGTGAGGGA  1020
CATCCACAAGAGATTTCAAAATTCTTGACTGATACACTGACTATTCAGAACGCAAATGAG  1080
GAATGTAGAAATGCTATGAGACATTTAAGACCAGAGGATACATTAGAAGAGAAATGTAT   1140
GCTTGCAGAGACATTGGAACTACAGGCCATAAAGCAAGAGTTTTGGCTGAAGCAATGAGC  1200
CAAGTAACTGGTCTTGCGGGCCCATTTAAAGGTGGAGCCTTGAAAGGAGGGCCACTAAAG  1260
GCAGCACAAACATGTTATAACTGTGGGAAGCCAGGACATTTATCTAGTCAATGTAGAGCA  1320
CCTAAAGTCTGTTTTAAATGTAAACAGCCTGGACATTTCTCAAAGCAATGCAGAAGTGTT  1380
CCAAAAAACGGGAAGCAAGGGCTCAAGGGAGGCCCCAGAAACAAACTTTCCCGATACAA   1440
CAGAAGAGTCAGCACAACAAATCTGTTGTACAAGAGACTCCTCAGACTCAAAATCTGTAC  1500
CCAGATCTGAGCGAAATAAAAAGGAATACAATGTCAAGGAGAAGGATCAAGTAGAGGAT   1560
CTCAACCTGGACAGTTTGTGGGAGTAA                                   1587
```

10H. Nucleotide Sequence of GAG gene of Chimeric Bovine
Immunodeficiency Virus (BIV) containing the HIV1 CA-SP1 region

```
ATGAAGAGAAGGGAGTTAGAAAAGAAGCTTCGTAAGGTTAGGGTGACACCCCAACAGGAT    60
AAATATTATACTATAGGGAATCTTCAATGGGCCATTAGAATGATAAATCTAATGGGGATC   120
AAATGTGTGTGTGACGAGGAGTGCTCGGCAGCAGAGGTAGCCCTTATCATAACCCAATTT   180
TCAGCTTTAGACTTAGAAAATTCTCCTATCAGAGGTAAGGAGGAGGTGGCCATAAAAAAT   240
ACTCTGAAGGTTTTCTGGTCCCTGCTGGCGGGGTACAAACCAGAGAGTACAGAAACGGCC   300
CTAGGATATTGGGAGGCCTTTACATATAGAGAAAGGGAGGCCAGAGCTGATAAGGAAGGC   360
GAAATTAAGAGTATTTACCCTTCCCTAACACAGAACACACAGAATAAGAAGCAGACATCG   420
AATCAGACAAACACTCAATCATTACCAGCTATCACTACTCAAGATGGTACTCCTAGGTTT   480
GATCCTGACCTCATGAAGCAGCTTAAGATCTGGTCAGACGCCACTGAAAGAAATGGGGTT   540
GACCTTCATGCAGTGAATATATTAGGGGTCATTACAGCAAACCTAGTACAGGAAGAAATT   600
AAACTCCTCTTGAATAGTACACCCAAGTGGAGATTAGATGTACAACTTATAGAATCAAAA   660
GTAAGAGAGAAAGAAAATGCCCACAGAACGTGGAAACAGCATCATCCAGAAGCCCCAAAA   720
ACAGATGAAATCATCGGTAAGGGCTTAGTTCTGCTGAACAAGCCACCCTGATCTCAGTA   780
GAATGCAGAGAAACTTTCAGACAGTGGGTGCTGCAGGCAGCTATGGAGGTGGCACAGGCA   840
AAACATGCTACCCCAGGTCCCATCAACATTCATCAGGGACCCAAGGAGCCGTACACAGAC   900
TTTATAAATAGATTAGTGGCAGCCCTTGAAGGTATGGCGGCTCCAGAAACCACAAAAGAA   960
TACTTACTCCAACATCTATCTATTGATCATGCCAATGAAGACTGCCAGTCTATTCTAAGA  1040
CCTTTGGGACCCAACACCCCAATGGAGAAAAAATTAGAAGCATGTAGGGTAGTGGGATCT  1100
CAGGGCCATAAAGCAAGAGTTTTGGCTGAAGCAATGAGCCAAGTAGGGATCCAATCACCA  1160
ATTCCAGCAGTCTTGCCTCACACACCAGAAGCATATGCCTCCCAAACCTCAGGGCCCGAG  1240
GATGGTAGGAGATGTTACGGATGTGGGAAGACAGGACATTTGAAGAGGAATTGTAAACAG  1300
CAAAAATGCTACCATTGTGGCAAACCTGGCCACCAAGCAAGAAACTGCAGGTCAAAAAAC  1360
GGGAAGTGCTCCTCTGCCCCTTATGGGCAGAGGAGCCAACCACAGAACAATTTTCACCAG  1420
AGCAACATGAGTTCTGTGACCCCATCTGCACCCCTCTTATATTAGATTAG            1471
```

Figure 12

|  | | | | | SP1 | | | | | | | | |
|---|---|---|---|---|---|---|---|---|---|---|---|---|---|
| NL4-3 | A | E | A | M | S | Q | V | T | N | P | A | T | I | M |
| ΔE365 | - | Δ | - | - | - | - | - | - | - | - | - | - | - | - |
| ΔA366 | - | - | Δ | - | - | - | - | - | - | - | - | - | - | - |
| ΔM367 | - | - | - | Δ | - | - | - | - | - | - | - | - | - | - |
| ΔS368 | - | - | - | - | Δ | - | - | - | - | - | - | - | - | - |
| ΔQ369 | - | - | - | - | - | Δ | - | - | - | - | - | - | - | - |
| ΔV370 | - | - | - | - | - | - | Δ | - | - | - | - | - | - | - |
| ΔT371 | - | - | - | - | - | - | - | Δ | - | - | - | - | - | - |
| ΔN372 | - | - | - | - | - | - | - | - | Δ | - | - | - | - | - |
| ΔP373 | - | - | - | - | - | - | - | - | - | Δ | - | - | - | - |
| ΔA374 | - | - | - | - | - | - | - | - | - | - | Δ | - | - | - |
| ΔT375 | - | - | - | - | - | - | - | - | - | - | - | Δ | - | - |
| ΔI376 | - | - | - | - | - | - | - | - | - | - | - | - | Δ | - |
| ΔM377 | - | - | - | - | - | - | - | - | - | - | - | - | - | Δ |

Figure 13. Summary of particle production and infectivity of point deletions mutants

| Virus | Particle production[a] (HeLa cells) | Gag processing[b] (HeLa cells) | Infectivity (Relative $TCID_{50}$ in U87 CD4.CXCR4 cells)[c] |
|---|---|---|---|
| NL4-3 | ++++ | WT | ++++ |
| ΔE365 | + | WT | + |
| ΔA366 | + | WT | - |
| ΔM367 | + | WT | - |
| ΔS368 | ++ | WT | ++ |
| ΔQ369 | ++ | WT | ++ |
| ΔV370 | +++ | WT | ++++ |
| ΔT371 | +++ | WT | ++++ |
| ΔN372 | ++++ | WT | ++++ |
| ΔP373 | ++++ | WT | ++++ |
| ΔA374 | ++++ | WT | NT |
| ΔT375 | NT[d] | WT | NT |
| ΔI376 | +++ | Defective | NT |
| ΔM377 | NT | Defective | NT |

[a] Virus particle yield. The level of virus production by NL4-3 was arbitrarily set as "++++". The levels of virus production for point deletion mutants were normalized by comparing with NL4-3 and then scored as follows: "-", not detectable; "+", 25% of NL4-3 level; "++", 50% of NL4-3 level; "+++", 75% of NL4-3 level; "++++" 100% of NL4-3 level. The data were the average of at least two to four independent transfection experiments.

[b] "WT" indicates wild-type or normal Gag processing as visualized in SDS-PAGE/Western-Blot. "Defective" means that significant amount of Gag intermediate products were present in virus particle.

[c] TCID50/ml ranging from $10^6$-$10^5$ ++++, $10^4$-$10^3$ +++, $10^2$ ++, $10^1$ +.

[d] Indicates that experiment was not performed

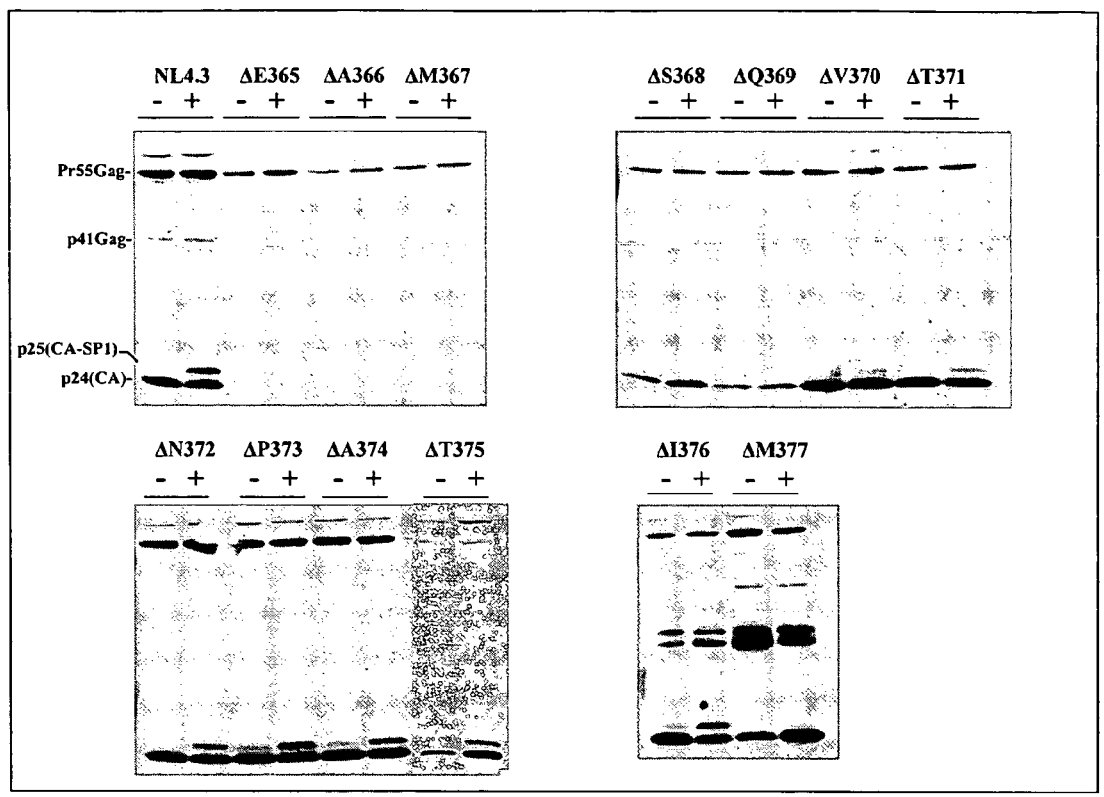
Figure 14. Western blots for viruses containing point deletions in SP1, in the presence (+) and absence (-) of DSB.

Figure 16. Cloning Strategy: Substituting HIV-1 specific CA-SP1
residues into the corresponding Gag region of FIV or EIAV
or BIV

| Provirus DNA | Cloning site | | Chimeric HIV1CA-SP1 Lentivirus |
|---|---|---|---|
| SIV | Bam HI nt xxx | Sbf Int xxx | SHIV-CA-SP1 Chimera |
| FIV | Sac I nt 504 | Eco RI1872 | FIV-HIV-CA-SP1 Chimera |
| EIAV | Kas I nt 310 | Eco RV2744 | EIAV-HIV-CA-SP1 Chimera |
| BIV | BsrG I nt 954 | Bsr GI1511 | BIV-HIV-CA-SP1 Chimera |

FIGURE 17. HIV-1 NL4-3 SP1 TAGGED WITH A EPITOPE

1. Tag SP1 with HA epitope (YPYDVPDYA) (SEQ ID NO: 81)

| SP1     | A | E | A | M | S | Q | V | T | N | P |   | A | T | I | M | 14 aa |
|---------|---|---|---|---|---|---|---|---|---|---|---|---|---|---|---|-------|
| HA-SP1a | - | - | - | - | - | - | - | - | Y | - | YDVPDY | - | - | - | - | 20 aa |
| HA-SP1b | - | - | - | - | - | - | - | - | Y | - | YDVPDY | - | Δ | I | M | 19 aa |
| HA-SP1c | - | - | - | - | - | - | - | - | Δ | Y | - YDVPDY | - | - | - | - | 19 aa |
| HA-SP1d | - | - | - | - | - | - | - | - | Δ | Y | - YDVPDY | - | Δ | - | - | 18 aa |

2. Tag SP1 with Blue-tongue virus VP7 epitope (QYPALT) (SEQ ID NO: 82)

| SP1      | A | E | A | M | S | Q | V | T | N | P |   | A | T | I | M | 14 aa |
|----------|---|---|---|---|---|---|---|---|---|---|---|---|---|---|---|-------|
| BTV7-SP1a| - | - | - | - | - | - | - | - | Q | Y | - | AL | - | - | - | 15 aa |
| BTV7-SP1b| - | - | - | - | - | - | - | - | Q | Y | - | ALT | - | - | - | 17 aa |

3. Tag SP1 with α–tubulin epitope (EEF)

| SP1    | A | E | A | M | S | Q | V | T | N | P |   | A | T | I | M | 14 aa |
|--------|---|---|---|---|---|---|---|---|---|---|---|---|---|---|---|-------|
| Tu-SP1a| - | - | - | - | - | - | - | - | - | - | - EEF | - | - | - | - | 17 aa |
| Tu-SP1b| - | - | - | - | - | - | - | - | - | - | EEFEEF | - | - | - | - | 18 aa |

4. Tag SP1 with Flag epitope (DYKDDDDK) (SEQ ID NO: 83)

| SP1      | A | E | A | M | S | Q | V | T | N | P |   | A | T | I | M |       |
|----------|---|---|---|---|---|---|---|---|---|---|---|---|---|---|---|-------|
|          |   |   |   |   |   |   |   |   |   |   |   |   |   |   |   | 14 aa |
| Flag-SP1a| - | - | - | - | - | - | - | - | - | - | DYKDDDDK | - | - | - | - | 20 aa |
| Flag-SP1b| - | - | - | - | - | - | - | - | D | Y | KDDD | D | K | - | - | 18 aa |
| Flag-SP1c| - | - | - | - | - | - | - | - | - | - | - | - | D Y KDDD | D | I | M | 23 aa |

5. Tag SP1 with VSV-G-tag construct (YTDIEMNRLGK) (SEQ ID NO: 84)

| SP1     | A | E | A | M | S | Q | V | T | N | P |   | A | T | I | M | 14 aa |
|---------|---|---|---|---|---|---|---|---|---|---|---|---|---|---|---|-------|
| VSV-SP1a| - | - | - | - | - | - | - | - | YTDIEMNRLGK | - | - | - | - | - | - | 23 aa |

Figure 18A

HIV-1 RF (HAT-3), genebank accession no: M17451 M12508
Polynuleotide sequence from position at 304 to 1809 (bold-type
and highlighted) encodes Gag protein (SEQ ID NO: 18)

Starcich,B.R., Hahn,B.H., Shaw,G.M., McNeely,P.D., Modrow,S., Wolf,H.,
Parks,E.S., Parks,W.P., Josephs,S.F., Gallo,R.C. and
Wong-Staal,F."Identification and characterization of conserved and variable
regions in the envelope gene of HTLV-III/LAV, the retrovirus of AIDS"; Cell 45
(5), 637-648 (1986)

```
   1 gagctctctg gctagctagg gaacccactg cttaagcctc aataaagctt gccttgagtg
  61 cttcaagtag tgtgtgcccg tctgttgtgt gactctggta actagagatc cctcagacct
 121 ctttagtcag tgtggaaaat ctctagcagt ggcgcccgaa cagggaccag aaagcgaaag
 181 tagaaccaga ggagatctct cgacgcagga ctcggcttgc tgaagcgcgc gcggcaagag
 241 gcgaggggcg gcgaacggtg agtacgccga aaattttgac tagcggaggc tagaaggaga
 301 gagatgggtg cgagagcgtc agtattaagc ggcggaaaat tagacaaatg ggaaaaaatt
 361 cggttaaggc caaggggaaa gaaagatat aagttaaaac atatagtatg ggcaagcagg
 421 gagctagaac gatttgctgt caatcctagc cttttagaga cagcagaggg ctgtagacaa
 481 atactgggac agctacaacc agcccttcag acaggatcag aagaacttaa atcattatat
 541 aatgcagtag caaccctcta ttgtgtacat caaaatatag aggtaagaga caccaaggaa
 601 gctttagaca agatagagga agagcaaaac aaaagtaaga aaaagcaca gcaagcagca
 661 gctgacacag gaaacggcag ccaggtcagc caaaattacc ctatagtgca gaaccttcag
 721 gggcaaatgg tacatcaagc catatcacct agaactttaa atgcatgggt aaaagtagta
 781 gaagagaagg cttttagccc agaagtaata cccatgtttt cagcattatc agaggagcc
 841 accccacaag atttaaacac catgctaaac acagtggggg gacatcaagc agccatgcaa
 901 atgttaaaag agactatcaa tgaggaagct gcagaatggg atagattgca tccagtgcat
 961 gcagggccta ttgcaccagg tcagatgaga gaaccaaggg gaagtgacat agcaggaacc
1021 actagtaccc ttcaggaaca aataggatgg atgacaaata tccacctat cccagtagga
1081 gaaatctata aaggtggat aattctggga ttaaataaaa tagtaagaat gtatagcccc
1141 atcagcattc tggacataag acaaggacct aaggaaccct ttagagacta tgtagaccgg
1201 ttctataaaa ctctaagagc cgagcaagct tcacaggatg taaaaaattg gatgacagaa
1261 accttcctgg tccaaaatgc gaacccagat tgtaaaacta ttttaaaagc attgggacca
1321 gcagctacac tagaagaaat gatgacagca tgtcagggag taggggggacc cagccataaa
1381 gcaagaattt tggctgaagc aatgagccaa gtaacaaatt cagctaccat aatgctgcag
1441 aaaggtaatt ttaggggacca agaaaaaatt gttaagtgtt tcaactgtgg caaagtaggg
1501 cacatagcca aaaattgcag ggcccctagg aaaaagggct gttggaaatg tggaaaggaa
1561 ggacaccaaa tgaaagattg cactaatgag gacgacagg ctaattttt agggaaaatc
1621 tggccttccc acaagggaag gccagggaac tttcttcaga gcagaccaga gccaacagcc
1681 ccaccagaag agagcttcag gtttggggaa gagacaactc cctctcagaa gcaggagaag
1741 atagacaagg aactgtatcc tttagcttcc ctcaaatcac tctttggcaa cgacccatcg
1801 tcacagtaaa gatagggggg caattaaagg aagctctatt agatacagga gcagatgata
1861 cagtattaga aaaatgaat ttgccaggaa aatggaaacc aaaaatgata gggggaattg
1921 gaggttttat caaagtgaga cagtatgatc aaatactcat agaaatctgt ggacataaag
1981 ctataggtac agtattagta ggacctacac ctgtcaacat aattggaaga aatctgttga
2041 ctcagattgg ttgcacttta aattttccca ttagtcctat tgaaactgta ccagtaaaat
2101 taaagccagg aatggatggc ccaaaagtta acaatggcc attgacagag gaaaaaataa
2161 aagcattggt agaaatttgt acagaaatgg aaaggaagg aaaaatttcc aaaattgggc
2221 ctgaaaatcc atacaatact ccagtatttg ccataaagaa aaagacagt actaaatgga
2281 gaaaattagt agatttcaga gaacttaata agagaactca agacttctgg gaagttcagt
2341 taggaatacc acatcctgca gggttaaaaa agaagaaatc agtaacagta ttggatgtgg
2401 gtgatgcata ttttcagtt cccttagata aagagttcag gaagtatact gcatttacca
2461 tacctagtat aaacaatgaa acaccacgga ttagatatca gtacaatgtg cttccacaag
2521 ggtggaaagg atcaccagca atattccaaa gtagtatgac aaaaatctta gagccttta
2581 aaaacaaaa tccagaaata gttatctatc aatacatgga tgatttgtat gtaggatctg
```

Figure 18B

```
2641 atttagaaat agggcagcat agaataaaaa tagaggaact gagagaacat ctgttaaagt
2701 gggggtttac cacaccggac aagaaacatc agaaagaacc tccatttctt tggatgggtt
2761 atgaactcca tcctgataaa tggacagtac agcctatagt gctgccagaa aaagacagct
2821 ggactgtcaa tgacatacag aagttagtgg gaaaattgaa ttgggcaagt cagatttatg
2881 cagggattaa agtaaagcaa ttatgtaaac tccttagggg aaccaaagca ctaacagaag
2941 tagtacaact aacaaaagaa gcagagctag aactggcaga aaatagggag attctaaaag
3001 aaccagtaca tggagtgtat tatgacccat caaaagactt aatagcagaa atacagaagc
3061 aggggcaagg ccaatggaca taccaaattt atcaagagcc atttaaaaac ctgaaaacag
3121 gaaagtatgc aagaatgagg ggtgcccaca ctaatgatgt aaaacaatta acagaggcag
3181 tacaaaaagt agccacagaa agcatagtaa tatggggaaa gactcctaaa tttaaactac
3241 ccatacaaaa agaaacatgg gaggcatggt ggacagagta ttggcaagcc acctggattc
3301 ctgagtggga gtttgtcaat acccctccct tagtaaaatt gtggtaccag ttagaaaaag
3361 aacccataat aggagcagaa actttctatg tagatggggc agctaataga gagactaaat
3421 taggaaaagc aggatatgtt actgacagag gaagacaaaa agttgtctcc ctaactgaca
3481 caacaaatca gaagactgag ttacaagcaa ttcatctagc tttgcaggat tcgggattag
3541 aagtaaacat agtaacagac tcacaatatg cattgggaat cattcaagca aaccagata
3601 aaagtgaatc agagttagtc agtcagataa tagagcagtt aataaaaaag gaaaaggtct
3661 acctggcatg ggtaccagca cacaaaggga ttggaggaaa tgaacaagta gatagattag
3721 tcagtactgg aatcaggaaa gtactatttt tggatggaat agataaggcc caagatgaac
3781 atgagaaata tcacagtaat tggagagcaa tggctagtga ttttaacctg ccacctgtag
3841 tagcaaaaga aatagtagcc agctgtgata atgtcagct aaaaggagaa gccatgcatg
3901 gacaagtaga ttgtagtcca ggaatatggc aactagattg tacacatcta gaaggaaaaa
3961 ttatcctggt agcagttcat gtagccagtg gctatataga agcagaagtt attccagcag
4021 aaacaggaca ggaaacagca tactttatct taaaattagc aggaagatgg ccagtaaaag
4081 taatacatac agacaatggc agcaatttca ccagtactac agttaaggcc gcctgttggt
4141 gggcagggat caagcaggaa tttggcattc cctacaatcc ccaaagtcaa ggagtagtag
4201 aatctatgaa taaacaatta agcaaatta taggacaggt aagagatcag gctgaacatc
4261 ttaagacagc agtacaaatg gcagtattca tccacaattt taaaagaaaa gggggattg
4321 ggggtacag tgcagggaa agaatagtag acataatagc aacagacata caaactaaag
4381 aactacaaaa acaaattaca aaaattcaaa attttcgggt ttattacagg gacagcagag
4441 atccactttg gaaaggacac gcaaagcttc tctggaaagg tgaaggggca gtagtaatac
4501 aagataatag tgacataaaa gtagtgccaa gaagaaaagc aaagatcatt agggattatg
4561 gaaaacagat ggcaggtgat gattgtgtgg caagtagaca ggatgaggat tagaacatgg
4621 aaaagtttag taaaacacca tatgtatatt tcaaggaaag ctaagggatg gttttataga
4681 catcactatg aaagcactca tccaagaata agttcagagg tacacatccc accaggggat
4741 gaaaggttgg taataacaac atattggggt ctgcatacag gagaaagaga ctggcatttg
4801 ggtcagggag tctccataga atggaggaaa aggagatata gcacacaagt agaccctgac
4861 ctagcagacc aactaattca cctgtactat tttgattgtt tttcagaatc tgctataaga
4921 aagccatcat taggacatat agttagtcct aggtgtgaat atcaagcagg acataacaag
4981 gtaggatctc tacagtacct ggcactagca gcattaacaa caccaaaaaa gataaagcca
5041 cctttgccta gtgttaagaa actgacagag gatagatgga acaagcccca gaagaccaag
5101 ggccacagag ggagccatac aatgaatgga cactagagct tttagaggag cttaagagtg
5161 aagctgtcag acatttccct aggctatggc tccatagctt aggacaacat atctatgaaa
5221 cttatgggga tacatgggca ggagtggaag ctataataag aattctgcaa caactgctgt
5281 ttattcattt cagaattggg tgtcaacata gcagaatagg cattactcga caaagaagag
5341 caagaaatgg agccagtaga tcctagacta gagccctgga agcatccagg aagtcagcct
5401 aagactgctt gtaacaattg ctattgtaaa aagtgttgct atcattgcca gtttgcttc
5461 ttaacaaaag gcttaggcat ctcctatggc aggaagaaga ggagacagcg acgaggacct
5521 cctcaaggca gtcagactca tcaagtctct ttatcaaagc agtaagtagt atatgtaatg
5581 caatctttag aaatattagc aatagtagca ttagtagtag cagcaatact agcaatagtt
5641 gtgtggacca tagttggcat agaaattagg aaaacattaa ggcaaaaaaa aaaatagaca
5701 ggttaattga tagaataaga gaaagagcag aagacagtgg caatgagagt gatggagatg
5761 aggaagaatt gtcagcactt gtggaaatgg ggcaccatgc tccttgggat gttgatgatc
5821 tgtagtgctg cagaggactt gtgggtcaca gtctattatg ggtacctgt gtggaagaa
5881 gcaaccacca ctctattttg tgcatcagaa gctaaagcat ataaaacaga ggtacataat
5941 gtctgggcca aacatgcttg tgtacctaca gaccccaacc cacaagaagt actattggaa
```

Figure 18C

```
6001 aatgtgacag aaaattttaa catgtggaaa aataacatgg tagaacagat gcatgaggat
6061 ataatcagtt tatgggatca aagcctaaag ccatgtgtaa aattaacccc actctgtgtt
6121 actttaaatt gcactgatgc taacttgaat ggtactaatg tcactagtag tagcggggga
6181 acaatgatgg agaacggaga aataaaaaac tgctctttcc aagttaccac aagtagaaga
6241 gataagacgc agaaaaaata tgcactttt tataaacttg atgtggtacc aatagagaag
6301 ggtaatatta gccctaagaa taatactagc aataatacta gctatggtaa ctatacattg
6361 atacattgta attcctcagt cattacacag gcctgtccaa aggtatcctt tgagccaatt
6421 cccatacatt attgcacccc ggctggtttt gcgattctaa agtgtaatga taagaagttc
6481 aatggaacag gaccatgtaa aaatgtcagc acagtacaat gtacacatgg aattaggcca
6541 gtagtgtcaa ctcaactgct gttaaatggc agtctagcag aagaagaggt agtaattaga
6601 tctgaaaatt tcacggacaa tgttaaaacc ataatagtac agctgaatgc atctgtacaa
6661 attaattgta caagacccaa caacaataca agaaaaagta taactaaggg accagggaga
6721 gtaatttatg caacaggaca aataatagga gatataagaa agcacattg taaccttagt
6781 agagcacaat ggaataacac tttaaaacag gtagttacaa aattaagaga acaatttgac
6841 aataaaacaa tagtctttac gtcatcctca ggaggggacc cagaaattgt acttcacagt
6901 tttaattgtg gaggggaatt tttctactgt aatacaacac aactgtttaa tagtacttgg
6961 aatagtactg aagggtcaaa taacactgga ggaaatgaca caatcacact cccatgcaga
7021 ataaaacaaa ttgtaaacat gtggcaggaa gtaggaaaag caatgtatgc cctcccatc
7081 agtggacaaa ttaaatgtat atcaaatatt acagggctac tattaacaag agatggggt
7141 gaagatacaa ctaatactac agagatcttc agacttggag gaggaaatat gagggacaat
7201 tggagaagtg aattatataa atataaagtg gtaagaattg agccattagg agtggcaccc
7261 actagggcaa agagaagagt ggtgcaaaga gaaaaaagag cagtgggaac aataggagct
7321 atgttccttg ggttcttggg agcagcagga agcactatgg gcgcaggctc aataacgcta
7381 acggtacagg ccagacactt attgtctggt atagtgcaac agcaaaacaa tttgctgagg
7441 gctattgagg cgcaacagca tctgttgcaa ctcacggtct gggcatcaa acagctccag
7501 gcaagagtcc tggctgtgga aagatacct agggatcaac agctcctagg aatttgggga
7561 tgctctggaa aactcatttg caccactact gtgccttgga atgctagttg gagtaataaa
7621 tctctgaata tgatttggaa taacatgacc tggatgcagt gggaaagaga aattgacaat
7681 tacacaggca taatatacaa cttacttgaa gaatcgcaga accagcaaga aaagaatgaa
7741 caagaattat tggaattgga taaatgggca aatttgtgga attggtttga cataacacaa
7801 tggctgtggt atataagaat attcataatg atagtaggag gcttggtagg tctaaaaata
7861 gtttttgctg tgctttctat agtgaataga gttaggcagg gatactcacc attatcattt
7921 cagacccacc tcccagcccc gaggggaccc gacaggcccg aaggaatcga aggagaaggt
7981 ggagagagag acagagacag atccggcggt gcagtgaatg gattcttgac acttatctgg
8041 gacgatctgt ggaccctgtg cagcttcagc taccaccgct tgagagactt actcttgata
8101 gtagtgagga ttgtggaact tctgggacgc aggggtgg aagccctcaa gtattggtgg
8161 aatctcctgc agtattggag tcaggagcta aagaatagtg ctgttagctt gcttaatacc
8221 acagcaatag cagtagctga agggacagat aggattatag aagtagcaca aagaattctt
8281 agagcttttc ttcacatacc tagaagaata agacagggct tagaaagggc tttgctgtaa
8341 aatgggtggc aagtggtcaa aaagtaagat gggtggatgg cctgctgtaa gggaaagaat
8401 gcaaaaagct gagccagcag cagatggggt gggagcagca tctcgagacc tggagaaaca
8461 tggaacaatc acaagtagca atacagcagc taataatgct gcttgcacct ggctagaagc
8521 acaagaggat gaggatgagg aggtgggttt tccagtcaga cctcaggtac ctttaaggcc
8581 tatgactttc aaggcagctg tagatcttag ccactttta aaagaaaagg ggggactgga
8641 tgggctagtg ttctcccaga aaagacaaga tatccttgat ctgtgggttt accacacaca
8701 aggctacttc cctgactggc agaactacac accagggcca gggaccagat atccactgac
8761 ctttggatgg tgcttcaagc tagtaccagt tgagccagat aaggtagaag aggccactga
8821 aggagagaac aacagcttgt tacaccctat atgcctgcat gggatggatg acccagagaa
8881 agaagtgtta gtgtggaagt ttgacagccg cctcgcattt catcacgtcg cccgagagaa
8941 gcatccggag tactacaaag actgctgaca tcgagttttc tacaagggac tttccgctgg
9001 ggactttcca gggaggtgtg gcctgggcgg gactggggag tggcgagccc tcagatgctg
9061 catataagca gctgcttttt gcctgtactg ggtctctctg gttagaccag atctgagctt
9121 gggagctc
```

Figure 19A

HIV-1 NL4-3, Genebank accession No: AF324493
Polynucleotide sequence from position at 790 to 2292 (bold-type and highlighted) encodes Gag protein  (SEQ ID NO: 19)

Adachi,A., Gendelman,H.E., Koenig,S., Folks,T., Willey,R., Rabson,A. and Martin,M.A. "Production of acquired immunodeficiency syndrome-associated retrovirus in human and nonhuman cells transfected with an infectious molecular clone"; JOURNAL   J. Virol. 59 (2), 284-291 (1986)

```
   1 tggaagggct aatttggtcc caaaaaagac aagagatcct tgatctgtgg atctaccaca
  61 cacaaggcta cttccctgat tggcagaact acacaccagg gccagggatc agatatccac
 121 tgacctttgg atggtgcttc aagttagtac cagttgaacc agagcaagta gaagaggcca
 181 aataaggaga gaagaacagc ttgttacacc ctatgagcca gcatgggatg gaggacccgg
 241 agggagaagt attagtgtgg aagtttgaca gcctcctagc atttcgtcac atgcccgag
 301 agctgcatcc ggagtactac aaagactgct gacatcgagc tttctacaag ggactttccg
 361 ctggggactt tccagggagg tgtggcctgg gcgggactgg ggagtggcga gccctcagat
 421 gctacatata agcagctgct ttttgcctgt actgggtctc tctggttaga ccagatctga
 481 gcctgggagc tctctggcta actagggaac ccactgctta agcctcaata agcttgcct
 541 tgagtgctca aagtagtgtg tgcccgtctg ttgtgtgact ctggtaacta gagatccctc
 601 agaccctttt agtcagtgtg gaaaatctct agcagtggcg cccgaacagg gacttgaaag
 661 cgaaagtaaa gccagaggag atctctcgac gcaggactcg gcttgctgaa gcgcgcacgg
 721 caagaggcga ggggcggcga ctggtgagta cgccaaaaat tttgactagc ggaggctaga
 781 aggagagaga tgggtgcgag agcgtcggta ttaagcgggg gagaattaga taaatgggaa
 841 aaaattcggt taaggccagg gggaaagaaa caatataaac taaaacatat agtatgggca
 901 agcagggagc tagaacgatt cgcagttaat cctggccttt tagagacatc agaaggctgt
 961 agacaaatac tgggacagct acaaccatcc cttcagacag gatcagaaga acttagatca
1021 ttatataata caatagcagt cctctattgt gtgcatcaaa ggatagatgt aaaagacacc
1081 aaggaagcct tagataagat agaggaagag caaaacaaaa gtaagaaaaa ggcacagcaa
1141 gcagcagctg acacaggaaa caacagccag gtcagccaaa attaccctat agtgcagaac
1201 ctccaggggc aaatggtaca tcaggccata tcacctagaa ctttaaatgc atgggtaaaa
1261 gtagtagaag agaaggcttt cagcccagaa gtaataccca tgttttcagc attatcagaa
1321 ggagccaccc cacaagattt aaataccatg ctaaacacag tggggggaca tcaagcagcc
1381 atgcaaatgt taaaagagac catcaatgag gaagctgcag aatgggatag attgcatcca
1441 gtgcatgcag ggcctattgc accaggccag atgagagaac caaggggaag tgacatagca
1501 ggaactacta gtacccttca ggaacaaata ggatggatga cacataatcc acctatccca
1561 gtaggagaaa tctataaaag atggataatc ctgggattaa ataaaatagt aagaatgtat
1621 agccctacca gcattctgga cataagacaa ggaccaaagg aacccttag agactatgta
1681 gaccgattct ataaaactct aagagccgag caagcttcac aagaggtaaa aaattggatg
1741 acagaaacct tgttggtcca aaatgcgaac ccagattgta agactatttt aaaagcattg
1801 ggaccaggag cgacactaga agaaatgatg acagcatgtc agggagtggg gggacccggc
1861 cataaagcaa gagttttggc tgaagcaatg agccaagtaa caaatccagc taccataatg
1921 atacagaaag gcaattttag gaaccaaaga aagactgtta agtgtttcaa ttgtggcaaa
1981 gaagggcaca tagccaaaaa ttgcagggcc cctaggaaaa agggctgttg gaaatgtgga
2041 aaggaaggac accaaatgaa agattgtact gagagacagg ctaattttt agggaagatc
2101 tggccttccc acaagggaag gccagggaat tttcttcaga gcagaccaga gccaacagcc
2161 ccaccagaag agagcttcag gtttggggaa gagacaacaa ctccctctca gaagcaggag
2221 ccgatagaca aggaactgta tcctttagct tccctcagat cactctttgg cagcgacccc
2281 tcgtcacaat aaagataggg ggcaattaa ggaagctct attagataca ggagcagatg
2341 atacagtatt agaagaaatg aatttgccag gaagatggaa accaaaaatg atagggggaa
2401 ttggaggttt tatcaaagta agacagtatg atcagatact catagaaatc tgcggacata
2461 aagctatagg tacagtatta gtaggaccta cacctgtcaa cataattgga agaaatctgt
2521 tgactcagat tggctgcact ttaaattttc ccattagtcc tattgagact gtaccagtaa
2581 aattaaagcc aggaatggat ggcccaaaag ttaaacaatg gccattgaca gaagaaaaa
2641 taaaagcatt agtagaaatt tgtacagaaa tggaaaagga aggaaaaatt tcaaaaattg
2701 ggcctgaaaa tccatacaat actccagtat ttgccataaa gaaaaaagac agtactaaat
2761 ggagaaaatt agtagatttc agagaactta ataagagaac tcaagatttc tgggaagttc
2821 aattaggaat accacatcct gcagggttaa aacagaaaaa atcagtaaca gtactggatg
```

Figure 19B

```
2881 tgggcgatgc atatttttca gttcccttag ataaagactt caggaagtat actgcattta
2941 ccatacctag tataaacaat gagacaccag ggattagata tcagtacaat gtgcttccac
3001 agggatggaa aggatcacca gcaatattcc agtgtagcat gacaaaaatc ttagagcctt
3061 ttagaaaaca aaatccagac atagtcatct atcaatacat ggatgatttg tatgtaggat
3121 ctgacttaga aatagggcag catagaacaa aaatagagga actgagacaa catctgttga
3181 ggtggggatt taccacacca gacaaaaaac atcagaaaga acctccattc ctttggatgg
3241 gttatgaact ccatcctgat aaatggacag tacagcctat agtgctgcca gaaaaggaca
3301 gctggactgt caatgacata cagaaattag tgggaaaatt gaattgggca agtcagattt
3361 atgcagggat taaagtaagg caattatgta aacttcttag gggaaccaaa gcactaacag
3421 aagtagtacc actaacagaa gaagcagagc tagaactggc agaaaacagg gagattctaa
3481 aagaaccggt acatggagtg tattatgacc catcaaaaga cttaatagca gaaatacaga
3541 agcaggggca aggccaatgg acatatcaaa tttatcaaga gccatttaaa aatctgaaaa
3601 caggaaaata tgcaagaatg aagggtgccc acactaatga tgtgaaacaa ttaacagagg
3661 cagtacaaaa aatagccaca gaaagcatag taatatgggg aaagactcct aaatttaaat
3721 tacccataca aaaggaaaca tgggaagcat ggtggacaga gtattggcaa gccacctgga
3781 ttcctgagtg ggagtttgtc aatacccctc ccttagtgaa gttatggtac cagttagaga
3841 aagaacccat aataggagca gaaactttct atgtagatgg ggcagccaat agggaaacta
3901 aattaggaaa agcaggatat gtaactgaca gaggaagaca aaaagttgtc cccctaacgg
3961 acacaacaaa tcagaagact gagttacaag caattcatct agctttgcag gattcgggat
4021 tagaagtaaa catagtgaca gactcacaat atgcattggg aatcattcaa gcacaaccag
4081 ataagagtga atcagagtta gtcagtcaaa taatagagca gttaataaaa aaggaaaaag
4141 tctacctggc atgggtacca gcacacaaag gaattggagg aaatgaacaa gtagatggt
4201 tggtcagtgc tggaatcagg aaagtactat ttttagatgg aatagataag gcccaagaag
4261 aacatgagaa atatcacagt aattggagag caatggctag tgattttaac ctaccacctg
4321 tagtagcaaa agaaatagta gccagctgtg ataaatgtca gctaaaaggg gaagccatgc
4381 atggacaagt agactgtagc ccaggaatat ggcagctaga ttgtacacat ttagaaggaa
4441 aagttatctt ggtagcagtt catgtagcca gtggatatat agaagcagaa gtaattccag
4501 cagagacagg gcaagaaaca gcatacttcc tcttaaaatt agcaggaaga tggccagtaa
4561 aaacagtaca tacagacaat ggcagcaatt tcaccagtac tacagttaag gccgcctgtt
4621 ggtgggcggg gatcaagcag gaatttggca ttccctacaa tccccaaagt caaggagtaa
4681 tagaatctat gaataaagaa ttaaagaaaa ttataggaca ggtaagagat caggctgaac
4741 atcttaagac agcagtacaa atggcagtat tcatccacaa ttttaaaaga aaggggggga
4801 ttggggggta cagtgcaggg gaaagaatag tagacataat agcaacagac atacaaacta
4861 aagaattaca aaaacaaatt acaaaaattc aaaattttcg ggtttattac agggacagca
4921 gagatccagt ttggaaagga ccagcaaagc tcctctggaa aggtgaaggg gcagtagtaa
4981 tacaagataa tagtgacata aaagtagtgc caagaagaaa agcaaagatc atcagggatt
5041 atggaaaaca gatggcaggt gatgattgtg tggcaagtag acaggatgag gattaacaca
5101 tggaaaagat tagtaaaaca ccatatgtat atttcaagga agctaagga ctggttttat
5161 agacatcact atgaaagtac taatccaaaa ataagttcag aagtacacat cccactaggg
5221 gatgctaaat tagtaataac aacatattgg ggtctgcata caggagaaag agactggcat
5281 ttgggtcagg gagtctccat agaatggagg aaaaagagat atagcacaca agtagaccct
5341 gacctagcag accaactaat tcatctgcac tattttgatt gtttttcaga atctgctata
5401 agaaatacca tattaggacg tatagttagt cctaggtgtg aatatcaagc aggacataac
5461 aaggtaggat ctctacagta cttggcacta gcagcattaa taaaccaaa acagataaag
5521 ccacctttgc ctagtgttag gaaactgaca gaggacagat ggaacaagcc ccagaagacc
5581 aagggccaca gagggagcca tacaatgaat ggacactaga gcttttagag gaacttaaga
5641 gtgaagctgt tagacatttt cctaggatat ggctccataa cttaggacaa catatctatg
5701 aaacttacgg ggatacttgg gcaggagtgg aagccataat aagaattctg caacaactgc
5761 tgtttatcca tttcagaatt gggtgtcgac atagcagaat aggcgttact cgacagagga
5821 gagcaagaaa tggagccagt agatcctaga ctagagccct ggaagcatcc aggaagtcag
5881 cctaaaactg cttgtaccaa ttgctattgt aaaaagtgtt gctttcattg ccaagtttgt
5941 ttcatgacaa aagccttagg catctcctat ggcaggaaga gcggagaca gcgacgaaga
6001 gctcatcaga acagtcagac tcatcaagct tctctatcaa gcagtaagt agtacatgta
6061 atgcaaccta taatagtagc aatagtagca ttagtagtag caataataat agcaatagtt
6121 gtgtggtcca tagtaatcat agaatatagg aaaatattaa gacaagaaa aatagacagg
6181 ttaattgata gactaataga aagagcagaa gacagtggca atgagagtga aggagaagta
6241 tcagcacttg tggagatggg ggtggaaatg gggcaccatg ctccttggga tattgatgat
6301 ctgtagtgct acagaaaaat tgtgggtcac agtctattat ggggtacctg tgtggaagga
```

Figure 19C

```
6361 agcaaccacc actctatttt gtgcatcaga tgctaaagca tatgatacag aggtacataa
6421 tgtttgggcc acacatgcct gtgtacccac agaccccaac ccacaagaag tagtattggt
6481 aaatgtgaca gaaaatttta acatgtggaa aatgacatg gtagaacaga tgcatgagga
6541 tataatcagt ttatgggatc aaagcctaaa gccatgtgta aaattaaccc cactctgtgt
6601 tagtttaaag tgcactgatt tgaagaatga tactaatacc aatagtagta gcgggagaat
6661 gataatggag aaaggagaga taaaaaactg ctctttcaat atcagcacaa gcataagaga
6721 taaggtgcag aaagaatatg cattctttta taaacttgat atagtaccaa tagataatac
6781 cagctatagg ttgataagtt gtaacacctc agtcattaca caggcctgtc caaaggtatc
6841 ctttgagcca attcccatac attattgtgc cccggctggt tttgcgattc taaaatgtaa
6901 taataagacg ttcaatggaa caggaccatg tacaaatgtc agcacagtac aatgtacaca
6961 tggaatcagg ccagtagtat caactcaact gctgttaaat ggcagtctag cagaagaaga
7021 tgtagtaatt agatctgcca atttcacaga caatgctaaa accataatag tacagctgaa
7081 cacatctgta gaaattaatt gtacaagacc caacaacaat acaagaaaaa gtatccgtat
7141 ccagagggga ccagggagag catttgttac aataggaaaa ataggaaata tgagacaagc
7201 acattgtaac attagtagag caaaatggaa tgccacttta aaacagatag ctagcaaatt
7261 aagagaacaa tttggaaata taaaacaat aatctttaag caatcctcag gaggggaccc
7321 agaaattgta acgcacagtt taattgtgg aggggaattt ttctactgta attcaacaca
7381 actgtttaat agtacttggt taatagtac ttggagtact gaagggtcaa ataacactga
7441 aggaagtgac acaatcacac tcccatgcag aataaaacaa tttataaaca tgtggcagga
7501 agtaggaaaa gcaatgtatg cccctcccat cagtggacaa attagatgtt catcaaatat
7561 tactgggctg ctattaacaa gagatggtgg taataacaac aatgggtccg agatcttcag
7621 acctggagga ggcgatatga gggacaattg gagaagtgaa ttatataaat ataaagtagt
7681 aaaaattgaa ccattaggag tagcacccac caaggcaaag agaagagtgg tgcagagaga
7741 aaaagagca gtgggaatag gagctttgtt ccttgggttc tgggagcag caggaagcac
7801 tatgggctgc acgtcaatga cgctgacggt acaggccaga caattattgt ctgatatagt
7861 gcagcagcag aacaatttgc tgagggctat tgaggcgcaa cagcatctgt tgcaactcac
7921 agtctgggc atcaaacagc tccaggcaag aatcctggct gtggaaagat acctaaagga
7981 tcaacagctc ctggggattt ggggttgctc tggaaaactc atttgcacca ctgctgtgcc
8041 ttggaatgct agttggagta ataaatctct ggaacagatt tggaataaca tgacctggat
8101 ggagtgggac agagaaatta acaattacac aagcttaata cactccttaa ttgaagaatc
8161 gcaaaccag caagaaaaga atgaacaaga attattggaa ttagataaat gggcaagttt
8221 gtggaattgg tttaacataa caaattggct gtggtatata aaattattca taatgatagt
8281 aggaggcttg gtaggtttaa gaatagtttt tgctgtactt tctatagtga atagagttag
8341 gcagggatat tcaccattat cgtttcagac ccacctccca atcccgaggg gacccgacag
8401 gcccgaagga atagaagaag aaggtggaga gagagacaga gacagatcca ttcgattagt
8461 gaacggatcc ttagcactta tctgggacga tctgcggagc ctgtgcctct tcagctacca
8521 ccgcttgaga gacttactct tgattgtaac gaggattgtg gaacttctgg gacgcagggg
8581 gtgggaagcc ctcaaatatt ggtggaatct cctacagtat tggagtcagg aactaaagaa
8641 tagtgctgtt aacttgctca atgccacagc catagcagta gctgagggga cagatagggt
8701 tatagaagta ttacaagcag cttatagagc tattcgccac atacctagaa gaataagaca
8761 gggcttggaa aggattttgc tataagatgg gtggcaagtg gtcaaaaagt agtgtgattg
8821 gatggcctgc tgtaagggaa agaatgagac gagctgagcc agcagcagat ggggtgggag
8881 cagtatctcg agacctagaa aaacatggag caatcacaag tagcaataca gcagctaaca
8941 atgctgcttg tgcctggcta gaagcacaag aggaggaaga ggtgggtttt ccagtcacac
9001 ctcaggtacc tttaagacca atgacttaca aggcagctgt agatcttagc cactttttaa
9061 aagaaaaggg gggactggaa gggctaattc actcccaaag aagacaagat atccttgatc
9121 tgtggatcta ccacacacaa ggctacttcc ctgattggca gaactacaca ccagggccag
9181 gggtcagata tccactgacc tttggatggt gctacaagct agtaccagtt gagccagata
9241 aggtagaaga ggccaataaa ggagagaaca ccagcttgtt acaccctgtg agcctgcatg
9301 gaatggatga ccctgagaga gaagtgttag agtggaggtt tgacagccgc ctagcatttc
9361 atcacgtggc ccgagagctg catccggagt acttcaagaa ctgctgacat cgagcttgct
9421 acaagggact ttccgctggg gactttccag gaggcgtgg cctgggcggg actggggagt
9481 ggcgagccct cagatgctgc atataagcag ctgcttttttg cctgtactgg gtctctctgg
9541 ttagaccaga tctgagcctg ggagctctct ggctaactag ggaacccact gcttaagcct
9601 caataaagct tgccttgagt gcttcaagta gtgtgtgccc gtctgttgtg tgactctggt
9661 aactagagat ccctcagacc ctttttagtca gtgtggaaaa tctctagcac ccaggaggta
9721 gaggttgcag tgagccaaga tcgcgccact gcattccagc ctgggcaaga aaacaagact
9781 gtctaaaata ataataataa gttaagggta ttaaatatat ttatacatgg aggtcataaa
```

Figure 19D

```
 9841 aatatatata tttgggctgg gcgcagtggc tcacacctgc gcccggccct ttgggaggcc
 9901 gaggcaggtg gatcacctga gtttgggagt tccagaccag cctgaccaac atggagaaac
 9961 cccttctctg tgtattttta gtagatttta ttttatgtgt attttattca caggtatttc
10021 tggaaaactg aaactgtttt tcctctactc tgataccaca agaatcatca gcacagagga
10081 agacttctgt gatcaaatgt ggtgggagag ggaggttttc accagcacat gagcagtcag
10141 ttctgccgca gactcggcgg gtgtccttcg gttcagttcc aacaccgcct gcctggagag
10201 aggtcagacc acagggtgag ggctcagtcc caagacata aacacccaag acataaacac
10261 ccaacaggtc caccccgcct gctgcccagg cagagccgat tcaccaagac gggaattagg
10321 atagagaaag agtaagtcac acagagccgg ctgtgcggga aacggagtt ctattatgac
10381 tcaaatcagt ctccccaagc attcggggat cagagttttt aaggataact tagtgtgtag
10441 ggggccagtg agttggagat gaaagcgtag ggagtcgaag gtgtccttt gcgccgagtc
10501 agttcctggg tgggggccac aagatcggat gagccagttt atcaatccgg gggtgccagc
10561 tgatccatgg agtgcagggt ctgcaaaata tctcaagcac tgattgatct taggttttac
10621 aatagtgatg ttaccccagg aacaatttgg ggaaggtcag aatcttgtag cctgtagctg
10681 catgactcct aaaccataat ttctttttg ttttttttt ttattttg agacagggtc
10741 tcactctgtc acctaggctg gagtgcagtg gtgcaatcac agctcactgc agcctcaacg
10801 tcgtaagctc aagcgatcct cccacctcag cctgcctggt agctgagact acaagcgacg
10861 ccccagttaa tttttgtatt tttggtagag cagcgtttt gccgtgtggc cctggctggt
10921 ctcgaactcc tgggctcaag tgatccagcc tcagcctccc aaagtgctgg acaaccggg
10981 cccagtcact gcacctggcc ctaaaccata atttctaatc ttttggctaa tttgttagtc
11041 ctacaaaggc agtctagtcc ccagcaaaaa gggggtttgt ttcgggaaag ggctgttact
11101 gtctttgttt caaactataa actaagttcc tcctaaactt agttcggcct acacccagga
11161 atgaacaagg agagcttgga ggttagaagc acgatggaat tggttaggtc agatctcttt
11221 cactgtctga gttataattt tgcaatggtg gttcaaagac tgcccgcttc tgacaccagt
11281 cgctgcatta atgaatcggc caacgcgcgg ggagaggcgg tttgcgtatt gggcgctctt
11341 ccgcttcctc gctcactgac tcgctgcgct cggtcgttcg gctcggcga gcggtatcag
11401 ctcactcaaa ggcggtaata cggttatcca cagaatcagg ggataacgca ggaaagaaca
11461 tgtgagcaaa aggccagcaa aaggccagga accgtaaaaa ggccgcgttg ctggcgtttt
11521 tccataggct ccgccccct gacgagcatc acaaaaatcg acgctcaagt cagaggtggc
11581 gaaacccgac aggactataa agataccagg cgtttccccc tggaagctcc ctcgtgcgct
11641 ctcctgttcc gaccctgccg cttaccggat acctgtccgc ctttctccct cgggaagcg
11701 tggcgctttc tcatagctca cgctgtaggt atctcagttc ggtgtaggtc gttcgctcca
11761 agctgggctg tgtgcacgaa ccccccgttc agcccgaccg ctgcgcctta ccggtaact
11821 atcgtcttga gtccaacccg gtaagacacg acttatcgcc actggcagca gccactggta
11881 acaggattag cagagcgagg tatgtaggcg gtgctacaga gttcttgaag tggtggccta
11941 actacggcta cactagaagg acagtatttg gtatctgcgc tctgctgaag ccagttacct
12001 tcggaaaaag agttggtagc tcttgatccg gcaaacaaac caccgctggt agcggtggtt
12061 tttttgtttg caagcagcag attacgcgca gaaaaaagg atctcaagaa gatcctttga
12121 tcttttctac ggggtctgac gctcagtgga cgaaaactc acgttaaggg attttggtca
12181 tgagattatc aaaaaggatc ttcacctaga tccttttaaa ttaaaaatga agttttaaat
12241 caatctaaag tatatatgag taaacttggt ctgacagtta ccaatgctta atcagtgagg
12301 cacctatctc agcgatctgt ctatttcgtt catccatagt tgcctgactc cccgtcgtgt
12361 agataactac gatacgggag ggcttaccat ctggccccag tgctgcaatg ataccgcgag
12421 acccacgctc accggctcca gatttatcag caataaacca gccagccgga agggccgagc
12481 gcagaagtgg tcctgcaact ttatccgcct ccatccagtc tattaattgt tgccgggaag
12541 ctagagtaag tagttcgcca gttaatagtt tgcgcaacgt tgttgccatt gctacaggca
12601 tcgtggtgtc acgctcgtcg tttggtatgg cttcattcag ctccggttcc caacgatcaa
12661 ggcgagttac atgatccccc atgttgtgca aaaaagcggt tagctccttc ggtcctccga
12721 tcgttgtcag aagtaagttg gccgcagtgt tatcactcat ggttatggca gcactgcata
12781 attctcttac tgtcatgcca tccgtaagat gcttttctgt gactggtgag tactcaacca
12841 agtcattctg agaatagtgt atgcggcgac cgagttgctc ttgcccggcg tcaatacggg
12901 ataataccgc gccacatagc agaactttaa aagtgctcat cattggaaaa cgttcttcgg
12961 ggcgaaaact ctcaaggatc ttaccgctgt tgagatccag ttcgatgtaa cccactcgtg
13021 cacccaactg atcttcagca tcttttactt tcaccagcgt ttctgggtga gcaaaaacag
13081 gaaggcaaaa tgccgcaaaa aagggaataa gggcgacacg gaaatgttga atactcatac
13141 tcttcctttt tcaatattat tgaagcattt atcagggtta ttgtctcatg agcggataca
13201 tatttgaatg tatttagaaa aataaacaaa tagggggttcc gcgcacattt ccccgaaaag
```

Figure 19E

```
13261 tgccacctga cgtctaagaa accattatta tcatgacatt aacctataaa aataggcgta
13321 tcacgaggcc ctttcgtctc gcgcgtttcg gtgatgacgg tgaaaacctc tgacacatgc
13381 agctcccgga gacggtcaca gcttgtctgt aagcggatgc cgggagcaga caagcccgtc
13441 agggcgcgtc agcgggtgtt ggcgggtgtc ggggctggct taactatgcg gcatcagagc
13501 agattgtact gagagtgcac catatgcggt gtgaaatacc gcacagatgc gtaaggagaa
13561 aataccgcat caggcgccat tcgccattca ggctgcgcaa ctgttgggaa gggcgatcgg
13621 tgcgggcctc ttcgctatta cgccagggga ggcagagatt gcagtaagct gagatcgcag
13681 cactgcactc cagcctgggc gacagagtaa gactctgtct caaaaataaa ataaataaat
13741 caatcagata ttccaatctt ttcctttatt tatttattta ttttctattt tggaaacaca
13801 gtccttcctt attccagaat tacacatata ttctattttt ctttatatgc tccagttttt
13861 tttagacctt cacctgaaat gtgtgtatac aaaatctagg ccagtccagc agagcctaaa
13921 ggtaaaaaat aaaataataa aaaataaata aaatctagct cactccttca catcaaaatg
13981 gagatacagc tgttagcatt aaataccaaa taacccatct tgtcctcaat aattttaagc
14041 gcctctctcc accacatcta actcctgtca aaggcatgtg ccccttccgg gcgctctgct
14101 gtgctgccaa ccaactggca tgtggactct gcagggtccc taactgccaa gccccacagt
14161 gtgccctgag gctgccccctt ccttctagcg gctgccccca ctcggctttg ctttccctag
14221 tttcagttac ttgcgttcag ccaaggtctg aaactaggtg cgcacagagc ggtaagactg
14281 cgagagaaag agaccagctt tacagggggt ttatcacagt gcacctgac agtcgtcagc
14341 ctcacagggg gtttatcaca ttgcacctg acagtcgtca gcctcacagg gggtttatca
14401 cagtgcaccc ttacaatcat tccatttgat tcacaatttt tttagtctct actgtgccta
14461 acttgtaagt taaatttgat cagaggtgtg ttcccagagg ggaaaacagt atatacaggg
14521 ttcagtacta tcgcatttca ggcctccacc tgggtcttgg aatgtgtccc ccgaggggtg
14581 atgactacct cagttggatc tccacaggtc acagtgacac aagataacca agacacctcc
14641 caaggctacc acaatgggcc gccctccacg tgcacatggc cggaggaact gccatgtcgg
14701 aggtgcaagc acacctgcgc atcagagtcc ttggtgtgga gggagggacc agcgcagctt
14761 ccagccatcc acctgatgaa cagaacctag ggaaagcccc agttctactt acaccaggaa
14821 aggc
```

INHIBITION OF HIV-1 REPLICATION BY DISRUPTION OF THE PROCESSING OF THE VIRAL CAPSID-SPACER PEPTIDE 1 PROTEIN

CROSS REFERENCE TO RELATED APPLICATIONS

This application is a continuation-in-part of U.S. application Ser. No. 10/766,528, filed Jan. 29, 2004, which claims priority to U.S. Provisional Application Nos. 60/496,660, filed Aug. 21, 2003, and 60/443,180, filed Jan. 29, 2003, all of which are entirely incorporated by reference herein.

STATEMENT REGARDING FEDERALLY-SPONSORED RESEARCH AND DEVELOPMENT

The U.S. Government has a paid-up license in this invention and the right in limited circumstances to require the patent owner to license others on reasonable terms as provided for by the terms of Grant No. 2R44AI051047-02 awarded by NIH/NIAID.

BACKGROUND OF THE INVENTION

1. Field of the Invention

The invention includes methods of inhibiting, inhibitors and methods of discovery of inhibitors of HIV infection.

2. Background

Human Immunodeficiency Virus (HIV) is a member of the lentiviruses, a subfamily of retroviruses. The viral genome contains many regulatory elements which allow the virus to control its rate of replication in both resting and dividing cells. Most importantly, HIV infects and invades cells of the immune system; it breaks down the body's immune system and renders the patient susceptible to opportunistic infections and neoplasms. The immune defect appears to be progressive and irreversible, with a high mortality rate that approaches 100% over several years.

HIV-1 is trophic and cytopathic for T4 lymphocytes, cells of the immune system which express the cell surface differentiation antigen CD4, also known as OKT4, T4 and leu3. The viral tropism is due to the interactions between the viral envelope glycoprotein, gp120, and the cell-surface CD4 molecules (Dalgleish et al., *Nature* 312:763-767 (1984)). These interactions not only mediate the infection of susceptible cells by HIV, but are also responsible for the virus-induced fusion of infected and uninfected T cells. This cell fusion results in the formation of giant multinucleated syncytia, cell death, and progressive depletion of CD4 cells in HIV-infected patients. These events result in HIV-induced immunosuppression and its subsequent sequelae, opportunistic infections and neoplasms.

In addition to CD4+ T cells, the host range of HIV includes cells of the mononuclear phagocytic lineage (Dalgleish et al., supra), including blood monocytes, tissue macrophages, Langerhans cells of the skin and dendritic reticulum cells within lymph nodes. HIV is also neurotropic, capable of infecting monocytes and macrophages in the central nervous system causing severe neurologic damage. Macrophage and monocytes are major reservoirs of HIV. They can interact and fuse with CD4-bearing T cells, causing T cell depletion and thus contributing to the pathogenesis of AIDS.

Considerable progress has been made in the development of drugs for HIV-1 therapy. Therapeutic agents for HIV can include, but are not are not limited to, at least one of AZT, 3TC, ddC, d4T, ddI, tenofovir, abacavir, nevirapine, delavirdine, emtricitabine, efavirenz, saquinavir, ritonavir, indinavir, nelfinavir, lopinavir, amprenavir, atazanavir and fosamprenavir, or any other antiretroviral drugs or antibodies in combination with each other, or associated with a biologically based therapeutic, such as, for example, gp41-derived peptides enfuvirtide (Fuzeon; Timeris-Roche) and T-1249 (Trimeris), or soluble CD4, antibodies to CD4, and conjugates of CD4 or anti-CD4, or as additionally presented herein. Combinations of these drugs are particularly effective and can reduce levels of viral RNA to undetectable levels in the plasma and slow the development of viral resistance, with resulting improvements in patient health and life span.

Despite these advances, there are still problems with the currently available drug regimens. Many of the drugs exhibit severe toxicities, have other side-effects (e.g., fat redistribution) or require complicated dosing schedules that reduce compliance and thereby limit efficacy. Resistant strains of HIV often appear over extended periods of time even on combination therapy. The high cost of these drugs is also a limitation to their widespread use, especially outside of developed countries.

There is still a major need for the development of additional drugs to circumvent these issues. Ideally these would target different stages in the viral life cycle, adding to the armamentarium for combination therapy, and exhibit minimal toxicity, yet have lower manufacturing costs.

HIV virion assembly takes place at the surface membrane of the infected cell where the viral Gag polyprotein accumulates, leading to the assembly of immature virions that bud from the cell surface. Within the virion, Gag is cleaved by the viral proteinase (PR) into the matrix (MA), capsid (CA), nucleocapsid (NC), and C-terminal p6 structural proteins (Wiegers K. et al., *J. Virol.* 72:2846-2854 (1998)). Gag processing induces a reorganization of the internal virion structure, a process termed "maturation." In mature HIV particles, MA lines the inner surface of the membrane, while CA forms the conical core which encases the genomic RNA that is complexed with NC. Cleavage and maturation are not required for particle formation but are essential for infectivity (Kohl, N. et al., *Proc. Natl. Acad. Sci. USA* 85:4686-4690, (1998)).

CA and NC as well as NC and p6 are separated on the Gag polyprotein by short spacer peptides of 14 and 10 amino acids (p2), respectively (spacer peptide 1 (SP1) and SP2, respectively) (Wiegers K. et al., *J. Virol.* 72:2846-2854 (1998), Pettit, S. C. et al., *J. Virol.* 68:8017-8027 (1994), Liang et al. *J. Virol.* 76:11729-11737 (2002)). These spacer peptides are released by PR-mediated cleavages at their N and C termini during particle maturation. The individual cleavage sites on the HIV Gag and Gag-Pol polyproteins are processed at different rates and this sequential processing results in Gag intermediates appearing transiently before the final products. Such intermediates may be important for virion morphogenesis or maturation but do not contribute to the structure of the mature viral particle (Weigers et al. and Pettit, et al., supra). The initial Gag cleavage event occurs at the C terminus of SP1 and separates an N-terminal MA-CA-SP1 intermediate from a C-terminal NC-SP2-p6 intermediate. Subsequent cleavages separating MA from CA-SP1 and NC-SP2 from p6 occur at an approximately 10-fold-lower rate. Cleavage of SP1 from the C terminus of CA is a late event and occurs at a 400-fold-lower rate than cleavage at the SP1-NC site (Weigers et al. and Pettit, et al., supra). The uncleaved CA-SP1 intermediate protein is alternatively termed "p25," whereas the cleaved CA protein is alternatively termed "p24" and the cleaved SP1 peptide is alternatively termed "p2".

Cleavage of SP1 from the C terminus of CA appears to be one of the last events in the Gag processing cascade and is required for final capsid condensation and formation of mature, infectious viral particles. Electron micrographs of mature virions reveal particles having electron dense conical cores. On the other hand, electron microscopy studies of viral particles defective for CA-SP1 cleavage show particles having a spherical electron-dense ribonucleoprotein core and a crescent-shaped, electron-dense layer located just inside the viral membrane (Weigers et al., supra). Mutations at or near the CA-SP1 cleavage site have been shown to inhibit Gag processing and disrupt the normal maturation process, thereby resulting in the production of non-infectious viral particles (Weigers et al., supra). Phenotypically, these particles exhibit a defect in Gag processing (which manifests itself in the presence of a p25 (CA-SP1) band in Western blot analysis) and the aberrant particle morphology described above which results from defective capsid condensation.

Previously, betulinic acid and platanic acid were isolated from *Syzigium claviflorum* and were determined to have anti-HIV activity. Betulinic acid and platanic acid exhibited inhibitory activity against HIV-1 replication in H9 lymphocyte cells with $EC_{50}$ values of 1.4 μM and 6.5 μM, respectively, and therapeutic index (T.I.) values of 9.3 and 14, respectively. Hydrogenation of betulinic acid yielded dihydrobetulinic acid, which showed slightly more potent anti-HIV activity with an $EC_{50}$ value of 0.9 and a T.I. value of 14 (Fujioka, T., et al., *J. Nat. Prod.* 57:243-247 (1994)). Esterification of betulinic acid with certain substituted acyl groups, such as 3',3'-dimethylglutaryl and 3',3'-dimethylsuccinyl groups produced derivatives having enhanced activity (Kashiwada, Y., et al., *J. Med. Chem.* 39:1016-1017 (1996)). Acylated betulinic acid and dihydrobetulinic acid derivatives that are potent anti-HIV agents are also described in U.S. Pat. No. 5,679,828. Anti-HIV assays indicated that 3-O-(3',3'-dimethylsuccinyl)-betulinic acid (DSB) and the dihydrobetulinic acid analog both demonstrated extremely potent anti-HIV activity in acutely infected H9 lymphocytes with $EC_{50}$ values of less than $1.7 \times 10^{-5}$ μM, respectively. These compounds exhibited remarkable T.I. values of more than 970,000 and more than 400,000, respectively.

U.S. Pat. No. 5,468,888 discloses 28-amido derivatives of lupanes that are described as having a cytoprotecting effect for HIV-infected cells.

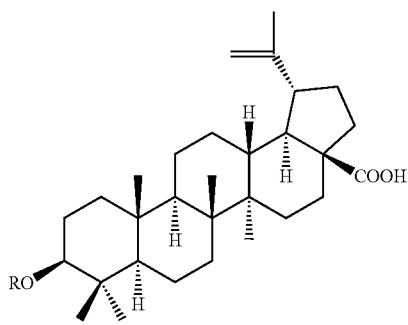

R═H (Betulinic acid)

Japanese Patent Application No. JP 01 143,832 discloses that betulin and 3,28-diesters thereof are useful in the anti-cancer field.

U.S. Pat. No. 6,172,110 discloses betulinic acid and dihydrobetulin derivatives which have the following formulae or pharmaceutically acceptable salts thereof, Betulin and Dihydrobetulin Derivatives

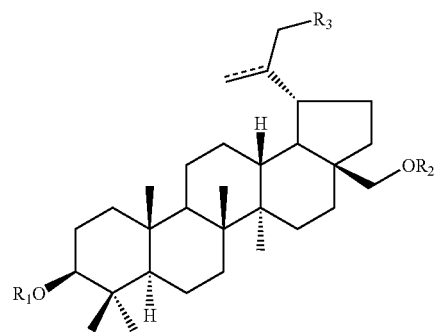

wherein $R_1$ is a $C_2$-$C_{20}$ substituted or unsubstituted carboxyacyl, $R_2$ is a $C_2$-$C_{20}$ substituted or unsubstituted carboxyacyl; and $R_3$ is hydrogen, halogen, amino, optionally substituted mono- or di-alkylamino, or —$OR_4$, where $R_4$ is hydrogen, $C_{1-4}$ alkanoyl, benzoyl, or $C_2$-$C_{20}$ substituted or unsubstituted carboxyacyl; wherein the dashed line represents an optional double bond between C20 and C29.

U.S. Patent Application No. 60/413,451 discloses 3,3-dimethylsuccinyl betulin and is herein incorporated by reference. Zhu, Y-M. et al., *Bioorg. Chem Lett.* 11:3115-3118 (2001); Kashiwada Y. et al., *J. Nat. Prod.* 61:1090-1095 (1998); Kashiwada Y. et al., *J. Nat. Prod.* 63:1619-1622 (2000); and Kashiwada Y. et al., *Chem. Pharm. Bull.* 48:1387-1390 (2000) disclose dimethylsuccinyl betulinic acid and dimethylsuccinyl oleanolic acid. Esterification of the 3' carbon of betulin with succinic acid produced a compound capable of inhibiting HIV-1 activity (Pokrovskii, A. G. et al., *Gos. Nauchnyi Tsentr Virusol. Biotekhnol. "Vector,"* 9:485-491 (2001)).

Published International Application No. WO 02/26761 discloses the use of betulin and analogs thereof for treating fungal infections.

There exists a need for new HIV inhibition methods that are effective against drug resistant strains of the virus. The strategy of this invention is to provide therapeutic methods and compounds that inhibit the virus in different ways from approved therapies.

The compound and methods of the present invention have a novel mechanism of action and therefore are active against HIV strains that are resistant to current reverse transcriptase and protease inhibitors. As such, this invention offers a completely new approach for treating HIV/AIDS.

BRIEF SUMMARY OF THE INVENTION

Generally, the invention provides methods of inhibiting, inhibitory compounds and methods of identifying inhibitory compounds that target proteolytic processing of the HIV-1 Gag protein. In one embodiment, such compounds may directly or indirectly inhibit the interaction of a protease enzyme with HIV-1 Gag protein. In another embodiment, such inhibition of interaction occurs via the binding of a compound to Gag. The inhibition of protease cleavage of the CA-SP1 protein of HIV-1 Gag by 3-O-(3',3'-dimethylsuccinyl)betulinic acid (DSB) is one example, but other proteolytic cleavage sites can be targeted by a similar approach using inhibitory compounds that interact with the substrate in a manner similar to that in which DSB interacts with Gag.

Another aspect of the invention is directed to a method of inhibiting the processing of the viral Gag p25 protein (CA-SP1) to p24 (CA), but having no effect on other Gag processing steps.

A further aspect of the invention is directed to a method for identifying compounds that inhibit processing of the viral Gag p25 protein (CA-SP1) to p24 (CA), but have no effect on other Gag processing steps.

In one aspect, the invention is drawn to a compound or pharmaceutical composition identified by the method for identifying compounds that inhibit HIV-1 replication disclosed herein.

In another aspect, the present invention is directed to a polynucleotide comprising a sequence which encodes an amino acid sequence containing a mutation in the Gag p25 protein, said mutation resulting in a decrease in the inhibition of processing of p25 to p24 by 3-O-(3',3'-dimethylsuccinyl) betulinic acid. This aspect of the invention is also directed to a vector, virus and host cell comprising said polynucleotide, and a method of making said protein.

A further aspect of the present invention is directed to an amino acid sequence containing a mutation in the Gag p25 protein, said mutation resulting in a decrease in the inhibition of processing of p25 to p24 by 3-O-(3',3'-dimethylsuccinyl) betulinic acid.

An additional aspect of the invention is directed to an antibody which selectively binds an amino acid sequence containing a mutation in the Gag p25 protein, said mutation resulting in a decrease in the inhibition of processing of p25 to p24 by 3-O-(3',3'-dimethylsuccinyl)betulinic acid. Also included in this aspect of the invention are a method of making said antibody, a hybridoma producing said antibody and a method of making said hybridoma.

In a further embodiment, the invention is directed to a kit comprising a polynucleotide, polypeptide or antibody disclosed herein.

The invention further relates to a method of inhibiting HIV-1 infection in cells of an animal by contacting said cells with a compound that blocks the maturation of virus particles released from treated infected cells. In one embodiment, the released virus particles exhibit non-condensed cores and a distinctive thin electron-dense layer near the viral membrane and have reduced infectivity. A method is included of contacting animal cells with a compound that both inhibits processing of the viral Gag p25 protein and that disrupts the maturation of virus particles. Also, included is a method of treating HIV-infected cells, wherein the HIV infecting said cells does not respond to other HIV therapies.

This invention further includes a method for identifying compounds that inhibit processing of the viral Gag p25 protein (CA-SP1) to p24 (CA), but have no significant effect on other Gag processing steps. The method involves contacting HIV-1 infected cells with a test compound, and thereafter analyzing virus particles that are released to detect the presence of p25. Methods to detect p25 include western blotting of viral proteins and detecting using an antibody to p25, gel electrophoresis, and imaging of metabolically labeled proteins. Methods to detect p25 also include immunoassays using an antibody to p25 or SP1 (p2) or to an epitope tag inserted into the SP1 sequence.

The invention is further directed to a method for identifying compounds involving contacting HIV-1 infected cells with a compound, and thereafter analyzing virus particles released by the contacted cells, by thin-sectioning and transmission electron microscopy, and determining whether viral particles with non-condensed cores and a distinctive thin electron-dense layer near the viral membrane are present.

The invention is also directed to compounds identified by the aforementioned screening methods. In additional embodiments, the invention is drawn to a method of treating HIV-1 infection in a patient by administering a compound that inhibits processing of the viral Gag p25 protein (CA-SP1) to p24 (CA), but does not significantly affect other Gag processing steps. In related embodiments, such inhibition may be accompanied by a different observable phenotypes. For example, inhibition may not necessarily significantly reduce the quantity of virions released from treated infected cells; and/or said inhibition may have little or no significant effect on the amount of RNA incorporation into the released virions; and/or said inhibition disrupts the maturation of virions released from infected cells treated with said compound. In related embodiments, the virion structure may be affected, and a majority of virions released from treated infected cells exhibit spherical, electron-dense cores that are acentric with respect to the viral particle; and/or possess crescent-shaped electron-dense layers lying just inside the viral membrane; and/or and have reduced or no infectivity.

In additional embodiments, the invention is drawn to a method of treating HIV-1 infection in a patient by administering a compound that inhibits the interaction of HIV protease with CA-SP1, which results in the inhibition of the processing of the viral Gag p25 protein (CA-SP1) to p24 (CA), but has no significant effect on other Gag processing steps. Such inhibition may be direct or, alternatively, indirect; and/or may involve said compound binding to the viral Gag protein such that interaction of HIV protease with CA-SP1 is inhibited. The invention is also drawn to a method of treating HIV in a patient with a compound that binds at or near the site of cleavage of the viral Gag p25 protein (CA-SP1) to p24 (CA), thereby inhibiting the interaction of HIV protease with the CA-SP1 cleavage site and resulting in the inhibition of processing of p25 to p24.

In other embodiments, the invention is drawn to a method of treating HJV-1-infection in a patient by administering a compound that inhibits processing of the viral Gag p25 protein (CA-SP1) to p24 (CA), wherein said compound binds to a polypeptide with an amino acid sequence having at least about 40%, 50%, 60%, 70%, 80%, 90% identity, or which is identical to a sequence selected from the group consisting of:

(a) KNWMTETFLVQNANPDCKTILKALGPAATLEEMMTACQGVGGPS

HKARILAEAMSQVTNSATIM;                                          (SEQ D NO: 21)

(b) KNWMTETLLVQNANPDCKTILKALGPGATLEEMMTACQGVGGPG

HKARVLAEAMSQVTNPATIM;                                          (SEQ ID NO: 22)

```
(c) TACQGVGGPSHKARILAEAMSQVTNSATIM;            (SEQ ID NO: 23)

(d) MTACQGVGGPGHKARVLAEAMSQVTNPATIM;           (SEQ ID NO: 24)

(e) SHKARILAEAMSQV                             (SEQ ID NO: 25)
and (f) GHKARVLAEAMSQV.                            (SEQ ID NO: 26)
```

In other embodiments, the invention is drawn to a method of treating HIV-1-infection in a patient by administering a compound that inhibits processing of the viral Gag p25 protein (CA-SP1) to p24 (CA), wherein said compound binds to a polypeptide encoded by a polynucleotide sequence having at least about 40%, 50%, 60%, 70%, 80%, 90% identity, or which is identical to a polynucleotide selected from the group consisting of: (a) about nucleotides 1243-1435 of; (b) about nucleotides 1729-1920 of SEQ ID NO: 19; (c) about nucleotides 1344-1435 of SEQ ID NO: 18; (d) about nucleotides 1828-1920 of SEQ ID NO: 19; (e) about nucleotides 1370-1413 of SEQ ID NO: 18; and (f) about nucleotides 1857-1899 of SEQ ID NO: 19.

In another aspect, the invention is drawn to a method of inhibiting processing of the viral Gag p25 protein (CA-SP1) by administration of a compound. In related embodiments, such a compound binds to a polypeptide with an amino acid sequence having at least about 40%, 50%, 60%, 70%, 80%, 90% identity, or which is identical to a sequence selected from the group consisting of:

used to treat HIV infection. In one application, the HIV is resistant to a protease inhibitor, a polymerase inhibitor, a nucleoside analog, a vaccine, a binding inhibitor, an immunomodulator, or any other inhibitor. In another embodiment, methods of the invention are practiced on a subject infected with an HIV that is resistant to a drug used to treat HIV infection is selected from the group consisting of zidovudine, lamivudine, didanosine, zalcitabine, stavudine, abacavir, nevirapine, delavirdine, emtricitabine, efavirenz, saquinavir, ritonavir, indinavir, nelfinavir, tenofovir, amprenavir, adefovir, atazanavir, fosamprenavir, hydroxyurea, AL-721, ampligen, butylated hydroxytoluene; polymannoacetate, castanospermine; contracan; creme pharmatex, CS-87, penciclovir, famciclovir, acyclovir, cytofovir, ganciclovir, dextran sulfate, D-penicillamine trisodium phosphonoformate, fusidic acid, HPA-23, eflonithine, nonoxynol, pentamidine isethionate, peptide T, phenytoin, isoniazid, ribavirin, rifabutin, ansamycin, trimetrexate, SK-818, suramin, UA001, and combinations thereof.

```
(a) KNWMTETFLVQNANPDCKTILKALGPAATLEEMMTACQGVGGPS

HKARILAEAMSQVTNSATIM;                      (SEQ D NO: 21)

(b) KNWMTETLLVQNANPDCKTILKALGPGATLEEMMTACQGVGGPG

HKARVLAEAMSQVTNPATIM;                      (SEQ ID NO: 22)

(c) TACQGVGGPSHKARILAEAMSQVTNSATIM;            (SEQ ID NO: 23)

(d) MTACQGVGGPGHKARVLAEAMSQVTNPATIM;           (SEQ ID NO: 24)

(e) SHKARILAEAMSQV                             (SEQ ID NO: 25)
and (f) GHKARVLAEAMSQV.                            (SEQ ID NO: 26)
```

In related embodiments; the invention is drawns to a method of inhibiting processing of the viral Gag p25 protein (CA-SP1) by administration of a compound wherein said compound binds to a polypeptide encoded by a polynucleotide sequence having at least about 40%, 50%, 60%, 70%, 80%, 90% identity, or which is identical to a polynucleotide selected from the group consisting of:

(a) about nucleotides 1243-1435 of SEQ ID NO: 18; (b) about nucleotides 1729-1920 of SEQ ID NO: 19; (c) about nucleotides 1344-1435 of SEQ ID NO: 18; (d) about nucleotides 1828-1920 of SEQ ID NO: 19; (e) about nucleotides 1370-1413 of SEQ ID NO: 18; and (f) about nucleotides 1857-1899 of SEQ ID NO: 19.

The invention may be useful in the treatment of HIV in patients who are not adequately treated by other HIV-1 therapies. Accordingly, the invention is also drawn to a method of treating a patient in need of therapy, wherein the HIV-1 infecting said cells does not respond to other HIV-1 therapies. In another embodiment, methods of the invention are practiced on a subject infected with an HIV that is resistant to a drug Compounds of the invention are also useful as part of combination of therapies. Accordingly, in one aspect the invention is drawn to a method of treating HIV in a patient, wherein said patient is administered said compound in combination with at least one anti-viral agent. Anti-viral agents suitable include, but are not limited to: zidovudine, lamivudine, didanosine, zalcitabine, stavudine, abacavir, nevirapine, delavirdine, emtricitabine, efavirenz, saquinavir, ritonavir, indinavir, nelfinavir, amprenavir, tenofovir, adefovir, atazanavir, fosamprenavir, hydroxyurea, AL-721, ampligen, butylated hydroxytoluene; polymannoacetate, castanospermine; contracan; creme pharmatex, CS-87, penciclovir, famciclovir, acyclovir, cytofovir, ganciclovir, dextran sulfate, D-penicillamine trisodium phosphonoformate, fusidic acid, HPA-23, eflornithine, nonoxynol, pentamidine isethionate, peptide T, phenytoin, isoniazid, ribavirin, rifabutin, ansamycin, trimetrexate, SK-818, suramin, UA001, enfuvirtide, gp41-derived peptides, antibodies to CD4, soluble CD4, CD4-containing molecules, CD4-IgG2, and combinations thereof. In another embodiment, the patient is administered said compound in combination with an immunomodulating agent, anticancer agent, antibacterial agent, antifungal agent, or a combination thereof.

The invention is also directed to compounds. Such compounds are useful in a method of treating patients infected with HIV; in a method for inhibiting processing of the viral Gag p25 protein (CA-SP1) to p24 (CA), or in a method for treating human blood and human blood products. Such compounds useful in the present invention include, but are not limited to derivatives of dimethylsuccinyl betulinic acid or dimethylsuccinyl betulin, or is selected from the group consisting of 3-O-(3',3'-dimethylsuccinyl)betulinic acid, 3-O-(3',3'-dimethylsuccinyl) betulin, 3-O-(3',3'-dimethylglutaryl) betulin, 3-O-(3',3'-dimethylsuccinyl)dihydrobetulinic acid, 3-O-(3',3'-dimethylglutaryl)betulinic acid, (3',3'-dimethylglutaryl)dihydrobetulinic acid, 3-O-diglycolyl-betulinic acid, 3-O-diglycolyl-dihydrobetulinic acid and combinations thereof.

Compounds of the invention may be used alone, or administered with additional compounds, including zidovudine, lamivudine, didanosine, zalcitabine, stavudine, abacavir, nevirapine, delavirdine, emtricitabine, efavirenz, saquinavir, ritonavir, indinavir, nelfinavir, amprenavir, tenofovir, adefovir, atazanavir, fosamprenavir, hydroxyurea, AL-721, ampligen, butylated hydroxytoluene; polymannoacetate, castanospermine; contracan; creme pharmatex, CS-87, penciclovir, famciclovir, acyclovir, cytofovir, ganciclovir, dextran sulfate, D-penicillamine trisodium phosphonoformate, fusidic acid, HPA-23, eflornithine, nonoxynol, pentamidine isethionate, peptide T, phenytoin, isoniazid, ribavirin, rifabutin, ansamycin, trimetrexate, SK-818, suramin, UA001, enfuvirtide, gp41-derived peptides, antibodies to CD4, soluble CD4, CD4-containing molecules, CD4-IgG2, and combinations thereof; an antiviral, an immunomodulating agent, anti-cancer agent, antibacterial agent, an anti-fungal agent, or combinations thereof.

In further embodiments, the invention is directed to a method of treating human blood products comprising contacting said blood products with a compound that inhibits processing of the viral Gag p25 protein (CA-SP1) to p24 (CA). In one aspect, said compound does not significantly affect other Gag processing steps. In related embodiments of this method, said inhibition does not significantly reduce the quantity of virions released from treated infected cell; and/or has little or no significant effect on the amount of RNA incorporation into the released virions; and/or inhibits the maturation of virions released from infected cells treated with said compound; and/or affects viral morphology. Such effects on viral morphology include, but are not limited to: the virions released from treated infected cells to exhibit spherical, electron-dense cores that are acentric with respect to the viral particle; and/or possess crescent-shaped electron-dense layers lying just inside the viral membrane; and/or and have reduced or no infectivity. In related embodiments, the method involves the administration of the compound which inhibits the interaction of HIV protease with CA-SP1, which results in the inhibition of the processing of the viral Gag p25 protein (CA-SP1) to p24 (CA) but has no significant effect on other Gag processing steps. This may be via direct, or indirect inhibition of the interaction of HIV protease with CA-SP1; and/or may involve said compound binds to the viral Gag protein such that interaction of HIV protease with CA-SP1 is inhibited; and/or said compound binds at or near the site of cleavage of the viral Gag p25 protein (CA-SP1) to p24 (CA), thereby inhibiting the interaction of HIV protease with the CA-SP1 cleavage site and resulting in the inhibition of processing of p25 to p24.

In a further embodiment, the invention is drawn to a method of treating human blood products comprising contacting said blood products with a compound that inhibits processing of the viral Gag p25 protein (CA-SP1) to p24 (CA), wherein said compound binds to a polypeptide with an amino acid sequence having at least about 40%, 50%, 60%, 70%, 80%, 90% identity, or which is identical to a sequence selected from the group consisting of:

(a) KNWMTETFLVQNANPDCKTILKALGPAATLEEMMTACQGVGGPS

HKARILAEAMSQVTNSATIM; (SEQ D NO: 21)

(b) KNWMTETLLVQNANPDCKTILKALGPGATLEEMMTACQGVGGPG

HKARVLAEAMSQVTNPATIM; (SEQ ID NO: 22)

(c) TACQGVGGPSHKARILAEAMSQVTNSATIM; (SEQ ID NO: 23)

(d) MTACQGVGGPGHKARVLAEAMSQVTNPATIM; (SEQ ID NO: 24)

(e) SHKARILAEAMSQV (SEQ ID NO: 25)
and (f) GHKARVLAEAMSQV. (SEQ ID NO: 26)

In a related embodiment, the invention is drawn to a method of treating human blood products comprising contacting said blood products with a compound that inhibits processing of the viral Gag p25 protein (CA-SP1) to p24 (CA), wherein said compound binds to a polypeptide encoded by a polynucleotide sequence having at least about 40%, 50%, 60%, 70%, 80%, 90% identity, or which is identical a polynucleotide selected from the group consisting of:

(a) about nucleotides 1243-1435 of SEQ ID NO: 18; (b) about nucleotides 1729-1920 of SEQ ID NO: 19; (c) about nucleotides 1344-1435 of SEQ ID NO: 18; (d) about nucleotides 1828-1920 of SEQ ID NO: 19; (e) about nucleotides 1370-1413 of SEQ ID NO: 18; and (f) about nucleotides 1857-1899 of SEQ ID NO: 19.

The invention also embodies methods for identifying compounds that inhibit HIV-1 replication. Accordingly, the invention also includes a method of identifying compounds that inhibit HIV-1 replication in cells of an animal, comprising: contacting a Gag protein comprising a CA-SP1 cleavage site with a test compound; adding a labeled substance that selectively binds near the CA-SP1 cleavage site; and measuring competition between the binding of the test compound and the labeled substance to the CA-SP1 cleavage site. In further embodiments of this method, the compounds inhibits the interaction of HIV-1 protease with a target site by binding to said target site.

These methods also include embodiments wherein the CA-SP1 cleavage site region is contained within a polypeptide fragment or recombinant peptide; and/or wherein the labeled substance is a labeled antibody specific for CA-SP1, and measuring the change in the amount of labeled antibody bound to the protein in the presence of test compound compared with a control. Labels include, but are not limited to, an enzyme, fluorescent substance, chemiluminescent substance, horseradish peroxidase, alkaline phosphatase, biotin, avidin, electron dense substance, radioisotope and a combination thereof.

The method of identifying compounds that inhibit HIV-1 replication in cells of an animal also comprises, in one embodiment, measuring the change in the amount of labeled 3-O-(3',3'-dimethylsuccinyl)betulinic acid bound to the protein in the presence of test compound, compared with a control, and wherein the labeled substance is 3-O-(3',3'-dimethylsuccinyl)betulinic acid.

In an alternative embodiment, the invention comprises a method for identifying compounds that inhibit HIV-1 replication in the cells of an animal which comprises: contacting a polypeptide comprising a CA-SP1 cleavage site, with a protease in the presence of a test compound. Preferably the protease is related to HIV-1 protease, or is HIV protease. In one embodiment, the method comprises ; contacting a polypeptide comprising a wild type CA-SP1 cleavage site, with a protease in the presence of a test compound and also contacting a polypeptide comprising a mutant CA-SP1 cleavage site or a protein comprising an alternative protease cleavage site with HIV-1 protease in the presence of the test compound, detecting the cleavage, and comparing the amount of cleavage of the native wild-type polypeptide to the amount of cleavage of the mutant polypeptide or to amount of cleavage of the protein comprising an alternative protease cleavage site. In a related aspect of this method, the wild-type CA-SP1 or mutant CA-SP1 or alternative protease cleavage site region is contained within a polypeptide fragment or recombinant peptide. In a further related aspect, the polypeptide is labeled with a fluorescent moiety and a fluorescence quenching moiety, each bound to opposite sides of the CA-SP1 cleavage site, and wherein said detecting comprises measuring the signal from the fluorescent moiety. In another related embodiment, the polypeptide is labeled with two fluorescent moieties, each bound to opposite sides of the CA-SP1 cleavage site, and wherein said detecting comprises measuring the transfer of fluorescent energy from one moiety to the other in the presence of the test compound. In a further embodiment, the effect of the test compound on cleavage of the polypeptide is detected by measuring the amount of a labeled antibody that is bound to SP1 or p24 (CA). In a related aspect, the labeled antibody that binds CA, or the antibody that binds SP1 is labeled with a molecule selected from the group consisting of enzyme, fluorescent substance, chemiluminescent substance, horseradish peroxidase, alkaline phosphatase, biotin, avidin, electron dense substance, radioisotope, and combinations thereof.

The invention is also directed to a method for identifying compounds that inhibit HIV-1 replication in cells of an animal. In one embodiment, the method comprises: contacting a test compound with cells infected with wild-type virus isolates and with cells infected with virus isolates having significantly reduced sensitivity to 3-O-(3',3'-dimethylsuccinyl) betulinic acid; and selecting test compounds that are more active against the wild-type virus isolate compared with virus isolates that have reduced sensitivity to 3-O-(3',3'-dimethylsuccinyl)betulinic acid. In another embodiment, the method comprises contacting HIV-1 infected cells with a test compound; lysing the infected cells or the released viral particles to form a lysate, and analyzing the lysate to determine whether cleavage of the CA-SP1 protein has occurred. In this latter embodiment, said analyzing may comprise measuring the presence or absence of p25; and or performing a western blot of viral proteins and detecting p25 using an antibody to p25; and/or performing a gel electrophoresis of viral proteins and imaging of metabolically labeled proteins; and/or performing an immunoassay. Such an immunoassay may be performed by any methods known in the art, including, but not limited to:

(a) capturing p25 and p24 on a substrate using an antibody that selectively binds p24; and (b) detecting the presence or absence of p25 on the substrate by using an antibody that selectively binds p25. The invention also includes such modifications of the above assay as would be obvious to one of ordinary skill in the art.

In a further embodiment, the method of identifying a compound according to the invention comprises the use of an epitope tag sequence inserted into SP1 and the selective detection of p25 is performed using an antibody to the epitope tag.

The invention is also directed to a method for identifying compounds that inhibit HIV-1 replication in the cells of an animal comprising: contacting HIV-1 infected cells with a test compound and thereafter analyzing the virus particles using transmission electron microscopy. Such analysis includes for example, looking for the presence of spherical cores that are acentric with respect to the viral particle; and/or having crescent-shaped, electron-dense layers lying just inside the viral membrane.

In additional aspects, the invention is drawn to an isolated polynucleotide comprising a sequence which encodes an amino acid sequence containing a mutation in an HIV Gag p25 protein (CA SP1), said mutation resulting in a decrease in inhibition of processing of p25 (CA-SP1) to p24 (CA) by 3-O-(3',3'-dimethylsuccinyl)betulinic acid (DSB). This inhibition of processing of p25 may be due to a decrease in inhibition of the interaction of HIV-1 protease with Gag; and/or a decrease in the binding of 3-O-(3',3'-dimethylsuccinyl)betulinic acid to Gag; and/or a decrease in the binding of DSB at or near the CA-SP1 cleavage site of Gag. Suitable polynucleotides also include those encoding a mutation at or near the CA-SP1 cleavage site or in the SP1 domain of CA-SP1; and/or those encoding a mutation at or near the amino acid sequence G/SHKARV/ILAEAMSQV (SEQ ID NO: 1); and/or those encoding the amino acid sequences GHKARV-LVEAMSQV (SEQ ID NO: 2) or SHKARILAEAMSQV (SEQ ID NO: 3); and/or isolated polynucleotide which is selected from the group consisting of SEQ ID NO: 4, SEQ ID NO: 6, SEQ ID NO: 8 and SEQ ID NO: 9; and/or having at least about 95% identity to a polynucleotide selected from the group consisting of SEQ ID NO: 4, and SEQ ID NO: 6; and/or having at least about 80% identity to a polynucleotide selected from the group consisting of SEQ ID NO: 8 and SEQ ID NO: 9; and/or having at least about 95% identity to a polynucleotide selected from the group consisting of SEQ NO: 5 and SEQ ID NO: 7; and/or having at least about 80% identity to a polynucleotide of SEQ ID NO: 10. In additional embodiments, the polynucleotide having more than about 40%, 50%, 60%, 70%, 80%, 90%, 95%, 99% identity or which is identical to the polynucleotide sequences listed above.

The invention is also drawn to vectors comprising such polynucleotides as described above; to a host cell comprising such a vector; and to a method of producing a polypeptide comprising incubating the host cell containing such a vector in a medium and recovering the polypeptide from said medium.

In one embodiment, the invention is directed to an antibody. Such an antibody may bind to a polypeptide with an amino acid sequence having at least about 40%, 50%, 60%, 70%, 80%, 90% identity, or which is identical to a sequence selected from the group consisting of:

```
(a) KNWMTETFLVQNANPDCKTILKALGPAATLEEMMTACQGVGGPS

HKARILAEAMSQVTNSATIM;                    (SEQ D NO: 21)

(b) KNWMTETLLVQNANPDCKTILKALGPGATLEEMMTACQGVGGPG

HKARVLAEAMSQVTNPATIM;                    (SEQ ID NO: 22)

(c) TACQGVGGPSHKARILAEAMSQVTNSATIM;          (SEQ ID NO: 23)

(d) MTACQGVGGPGHKARVLAEAMSQVTNPATIM;         (SEQ ID NO: 24)

(e) SHKARILAEAMSQV                           (SEQ ID NO: 25)
and (f) GHKARVLAEAMSQV.                          (SEQ ID NO: 26)
```

In a further related embodiment, the invention is drawn to an antibody which binds to a polypeptide encoded by a polynucleotide sequence having at least about 40%, 50%, 60%, 70%, 80%, 90% identity, or which is identical to a polynucleotide with a sequence selected from the group consisting of: (a) about nucleotides 1243-1435 of SEQ ID NO: 18; (b) about nucleotides 1729-1920 of SEQ ID NO: 19; (c) about nucleotides 1344-1435 of SEQ ID NO: 18; (d) about nucleotides 1828-1920 of SEQ ID NO: 19; (e) about nucleotides 1370-1413 of SEQ ID NO: 18; and (f) about nucleotides 1857-1899 of SEQ ID NO: 19.

In one embodiment, the antibody binds to amino acids of the CA-SP1 region of the HIV-1 Gag polypeptide, wherein said amino acids comprise: SHKARILAEAMSQV (SEQ ID NO: 25) or GHKARVLAEAMSQV (SEQ ID NO: 26).

In one embodiment, the invention is drawn to an antibody that inhibits the binding of 3-O-(3',3'-dimethylsuccinyl)betulinic acid to the CA-SP1 region of the Gag polypeptide.

The invention is also drawn to mutant HIV-1 viruses. In one such embodiment, the invention is an isolated mutant recombinant HIV-1 virus, wherein the processing of the viral Gag p25 protein (CA-SP1) to p24 (CA) in said virus is not significantly inhibited by 3-O-(3',3'-dimethylsuccinyl)betulinic acid. In related embodiments, this virus is not inhibited by 3-O-(3',3'-dimethylsuccinyl)betulinic acid. In another embodiment, 3-O-(3',3'-dimethylsuccinyl)betulinic acid does not inhibit the interaction of protease with the Gag polypeptide in this virus. In another, the virus does not bind to 3-O-(3',3'-dimethylsuccinyl)betulinic acid. In further embodiments the invention is drawn to viruses wherein the amino acids of the CA-SP1 region are replaced with alternative amino acids, or amino acids are added to the CA-SP1 region, or where amino acids are deleted. In one embodiment, ; one or more amino acids are deleted from the AEAMSQV (amino acid no. 8-14 of SEQ ID NO:26) amino acid sequence in the CA-SP1 region.

A mutant viruses may be used in the methods of the invention described elsewhere herein. For example, such viruses are useful in a method of identifying a compound which inhibits processing of the viral Gag p25 protein (CA-SP1) to p24 (CA), the method comprising comparing the ability of said compound to inhibit HIV-1 replication compared with the replication of a the mutant virus outlined above. Such inhibition may be examined in a cell, or in an animal, or in vitro.

The invention is also drawn to non-HIV-1 retroviruses that are sensitive to 3-O-(3',3'-dimethylsuccinyl)betulinic acid. In some embodiment, said retrovirus encodes a CA-SP1 polypeptide with an amino acid sequence comprising the sequence AEAMSQV (amino acid no. 8-14 of SEQ ID NO: 26) at or near the CA-SP1 cleavage site. In another embodiment, the retrovirus encodes a CA-SP1 polypeptide with an amino acid sequence comprising the sequence VLAEAMSQV (amino acid no. 6-14 of SEQ ID NO: 26) at or near the CA-SP1 cleavage site. In another embodiment, the retrovirus encodes a CA-SP1 polypeptide with an amino acid sequence comprising the sequence GHKARVLAEAMSQV (SEQ ID NO: 26) at or near the CA-SP1 cleavage site; in another the retrovirus comprises the amino acid sequence having at least 60%, 70%, 80%, 90% identity or which is identical to the sequence enocoded by the polynucleotide of SEQ ID NO:26, SEQ ID NO: 90; SEQ ID NO: 92; SEQ ID NO: 94; SEQ ID NO: 96; or SEQ ID NO: 98; in another embodiment the retrovirus comprises the amino acid sequence having at least 60%, 70%, 80%, 90% identity or which is identical to the sequence of SEQ ID NO: 91; SEQ ID NO: 93; SEQ ID NO: 95; SEQ ID NO: 97; or SEQ ID NO: 99. In another embodiment, the retrovirus comprises the nucleic acid sequence having at least 70%, 80%, 90% or which is identical to the sequence of SEQ ID NO: 90; SEQ ID NO: 92; SEQ ID NO: 94; SEQ ID NO: 96; or SEQ ID NO: 98.

Retroviruses of this embodiment of the invention include, but are not limited to HIV-2, HTLV-I, HTLV-II, SIV, avian leukosis virus (ALV), endogenous avian retrovirus (EAV), mouse mammary tumor virus (MMTV), feline immunodeficiency virus (FIV), Bovine immunodeficiency virus (BIV), caprine arthritis encephalitis virus (CAEV), Visna-maedi virus, or feline leukemia virus (FeLV).

In a related embodiment, the invention is drawn to a method of making a recombinant non-HIV-1 lentivirus sensitive to DSB. This method comprises: deleting from the genome of said lentivirus the nucleotides which correspond to nucleotides 1370-1413 from SEQ ID NO: 18, in HIV-1; and inserting nucleotides 1370-1413 from SEQ ID NO: 18 or nucleotides 1857-1899 of SEQ ID NO: 19 into said region of said non-HIV-1 lentivirus.

Examples of chimeric lentiviruses that were, are or may be constructed by this method are described in FIG. 10.

Such viruses may be used in the methods of the invention described elsewhere herein. For example, such recombinant non-HIV-1 lentiviruses may be used in a method of identifying a compound which inhibit processing of the viral Gag p25 protein (CA-SP1) to p24 (CA), the method consisting of comparing of the ability of said compound to inhibit replication of a wild-type non-HIV-1 lentivirus with the DSB-sensitive recombinant variant thereof. Such inhibition may occur in a cell; in an animal; or in vitro.

The invention is also drawn to an animal model of lentivirus infection comprising a suitable non-human animal host infected with a lentivirus sensitive to 3-O-(3',3'-dimethylsuccinyl)betulinic acid. In such an embodiment, the lentivirus may include, but is not limited to SIV; FIV; EIAV; BIV; CAEV; and Visna-Maedi virus.

The invention is also drawn to isolated polypeptides. In one embodiment, the invention is drawn to a polypeptide containing a mutation in an HIV CA-SP1 protein, said mutation which results in a decrease in inhibition of processing of p25 by 3-O-(3',3'-dimethylsuccinyl)betulinic acid. In a related embodiment, this polypeptide is encoded by a polynucleotide that contains a mutation located at or near the CA-SP1 cleavage site or in the SP1 domain encoded by SEQ ID NO: 5, SEQ ID NO: 7, or SEQ ID NO: 10 and/or is encoded by a polynucleotide selected from the group consisting of SEQ ID NO: 4, SEQ ID NO: 6, SEQ ID NO: 8 and SEQ ID NO: 9; and/or comprises a sequence that is selected from the group consisting of GHKARVLVEAMSQV (SEQ ID NO: 2) or SHKARILAEVMSQV (SEQ ID NO: 3); and/or is encoded by an isolated polynucleotide which hybridizes under stringent conditions to a polynucleotide selected from the group consisting of SEQ ID NO: 5, SEQ ID NO: 7, and 10; and/or is part of a chimeric or fusion protein.

The invention is also drawn to antibodies which selectively bind to an amino acid sequence containing a mutation in an HIV CA-SP1 protein which results in a decrease in the inhibition of processing of p25 (CA-SP1) to p24 (CA) by 3-O-(3'3'-dimethylsuccinyl)betulinic acid. In one such embodiment, the antibody selectively binds to a mutation located at or near the CA-SP1 cleavage site or in the SP1 domain of CA-SP1; in another, the antibody selectively binds to a mutation comprising a sequence that is selected from the group consisting of GHKARVLVEAMSQV (SEQ ID NO: 2) or SHKARILAEVMSQV (SEQ ID NO: 3); in another embodiment, the antibody selectively binds an amino acid sequence selected from the group consisting of SEQ ID NO: 2 and SEQ ID NO: 3.

In another embodiment, the invention is drawn to an antibody that selectively binds SP1 but not CA-SP1; another that selectively binds CA-SP1 but not CA; another that selectively binds CA but not CA-SP1; and a further antibody that selectively binds at or near the CA-SP1 cleavage site.

The invention is also directed to a compound identified by any of the methods elucidated herein. In one embodiment, the compounds is not a compound selected from the group consisting of 3-O-(3',3'-dimethylsuccinyl)betulinic acid, 3-O-(3', 3'-dimethylsuccinyl)betulin, 3-O-(3',3'-dimethylglutaryl) betulin, 3-O-(3',3'-dimethylsuccinyl)dihydrobetulinic acid, 3-O-(3',3'-dimethylglutaryl)betulinic acid, (3',3'-dimethylglutaryl)dihydrobetulinic acid, 3-O-diglycolyl-betulinic acid, 3-O-diglycolyl-dihydrobetulinic acid, and combinations thereof.

The invention is also drawn to a pharmaceutical composition. In one embodiment, the pharmaceutical composition comprises derivatives of dimethylsuccinyl betulinic acid or dimethylsuccinyl betulin; in another, the pharmaceutical composition comprises a compound selected from the group consisting of 3-O-(3',3'-dimethylsuccinyl)betulinic acid, 3-O-(3',3'-dimethylsuccinyl)betulin, 3-O-(3',3'-dimethylglutaryl)betulin, 3-O-(3',3'-dimethylsuccinyl)dihydrobetulinic acid, 3-O-(3',3'-dimethylglutaryl)betulinic acid, (3',3'-dimethylglutaryl)dihydrobetulinic acid, 3-O-diglycolyl-betulinic acid, 3-O-diglycolyl-dihydrobetulinic acid, and combinations thereof. In another embodiment, the pharmaceutical composition comprises one or more compounds identified according to the methods of the invention which are not otherwise listed; or any pharmaceutically acceptable salt, ester or prodrug thereof, and a pharmaceutically acceptable carrier. In another embodiment, the pharmaceutical composition further comprising an anti-viral agent which may include any one of zidovudine, lamivudine, didanosine, zalcitabine, stavudine, abacavir, nevirapine, delavirdine, emtricitabine, efavirenz, saquinavir, ritonavir, indinavir, nelfinavir, tenofovir, amprenavir, adefovir, atazanavir, fosamprenavir, hydroxyurea, AL-721, ampligen, butylated hydroxytoluene; polymannoacetate, castanospermine; contracan; creme pharmatex, CS-87, penciclovir, famciclovir, acyclovir, cytofovir, ganciclovir, dextran sulfate, D-penicillamine trisodium phosphonoformate, fusidic acid, HPA-23, eflornithine, nonoxynol, pentamidine isethionate, peptide T, phenytoin, isoniazid, ribavirin, rifabutin, ansamycin, trimetrexate, SK-818, suramin, UA001, combinations thereof, any other antiviral, immunomodulating agent, anti-cancer agent, anti-fungal agent, anti-bacterial agent, or combinations thereof.

The invention is also drawn to a method of determining if an individual is infected with HIV-1 that is susceptible to treatment by a compound that inhibits p25 processing. In one embodiment, the method involves taking blood from the patient, genotyping the viral RNA and determining whether the viral RNA contains mutations in the sequence encoding the region of the CA-SP1 cleavage site.

The invention is also drawn to a method of treating a disease in a patient in need thereof comprising:

identifying a compound which inhibits the processing of viral Gag p25 protein (CA-SP1) to p24 (CA), but has no significant effect on other Gag processing steps;

obtaining regulatory approval for the sale and use of said compound;

packaging the compound for sale and treatment of a disease in a patient in need thereof.

BRIEF DESCRIPTION OF THE DRAWINGS

FIG. 4 depicts amino acid sequences in the region of the CA-SP1 cleavage site from DSB-sensitive HIV-1 isolates NL4-3 and RF (#1; SEQ ID NO: 1) and DSB-resistant HIV-1 isolates (#2; SEQ ID NO: 2 (NL4-3), and #3; SEQ ID NO: 3 (RF)). The differences between the native and DSB-resistant sequences involve an alanine to valine change at the first downstream residue (#2) and an alanine to valine change in the third downstream residue (#3) from the CA-SP1 cleavage site (-|-). These residues are underlined and bolded for ease of identification.

FIG. 5 depicts the + sense consensus sequence for the A364V DSB-resistant NL4-3 mutant (SEQ ID NO: 4) beginning with the start of gag and continuing into pol, including the entire protease coding region. Missense mutations not found in the wild-type NL4-3 GENBANK M19921 sequence are in bold and gray shadowing. The coding sequence for the consensus CA-SP1 cleavage site region is underlined. The shaded area including the cleavage site denotes the SP1 sequence. The first mutation is the A364V mutation.

Figure 1:
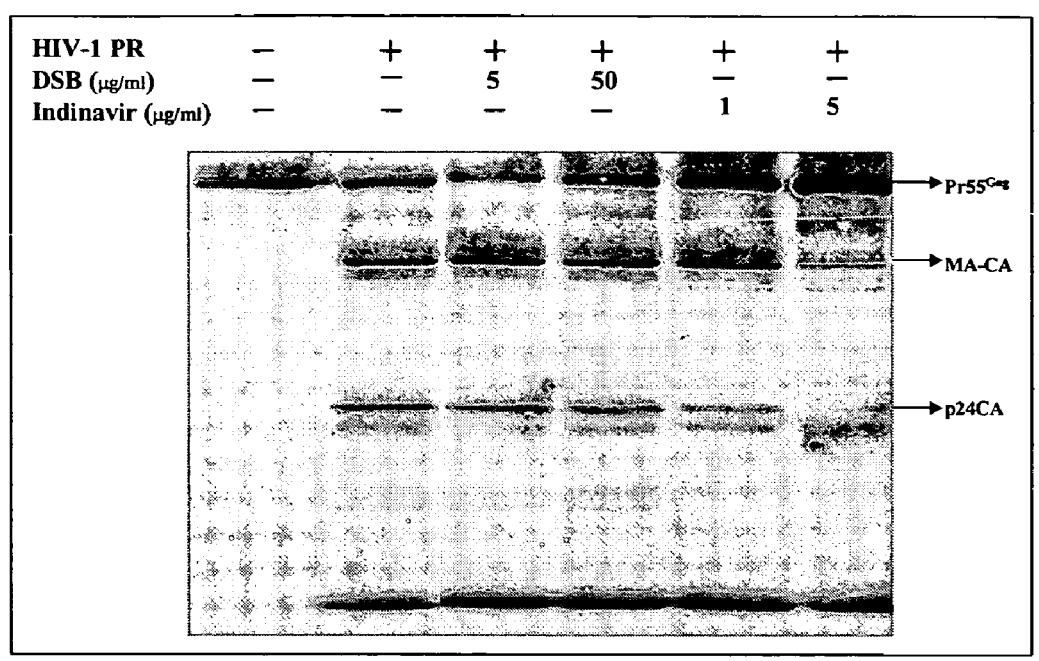
FIG. 1. DSB does not disrupt the activity of HIV-1 protease at a concentration of 50 µg/mL. In DSB-containing samples recombinant Gag is processed correctly. In contrast, indinavir blocks protease activity at 5 µg/mL as evidenced by the absence of bands corresponding to p24 and the MA-CA precursor.

The second amino acid change (in protease) was also found in the parental clone and has been confirmed to correspond to a sequencing error in the original GENBANK entry. Therefore, no mutations actually occurred in protease.

FIG. 6 depicts the + sense consensus sequence for the DSB-sensitive NL4-3 parental isolate (SEQ ID NO: 5) that was passaged in the absence of drug in parallel with the A364V mutant isolate.

FIG. 7 depicts the + sense consensus sequence for the A366V DSB-resistant HIV-1 RF mutant (SEQ ID NO: 6) beginning with the start of the gag and continuing into pol, including the entire protease coding region. Missense mutations not found in the wild-type HIV-1 RF GENBANK M17451 sequence are shadowed in gray. The region of the CA-SP1 cleavage site is underlined. The only missense mutation not also found in the identically passaged DSB-sensitive isolate is the A366V mutation in the CA-SP1 cleavage site.

FIG. 8 depicts the + sense consensus sequence for the DSB-sensitive HIV-1 RF parental isolate (SEQ ID NO: 7), that was passaged in the absence of drug in parallel with the A366V mutant isolate.

FIG. 9 depicts the polynucleotide sequences, SEQ ID NO: 8 and SEQ ID NO: 9, which encode the polypeptides designated herein as SEQ ID NO: 2 and SEQ ID NO: 3, respectively. SEQ ID NO: 10 and 12 depict the nucleotide sequences that encode the parental polypeptide sequences designated as SEQ ID NO: 1. SEQ ID NO: 1 is a consensus sequence based on the sequences of the region from NL4-3 and RF

FIG. 10:

10A. Amino acid sequences in the CA-SP1 region of lentiviruses. (SEQ ID NO: 13; SEQ ID NO: 11; SEQ ID NO: 14; SEQ ID NO: 15; SEQ ID NO: 20; SEQ ID NO: 27; SEQ ID NO: 28; SEQ ID NO: 29; SEQ ID NO: 30; SEQ ID NO: 30; respectively)

10B: Amino acid sequences of the CA-SP1 region in HIV-1 strains RF (SEQ ID NO: 11) and NL4-3 (SEQ ID NO: 13).

10C-10D: Nucleotide sequences of gag gene chimeric SIVs. The 42 nucleotide sequence encoding the seven amino acids upstream and seven amino acids downstream of the CA-SP1 cleavage site is underlined and in bold.

10E-H Nucleotide sequences of gag gene of chimeric FIV, EIAV and BIV to be made according to the invention. The 42 nucleotide sequences encoding the seven amino acids upstream and seven amino acids downstream of the CA-SP1 cleavage sites are underlined and in bold (nucleotide sequence: SEQ ID NO: 16; amino acid sequence SEQ ID NO: 17).

10F. Nucleotide sequence of GAG gene of Chimeric Feline Immunodeficiency Virus (FIV) containing the HIV CA-SP1 region: Chimeric FIV-GAG gene nucleotides 1-1353 corresponds to nucleotides 628-1980 in Chimeric FIV genome. Nucleotide sequence SEQ ID NO: 94 encoding amino acids SEQ ID NO: 95.

10G. Nucleotide Sequence of GAG gene of Chimeric Equine Infectious Anemia Virus (EIAV) containing the HIV1 CA-SP1 region: Chimeric EIAV-GAG gene nucleotide 1-1587 corresponds to nucleotides 450-1910 in Chimeric EIAV genome. Nucleotide SEQ ID NO: 96 encoding amino acids SEQ ID NO: 97

10H. Nucleotide Sequence of GAG gene of Chimeric Bovine Immunodeficiency Virus (BIV) containing the HIV1 CA-SP1 region: Chimeric BIV-GAG gene nucleotides 1-1471 corresponds to nucleotides 316-1746 in Chimeric BIV genome. Nucleotide SEQ ID NO: 98 encoding amino acids SEQ ID NO: 99

Figure 11:
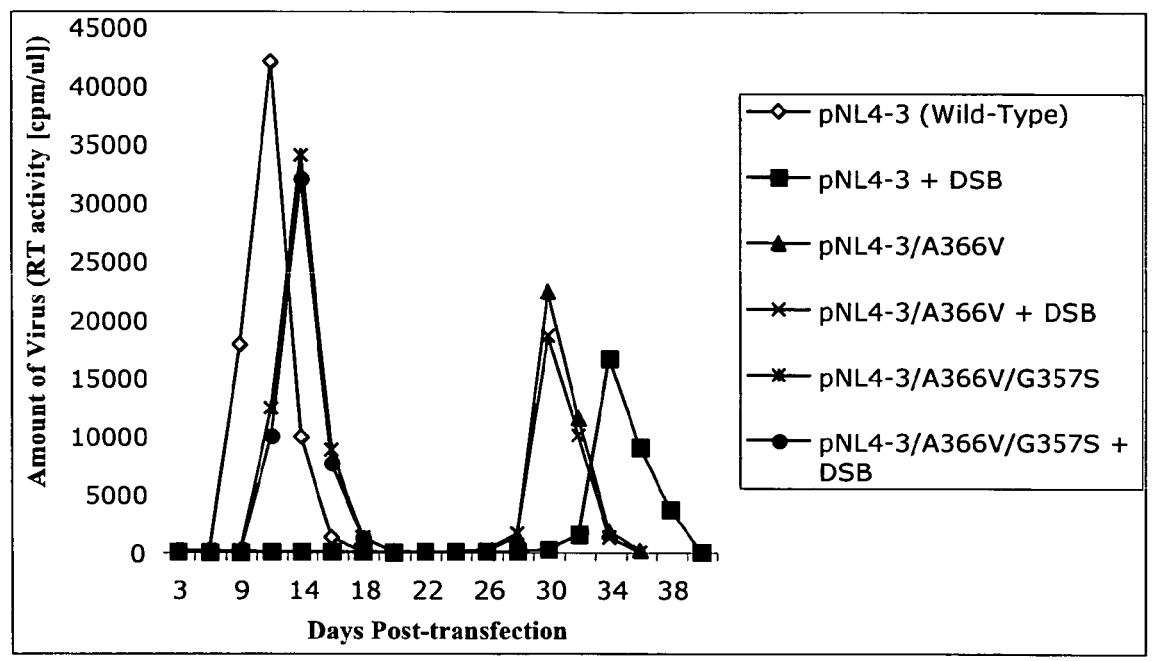

FIG. 11: Replication kinetics of PA-457 (DSB)-resistant mutants

FIG. 12: Sequential SP1 point deletions in the context of NL4-3 used to identify residues necessary for DSB activity. The amino acid sequence of SP1 domain in NL4-3 is shown. "Δ" indicates the deletion and "-" means identical residues between point deletion mutants and NL4-3 (SEQ ID NO: 13; SEQ ID NO: 33; SEQ ID NO: 34; SEQ ID NO: 35; SEQ ID NO: 36; SEQ ID NO: 85; SEQ ID NO: 86; SEQ ID NO: 87; SEQ ID NO: 88; SEQ ID NO: 89; SEQ ID NO: 100; SEQ ID NO: 101; SEQ ID NO: 102; SEQ ID NO: 103; respectively).

FIG. 13. Summary of particle production and infectivity of point deletions mutants.

FIG. 14. Western blots for viruses containing point deletions in SP1, in the presence (+) and absence (−) of DSB.

Figure 15:
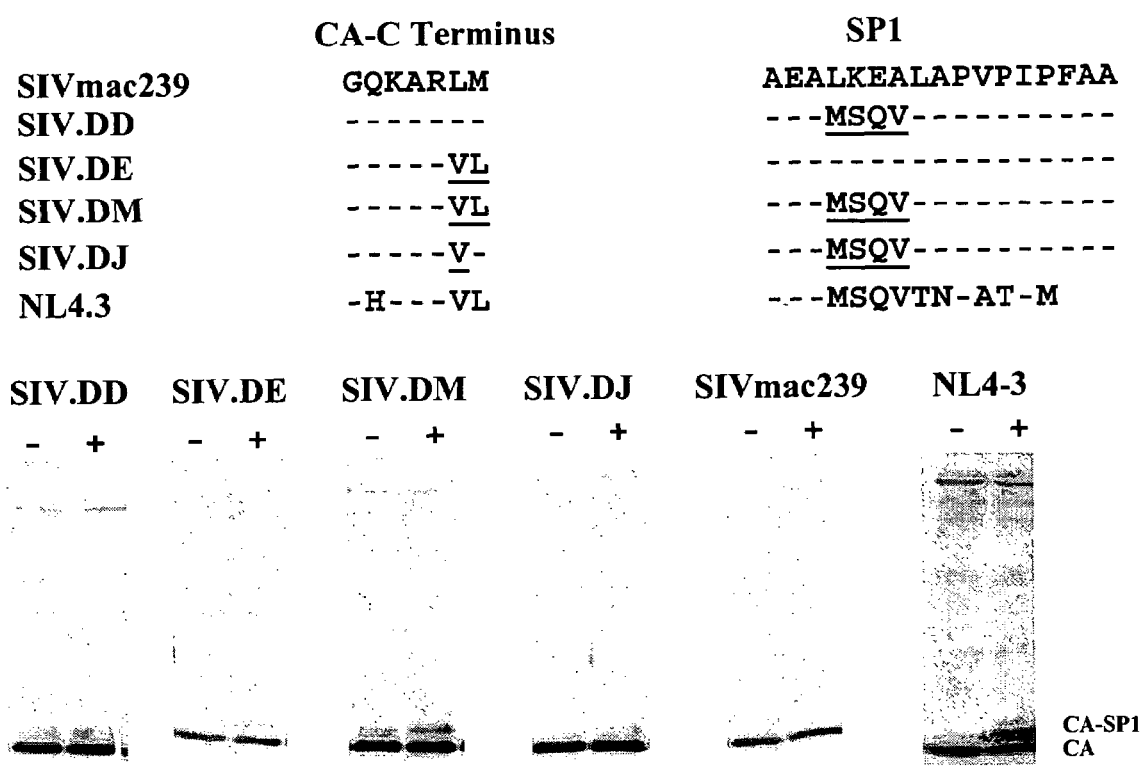

FIG. 15. Substitution of HIV-1 CA-SP1 residues VL-AE-AMSQV (SEQ ID NO:32) into SIVmac239 backbone renders SJVmac239 sensitive to DSB (SEQ ID NO: 14; SEQ ID NO: 15; SEQ ID NO: 20; SEQ ID NO: 27; SEQ ID NO: 28; SEQ ID NO: 13; respectively).

(Top panel) Amino acid sequences near the CA-SP1 cleavage site (including entire SP1 region) are shown for SIVmac239, HIV-1 NL4-3 and a series of SIV mutants into which various NL4-3 residues (underlined) were inserted. Dashes ("-") indicates the residues are the same as those in SIVmac239.

(Bottom panel) Western blots showing the CA and CA-SP1 proteins for this series of viruses in the presence (+) or absence (−) of DSB.

FIG. 16: Sequence conservation in the CA-SP1 region of Lentiviruses. Cloning Strategy: Substituting HIV-1 specific CA-SP1 residues into the corresponding Gag region of FIV, EIAV or BIV.

FIG. 17. HIV-1 NL4-3 SP1 tagged with an epitope. Sequences of SP1 peptides with peptide tags inserted are shown. "Δ" indicates deleted residue and "-" indicates that the residue is identical to that in NL4-3 SP1. (FIG. 17 (1): SEQ ID NO: 15; SEQ ID NO: 104; SEQ ID NO: 105; SEQ ID NO: 106; SEQ ID NO: 107; respectively): (FIG. 17 (2): SEQ ID NO: 15; SEQ ID NO: 108; SEQ ID NO: 109; respectively): (FIG. 17 (3): SEQ ID NO: 15; SEQ ID NO: 110; SEQ ID NO: 111; respectively): (FIG. 17 (4): SEQ ID NO: 15; SEQ ID NO: 112; SEQ ID NO: 113; SEQ ID NO: 114; respectively); (FIG. 17 (5): SEQ ID NO: 15; SEQ ID NO: 115; respectively).

FIGS. 18A-C: HIV-1 strain RF polynucleotide sequence. The nucleotide sequence of the Gag polyprotein is underlined and in bold. The 42 nucleotide sequence encoding the seven amino acids upstream and seven amino acids downstream of the CA-SP1 cleavage site is highlighted in green. An additional 129 nucleotides (43 amino acid residues) upstream of the cleavage site in CA and the remaining 21 nucleotides (seven amino acids residues) in SP1 are highlighted.

FIGS. 19A-E: HIV-1 strain NL4-3 polynucleotide sequence. The nucleotide sequence of the Gag polyprotein is underlined and in bold. The 42 nucleotide sequence encoding the seven amino acids upstream and seven amino acids downstream of the CA-SP1 cleavage site is highlighted in green. An additional 129 nucleotides (43 amino acid residues) upstream of the cleavage site in CA and the remaining 21 nucleotides (seven amino acids residues) in SP1 are highlighted.

DETAILED DESCRIPTION OF THE INVENTION

The present invention is directed to methods of inhibiting HIV-1 replication in the cells of an animal. More specifically, the invention involves methods of inhibiting HIV-1 replication in the cells of a mammal by contacting infected cells with a compound that inhibits the processing of the viral Gag p25 protein (CA-SP1) to the p24 protein (CA). More specifically, such compounds inhibit the processing of the viral Gag p25 protein (CA-SP1) to the p24 protein (CA) without significantly affecting other Gag processing steps.

"A compound that does not significantly affect other Gag processing steps" means that the compound in question predominantly inhibits processing of p25 to p24, but does not necessarily preclude the possibility of having additional minor effects on other Gag processing steps.

"Significant" or "Significantly," where not otherwise defined herein, means an observable or measurable change compared to the process in the absence of a compound. However, not all observable or measureable changes may necessarily be significant.

A number of viral phenotypes may also be observed in practicing the method of the invention. One result of contacting an infected cell with the compounds of the invention may be the formation of noninfectious viral particles. Alternatively, or in addition, contacting infected cells with a compound that inhibits p25 to p24 processing, results in the formation of non-infectious viral particles, but where there is no significant effect on other Gag processing steps. This may not significantly reduce the quantity of virus released from treated cells and/or has no little or no significant effect on the amount of RNA incorporation into the released virions.

Accordingly, the invention is also drawn to a method of inhibiting HIV infection in cells of an animal comprising contacting said cells with a compound that inhibits p25 processing and also affects other viral phenotypes, discribed above.

Mutant viruses defective in CA-SP1 cleavage have been shown to be non-infectious (Wiegers K. et al., *J. Virol.* 72:2846-2854 (1998)). 3-O-(3',3'-dimethylsuccinyl)betulinic acid (DSB) is an example of a compound that disrupts p25 to p24 processing and potently inhibits HIV-1 replication. This compound's activity is specific for the p25 to p24 processing step, not other steps in Gag processing. Furthermore, DSB treatment results in the aberrant HIV particle morphology as described in FIG. 3.

Identification of HIV-1 Determinants Associated with Sensitivity to 3-O-(3',3'-dimethylsuccinyl)betulinic acid Generation and Selection of HIV-1 Viruses Resistant to DSB.

Mutant forms of HIV-1 have been generated in which the amino acid sequence in the region of the CA-SP1 cleavage site is modified, decreasing the sensitivity of these strains to compounds that disrupt CA-SP1 processing. Data on these mutant viruses have been used to identify the amino acid residues in wild-type Gag that are implicated in the antiviral activity of these compounds. In one embodiment, compounds that disrupt CA-SP1 processing directly or indirectly inhibit the interaction of HIV-1 protease with the region of the Gag protein containing these amino acid residues. In another embodiment, compounds that disrupt CA-SP1 processing bind to the region containing these amino acid residues. As used herein, the terms "bind," "bound" or "binding" refers to binding or attachment including, e.g., ionic interactions, electrostatic hydrophobic interactions, hydrogen bonds, etc; and also includes associations that may be covalent, e.g., by chemically coupling. Covalent bonds can be, for example, ester, ether, phosphoester, thioester, thioether, urethane, amide, amine, peptide, imide, hydrazone, hydrazide, carbon-sulfur bonds, carbon-phosphorus bonds, and the like. The term "bound" is broader than and includes terms such as "coupled," "conjugated" and "attached."

In another embodiment, compounds that disrupt CA-SP1 processing bind to another region of Gag and thereby inhibit the interaction of HIV-1 protease with the region of the CA-SP1 cleavage site. In another embodiment, viruses or recombinant proteins that contain mutations in the region of the CA-SP1 cleavage site can be used in screening assays to identify compounds that disrupt CA-SP1 processing.

In one set of experiments, amino acid residues in HIV-1 Gag that are involved in the disruption of CA-SP1 processing by 3-O-(3',3'-dimethylsuccinyl)betulinic acid (DSB) were identified by sequencing the gag-pol gene of virus isolates that had been selected for resistance to DSB. The amino acid sequences from these resistant viruses were compared with the gag-pol gene sequences from DSB-sensitive HIV-1 isolates. Two single amino acid changes were identified in the DSB-resistant viruses, an alanine (Ala) to valine (Val) substitution at residue 364 (SEQ ID NO: 4) and in a second isolate, at residue 366 (SEQ ID NO: 6), in the Gag polyprotein (see FIG. 4). These residues are located immediately downstream of the CA-SP1 cleavage site (at the N-terminus of SP1). Alanine is highly conserved at these positions throughout all HIV-1 subtypes listed in the Los Alamos National Laboratory database. The five amino acid residues upstream and downstream of the CA-SP1 cleavage site are also highly conserved among the various subtypes. However, isoleucine replaces valine at the position two residues upstream of the cleavage site in a number of clades (c.f., FIG. 4, SEQ ID NO: 1). ("*HIV Sequence Compendium* 2002," Kuiken et al. eds. Los Alamos National Laboratory, Los Alamos, N. Mex.)

In order to more extensively map the viral genetic determinants for DSB resistance, additional experiments were performed to select for viruses in vitro that are drug resistant. Multiple parallel cultures of Jurkat T cells ($5\times10^5$ each) were transfected with the proviral DNA clone pNL4-3 in the presence or absence of 10-50 ng/ml DSB. The cells were passaged every two days, and fresh drug was added at each passage. Virus replication was monitored by measuring reverse transcriptase activity in culture supernatants. Virus was isolated from culture supernatants harvested at selected timepoints, and genomic DNA was amplified by RT-PCR using primers that spanned the coding region between the N-terminus of CA and the N-terminus of RT. The amplified product was then sequenced using the same set of primers.

In one experiment, an A366V mutation was identified in the SP1 region of NL4-3 virus cultured in the presence of DSB (note: numbering is relative to the Gag polyprotein). Upon further passaging, a double mutant was identified that contained a G357S mutation in CA as well as the A366V mutation in SP1. The A366V mutation was identified previously in experiments selecting for resistant variants of the RF isolate. Interestingly, the wild-type RF sequence also contains a serine residue at position 357 in CA (FIG. 4). Since serine is present at this position in isolates (such as RF) that are sensitive to DSB, the CA G357S mutation alone is not sufficient to confer resistance to DSB. To determine the contribution of each of these mutations to drug resistance, the A366V mutation and the A366V/G357S double mutation were re-engineered into the wild-type NL4-3 backbone by site-directed mutagenesis. The resulting constructs were transfected into Jurkat T cells and characterized in a virus replication assay as described above for the selection of resistance. SDS-PAGE analysis of transfected cell lysates and virus released into the media demonstrated that the A366V mutant Gag was processed and released from cells inefficiently (data not shown) and thus replicated very poorly even in the absence of drug (FIG. 11) However, the A366V/G357S double mutant replicated efficiently in the absence or presence of DSB. There data indicate that the resistant mutant, A366V, requires a serine at the 357 position in the CA region of Gag to compensate for a deleterious effect on virus replication (FIG. 11).

In a further experiment, ten different resistant isolates were generated. Sequencing of these isolates identified four additional mutations not previously seen in resistance selection experiments. These were H358Y, L363F and L363M in CA, and A402T in the NC region of Gag. None of these mutations are present in the consensus sequences for HIV-1 clades A-O, reflecting the breadth of activity of DSB against genetically diverse clades of HIV-1. The L363M substitution in CA was found in the consensus sequence for HIV-2, which may, in part, explain the specificity of DSB for HIV-1.

These results demonstrate the presence of specific genetic determinants for DSB activity in HIV-1, and that these determinants are centered around the CA-SP1 cleavage site.

HIV-1 NL4-3 Deletion and SIV Insertion Studies Used to Identify Viral Genetic Determinants of DSB Sensitivity Results from in vitro resistance selection experiments indicated that the determinants of DSB HIV-1 inhibitory activity map to the region of Gag flanking the CA-SP1 cleavage site. In order to better define the viral genetic determinant for DSB, HIV-1 point-deletion mutagenesis and SIV insertion studies were undertaken to identify the specific amino acid residues associated with compound activity. The study was carried out as follows. Single residue deletions starting with residue E365 and continuing through residue M377 were engineered into the SP1 domain of the infectious HIV-1 molecular clone NL4-3 (FIG. 12). The effect of these point deletions on viral particle production, infectivity, Gag processing and sensitivity to DSB was determined. The results of these experiments were used to identify the Gag residues in the region of the CA-SP1 cleavage site that are associated with DSB activity. The residues associated with activity were inserted into the CA-SP1 cleavage site region of the DSB-resistant virus SIV (Mac 239 isolate) to generate a HIV-1, SIV chimeric virus (SHIV). Point substitution of HIV-1 residues from the N-terminus of the CA protein were made into this chimeric virus until the minimal sequence necessary to rescue DSB activity was identified. This minimal sequence necessary to gain DSB activity is considered a primary viral genetic determinant of DSB activity. It may suggest the molecular determinant of DSB activity.

Methods:

Construction of NL4-3 Single Point-Deletion Mutants.

Single point-deletion constructs were generated using the PCR-ligation-PCR (PLP) strategy as previously described. HIV-1 NL4-3 plasmid DNA was used as the template to perform all PCR reactions for generating point deletions spanning the complete Gag SP1 domain with the exception of the first residue of SP1.

ΔE365 was generated using NL4-3 as the template with Vent DNA polymerase (NEB) by using deletion-specific downstream primer (Primer 1) with universal upstream primer (Primer 2) (Table 1). The fragment derived from this was termed as a first flanking PCR fragment. A second flanking fragment was amplified using deletion-specific upstream primer (Primer. 3) and universal downstream primer (Primer 4) (Table 1). To generate other deletion constructs (ΔA366, ΔM367, ΔS368, ΔQ369, ΔV370, ΔT371, ΔN372, ΔP373, ΔA374, ΔT375, ΔI376, and ΔM377). PCR procedures were similarly performed by varying deletion-specific downstream and upstream primers corresponding to each specific point deletion (Table 1).

Each of these parallel two adjacent PCR fragments was gel purified, phosphorylated using T4 polynucelotide kinase (NEB), and ligated by using T4 DNA ligase (NEB). After inactivation at 65° C. for 15 minutes, the ligation reaction was used for a subsequent amplification with universal upstream primer (Primer. 2) and downstream primer (Primer. 4). This product was gel purified, digested with SpeI and ApaI, and then ligated into the SpeI and ApaI sites of NL4-3 proviral DNA clone.

Standard PCR conditions were used for the above-described reactions. These included, one cycle of denaturation at 95° C. for 1 minutes 30 seconds, followed by 30 cycles of denaturation at 95° C. for 30 seconds, 60° C. for 30 seconds and 72° C. for 30 seconds. The PCR reactions were set up using the following components:

5 μL 10×NEB Thermophilic buffer
2 μL 10 mM dNTPs
1 μL 100 nM MgSO$_2$
1 μL 50 pmol upstream primer
1 μL 50 pmol downstream primer
1 μL 50 ng/μL template DNA
0.5 μL Vent DNA polymerase
38.5 μL ddH$_2$O A 10 μL aliquot was run on a 1.0% agarose gel to make sure the correct size product was amplified. The PCR products were then gel isolated and purified with a Qiaex II gel extraction Kit (Qiagen). The gel-purified two adjacent PCR fragments were individually phosphorylated in the following reaction by using T4 polynucleotide kinase (NEB) prior to ligation. The phosphorylation reaction was set up as follows:

2 μL 10×T4 polynucleotide kinase buffer
2 μL 10 mM ATP
1 μL T4 polynucleotide kinase
15 μL gel purified DNA of each of these two adjacent PCR fragments The reaction was incubated at 37° C. for 1 hour. Following the inactivation at 65° C. for 10 minutes, the adjacent phosphorylated PCR fragments were then ligated together by using T4 DNA ligase (NEB) under following conditions:

3 μL 10×T4 DNA ligase buffer
13 μL of each two adjacent PCR fragments
1 μL T4 DNA ligase After overnight incubation at 16° C. the ligation reaction product was used in a second round PCR reaction to amplify the full-length PCR fragment spanning these two adjacent PCR products. The second round PCR reaction was performed as described above with the exception that only universal upstream primer (Primer. 2) and downstream primer (Primer. 4) were used. Again, a 10 µL aliquot was run on a agarose gel to make sure the correct product was amplified. The full-length PCR fragments were then gel isolated and purified using a Qiaex II kit. The purified full-length PCR fragment, together with NL4-3, were then cut with SpeI and ApaI under the following conditions:

2 µL 10×NE buffer 4 (NEB)
1 µL ApaI (NEB)
1 µL SpeI (NEB)
16 µL full length PCR product (1 µg) or NL4-3 (500 ng)

The above restriction enzyme digestion mixture was incubated at 37° C. for 2 hours. Digested DNA fragments for the full-length PCR product and the NL4-3 plasmid were individually gel isolated and purified using a Qiaex II kit. The digested vector NL4-3 and full length PCR fragment were ligated using T4 DNA ligase under the following procedure:

1 µL 10×T4 DNA ligase buffer
1 µL (25-50 ng) digested NL4-3 vector
7 µL digested (200 ng-400 ng) digested PCR fragment (700 bp)
1 µL T4 DNA ligase The ligation reaction was incubated at 16° C. overnight and the ligated products were transformed into *Escherichila coli* Max Efficiency Stbl2 (Invitrogen) by heat shock according to instruction (Invitrogen). The proviral DNA clones were then screened by automatically sequencing using a Taq Dye Deoxy Terminator cycle Sequencer Kit (Applied Biosystems) individually using internal primers (Primer 29 and 30) Following the verification the mutations the proviral DNA clones were used for various future studies.

Construction of SIV Chimeric Mutants

A panel of SIV chimeric constructs harboring various residues of NL4-3 CA-SP1 boundary region was generated using the SIVmac239 molecular clone by employing PCR and cloning procedures described above. These constructs and their amino acid sequences in the CA-SP1 boundary region are shown in FIG. 15. SIV mac239 was used to generate the SIV DD and DE constructs. The SIV DD construct was used to generate SIV DM. Different SIV chimeric constructs were produced in the PCR by varying respective mutagenic upstream and downstream primers corresponding to each chimera (Table 1). Each of these parallel two adjacent PCR fragments was gel purified and directly used without phosphorylation treatment for a subsequent amplification with universal upstream primer (Primer. 31) and downstream primer (Primer. 32). This product was gel purified, digested with BamHI and SbfI, and then ligated into the BamHI and SbfI sites of SIVmac239 proviral DNA clone. The proviral DNA clones were then screened by automatically sequencing using a Taq Dye Deoxy Terminator cycle Sequencer Kit (Applied Biosystems) individually using an internal primer (Primer. 39). Following the verification the mutations the proviral DNA clones were used for various future studies.

Cell Culture and DNA Transfection

HeLa cells were maintained in DMEM (Invitrogen) (10% FBS, 100 U/ml penicillin, and 100 µg/ml Streptomycin) and passaged upon confluence. Jurkat cells were cultured in RPMI 1640 (Invitrogen) (10% FBS, 100 U/ml penicillin, and 100 µg/ml Streptomycin) and passaged every two or three days.

To characterize the effect of deletion or substitution on viral particle production and Gag polyprotein processing, wild-type HIV-1 NL4-3 or SIVmac239 and respective mutant proviral DNAs were transfected into HeLa cells by employing FuGENE 6 transfection reagent (Roche). Briefly, cells were seeded into a 6-well plate (Corning) at a concentration of $0.5 \times 10^5$ per well the day before transfection to reach 60 to 80% confluence on the day of transfection. For each transfection, 3 µl of FuGENE 6 was diluted into 100 µl of serum-free DMEM followed by the addition of 1 µg of DNA. After gently mixing, the mixture of DNA-lipid complexes was gently added drop wise into the cells containing 2 ml of complete DMEM medium. Twenty-four hours post-transfection, medium containing DNA-FuGENE 6 complexes was removed, 2 ml of fresh DMEM was added into the transfected cells. At 48 h post-transfection, medium containing viral particles was collected and clarified by centrifugation at 2,000 rpm at 4° C. for 20 min in a Sorvall RT 6000B centrifuge. Virus particle-containing supernatants were then concentrated through a 20% sucrose cushion in a microcentrifuge at 13,000 rpm at 4° C. for 120 min and pellets were resuspended in a lysis buffer (150 mM Tris-HCl, 5% Triton X-100, 1% deoxycholate, pH 8.0). The level of viral particle production for wild type NL4-3 and point deletion mutants was determined by p24 antigen capture ELISA (ZeptoMetrix, Buffalo, N.Y.).

To examine the effect of deletion or substitution on Gag polyprotein processing (in the absence of DSB), SDS-PAGE and Western-Blot was performed. In brief, viral proteins were separated on a 12% NuPAGE Bis-Tris Gel (Invitrogen) and transferred to a nitrocellulose membrane (Invitrogen) followed by blocking in a PBS buffer containing 0.5% Tween and 5% dry milk. The membrane was incubated with immunoglobulin from HIV-1-infected patients (HIV-Ig) (NIH AIDS research and reference reagent program) and hybridized with goat anti-human horseradish peroxidase (Sigma). For the membrane containing SIV proteins, the membrane was incubated with a reference polyclonal immune serum from a SIV-infected monkey (NIH AIDS Research and Reference Reagent Program) and hybridized with goat-anti-monkey horseradish peroxidase (Sigma). The immune complex was visualized with an ECL system (Amersham Pharmacis Biotech) according to the instructions provided by the manufacturer.

To address the effect of deletion or substitution on the ability of DSB to inhibit CA-SP1 processing, HeLa cells were transfected with wild-type HIV-1 NL4-3 or SIVmac239 and respective mutant proviral DNAs by employing the procedure described above. DSB at a concentration of 1 µg/ml and DMSO control were maintained throughout the entire culture and SDS-PAGE/Western-Blot for analyzing viral proteins derived from these transfections were performed as described in the previous paragraph.

The 50%—Tissue Culture Infectious Dose ($TCID_{50}$) per ml was used as a measure of the infectivity of each deletion mutant. Mutant viruses derived from transfections in HeLa cells were used to infect U87 CD4.CXCR4 cells. Each virus stock was tested in triplicate at a starting dilution of 1:10, followed by four-fold serial dilutions. Cells were plated the day before infection at a density of $3 \times 10^3$ cells/well. On the day of infection, culture media was removed from the cell plate and 90 µl of diluted virus was added. On days 1, 3, and 6 post infection, virus was removed from plate and 200 µl of culture media was added. On days 6 and 8 post infection, supernatant was collected for p24 ELISA analysis. The virus dilution that caused 50% of the culture to be infected (TCID$_{50}$) was determined according to the method of Reed and Muench (Aldovini A. and B. Walker 1990; Dulbecco R. 1988).

Results

Viruses containing sequential point deletions within the Gag SP1 domain (FIG. 12) were characterized for particle production, infectivity, Gag processing and sensitivity to DSB. The results from these experiments were used to identify SP1 residues associated with DSB activity.

As expected, the effect of point deletions on viral particle production varied as a function of the proximity of the change from the proteolytic cleavage site. The results from these experiments are summarized in FIG. 13. Viruses with deletions at residues E366, A367 and M368 were most affected, generating <25% the number of particles normally observed in wild-type virus infection. In vitro infectivity assays were used to characterize the ability of the deletion mutants to support virus replication. These experiments indicated that deletion of single residues at any of the five positions E365 through Q369 resulted in a virus that was either non-infectious or significantly impaired for replication (FIG. 13). In contrast, starting with residue V370 and extending away from the CA-SP1 cleavage site, none of the characterized point deletions resulted in a decrease in virus infectivity (FIG. 13). With the exception of viruses with deletions at positions I376 and M377 all mutant viruses exhibited a normal or near normal Gag processing phenotype (FIG. 13). The results from these three sets of experiments permitted the design and interpretation of experiments to identify the genetic determinants of DSB activity.

Sensitivity to DSB was determined in experiments that characterized the effect of DSB on a late step in Gag processing, CA-SP1 cleavage.

Specifically, these assays measured the ability of DSB to disrupt CA-SP1 processing. As seen, e.g. Example 8, the DSB-induced defect in Gag processing correlates with the ability of the compound to inhibit virus replication. Results from these experiments indicate that deletion of a single residue at any of the six positions E365 through V370 significantly reduces the affect of DSB on CA-SP1 processing (FIG. 14). In contrast, starting with residue T372 and extending away from the CA-SP1 cleavage site, all of the characterized point deletions are fully sensitive to DSB-induced disruption of CA-SP1 processing (FIG. 14).

The SP1 residues associated with DSB activity consist of the contiguous residues E365 through V370.

Residues A364 through V370 were inserted into the analogous position of the Gag SP1 domain in the DSB-resistant retrovirus SIV (Mac 239 isolate). Additionally, the N-terminus of the CA protein of this chimeric virus was modified by cumulative substitution of residues found in SIV with HIV-1-specific residues. This approach is summarized in FIG. 15. Next, the effect of DSB on the Gag processing phenotype of each of the chimeric viruses was determined. As shown in FIG. 15, the SWV.DM virus displays a Gag processing phenotype indicative of sensitivity to DSB. Thus, the minimum sequence of HIV-1 CA-SP1-specific residues that needs to be inserted to rescue DSB activity in the SHIVs extends from V362 to V370

TABLE 1

PCR Mutagenesis Primers

| Primer ID | Sequence (5' to 3') | Construct | PCR application |
|---|---|---|---|
| 1 | agccaaaactcttgctttatggcc (SEQ ID NO: 37) | ΔE365 | First PCR fragment (with No. 2 primer) |
| 2 | agtcagtgtggaaaatctctagcagtgg (SEQ ID NO: 38) | All deletion constructs of NL4-3 | All first PCR fragments |
| 3 | gcaatgagccaagtaacaaatcca (SEQ ID NO: 39) | ΔE365 | Second PCR fragment (with No. 4 primer) |
| 4 | aggtatggtaaatgcagtatacttcctgaag (SEQ ID NO: 40) | All deletion constructs | All second PCR fragments |
| 5 | ttcagccaaaactcttgctttatggcc (SEQ ID NO: 41) | ΔA366 | First PCR fragment (with No. 2 primer) |
| 6 | atgagccaagtaacaaatccagc (SEQ ID NO: 42) | ΔA366 | Second PCR fragment (with No. 4 primer) |
| 7 | tgcttcagccaaaactcttgc (SEQ ID NO: 43) | ΔM367 | First PCR fragment (with No. 2 primer) |

TABLE 1-continued

PCR Mutagenesis Primers

| Primer ID | Sequence (5' to 3') | Construct | PCR application |
|---|---|---|---|
| 8 | agccaagtaacaaatccagct (SEQ ID NO: 44) | ΔM367 | Second PCR fragment (with No. 4 primer) |
| 9 | cattgcttcagccaaaactcttgc (SEQ ID NO: 45) | ΔS368 | First PCR fragment (with No. 2 primer) |
| 10 | caagtaacaaatccagctacca (SEQ ID NO: 46) | ΔS368 | Second PCR fragment (with No. 4 primer) |
| 11 | gctcattgcttcagccaaaactctt (SEQ ID NO: 47) | ΔQ369 | First PCR fragment (with No. 2 primer) |
| 12 | gtaacaaatccagctaccataa (SEQ ID NO: 48) | ΔQ369 | Second PCR fragment (with No. 4 primer) |
| 13 | acaaatccagctaccataatgatac (SEQ ID NO: 49) | ΔV370 | First PCR fragment (with No. 2 primer) |
| 14 | ttggctcattgcttcagccaaaactc (SEQ ID NO: 50) | ΔV370 | Second PCR fragment (with No. 4 primer) |
| 15 | tacttggctcattgcttcagccaa (SEQ ID NO: 51) | ΔT371 | First PCR fragment (with No. 2 primer) |
| 16 | aatccagctaccataatgatacag (SEQ ID NO: 52) | ΔT371 | Second PCR fragment (with No. 4 primer) |
| 17 | tgttacttggctcattgcttc (SEQ ID NO: 53) | ΔN372 | First PCR fragment (with No. 2 primer) |
| 18 | ccagctaccataatgatacagaaa (SEQ ID NO: 54) | ΔN372 | Second PCR fragment (with No. 4 primer) |
| 19 | atttgttacttggctcattgcttc (SEQ ID NO: 55) | ΔP373 | First PCR fragment (with No. 2 primer) |
| 20 | gctaccataatgatacagaaaggcaa (SEQ ID NO: 56) | ΔP373 | Second PCR fragment (with No. 4 primer) |
| 21 | tggatttgttacttggctcattgc (SEQ ID NO: 57) | ΔA374 | First PCR fragment (with No. 2 primer) |
| 22 | accataatgatacagaaaggc (SEQ ID NO: 58) | ΔA374 | Second PCR fragment (with No. 4 primer) |

TABLE 1-continued

PCR Mutagenesis Primers

| Primer ID | Sequence (5' to 3') | Construct | PCR application |
|---|---|---|---|
| 23 | agctggatttgttacttggctc (SEQ ID NO: 59) | ΔT375 | First PCR fragment (with No. 2 primer) |
| 24 | ataatgatacagaaaggcaatttagg (SEQ ID NO: 60) | ΔT375 | Second PCR fragment (with No. 4 primer) |
| 25 | ggtagctggatttgttacttg (SEQ ID NO: 61) | ΔI376 | First PCR fragment (with No. 2 primer) |
| 26 | atgatacagaaaggcaattttaggaacc (SEQ ID NO: 62) | ΔI376 | Second PCR fragment (with No. 4 primer) |
| 27 | tatggtagctggatttgttac (SEQ ID NO: 63) | ΔM377 | First PCR fragment (with No. 2 primer) |
| 28 | atacagaaaggcaattttagg (SEQ ID NO: 64) | ΔM377 | Second PCR fragment (with No. 4 primer) |
| 29 | ccacctatcccagtaggag (SEQ ID NO: 65) | Sequencing primer | For NL4-3 mutants |
| 30 | ggcacagcaagcagcagctg (SEQ ID NO: 66) | Sequencing primer | For NL4-3 mutants |
| 31 | gtagaccaacagcaccatctagcggcaga (SEQ ID NO: 67) | All substitution constructs of SIV | For SIV mutants |
| 32 | ggtaaagtaaaggcagtgtactgcctaa (SEQ ID NO: 68) | All substitution constructs of SIV | For SIV mutants |
| 33 | cactggtgcgaggacctgactcatggcttctgccatt (SEQ ID NO: 69) | SIV DD | First PCR fragment (with No. 31 primer) |
| 34 | aatggcagaagccatgagtcaggtcctcgcaccagtg (SEQ ID NO: 70) | SIV DD | Second PCR fragment (with No. 32 primer) |
| 35 | ggcttctgccagtactctagccttctgt (SEQ ID NO: 71) | SIV DE | First PCR fragment (with No. 31 primer) |
| 36 | acagaaggctagagtactggcagaagcc (SEQ ID NO: 72) | SIV DE | Second PCR fragment (with No. 32 primer) |
| 37 | ggcttctgccagtactctagccttctgt (SEQ ID NO: 73) | SIV DM | First PCR fragment (with No. 31 primer) |

TABLE 1-continued

PCR Mutagenesis Primers

| Primer ID | Sequence (5' to 3') | Construct | PCR application |
|---|---|---|---|
| 38 | acagaaggctagagtactggcagaagcc (SEQ ID NO: 74) | SIV DM | Second PCR fragment (with No. 32primer) |
| 39 | atccaactggggttgcaaaaatgtg (SEQ ID NO: 75) | Sequencing primer | For SIV mutant |

The resistance and mutagenesis data presented above suggest that the GHARVL-AEAMSQV amino acid sequence in the region of the HIV-1 Gag CA-SP1 cleavage site serves as a genetic determinant of viral sensitivity to DSB.

Extending the Determinants of Pa-457DSB Sensitivity to Other Lentiviruses: CA-SP1 Chimeras as Animal Efficacy Models for Development of Maturation Inhibitors The development of anti-HIV therapeutics has been hindered by the lack of an animal efficacy model. This lack of an animal model is primarily due to the inability of most HIV-1 strains to replicate and cause disease in non-human primates. In some instances this problem has been overcome through the use of chimeric viruses that incorporate the region(s) of interest from the HIV-1 viral target into an SIV viral backbone that will support replication in a non-human primate. The most notable example of this approach involves the HIV-1/SIV (SHIV) chimeric viruses in which the proteins making up the infectious virus are exclusively SIV in origin with the exception of Env (gp120/gp41) which is derived form HIV-1. These SHIV envelope chimeras have been used extensively in HIV-1 vaccine development.

HIV-1 maturation inhibitors disrupt Gag CA-SP1 processing, which results in the formation and release of non-infectious viral particles exhibiting aberrant core morphology. See e.g. Li et al. *Proc Natl Acad Sci USA*. 100:13555-60 (2003). The betulinic acid derivative PA-457 DSB is an example of this class of inhibitors. The viral genetic determinants critical that are associated with the activity of maturation inhibitors map to amino acid residues flanking the HIV-1 CA-SP1 cleavage site. When this determinant is introduced into the CA-SP1 cleavage sites of PA-457DSB-resistant non-HIV-1 viruses, maturation inhibitor sensitive chimeras result. These CA-SP1 chimeric viruses serve as the basis for an animal efficacy model for HIV-1 maturation inhibitors.

The region of HIV-1 CA-SP1 necessary for maturation inhibitor sensitivity is introduced into selected lentiviruses. Amino acid residues from HIV-1 CA-SP1 junction that are determinants of PA-457DSB sensitivity were used to replace the corresponding CA-SP1 amino acids in the genome of Simian Immunodeficiency (SIV). Similarly, the amino acid residues from HIV-1 CA-SP1 junction that are determinants of PA-457DSB can be replaced in Feline Immunodeficiency virus (FIV), Bovine Immunodeficiency virus (BIV), Equine Infectious Anemia Virus (EIAV), Visna-Maedi, and Caprine Arthritis Encephalitis virus (CAEV). Table 2 depicts the Gag polypeptide sequence for HIV-1, SIV, FIV, EIAV and BIV in the region of the CA-SP1 cleavage site.

TABLE 2

Sequence comparison in the region of the CA-SP1 cleavage site region of HIV-1 with SIV, FIV, EIAV and BIV

| | CA | SP1 | NC |
|---|---|---|---|
| HIV-1 (SEQ ID NO: 76) | GHKARVL | AEAMSQVTNPATIM | IQKG |
| FIV (SEQ ID NO: 77) | GYKMQLL | AEALTKVQ | VVQS |
| EIAV (SEQ ID NO: 78) | KQKMMLL | AKALQ | TGLA |
| BIV (SEQ ID NO: 79) | KSKMQFL | VAAMKEMGIQSPIPAVLPHTPEAYA | SQTS |

The HIV-1 CA-SP1 sequence used for replacement is as follows:

| CA | SP1 | |
|---|---|---|
| GHKARVL | AEAMSQV | (SEQ ID NO: 80) |

The method described above for generating the SHIV CA-SP1 chimeric provirus DNA clone is used to generate FIV, EIAV and BIV provirus clones containing selected residues or extended region from CA-SP1 region of HIV-1 replacing the corresponding wild-type sequence (FIG. 16).

The SHIV CA-SP1 chimeric-provirus DNA clone was generated by site-directed mutagenesis employing standard molecular biology techniques. Briefly, the unique restriction enzyme sites in the SIV Gag that surrounding the CA-SP1 region were identified i.e., BamHI (in matrix) and Sbf-I (in NC). Starting from the CA-SP1 region where the mutagenisis is intended two overlapping primers, a forward and a reverse primer incorporating the mutated sequence i.e., HIV CA-SP1 at their 5' ends were synthesized. Using the wild-type SW provirus DNA as a template, two separate PCR reactions were set up to amplify SIV-Gag fragments in either direction from the site of mutagenisis (CA-SP1 region), i.e., yield two amplified fragments that overlapped in the mutated CA-SP1 region, a Bam HI-CA-SP1 fragment and a CA-SP1-Sbf-I fragment. In a third PCR reaction, the fragments, Bam HI-CA-SP1 and CA-SP1-Sbf-I were annealed at their common HIV-CA-SP1 sequence and amplified with a forward SIV Bam HI primer and a reverse SIV Sbf-I primer to generate a full-length chimeric SHIV CA-SP1 gag fragment. The chimeric SHIV CA-SP1 PCR fragment was cloned into BamHI—Sbf-I window of SIV provirus clone replacing the SIV-Gag wild-type sequence to yield the SHIV CA-SP1 provirus cDNA clone.

Similarly, unique restriction enzyme cloning sites surrounding the CA-SP1 regions in FIV (Genbank Accession # NC_001482), EIAV (GA# AF016316), and BIV (GA# M32690) genome have been identified (FIG. 16). Specific FIV/EIAV/BIV-HIV1CA-SP1 chimeric primers along with genome specific primers of FIV, EIAV or BIV incorporating the specific cloning site sequence are synthesized. These primers along with corresponding provirus DNA clone as template (FIV, EIAV or BIAV) in PCR reactions to generate the Chimeric HIV-1 CA-SP1 fragment. The chimeric HIV-1 CA-SP1 fragment is digested with the appropriate restriction enzyme and cloned into SacI-EcoRI window of FIV provirus; or (ii) KasI-EcoRV window of EIAV provirus; or (iii) BsrGI-ApaI window of BIV provirus replacing the corresponding wild type sequence (FIG. 16). The chimeric FIV/EIAV/BIV-HIV-1CA-SP1 provirus DNA clones are sequenced to confirm the presence of intended mutations. Based on observed results that indicate the transfer of PA-457DSB sensitivity, additional constructs are generated employing the above strategy in order to optimize the results.

In summary, a chimeric virus was generated in which the CA-SP1 determinant of HIV-1 maturation inhibitor sensitivity has replaced the analogous region of Gag in the maturation inhibitor-resistant simian immunodeficiency virus (SIV). Transfer of this region of HIV-1 into the genome of SIV results in a maturation inhibitor-sensitive phenotype. Infection of a non-human primate with this HIV-1/SIV chimeric virus should result in an animal efficacy model for therapeutic development of maturation inhibitors.

Analogous approaches are used to prepare and characterize HIV-1 CA-SP1 chimeras with FIV, BIV and EIAV. These additional DSB-sensitive chimeric viruses should enable the development of additional animal efficacy models for the study of HIV-1 maturation inhibitors.

Uses of Mutant and Chimeric Viruses

The mutant and chimeric viruses of the present invention, as described above, are useful in a variety of cell based as well as animal based assays.

By comparing the phenotypes associated with a virus that is resistant to DSB, with a virus that is sensitive DSB, one may identify compounds that act by a mechanism similar to that of DSB. Thus the invention includes a method of identifying a compound that inhibits cleavage of p25 to p24 in wild type HIV-1, but does not inhibit CA-SP1 processing in HIV-1 containing a deletion in the CA-SP1 region. Compounds obtained by such a method are also included in the present invention.

Chimeras of SIV and other lentiviruses that do not readily infect humans have additional advantages. Firstly, these viruses pose a lesser safety hazard to laboratory workers. As a result, cell based assays to identify novel compounds that inhibit CA-SP1 processing, for example, can be conducted with less risk. The lower risk may allow assays to be performed that cannot be performed readily or safely with HIV, and may also lower the cost of such assays.

Furthermore, such chimeric viruses are useful in animal models. For example chimeric SIV that is sensitive to DSB may be used to identify novel compounds that inhibit CA-SP1 processing, for example; to identify pharmaceutical compositions, routes of administration and dosage regimes for treatment of disease; and for studying the effect of combination therapies, such as DSB with protease inhibitors.

As SIV is generally limited to infection of monkeys, the generation of additional lentiviral chimeras allows animal studies to be performed in animals that are less expensive, easier to handle, have a faster disease progression or otherwise more appropriate for a particular aspect of human disease, for example.

Furthermore, animal models may be used to identify appropriate pharmaceutical compositions for the treatment of animal diseases, of interest in the treatment of companion animals and other high value animals, such as agricultural breeding stock and race horses.

Chimeric viruses may be derived from any retrovirus. For example, derived HIV-2, HTLV-I, HTLV-II, SIV, avian leukosis virus (ALV), endogenous avian retrovirus (EAV), mouse mammary tumor virus (MMTV), feline immunodeficiency virus (FIV), Bovine immunodeficiency virus (BIV), caprine arthritis encephalitis virus (CAEV), Equine infectious anemia virus (EIAV), Visna-maedi virus, or feline leukemia virus (FeLV).

Such chimeric viruses may be used in the methods of the invention described elsewhere herein. For example, such recombinant non-HIV-1 lentiviruses may be used in a method of identifying a compound which inhibit processing of the viral Gag p25 protein (CA-SP1) to p24 (CA), the method consisting of comparing of the ability of said compound to inhibit replication of a wild-type non-HIV-1 lentivirus with the DSB-sensitive recombinant variant thereof. Such inhibition may occur in a cell; in an animal; or in vitro.

Construction and use of Viruses or Polypeptides with Epitope Tags

The present invention is also drawn to recombinant retroviruses with epitope tags in the CA-SP1 region of Gag. Epitope tags may be inserted in the CA domain and/or in the SP1 domain. Suitable tags are well known to those of ordinary skill in the art, and include haemagglutinin epitope HA (YPYDVPDYA) (SEQ ID NO: 81), bluetongue virus epitope VP7 (QYPALT) (SEQ ID NO: 82), α-tubulin epitope (EEF), Flag (DYKDDDDK) (SEQ ID NO: 83), and VSV-G (YTDIEMNRLGK) (SEQ ID NO: 84). Examples of SP1 containing epitope tags are illustrated in FIG. 17.

Such epitope tagged viruses and fragments thereof are useful in identifying novel compounds that inhibit CA-SP1 processing in vitro, in cell based assays, and in vivo, including in animal models. Additional uses of such epitope tagged viruses and fragments thereof are described elsewhere herein.

Polynucleotides, Polypeptides and Antibodies of the Invention

The invention also includes isolated polypeptides and polynucleotides. In one embodiment, the invention includes polypeptides at least about 40%, 50%, 60%, 70%, 80%, 90%, 99% or 100% identical to an amino acid sequence selected from the group consisting of:

(a) KNWMTETFLVQNANPDCKTILKALGPAATLEEMMTACQGVGGPS

HKARILAEAMSQVTNSATIM; (SEQ D NO: 21)

(b) KNWMTETLLVQNANPDCKTILKALGPGATLEEMMTACQGVGGPG

HKARVLAEAMSQVTNPATIM; (SEQ ID NO: 22)

(c) TACQGVGGPSHKARILAEAMSQVTNSATIM; (SEQ ID NO: 23)

(d) MTACQGVGGPGHKARVLAEAMSQVTNPATIM; (SEQ ID NO: 24)

(e) SHKARILAEAMSQV (SEQ ID NO: 25)
and (f) GHKARVLAEAMSQV. (SEQ ID NO: 26)

In another embodiment the invention includes polynucleotides encoding the above polypeptides. Polynucleotides of the invention include degenerate variants, such as those that differ in the third base of the codon but nevertheless encodes the same amino acid due to coding "degeneracy".

The term "about" as used herein refers to a value that is 10% more or less than the stated value, and preferably is 5% more or less.

The polypeptides and polynucleotides of the invention are useful in the methods of the invention. In one aspect, they may be used in an in vitro assay to identify compounds that bind to the CA-SP1 region of Gag. In another, they may be used in the production of antibodies useful in other methods described elsewhere herein. In another, a polynucleotide may be inserted into a vector and thereupon into a host cell for production of polypeptide. The above embodiments are exemplary and are not intended to be limiting.

The present invention comprises a polynucleotide comprising a sequence which encodes an amino acid sequence containing a mutation in the HIV Gag p25 protein (CA-SP1), said mutation resulting in a decrease in the inhibition of processing of p25 (CA-SP1) to p24 (CA) by DSB. The polynucleotide of the invention includes a mutation which is optionally located at or near the CA-SP1 cleavage site or located in the SP1 domain of CA-SP1. Said mutation can be present in an amino acid sequence that is selected from the group consisting of GHKARVLVEAMSQV (SEQ ID NO: 2) and SHKARILAEVMSQV (SEQ ID NO: 3). The polynucleotide of this invention is also drawn to sequences designated as SEQ ID NO: 4, SEQ ID NO: 6, SEQ ID NO: 8 and SEQ ID NO: 9. The invention also includes a vector comprising said polynucleotide, a host cell comprising said vector and a method of producing said polypeptides comprising incubating said host cell in a medium and recovering the polypeptide from the medium.

The invention further includes a polynucleotide that hybridizes under stringent conditions to a polynucleotide selected from the group consisting of SEQ ID NO: 4, SEQ ID NO: 6, SEQ ID NO: 8 and SEQ ID NO: 9. The invention also includes a polynucleotide which hybridizes to SEQ NO: 5, SEQ ID NO: 7 or SEQ ID NO: 10 or 12, which contains a mutation which results in the decrease in the inhibition of processing of p25 to p24 by 3-O-(3',3'-dimethylsuccinyl) betulinic acid, and also wherein said mutation is optionally located at or near the CA-SP1 cleavage site or in the SP1 domain of CA-SP1. The invention is also directed to a vector comprising said polynucleotides, a host cell comprising said vector and a method of producing said polypeptides, comprising incubating said host cell in a medium and recovering said polypeptide from the medium.

"Near" or "adjacent," as used herein in reference to polypeptides is meant to include about 50, about 25, about 20, or about 15 residues from the point of reference. For example, near may encompass about 50, about 25, about 20 or about 15 residues on either side of the HIV-1 Gag CA-SP1 cleavage site; more preferably about ten residues on either side of the HIV-1 Gag CA-SP1 cleavage site; and most preferably about seven residues on either side of the HIV-1 Gag CA-SP1 cleavage site. In reference to polynucleotides, the terms "near" or "adjacent refer to about 150, about 75, about 60, about 45, or about 30 nucleotides from the point of reference.

"Isolated" means altered "by the hand of man" from the natural state. If an "isolated" composition or substance occurs in nature, it has been changed or removed from its original environment, or both. Also, "isolated" nucleic acid molecule(s) of the invention is intended a nucleic acid molecule, DNA or RNA, which has been removed from its native environment For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

"Polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single-and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritiated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from post-translation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

"Mutant" as the term is used herein, is a polynucleotide or polypeptide that differs from a reference polynucleotide or polypeptide respectively. A typical mutant of a polynucleotide differs in nucleotide sequence from another, reference polynucleotide. Changes in the nucleotide sequence of the mutant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical mutant of a polypeptide differs in amino acid sequence from another, reference polypeptide. Generally, differences are limited so that the sequences of the reference polypeptide and the variant are closely similar overall and, in many regions, identical. A mutant and reference polypeptide may differ in amino acid sequence by one or more substitutions, additions, deletions in any combination. A substituted or inserted amino acid residue may or may not be one encoded by the genetic code. A mutant of a polynucleotide or polypeptide may be a naturally occurring such as an allelic variant, or it may be a mutant that is not known to occur naturally. Non-naturally occurring mutants of polynucleotides and polypeptides may be made by mutagenesis techniques or by direct synthesis.

Thus, the mutant, (or fragments, derivatives or analogs) of a polypeptide encoded by any one of the polynucleotides described herein may be (i) one in which at least one or more of the amino acid residues are substituted with a conserved or non-conserved amino acid residue (a conserved amino acid residue(s), or at least one but less than ten conserved amino acid residues) and such substituted amino acid residue may or may not be one encoded by the genetic code, (ii) one in which one or more of the amino acid residues includes a substituent group, (iii) one in which the mature polypeptide is fused with another compound, such as a compound to increase the half-life of the polypeptide (for example, polyethylene glycol), or (iv) one in which the additional amino acids are fused to the mature polypeptide, such as an IgG:Fc fusion region peptide or leader or secretory sequence or a sequence which is employed for purification of the mature polypeptide or a proprotein sequence. Such mutants are deemed to be within the scope of those skilled in the art from the teachings herein. Polynucleotides encoding these mutants are also encompassed by the invention. "Mutant" as used herein is equivalent to the term "variant."

Substitutions of charged amino acids with another charged amino acids and with neutral or negatively charged amino acids are included. Additionally, one or more of the amino acid residues of the polypeptides of the invention (e.g., arginine and lysine residues) may be deleted or substituted with another residue to eliminate undesired processing by proteases such as, for example, furins or kexins. The prevention of aggregation is highly desirable. Aggregation of proteins not only results in a loss of activity but can also be problematic when preparing pharmaceutical formulations, because they can be immunogenic. (Pinckard et al., *Clin Exp. Immunol.* 2:331-340 (1967); Robbins et al., *Diabetes* 36:838-845 (1987); Cleland et al. *Crit. Rev. Therapeutic Drug Carrier Systems* 10:307-377 (1993)). Thus, the polypeptides of the present invention may include one or more amino acid substitutions, deletions or additions, either from natural mutations or human manipulation.

As indicated, changes are preferably of a minor nature, such as conservative amino acid substitutions that do not significantly affect the folding or activity of the protein (see Table 3).

TABLE 3

| Conservative Amino Acid Substitutions | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

However, in some embodiments, it is desirable to use non-conservative substitutions of amino acids. For example non-conservative substitution of amino acids is used to render a DSB sensitive virus resistant to DSB.

The polynucleotides encompassed by this invention may have at least about 40%, 45%, 50%, 55%, 60%, 65%, 70%, 75%, 80%, 85%, 90%, 95% or 100% identity with a reference sequence, providing the reference polynucleotide encodes an amino acid sequence containing a mutation in the CA-SP1 protein, said mutation which results in the decrease in the inhibition of processing of p25 to p24 by a 3-O-(3',3'-dimethylsuccinyl)betulinic acid. The polynucleotides also encompassed by this invention include those mutations which are "silent," in which different codons encode the same amino acid (wobble).

"Identity" is a measure of the identity of nucleotide sequences or amino acid sequences. The term "identity" is used interchangeably with the word "homology" herein. In general, the sequences are aligned so that the highest order match is obtained. "Identity" per se has an art-recognized meaning and can be calculated using published techniques. While there exist a number of methods to measure identity between two polynucleotide or polypeptide sequences, the term "identity" is well known to skilled artisans. Methods commonly employed to determine identity or similarity between two sequences include, but are not limited to, those disclosed in Baxevanis and Oullette, *Bioinformatics: A Practical Guide to the Analysis of Genes and Proteins, Second Edition*, Wiley-Interscience, New York, (2001). Methods to determine identity and similarity are codified in computer programs. Preferred computer program methods to determine identity and similarity between two sequences include, but are not limited to, GCS program package (Devereux, J. et al., *Nucleic Acids Research* 12(1):387, (1984)), BLASTP, BLASTN, FASTA (Atschul, S. F. et al., *J. Molec. Biol.* 215: 403, (1990)).

A polynucleotide having a nucleotide sequence having at least, for example, 95% "identity" to a reference nucleotide sequence is intended that the nucleotide sequence of the polynucleotide is identical to the reference sequence except that the polynucleotide sequence may include up to five point mutations per each 100 nucleotides of the reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

Similarly, by a polypeptide having an amino acid sequence having at least, for example, 95% "identity" to a reference amino acid sequence, is intended that the amino acid sequence of the polypeptide is identical to the reference sequence except that the polypeptide sequence may include up to five amino acid alterations per each 100 amino acids of the reference amino acid. To obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence. The reference (query) sequence may be the entire nucleotide sequence of any one of the nucleotide sequences of the invention or any polynucleotide fragment (e.g., a polynucleotide encoding the amino acid sequence of the invention and/or C terminal deletion).

Whether any particular nucleic acid molecule having at least 40%, 50%, 60%, 70%, 80%, 85%, 90%, 92%, 95%, 96%, 97%, 98%, 99% identity or which are identical to, for instance, the nucleotide sequences of the invention can be determined conventionally using known computer programs such as the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman, (*Advances in Applied Mathematics* 2:482-489 (1981)), to find the best segment of homology between two sequences. When using BESTFIT or any other sequence alignment program to determine whether a particular sequence is, for instance, 95% identical to a reference sequence according to the present invention, the parameters are set, such that the percentage of identity is calculated over the full length of the reference nucleotide sequence and that gaps in homology of up to 5% of the total number of nucleotides in the reference sequence are allowed.

In a specific embodiment, the identity between a sequence of the present invention and a subject sequence, also referred to as a global sequence alignment, is determined using the FASTDB computer program based on the algorithm of Brutlag et al. (*Comp. App. Biosci.* 6:237-245 (1990)). Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter. According to this embodiment, if the subject sequence is shorter than the reference sequence because of 5' or 3' deletions, not because of internal deletions, a manual correction is made to the results to take into consideration the fact that the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. A determination of whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of this embodiment. Only bases outside the 5' and 3' bases of the subject sequence, as displayed by the FASTDB alignment, which are not matched/aligned with the query sequence, are calculated for the purposes of manually adjusting the percent identity score. For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence, which are not matched/aligned with the query. In this case the percent identity calculated by FASTDB is not manually corrected. Only bases 5' and 3' of the subject sequence which are not matched/aligned with the query sequence are manually corrected. No other manual corrections are made for the purposes of this embodiment.

The present application is directed to nucleic acid molecules having at least about 40%, 50%, 60%, 70%, 80%, 85%, 90%, 92%, 95%, 96%, 97%, 98% or 99% identity or which is identical to the nucleic acid sequence disclosed herein, or fragments thereof, irrespective of whether they encode a polypeptide having the disclosed functional activity. This is because even where a particular nucleic acid molecule does not encode a polypeptide having the disclosed functional activity, one of skill in the art would still know how to use the nucleic acid molecule, for instance, as a hybridization probe or a polymerase chain reaction (PCR) primer. Uses of the nucleic acid molecules of the present invention that do not encode a polypeptide having the disclosed functional activity include, inter alia: (1) isolating the variants thereof in a cDNA library; (2) in situ hybridization (e.g., "FISH") to determine cellular location or presence of the disclosed sequences, and (3) Northern Blot analysis for detecting mRNA expression in specific tissues.

As used herein, the term "PCR" refers to the polymerase chain reaction that is the subject of U.S. Pat. Nos. 4,683,195 and 4,683,202 to Mullis et al., as well as improvements now known in the art. In accordance with the present invention there may be employed conventional molecular biology, microbiology, and recombinant DNA techniques within the skill of the art. Such techniques are explained fully in the literature. See, for example, Sambrook, J. and Russell, D. W. (2001) *Molecular Cloning: A Laboratory Manual,* 3rd Ed., Cold Spring Harbor Laboratory Press, Cold Spring Harbor, N.Y.

The term "stringent conditions," as used herein refers to homology in hybridization, is based upon combined conditions of salt, temperature, organic solvents, and other parameters typically controlled in hybridization reactions, and well known in the art (Sambrook, et al. supra). The invention includes an isolated nucleic acid molecule comprising, a polynucleotide which hybridizes under stringent hybridization conditions to a portion of the polynucleotide in a nucleic acid molecule of the invention described above, for instance, the sequence complementary to the coding and/or noncoding (i.e., transcribed, untranslated) sequence of any polynucleotide or a polynucleotide fragment as described herein. By "stringent hybridization conditions" is intended overnight incubation at 42° C. in a solution comprising, or alternatively consisting of: 50% formamide, 5×SSC (750 mM NaCl, 75 mM trisodium citrate), 50 mM sodium phosphate (pH 7.6), 5× Denhardt's solution, 10% dextran sulfate, and 20 µg/ml denatured, sheared salmon sperm DNA, followed by washing in 0.1×SSC at about 65° C. Polypeptides encoded by these polynucleotides are also encompassed by the invention.

The invention also includes a virus comprising the polynucleotides of the invention, and wherein the virus includes a retrovirus comprising said polynucleotides, and wherein the retrovirus may be a member of the group consisting of HIV-1, HIV-2, HTLV-I, HTLV-II, SIV, avian leukosis virus (ALV), endogenous avian retrovirus (EAV), mouse mammary tumor virus (MMTV), feline immunodeficiency virus (FIV), or feline leukemia virus (FeLV).

The invention further includes a polypeptide containing a mutation in the CA-SP1 protein, said mutation which results in the decrease in inhibition of processing of p25 to p24 by 3-O-(3',3'-dimethylsuccinyl)betulinic acid, and also wherein said mutation is optionally located at or near the CA-SP1 cleavage site or located in the SP1 domain of SEQ ID NO: 5 or SEQ ID NO: 7 (parental polynucleotide sequences) encoding the CA-SP1 protein. Said polypeptide may be encoded by a polynucleotide selected from the group consisting of SEQ ID NO: 4, SEQ ID NO: 6, SEQ ID NO: 8 and SEQ ID NO: 9, or may comprise a sequence that is selected from the group consisting of GHKARVLVEAMSQV (SEQ ID NO: 2) and SHKARILAEVMSQV (SEQ ID NO: 3). The polypeptide of this invention may further be encoded by a polynucleotide which hybridizes to a polynucleotide selected from the group consisting of SEQ ID NO: 4, SEQ ID NO: 6, SEQ ID NO: 8 and SEQ ID NO: 9. The invention also includes a polypeptide encoded by a polynucleotide which hybridizes to SEQ NO: 5, SEQ ID NO: 7 or SEQ ID NO: 10 or 12, which contains a mutation that results in decrease in inhibition of processing of p25 to p24 by 3-O-(3',3'-dimethylsuccinyl)betulinic acid, and also wherein said mutation is optionally located at or near the CA-SP1 cleavage site or in the SP1 domain of CA-SP1. The polypeptide of this invention further includes polypeptides that are part of a chimeric or fusion protein. Said chimeric proteins may be derived from species which include, but are not limited to: primates, including simian and human; rodentia, including rat and mouse; feline; bovine; ovine; including goat and sheep; canine; or porcine. Fusion proteins may include synthetic peptide sequences, bifunctional antibodies, peptides linked with proteins from the above species, or with linker peptides. Polypeptides of the invention may be further linked with detectable labels; metal compounds; cofactors; chromatography separation tags, such as, but not limited to: histidine, protein A, or the like, or linkers; blood stabilization moieties such as, but not limited to: transferrin, or the like; therapeutic agents, and so forth.

The invention also includes an antibody which selectively binds an amino acid sequence containing a mutation in the CA-SP1 protein that results in a decrease in the inhibition of processing of p25 (CA-SP1) to p24 (CA) by 3-O-(3',3'-dimethylsuccinyl)betulinic acid and also wherein said mutation is optionally located at or near the CA-SP1 cleavage site or in the SP1 domain of CA-SP1. The invention also includes an antibody which selectively binds the polypeptide having a mutation which comprises a sequence that is one of GHKARVLVEAMSQV (SEQ ID NO: 2), SHKARILAEVMSQV (SEQ ID NO: 3)., Said antibody can selectively bind the polypeptide encoded by a polynucleotide sequence selected from the group consisting of SEQ ID NO: 4, SEQ ID NO: 6, SEQ ID NO: 8 and SEQ ID NO: 9. Said antibody can also selectively bind the polypeptide encoded by a polynucleotide which hybridizes under highly stringent conditions to a polynucleotide selected from the group consisting of SEQ ID NO: 4, SEQ ID NO: 6, SEQ ID NO: 8 and SEQ ID NO: 9. The invention also includes an antibody that selectively binds SP1, which would enable one to distinguish SP1 from CA-SP1 (p25). The invention also includes an antibody that selectively binds CA (p24), which would enable one to distinguish CA from CA-SP1. The invention also includes an antibody that selectively binds CA-SP1, which would enable one to distinguish CA from CA-SP1. The invention additionally includes an antibody that selectively binds at or near the CA-SP1 cleavage site. The antibody of this invention may be a polyclonal antibody, a monoclonal antibody or said antibody may be chimeric or bifunctional, or part of a fusion protein. The invention further includes a portion of any antibody of this invention, including single chain, light chain, heavy chain, CDR, F(ab')$_2$, Fab, Fab', Fv, sFv, or dsFv, or any combinations thereof.

As used herein, an antibody "selectively binds" a target peptide when it binds the target peptide and does not significantly bind to unrelated proteins. The term "selectively binds" also comprises determining whether the antibody selectively binds to the target mutant sequence relative to a native target sequence. An antibody which "selectively binds" a target peptide is equivalent to an antibody which is "specific" to a target peptide, as used herein. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity. In another embodiment, the determination whether the antibody selectively binds to the mutant target sequence comprises: (a) determining the binding affinity of the antibody for the mutant target sequence and for the native target sequences; and (b) comparing the binding affinities so determined, the presence of a higher binding affinity for the mutant target sequence than for the native indicating that the antibody selectively binds to the mutant target sequence.

The invention is further drawn to an antibody immobilized on an insoluble carrier comprising any of the antibodies disclosed herein. The antibody immobilized on an insoluble carrier includes multiple well plates, culture plates, culture tubes, test tubes, beads, spheres, filters, electrophoresis material, microscope slides, membranes, or affinity chromatography medium.

The invention also includes labeled antibodies, comprising a detectable signal. The labeled antibodies of this invention are labeled with a detectable molecule, which includes an enzyme, a fluorescent substance, a chemiluminescent substance, horseradish peroxidase, alkaline phosphatase, biotin, avidin, an electron dense substance, and a radioisotope, or any combination thereof.

The invention further includes a method of producing a hybridoma comprising fusing a mammalian myeloma cell with a mammalian B cell that produces a monoclonal antibody which selectively binds an amino acid sequence containing a mutation in the CA-SP1 protein, said mutation resulting in a decrease in the inhibition of processing of p25 to p24 by 3-O-(3',3'-dimethylsuccinyl)betulinic acid and a hybridoma producing any of the monoclonal antibodies disclosed herein. The invention further includes a method of producing an antibody comprising growing a hybridoma producing the monoclonal antibodies disclosed herein in an appropriate medium and isolating the antibodies from the medium, as is well known in the art. The invention also includes the production of polyclonal antibodies comprising the injection, either one injection or multiple injections of any of the polypeptides of the inventions into any animal known in the art to be useful for the production of polyclonal antibodies, including, but not limited to mouse, rat, hamster, rabbit, goat, sheep, deer, guinea pig, or primate, and recovering the antibodies in sera produced therein. The invention includes high avidity or high affinity antibodies produced therein. The invention also includes B cells produced from the listed species to be further used in cell fusion procedures for the manufacture of monoclonal antibody-producing hybridomas as disclosed herein.

The invention is further drawn to a kit comprising the antibody or a portion thereof as disclosed herein, a container comprising said antibody and instructions for use, a kit comprising the polypeptides of this invention and instructions for use and a kit comprising the polynucleotide of the invention, a container comprising said polynucleotide and instructions for use, or any combinations thereof. These kits would include, but not be limited to nucleic acid detection kits, which may, or may not, utilize PCR and immunoassay kits. Such kits are useful for clinical diagnostic use and provide standardized reagents as required in current clinical practice. These kits could either provide information as to the presence or absence of mutations prior to treatment or monitor the progress of the patient during therapy. The kits of the invention may also be used to provide standardized reagents for use in research laboratory studies.

Compounds of the Invention

In one aspect, the invention is also directed to a compound, a method of using a compound, a method of identifying a compound and the like.

The term "a", "an" or "one", as used in the present invention may refer to either the singular or the plural. For example, "a compound" encompasses one or more compounds.

Compounds useful in the methods of the present invention include derivatives of betulinic acid and betulin that are presented in U.S. Pat. Nos. 5,679,828 and 6,172,110 respectively, and in U.S. application Ser. Nos. 60/443,180 and 10/670,797, which are herein incorporated by reference. Additional useful compounds include oleanolic acid derivatives disclosed by Zhu et al. (*Bioorg. Chem Lett.* 11:3115-3118 (2001)); oleanolic acid and pomolic acid derivatives disclosed by Kashiwada et al. (*J. Nat. Prod.* 61:1090-1095 (1998)); 3-O-acyl ursolic acid derivatives described by Kashiwada et al. (*J. Nat. Prod.* 63:1619-1622 (2000)); and 3-alkylamido-3-deoxy-betulinic acid derivatives, disclosed by Kashiwada et al. (*Chem. Pharm. Bull.* 48:1387-1390 (2000)). (All references incorporated by reference).

Compounds useful in the present invention include, but are not limited to those betulinic acid derivatives having the general Formula I and dihydrobetulinic acid derivatives of Formula II:

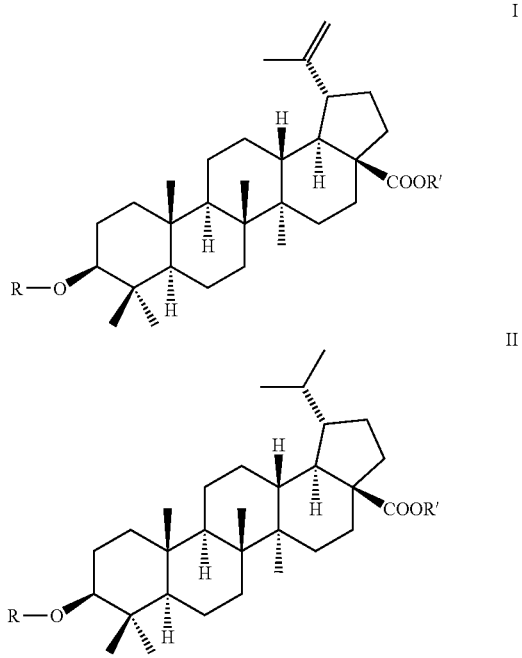

or a pharmaceutically acceptable salt thereof, wherein,

R is a $C_2$-$C_{20}$ substituted or unsubstituted carboxyacyl,

R' is hydrogen or a $C_2$-$C_{10}$ substituted and unsubstituted alkyl or aryl group. Preferred compounds are those wherein R is one of the substituents in Table 4, below, and R' is hydrogen.

Additional useful compounds include derivatives of betulin and dihydrobetulin of Formula III:

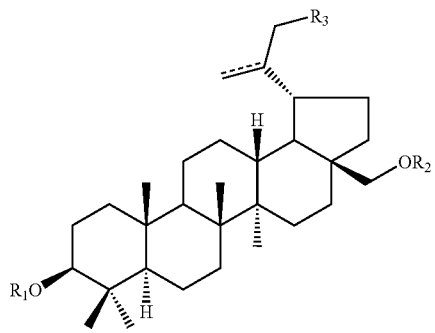

III or a pharmaceutically acceptable salt thereof, wherein, $R_1$ is a $C_2$-$C_{20}$ substituted or unsubstituted carboxyacyl, $R_2$ is hydrogen, $C(C_6H_5)_3$, or a $C_2$-$C_{20}$ substituted or unsubstituted carboxyacyl; and $R_3$ is hydrogen, halogen, amino, optionally substituted mono- or di-alkylamino, or —$OR_4$, where $R_4$ is hydrogen, $C_{1-4}$ alkanoyl, benzoyl, or $C_2$-$C_{20}$ substituted or unsubstituted carboxyacyl;

wherein the dashed line represents an optional double bond between C20 and C29.

Preferred compounds useful in the present invention are those where $R_1$ is one of the substituents in Table 4, $R_2$ is hydrogen or one of the substituents in Table 4 and $R_3$ is hydrogen.

TABLE 4

Preferred Substituents for $R_1$, $R_2$.

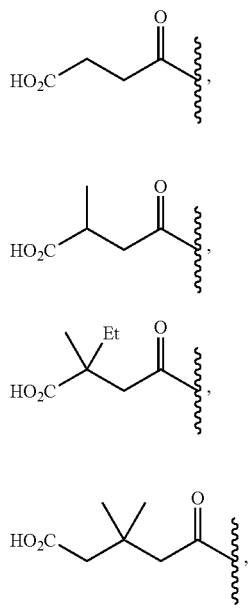

TABLE 4-continued

Preferred Substituents for $R_1$, $R_2$.

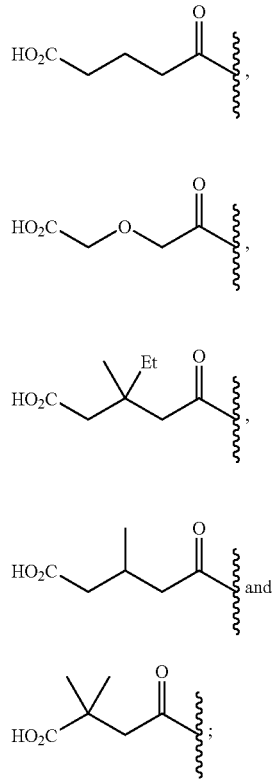

More preferred compounds are 3-O-(3',3'-dimethylsuccinyl)betulinic acid, 3-O-(3',3'-dimethylsuccinyl)dihydrobetulinic acid, 3-O-(3',3'-dimethylsuccinyl)betulin, and 3-O-(3', 3'-dimethylsuccinylglutaryl) dihydrobetulin.

A particularly preferred compound is 3-O-(3',3'-dimethylsuccinyl)betulinic acid.

Additional compounds useful in the present invention are described by the Formulas IV, V, VI and VI.

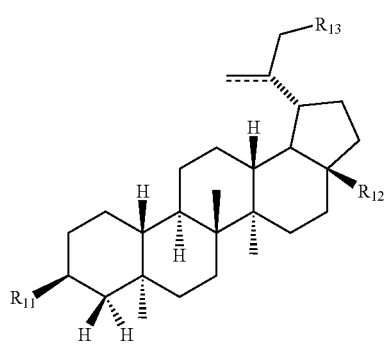

IV $R_{11}$=—$OR_{14}$ or —$NHR_{15}$;
$R_{12}$=$COOR_{17}$, $COO^-A^+$, or $CHOR_{17}$
$R_{13}$=—H, halogen, amino, optionally substituted mono-or di-alkylamino, or —$OR_{16}$;

$R_{14}$=—H, $C_2$-$C_{20}$ substituted or unsubstituted carboxyacyl;

$R_{15}$=—H, $C_2$-$C_{20}$ substituted or unsubstituted carboxyacyl;

$R_{16}$=—H, $C_4$-$C_7$ alkanoyl, benzyloyl, or $C_2$-$C_{20}$ substituted or unsubstituted carboxyacyl;

$R_{17}$=—H, $C(C_6H_5)_3$, or $C_2$-$C_{20}$ substituted or unsubstituted carboxyacyl;

wherein dashed line represents optional bond between $C_{20}$ and $C_{29}$, and wherein A=Na+, K+, or other cation

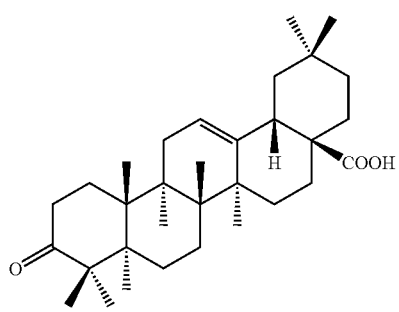
V

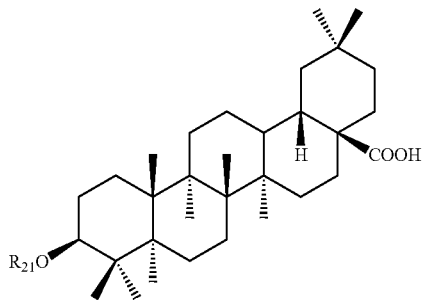
VI wherein $R_{21}$ = H,

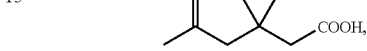

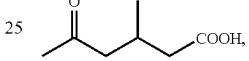, or

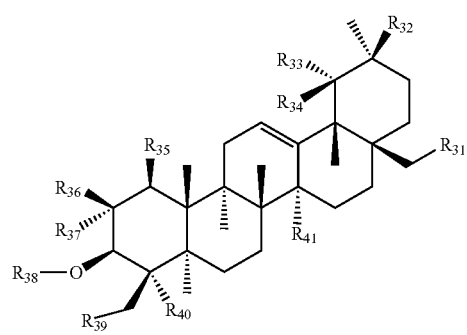
VII

| $R_{31}$ | $R_{32}$ | $R_{33}$ | $R_{34}$ | $R_{35}$ | $R_{36}$ | $R_{37}$ | $R_{38}$ | $R_{39}$ | $R_{40}$ | $R_{41}$ |
|---|---|---|---|---|---|---|---|---|---|---|
| 1 CH₂NH₂ | H | H | H | H | H | H | H | H | H | H |
| 2 ₂-CH₂-COOH) | H | H | H | H | H | H | ₂-CH₂-COOH) | H | H | H |
| 3 ![](CH₂NH-CO-CH₂-cyclopentyl-CH₂-COOH) | H | H | H | H | H | H | | H | H | H |
| 4 COOH | H | H | H | H | H | H | H | H | H | H |
| 5 COOH | H | H | H | H | H | H | | H | H | H |
| 6 COOH | H | H | H | H | H | H | -CH₂-COOH) | H | H | H |

-continued
VII
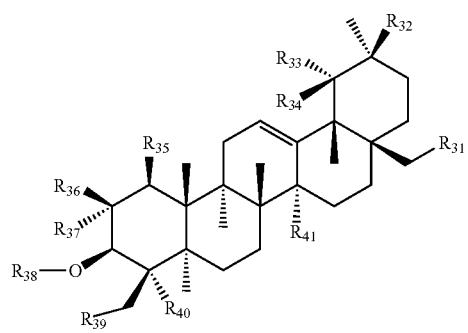
| R31 | R32 | R33 | R34 | R35 | R36 | R37 | R38 | R39 | R40 | R41 |
|---|---|---|---|---|---|---|---|---|---|---|
| 7 COOH | H | H | H | H | H | H |  | H | H | H |
| 8 COOH | H | H | H | H | H | H | 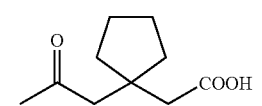 | H | H | H |
| 9 COOH | H | H | H | H | H | H | 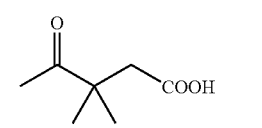 | H | H | H |
| 10 COOH | H | H | H | H | H | H | 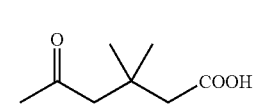 | H | H | H |
| 11 COOH | H | H | H | H | H | H |  | H | H | H |
| 12 COOH | H | H | H | H | H | H |  | H | H | H |
| 13 COOH | H | H | H | H | H | H |  | H | H | H |
| 14 COOH | H | H | H | H | H | H | 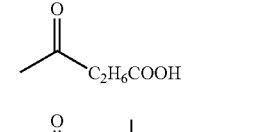 | H | H | H |
| 15 COOH | H | H | H | H | H | H | 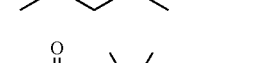 | H | H | H |
| 16 COOH | H | H | H | H | H | H | H | H | H | H |
| 17 COOH | H | H | H | H | H | OH | H | H | OH | H |
| 18 COOH | H | H | H | H | H | OH | H | OH | H | H |
| 19 COOH | H | H | H | H | H | H | H | H | H | OH |
| 20 COOH | H | OH | H | H | H | H | H | H | H | H |
| 21 COOH | H | H | H | H | H | H | H | H | H | H |
| 22 COOH | H | H | H | H | H | OH | H | H | H | H |

-continued

VII

[Structure of Formula VII shown with substituents R31-R41]

| | R31 | R32 | R33 | R34 | R35 | R36 | R37 | R38 | R39 | R40 | R41 |
|---|---|---|---|---|---|---|---|---|---|---|---|
| 23 | COOH | H | H | H | H | H | OH | H | OH | H | H |
| 24 | COOH | H | OH | H | H | H | OH | H | H | H | H |
| 25 | COOH | H | OH | H | H | O | | H | H | H | H |
| 26 | COOH | H | OH | H | OH | O | | H | H | H | H |
| 27 | COOH | H | OH | H | OH | OH | H | H | H | H | |
| 28 | COOH | H | OH | H | OH | H | OH | H | H | H | |
| 29 | COOH | H | OH | H | HH | | OH | H | H | H | |
| 30 | COOH | CH₃ | H | H | H | H | H | H | H | H | |
| 31 | COOH | CH₃ | H | H | H | H | 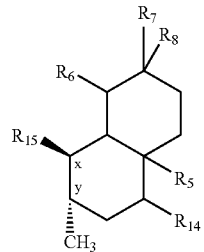 | | H | H | |
| 32 | COOH | H | H | CH₃ | H | H | H | H | H | H | H |
| 33 | COOH | H | H | H | H | H | H | 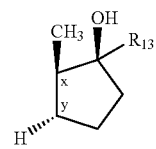 | H | H | H |

$R_{38}$ moieties other than hydrogen are attached to $R_{33}$ oxygen by a covalent bond to the carbonyl carbon.

Preferred compounds are those where R38 is not hydrogen.

Compounds useful in the methods of the invention also include those described in U.S. Provisional Application No. 60/559,358, which is entirely incorporated by reference. In one aspect, these compounds are described by reference to the following compounds VIII to XI:

Additional compounds useful in the present invention have the general Formula VIII:

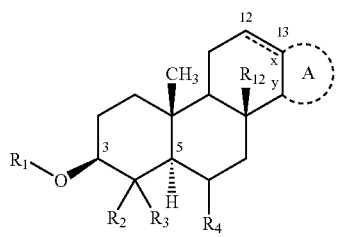

VIII or a pharmaceutically acceptable salt or ester thereof:

wherein A is a fused ring of formula

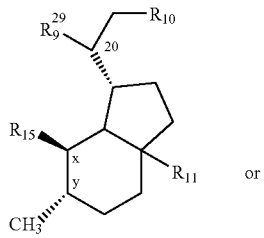

(i)

(ii)

or (iii)

wherein the ring carbons designated x and y in the formulas of A are the same as the ring carbons designated x and y in Formula VIII;

$R_1$ is a carboxyalkanoyl, where the alkanoyl chain can be optionally substituted by one or more hydroxy or halo, or can be interrupted by a nitrogen, sulfur or oxygen atom, or combinations thereof;

$R_2$, $R_3$ and $R_4$ are independently hydrogen, methyl, halogen, or hydroxy;

$R_5$ is carboxyalkoxycarbonyl, alkoxycarbonyl, alkanoyloxymethyl, carboxyalkanoyloxymethyl, alkoxymethyl or carboxyalkoxymethyl, any of which is optionally substituted by one or more hydroxy or halo, or $R_5$ is a carboxyl or hydroxymethyl;

$R_6$ is hydrogen, methyl, hydroxy or halogen;

$R_7$ and $R_8$ are independently hydrogen or $C_{1-6}$ alkyl;

$R_9$ is $CH_2$ or $CH_3$;

$R_{10}$ is hydrogen, hydroxy or methyl;

$R_{11}$ is methyl, methoxycarbonyl, carboxyalkoxycarbonyl, alkanoyloxymethyl, alkoxymethyl or carboxyalkoxymethyl, any of which is optionally substituted by one or more hydroxy or halo;

$R_{12}$ is hydrogen or methyl;

$R_{13}$ is hydrogen or methyl;

$R_{14}$ is hydrogen or hydroxy;

$R_{15}$ is hydrogen if C12 and C13 form a single bond, or $R_{15}$ is absent if C12 and C13 form a double bond; and wherein the straight dashed line represents an optional double bond between C12 and C13 or C20 and C29;

with the proviso that when A is

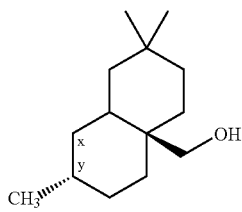

then $R_1$ cannot be glutaryl or succinyl when a double bond exists between C12 and C13;

when A is (ii) and $R_{11}$ is methyl, then $R_1$ cannot be succinyl;

when A is (iii) and $R_2$, $R_3$ and $R_{13}$ are each hydrogen, then $R_1$ cannot be succinyl; and with the proviso that A (i) cannot be

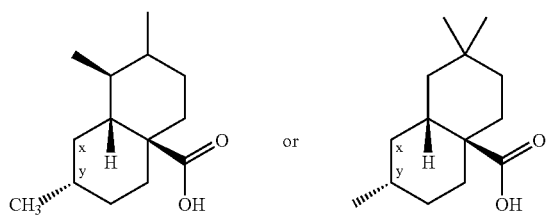

when $R_2$ and $R_3$ are both methyl and a double bond exists between C12 and C13.

In some embodiments, $R_1$ is a carboxy($C_{2-6}$)alkylcarbonyl group or a carboxy($C_{2-6}$)alkoxy($C_{1-6}$)alkylcarbonyl group. Suitable groups are selected from the group consisting of:

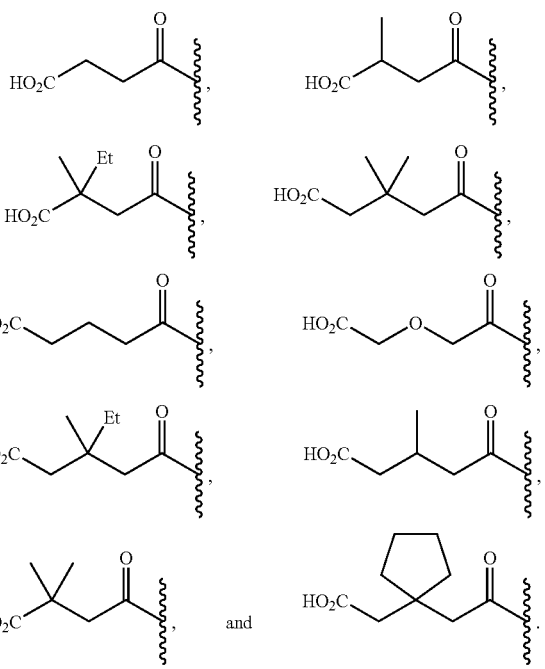

According to the invention, in some embodiments the compounds have Formula IX:

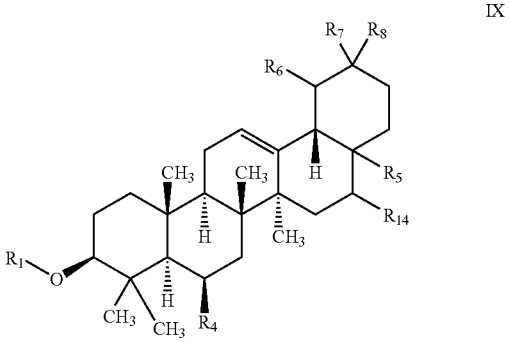

IX wherein $R_1$, $R_4$, $R_5$, $R_6$, $R_7$, $R_8$ and $R_{14}$ are as defined above for Formula VII. In one embodiment, $R_6$ is β-methyl, $R_8$ is hydrogen, $R_5$ is hydroxymethyl and $R_1$ is 3',3'-dimethylglutaryl, 3',3'-dimethylsuccinyl, glutaryl or succinyl. In another embodiment, $R_6$ is hydrogen, $R_7$ and $R_8$ are both methyl, $R_5$ is carboxyl and $R_1$ is 3',3'-dimethylglutaryl, 3',3'-dimethylsuccinyl, glutaryl or succinyl.

In some embodiments, $R_5$ is carboxyalkoxycarbonyl, alkoxycarbonyl, alkanoyloxymethyl, carboxyalkanoyloxymethyl, alkoxymethyl or carboxyalkoxymethyl, any of which is optionally substituted by one or more hydroxy or halo, or $R_5$ is a carboxyl or hydroxymethyl. In some embodiments, $R_5$ is selected from a group consisting of carboxyl, hydroxymethyl, —$CO_2(CH_2)_n$COOH, —$CO_2(CH_2)_n$CH$_3$, —$CH_2$OC(O)($CH_2)_n$CH$_3$, —$CH_2$OC(O)($CH_2)_n$COOH, —$CH_2$O($CH_2)_n$CH$_3$ and —$CH_2$O($CH_2)_n$COOH. In some embodiments, $R_5$ is selected from a group consisting of

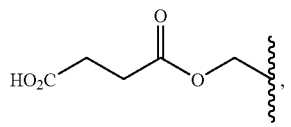

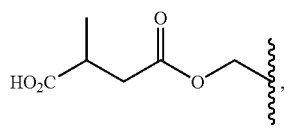

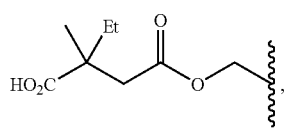

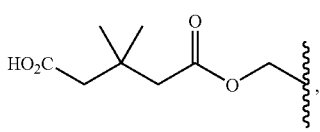

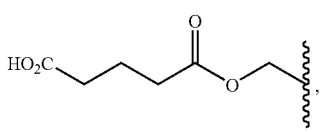

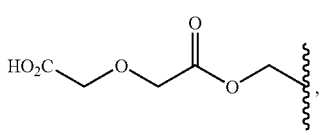

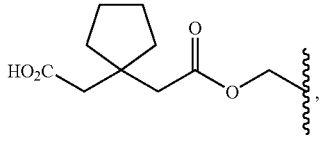

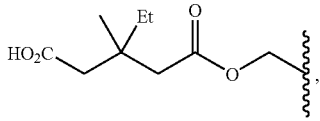

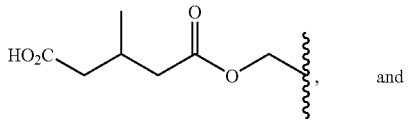 and

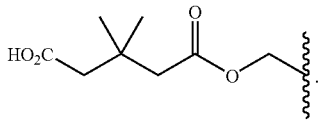

In some embodiments, $R_5$ is hydroxymethyl. In some embodiments, $R_5$ is carboxyl. In some embodiments, n is from 0 to 20. In some embodiments, n is from 1 to 10. In some embodiments, n is from 2 to 8. In some embodiments, n is from 1 to 6. In some embodiments, n is from 2 to 6.

In some embodiments, compounds useful in the present invention have the Formula X:

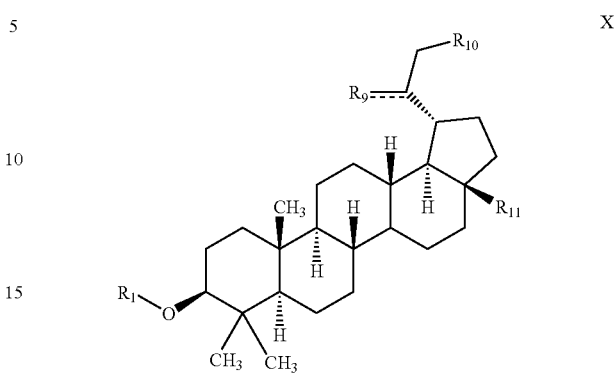

wherein $R_1$, $R_9$, $R_{10}$, and $R_{11}$ are as defined above for Formula VIII. In one embodiment, $R_1$ is 3',3'-dimethylglutaryl, 3',3'-dimethylsuccinyl, glutaryl or succinyl.

In some embodiments, $R_{11}$ is methyl, methoxycarbonyl, carboxyalkoxycarbonyl, alkanoyloxymethyl, alkoxymethyl or carboxyalkoxymethyl, any of which is optionally substituted by one or more hydroxy or halo. In some embodiments, $R_{11}$ is selected from the group consisting of methyl, $-CO_2(CH_2)_n COOH$, $-CH_2OC(O)(CH_2)_n CH_3$, $-CH_2O(CH_2)_n CH_3$ and $-CH_2O(CH_2)_n COOH$.

In some embodiments, n is from 0 to 20. In some embodiments, n is from 1 to 10. In some embodiments, n is from 2 to 8. In some embodiments, n is from 1 to 6. In some embodiments, n is from 2 to 6. In some embodiments, $R_{11}$ is methyl. In some embodiments, $R_{11}$ is methoxycarbonyl. In some embodiments, $R_{11}$ is selected from the group consisting of methoxymethyl and ethoxymethyl. In some embodiments, methyl groups found in $R_{11}$ can be substituted with a halogen or a hydroxy.

In some embodiments, the compounds useful in the present invention have Formula XI:

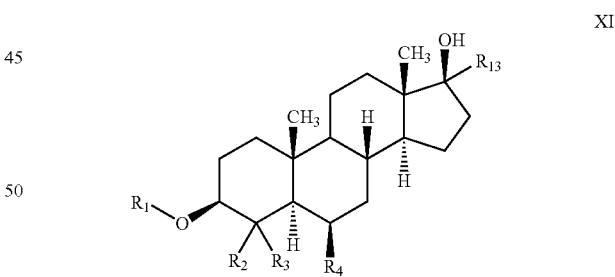

wherein $R_1$, $R_2$, $R_3$, $R_4$, and $R_{13}$ are as defined above for Formula VIII. In one embodiment, $R_1$ is 3',3'-dimethylglutaryl, 3',3'-dimethylsuccinyl, glutaryl or succinyl. In one embodiment, both $R_2$ and $R_3$ are methyl.

Any triterpene which falls within the scope of Formula VIII can be used. According to the invention, in some embodiments the compounds of Formula VIII are selected from the group consisting of derivatives of uvaol, ursolic acid, erythrodiol, echinocystic acid, oleanolic acid, sumaresinolic acid, lupeol, dihydrolupeol, betulinic acid methylester, dihydrobetulinic acid methylester, 17-α-methyl-androstanediol, androstanediol, and 4,4-dimethyl-androstanediol.

In some embodiments, the compounds of the present invention are defined as in Formula VIII, wherein $R_2$ and $R_3$ are both methyl. In some embodiments, the compounds of the present invention are defined as in Formula VIII, wherein $R_1$ is 3',3'-dimethylsuccinyl. In some embodiments, the compounds of the present invention are defined as in Formula VIII, wherein $R_1$ is succinyl, i.e.,

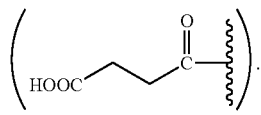

According to the invention, in some embodiments the stereochemistry of the sidechain substituents is important. In some embodiments, the compounds of the present invention are defined as in Formula VIII, wherein A is (i) and $R_5$ is in the β position. In some embodiments, the compounds of the present invention are defined as in Formula VIII, wherein A is (i) and $R_6$ is in the β position. In some embodiments, the compounds of the present invention are defined as in Formula VIII, wherein A is (i) and $R_{14}$ is in the α position. In some embodiments, the compounds of the present invention are defined as in Formula VIII, wherein A is (i), $R_7$ is α-methyl, and $R_8$ is hydrogen. In some embodiments, the compounds of the present invention are defined as in Formula VIII, wherein A is (i), $R_8$ is α-methyl, and $R_7$ is hydrogen. In some embodiments, the compounds of the present invention are defined as in Formula VIII, wherein A is (i) and both $R_7$ and $R_8$ are methyl. In some embodiments, the compounds of the present invention are defined as in Formula VIII, wherein A is (ii) and $R_{11}$ is in the β position.

In some embodiments, 3',3'-dimethylsuccinyl is at the C3 position. In some embodiments, the compounds of Formula IX are 3-O-(3',3'-dimethylsuccinyl)uvaol; 3-O-(3',3'-dimethylsuccinyl)erythrodiol; 3-O-(3',3'-dimethylsuccinyl)echinocystic acid or 3-O-(3',3'-dimethylsuccinyl)sumaresinolic acid. In some embodiments, the compounds of Formula X are 3-O-(3',3'-dimethylsuccinyl)lupeol; 3-O-(3',3'-dimethylsuccinyl)dihydrolupeol; 3-O-(3',3'-dimethylsuccinyl)17β-methylester-betulinic acid; or 3-O-(3',3'-dimethylsuccinyl)17β-methylester-dihydrobetulinic acid. In some embodiments, the compounds of Formula XI are 3-O-(3',3'-dimethylsuccinyl)4,4-dimethylandrostanediol; 3-O-(3',3'-dimethylsuccinyl)17α-methylandrostanediol; 3-O-(3',3'-dimethylsuccinyl)androstanediol.

Alkyl groups and alkyl containing groups of the compounds of the present invention can be straight chain or branched alkyl groups, preferably having one to ten carbon atoms. In some embodiments, the alkyl groups or alkyl containing groups of the present invention can be substituted with a $C_{3-7}$ cycloalkyl group. In some embodiments, the cycloalkyl group may include, but is not limited to, a cyclobutyl, cyclopentyl or cyclohexyl group.

Also, included within the scope of the present invention are the non-toxic pharmaceutically acceptable salts of the compounds of the present invention. These salts can be prepared in situ during the final isolation and purification of the compounds or by separately reacting the purified compound in its free acid form with a suitable organic or inorganic base and isolating the salt thus formed. These can include cations based on the alkali and alkaline earth metals, such as sodium, lithium, potassium, calcium, magnesium, and the like, as well as nontoxic ammonium, quaternary ammonium and amine cations including, but not limited to ammonium, tetramethylammonium, tetraethylammonium, methylamine, dimethylamine, trimethylamine, ethylamine, N-methyl glucamine and the like.

Also, included within the scope of the present invention are the non-toxic pharmaceutically acceptable esters of the compounds of the present invention. Ester groups are preferably of the type which are relatively readily hydrolyzed under physiological conditions. Examples of pharmaceutically acceptable esters of the compounds of the invention include $C_{1-6}$ alkyl esters wherein the alkyl group is a straight or branched chain. Acceptable esters also include $C_{5-7}$ cycloalkyl esters as well as arylalkyl esters, such as, but not limited to benzyl. $C_{1-4}$ alkyl esters are preferred. In some embodiments, the esters are selected from the group consisting of alkylcarboxylic acid esters, such as acetic acid esters, and mono- or dialkylphosphate esters, such as methylphosphate ester or dimethylphosphate ester. Esters of the compounds of the present invention can be prepared according to conventional methods.

Certain compounds within the scope of Formulae VIII, IX, X and XI are derivatives referred to as "prodrugs". The expression "prodrug" refers to compounds that are rapidly transformed in vivo by an enzymatic or chemical process, to yield the parent compound of the above formulas, for example, by hydrolysis in blood. A thorough discussion is provided by Higuchi, T. and V. Stella in *Pro-drugs as Novel Delivery Systems*, Vol. 14, A.C.S. Symposium Series, and in *Bioreversible Carriers in Drug Design*, Ed. Edward B. Roche, American Pharmaceutical Association, Pergamon Press, 1987. Useful prodrugs can be esters of the compounds of Formulae VIII, IX, X, and XI. In some prodrug embodiments, a lower alkyl group is substituted with one or more hydroxy or halo groups by a suitable acid. Suitable acids include, e.g., carboxylic acids, sulfonic acids, phosphoric acid or lower alkyl esters thereof, and phosphonic acid or lower alkyl esters thereof. For example, suitable carboxylic acids include alkylcarboxylic acids, such as acetic acid, arylcarboxylic acids and arylalkylcarboxylic acids. Suitable sulfonic acids include alkylsulfonic acids, arylsulfonic acids and arylalkylsulfonic acids. Suitable phosphoric and phosphonic acid esters are methyl or ethyl esters. In some embodiments, the C3 acyl groups having dimethyl groups or oxygen at the C3' position can be the most active compounds. This observation suggests that these types of acyl groups might be important to the enhanced anti-HIV activity.

In an additional embodiment, the invention includes compounds and methods that use compounds of Formula XII:

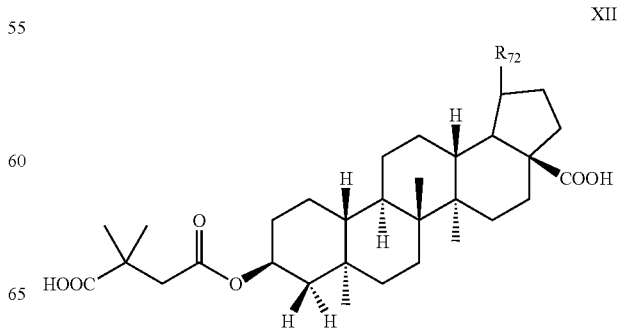

where $R_{72}$ is one of:

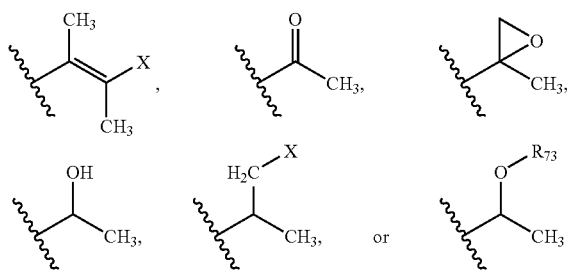

wherein

X is hydroxy or halogen; and $R_{73}$ is lower alkyl, such as methyl, ethyl or propyl.

In one embodiment, the invention is drawn to a method of treating HIV-1 infection in a patient by administering a compound that inhibits processing of the viral Gag p25 protein (CA-SP1) to p24 (CA), but does not significantly affect other Gag processing steps, wherein said compound is a compound of Formula I through XII In one embodiment, the invention is drawn to a method of treating HIV-1 infection in a patient by administering a compound that inhibits processing of the viral Gag p25 protein (CA-SP1) to p24 (CA), but does not significantly affect other Gag processing steps, wherein said compound is a compound of Formula I through XII, with the exception of DSB.

In one embodiment, the invention is drawn to a method of treating HIV-1 infection in a patient by administering a compound that inhibits processing of the viral Gag p25 protein (CA-SP1) to p24 (CA), but does not significantly affect other Gag processing steps, wherein said compound is other than a compound of Formula I through VI. In one embodiment, the invention is drawn to a method of treating HIV-1 infection in a patient by administering a compound that inhibits processing of the viral Gag p25 protein (CA-SP1) to p24 (CA), but does not significantly affect other Gag processing steps, wherein said compound is other than a compound of Formula I through XI.

In another embodiment, the invention is drawn to a method of inhibiting processing of the viral Gag p25 protein (CA-SP1) to p24 (CA) in a cell, but without significantly affect other Gag processing steps, wherein said compound is a compound of Formula Groups I through XII.

In another embodiment, the invention is drawn to a method of inhibiting processing of the viral Gag p25 protein (CA-SP1) to p24 (CA) in a cell, but without significantly affect other Gag processing steps, wherein said compound is other than a compound of Formula I through VII.

In another embodiment, the invention is drawn to a method of inhibiting processing of the viral Gag p25 protein (CA-SP1) to p24 (CA) in a cell, but without significantly affect other Gag processing steps, wherein said compound is other than a compound of Formula I through XI.

In another embodiment, the invention is drawn to a method of treating human blood or blood products by inhibiting processing of the viral Gag p25 protein (CA-SP1) to p24 (CA) in a cell, but without significantly affect other Gag processing steps, wherein said compound is a compound of Formula I through XII.

In another embodiment, the invention is drawn to a method of treating human blood or blood products by inhibiting processing of the viral Gag p25 protein (CA-SP1) to p24 (CA) in a cell, but without significantly affect other Gag processing steps, wherein said compound is other than a compound of Formula I through VII.

In another embodiment, the invention is drawn to a method of treating human blood or blood products by inhibiting processing of the viral Gag p25 protein (CA-SP1) to p24 (CA) in a cell, but without significantly affect other Gag processing steps, wherein said compound is other than a compound of Formula I through XI.

Synthesis Of DSB and Related Compounds

Reaction of betulinic acid and dihydrobetulinic acid with dimethylsuccinic anhydride produced a mixture of 3-O-(2', 2'-dimethylsuccinyl) and 3-O-(3',3'-dimethylsuccinyl)-betulinic acid and dihydrobetulinic acid, respectively. The mixtures were successfully separated by preparative scale HPLC yielding pure samples. The structures of these isomers were assigned by long-range $^1H$-$^{13}C$ COSY examinations.

The derivatives of betulinic acid and dihydrobetulinic acid of the present invention were all synthesized by refluxing a solution of betulinic acid or dihydrobetulinic acid, dimethylaminopyridine (1 equivalent mol), and an appropriate anhydride (2.5-10 equivalent mol) in anhydrous pyridine (5-10 mL). The reaction mixture was then diluted with ice water and extracted with $CHCl_3$. The organic layer was washed with water, dried over $MgSO_4$, and concentrated under reduced pressure. The residue was chromatographed using silica gel column or semi-preparative-scale HPLC to yield the product.

Preparation of 3-O-(3',3'-dimethylsuccinyl)betulinic acid: yield 70% (starting with 542 mg of betulinic acid); crystallization from MeOH gave colorless needles; mp 274°-276° C.; $[\alpha]_D^{19}$+23.5° (c=0.71), $CHCl_3$-MeOH [1:1]); Positive FABMS m/z 585 (M+H)$^+$; Negative FABMS m/z 583 (M−H)$^−$; HR-FABMS calcd for $C_{36}H_{57}O_6$ 585.4155, found m/z 585.4161; $^1H$ NMR (pyridine-$d_5$): 0.73, 0.92, 0.97, 1.01, 1.05 (each 3H, s; 4-(CH$_3$)$_2$, 8-CH$_3$, 10-CH$_3$, 14-CH$_3$), 1.55 (6H, s, 3'-CH$_3$×2), 1.80 (3H, s, 20-CH$_3$), 2.89, 2.97 (each 1H, d, J=15.5 Hz, H-2'), 3.53 (1H, m, H-19), 4.76 (1H, dd, J=5.0, 11.5 Hz, H-3), 4.78, 4.95 (each 1H, br s, H-30).

3-O-(3',3'-dimethylsuccinyl)dihydrobetulinic acid: yield 24.5% (starting with 155.9 mg of dihydrobetulinic acid); crystallization from MeOH—H$_2$O gave colorless needles; mp 291°-292° C.; $[\alpha]_D^{20}$-13.4° (c=1.1, $CHCl_3$—MeOH [1:1], $^1H$ NMR (pyridine-$d_5$): 0.85, 0.94 (each 3H, d, J=7.0 Hz; 20-(CH$_3$)$_2$), 0.75, 0.93, 0.97, 1.01, 1.03 (each 3H, s; 4-(CH$_3$)$_2$, 8-CH$_3$, 10-CH$_3$, 14-CH$_3$), 1.55 (6H, s; 3'-CH$_3$×2), 2.89, 2.97 (each 1H, d, J=15.5 Hz; H-2'), 4.77 (1H, dd, J=5.0, 11.0 Hz, H-3); Anal. Calcd for $C_{36}H_{58}O_6$.5/2H$_2$O: C 68.43, H 10.04; found C 68.64, H 9.78.

The synthesis of 3-O-(3',3'-dimethylglutaryl)betulinic acid was disclosed U.S. Pat. No. 5,679,828, as COMPOUND NO. 4.

3-O-(3',3'-dimethylglutaryl)dihydrobetulinic acid: yield 93.3% (starting with 100.5 mg of dihydrobetulinic acid); crystallization from needles MeOH—H$_2$O gave colorless needles; mp 287°-289° C.; $[\alpha]_D^{20}$-17.9° (c=0.5, $CHCl_3$—MeOH[1:1]); $^1H$-NMR (pyridine-$d_5$): 0.86, 0.93 (each 3H, d, J=6.5 Hz; 20-(CH$_3$)$_2$), 0.78, 0.92, 0.96, 1.02, 1.05 (each 3H, s; 4-(CH$_3$)$_2$, 8-CH$_3$, 10-CH$_3$, 14-CH$_3$), 1.38, 1.39 (each 3H, s; 3'-CH$_3$×2), 2.78 (4H, m, H$_2$-2' and 4'), 4.76 (1H, dd, J=4.5, 11.5 Hz; H-3). Anal. Calcd for $C_{37}H_{60}O_6$: C 73.96, H 10.06; found C 73.83, H 10.10.

The synthesis for 3-O-diglycolyl-betulinic acid was disclosed in U.S. Pat. No. 5,679,828, as COMPOUND NO. 5.

3-O-diglycolyl-dihydrobetulinic acid: yield 79.2% (starting with 103.5 mg of dihydrobetulinic acid); an off-white amorphous powder; $[\alpha]_D^{20}$-9.8° (c=1.1, CHCl$_3$—MeOH[1:1]); $^1$H-NMR (pyridine-d$_5$): 0.79, 0.87 (each 3H, d, J=6.5 Hz; 20-(CH$_3$)$_2$), 0.87, 0.88, 0.91, 0.98, 1.01 (each 3H, s; 4-(CH$_3$)$_2$, 8-CH$_3$, 10-CH$_3$, 14-CH$_3$), 4.21, 4.23 (each 2H, s, H$_2$-2' and 4'), 4.57 (1H, dd, J=6.5, 10.0 Hz, H-3); Anal. Calcd for C$_{34}$H$_{54}$O$_7$.2H$_2$O: C 66.85, H 9.57; found C 67.21, H 9.33.

The syntheses of 3-O-(3',3'-dimethylsuccinyl)betulin and 3-O-(3',3'-dimethylglutaryl)betulin were disclosed in U.S. application Ser. No. 10/670,797.

Methods of Inhibiting HIV with a Compound

Methods of "inhibiting HIV" or "inhibition of HIV" as used herein, means any interference in, inhibition of, and/or prevention of HIV using the methods of the invention. As such, methods of inhibition are useful in inhibiting with the infectivity of HIV, inhibition of p25 processing, inhibition of viral maturation, formation of virions that exhibit altered phenotypes, and the like. Preferably, methods of the invention act upon p25 processing in the cells of an animal, but are not limited by that method of action.

A method of inhibiting HIV with a compound may be relevant to a method of treating HIV infection in a patient. Therefore, a method of inhibiting HIV with a compound may similarly be used to treat a patient.

The methods of inhibiting HIV-1 replication in cells of an animal includes contacting infected cells with a compound of Formula I through XII, above. Related embodiments include a method of treating a HIV-1 infection in a patient comprising administration of a compound of Formula I through XII; a method of inhibiting p25 processing either in a cell, in vivo, and/or in vitro, by administration of a compound that inhibits said p25 processing; and a method of treating human blood or blood products by administering a compound of Formula I through XII. Also included are a method of identifying a compound that inhibits any one of p25 processing, HIV maturation, HIV infectivity, HIV virion phenotypes and the like.

In one embodiment, the compound is a derivative of betulinic acid, betulin, or dihydrobetulinic acid or dihydrobetulin and which includes the preferred substituents of Table 4. Preferred compounds include but are not limited to 3-O-(3',3'-dimethylsuccinyl)betulinic acid, 3-O-(3',3'-dimethylsuccinyl)betulin, 3-O-(3',3'-dimethylglutaryl)betulin, 3-O-(3',3'-dimethylsuccinyl)dihydrobetulinic acid, 3-O-(3',3'-dimethylglutaryl)betulinic acid, (3',3'-dimethylglutaryl)dihydrobetulinic acid, 3-O-diglycolyl-betulinic acid, and 3-O-diglycolyl-dihydrobetulinic acid.

In one embodiment, the invention is drawn to a method inhibiting HIV-1 replication in cells of an animal by contacting infected cells with a compound that inhibits processing of the viral Gag p25 protein (CA-SP1) to p24 (CA), but does not significantly affect other Gag processing steps, wherein said compound is a compound of Formulas I through XII above.

In one embodiment, the invention is drawn to a method of inhibiting HIV-1 replication in cells of an animal by contacting infected cells with a compound that inhibits processing of the viral Gag p25 protein (CA-SP1) to p24 (CA), but does not significantly affect other Gag processing steps, wherein said compound is compound of Formulas I through XII, with the exception of DSB.

In another embodiment, the invention is drawn to a method of inhibiting HIV-1 replication in cells of an animal by contacting infected cells with a compound that inhibits processing of the viral Gag p25 protein (CA-SP1) to p24 (CA), but does not significantly affect other Gag processing steps, wherein said compound is one that is excluded from those of Formulas I through VI. In one embodiment, the invention is drawn to a method of treating HIV-1 infection in a patient by administering a compound that inhibits processing of the viral Gag p25 protein (CA-SP1) to p24 (CA), but does not significantly affect other Gag processing steps, wherein said compound is one that is other than those of Formulas I through XI.

In another embodiment, the invention is drawn to a method of inhibiting processing of the viral Gag p25 protein (CA-SP1) to p24 (CA) in a cell, but without significantly affecting other Gag processing steps, wherein said compound is a compound of Formulas I through XII.

In another embodiment, the invention is drawn to a method of inhibiting processing of the viral Gag p25 protein (CA-SP1) to p24 (CA) in a cell, but without significantly affecting other Gag processing steps, wherein said compound is a compound other than those of Formulas I through VI.

In another embodiment, the invention is drawn to a method of inhibiting processing of the viral Gag p25 protein (CA-SP1) to p24 (CA) in a cell, but without significantly affecting other Gag processing steps, wherein said compound is a compound other than those of Formulas I through XI.

In another embodiment, the invention is drawn to a method of inhibiting processing of the viral Gag p25 protein (CA-SP1) to p24 (CA) in a cell, but without significantly affecting other Gag processing steps, wherein said compound is a compound other than those of Formulas I through XI. In another embodiment, the invention is drawn to a method of treating human blood or blood products by inhibiting processing of the viral Gag p25 protein (CA-SP1) to p24 (CA) in a cell, but without significantly affect other Gag processing steps, wherein said compound is a compound of Formulas I through XII.

In another embodiment, the invention is drawn to a method of treating human blood or blood products by inhibiting processing of the viral Gag p25 protein (CA-SP1) to p24 (CA) in a cell, but without significantly affect other Gag processing steps, wherein said compound is a compound other than those of Formulas I through VI.

In another embodiment, the invention is drawn to a method of treating human blood or blood products by inhibiting processing of the viral Gag p25 protein (CA-SP1) to p24 (CA) in a cell, but without significantly affect other Gag processing steps, wherein said compound is a compound other than those of Formulas I through XI.

The method disclosed herein, further comprises contacting said cells with one or more drugs selected from the group consisting of anti-viral agents, anti-fungal agents, anti-bacterial agents, anti-cancer agents, immunostimulating agents, and combinations thereof. The method may include the treatment of human blood products.

The invention may also be used in conjunction with a method of treating cancer comprising the administration to an animal of one or more anti-neoplastic agents, exposing an animal to a cancer cell-killing amount of radiation, or a combination of both.

Methods of Identifying Compounds

The invention further includes a method for identifying compounds that inhibit HIV-1 replication in cells of an animal disclosed herein. In one embodiment, said method comprises:

(a) contacting a Gag polypeptide comprising a CA-SP1 cleavage site with a test compound;

(b) adding a labeled substance that selectively binds at or near the CA-SP1 cleavage site; and (c) measuring the binding of the test compound at or near the CA-SP1 cleavage site.

Labeled substances or molecules include labeled antibodies or labeled DSB and the label includes an enzyme, fluorescent substance, chemiluminescent substance, horseradish peroxidase, alkaline phosphatase, biotin, avidin, electron dense substance, such as gold, osmium tetroxide, lead or uranyl acetate, and radioisotope, antibodies labeled with such substances of molecules or a combination thereof. The assays could include, but are not limited to ELISA, single and double sandwich techniques, immunodiffusion or immunoprecipitation techniques, as known in the art ("*Immunoassay Handbook, 2$^{nd}$ ed.*," D. Wild, Nature Publishing Group, (2001)). Said methods of identifying also could include, but are not limited to Western blot assays, colorimetric assays, light and electron microscopic techniques, confocal microscopy, or other techniques known in the art.

A method of identifying compounds that inhibit HIV replication in cells of an animal further comprises:

(a) contacting a Gag protein comprising a wild-type CA-SP1 cleavage site, with HIV-1 protease in the presence of a test compound;

(b) separately, contacting a Gag protein comprising a mutant CA-SP1 cleavage site or a protein comprising an alternative protease cleavage site with HIV-1 protease in the presence of the test compound; and (c) comparing the cleavage of the native wild-type Gag protein to the amount of cleavage of the mutant Gag protein or to the amount of cleavage of the peptide comprising an alternative protease cleavage site.

Step (b) above is performed as a control in order to eliminate compounds that might bind directly to, and therefore inhibit, the protease enzyme. The above method also includes the method wherein the wild-type CA-SP1, mutant CA-SP1 or alternative protease cleavage site is contained within a polypeptide fragment or recombinant peptide.

The method for identifying compounds that inhibit HIV-1 disclosed herein, also includes a method wherein said peptide or protein is labeled with a fluorescent moiety and a fluorescence quenching moiety, each bound to opposite sides of the CA-SP1 cleavage site, and wherein said detecting comprises measuring the signal from the fluorescent moiety, or wherein said peptide or protein is labeled with two fluorescent moieties, each bound to opposite sides of the CA-SP1 cleavage site, and wherein said detecting comprises measuring the transfer of fluorescent energy from one moiety to the other in the presence of the test compound and HIV-1 protease and comparing said transfer of fluorescent energy to that observed when the same procedure is applied to a peptide that comprises a sequence containing a mutation in the CA-SP1 cleavage site or that comprises a sequence containing another cleavage site. Examples of fluorescence-based assays of protease activity are well known in the art. In one such example, a protease substrate is labeled with green fluorescent dye molecules, which fluoresce when the substrate is cleaved by the protease enzyme (Molecular Probes, Protease Assay Kit).

The method of comparing the cleavage, above, also includes using a labeled antibody that selectively binds CA or SP1 or CA-SP1 in order to measure the extent to which the test compound inhibits CA-SP1 cleavage. The antibody can be labeled with a molecule selected from the group consisting of enzyme, fluorescent substance, chemiluminescent substance, horseradish peroxidase, alkaline phosphatase, biotin, avidin, electron dense substance, and radioisotope, or combinations thereof. The method also includes the use of an antibody to a specific epitope tag sequence to selectively detect CA-SP1 (p25) or SP1, into which the amino acid sequence for that epitope tag has been engineered according to standard methods in the art. Suitable tags are well known to those of ordinary skill in the art, and include haemagglutinin epitope HA (YPYDVPDYA) (SEQ ID NO: 81), bluetongue virus epitope VP7 (QYPALT) (SEQ ID NO: 82), α-tubulin epitope (EEF), Flag (DYKDDDDK) (SEQ ID NO: 83), and VSV-G (YTDOEMNRLGK) (SEQ ID NO: 84). Examples of SP1 containing epitope tags are illustrated in FIG. 17.

As an example, the sequence of the FLAG epitope tag (Sigma-Aldrich) is inserted into the p2 (SP1) region of Gag by oligonucleotide-directed mutagenesis of a Gag expression plasmid. The presence of the SP1 domain in the cell-expressed protein is then be detected using commercially available anti-FLAG monoclonal antibodies (Sigma-Aldrich). (Hopp, T. P. *Biotechnology* 6: 1204-1210 (1988)).

The method of identifying compounds that disrupt CA-SP1 cleavage also includes the addition of a compound to cells infected with HIV-1 and the detection of CA-SP1 cleavage products by lysing and analyzing the cells or the released virions. The method included in the invention can be performed using a western blot analysis of viral proteins and detecting p25 using an antibody to p25 or wherein said mixture is analyzed by performing a gel electrophoresis of viral proteins and imaging of metabolically labeled proteins, or wherein the mixture is analyzed using immunoassays that use an antibody that selectively binds p25 or an antibody that selectively binds in order to distinguish p25 from p24. The invention includes the use of an antibody to a specific epitope tag sequence inserted into the C-terminal domain of SP1 to selectively detect p25 or SP1. For example, a sandwich ELISA assay can be performed where p25 and p24 in detergent-solubilized virus are captured using an antibody that selectively binds to the CA region of Gag, which antibody is bound to a multiple well plate. Following a washing step, bound p25 is detected using an antibody to an epitope tag inserted in SP1, which is conjugated to an appropriate detection reagent (e.g. alkaline phosphatase for an enzyme-linked immunosorbent assay). Virus released by cells treated with compounds that act via this mechanism will generally have increased levels of p25 compared with untreated virions.

The disclosed method is drawn to an antibody that selectively binds p25, or an antibody that selectively binds SP1, or an antibody to an epitope tag sequence inserted into SP1, which is labeled with a molecule selected from the group consisting of enzyme, fluorescent substance, chemiluminescent substance, horseradish peroxidase, alkaline phosphatase, biotin, avidin, electron dense substance, and radioisotope, or combinations thereof.

"Infected cells," as used herein, includes cells infected naturally by membrane fusion and subsequent insertion of the viral genome into the cells, or transfection of the cells with viral genetic material through artificial means. These methods include, but are not limited to, calcium phosphate transfection, DEAE-dextran mediated transfection, microinjection, lipid-mediated transfection, electroporation or infection.

The invention may be practiced by infecting target cells in vitro with an infectious strain of HIV and in the presence of test compound, under appropriate culture conditions and for varying periods of time. Infected cells or supernatant fluid can be processed and loaded onto a polyacrylamide gel for the detection of virus levels, by methods that are well known in the art. Non-infected and non-treated cells can be used as negative and positive infection controls, respectively. Alternatively, the invention may be practiced by culturing the target cells in the presence of test compound prior to infecting the cells with an HIV strain.

The invention also includes a method for identifying compounds that inhibit HIV-1 replication in the cells of an animal, comprising:

(a) contacting a test compound with wild-type virus isolates and separately with virus isolates having redued sensitivity to 3-O-(3',3'-dimethylsuccinyl)betulinic acid; and (b) selecting test compounds that are more active against the wild-type virus isolate compared with virus isolates that have reduced sensitivity to 3-O-(3',3'-dimethylsuccinyl)betulinic acid.

This invention further includes a method for identifying compounds that act by any of the abovementioned mechanism, involving treating HIV-1 infected or transfected cells with a compound then analyzing the virus particles released by compound-treated cells by thin-sectioning and transmission electron microscopy, by standard methods well known in the art. A compound acts by the abovementioned mechanism if particles are detected that exhibit spherical condensed cores that are acentric with respect to the viral particle and/or a crescent-shaped electron-dense layer just inside the viral membrane.

For electron microscopic studies, infected cells or centrifuged virus pellets obtained from the supernatant fluid can be contacted with a fixative, such as glutaraldehyde or freshly-made paraformaldehyde, and/or osmium tetroxide or other electron microscopy compatible fixative that is known in the art. The virus from the supernatant fluid or the cells, is dehydrated and embedded in an electron-lucent polymer such as an epoxy resin or methacrylate, thin sectioned using an ultramicrotome, stained using electron dense stains such as uranyl acetate, and/or lead citrate, and viewed in a transmission electron microscope. Non-infected and non-treated cells can be used as negative and positive infection controls, respectively. Alternatively, the invention may be practiced by culturing the target cells in the presence of test compound prior to infecting the cells with an HIV strain. Maturation defects caused by the compounds of the present invention are determined by the presence of morphologically aberrant viral particles, compared with controls, as described herein.

For cell culture studies, the virus-infected cells may be observed for the formation of syncytia, or the supernatant may be tested for the presence of HIV particles. Virus present in the supernatant may be harvested to infect other naive cultures to determine infectivity.

Also included in the invention, is a method of determining if an individual is infected with HIV-1, is susceptible to treatment by a compound that inhibits p25 processing, the method involves taking blood from the patient, genotyping the viral RNA and determining whether the viral RNA contains mutations in the CA-SP1 cleavage site.

The invention also includes a method for identifying compounds that act by the abovementioned mechanisms, involving testing by a combination of the methods disclosed herein.

HIV Gag protein and fragments thereof for use in the aforementioned assays may be expressed or synthesized using a variety of methods familiar to those skilled in the art. Gag can be produced in an in vitro transcription and translation system using a rabbit reticulocyte lysate. Gag expressed in this system has been shown to be processed sequentially in a pattern similar to that observed in infected cells (Pettit, S. C. et al. *J. Virol.* 76:10226-10233 (2002)). Moreover, Gag expressed by this method is capable of assembling into immature viral particles when fused to a heterologous type D retroviral cytoplasmic self-assembly domain (Sakalian, M. et al., *J. Virol.* 76:10811-10820 (2002)). The plasmid pDAB72, available from the NIH AIDS Reagent Program can be used for this purpose (Erickson-Viitanen, S. et al., *AIDS Res. Hum. Retroviruses.* 5:577-91 (1989); Sidhu M. K. et al., *Biotechniques,* 18:20, 22, 24 (1995)). Other in vitro transcription/translation systems based on wheat germ or bacterial lysates can also be used for this purpose. HIV Gag may also be expressed in transfected cells using a variety of commercially available expression vectors. The plasmid p55-GAG/GFP, available from the NIH AIDS Reagent Program, may be used to express an HIV Gag-green fluorescent protein fusion protein in mammalian cells for drug interaction studies (Sandefur, S. et al., *J. Virol.* 72:2723-2732 (1998)). This construct would permit the capture and purification of Gag fusion protein using GFP-specific monoclonal antibodies. In addition, Gag may be expressed in cells using recombinant viral vectors, such as those used in the vaccinia virus, adenovirus, or baculovirus systems. Gag can also be expressed by infecting cells with HIV or by transfecting cells with proviral DNA. Finally, Gag may be expressed in yeast or bacterial cells transformed with the appropriate expression vectors.

In addition to Gag proteins expressed in cells or in vitro using cell lysates, peptides corresponding to various regions of Gag may be commercially synthesized from using standard peptide synthesis techniques.

The invention further encompasses compounds identified by the method of this invention and/or a compound which inhibits HIV-1 replication according to the methods of this invention and pharmaceutical compositions comprising one or more compounds as disclosed herein, or pharmaceutically acceptable salts, esters or prodrugs thereof, and pharmaceutically acceptable carriers.

Pharmaceutical Compositions

Compounds according to the present invention have been found to possess anti-retroviral, particularly anti-HIV, activity. The salts and other formulations of the present invention are expected to have improved water solubility, and enhanced oral bioavailability. Also, due to the improved water solubility, it will be easier to formulate the salts of the present invention into pharmaceutical preparations. Further, compounds according to the present invention are expected to have improved biodistribution properties.

In one embodiment, the compounds are those of Formula I through XII, in another they are compounds other than the compounds of Formula I through XI.

This invention also includes a pharmaceutical composition comprising a compound that inhibits processing of the viral Gag p25 protein (CA-SP1) to p24 (CA), but has no significant effect on other Gag processing steps, or that inhibits the maturation of virus particles released from treated infected cells, such as the compounds of Formula I through XII. The invention includes a pharmaceutical composition comprising one or more compounds disclosed herein, or pharmaceutically acceptable salts, esters or prodrugs thereof, and pharmaceutically acceptable carriers, wherein said compound is of Formulae I through XII above, or preferably, wherein said compound is selected from the group consisting of 3-O-(3',3'-dimethylsuccinyl)betulinic acid, 3-O-(3',3'-dimethylsuccinyl)betulin, 3-O-(3',3'-dimethylglutaryl)betulin, 3-O-(3',3'-dimethylsuccinyl)dihydrobetulinic acid, 3-O-(3',3'-dimethylglutaryl)betulinic acid, (3',3'-dimethylglutaryl) dihydrobetulinic acid, 3-O-diglycolyl-betulinic acid, and 3-O-diglycolyl-dihydrobetulinic acid. The pharmaceutical compositions according to the invention, further comprise one or more drugs selected from an anti-viral agent, anti-fungal agent, anti-cancer agent or an immunostimulating agent.

Pharmaceutical compositions of the present invention can comprise at least one of the compounds of Formulae I through XII disclosed herein. Pharmaceutical compositions according to the present invention can also further comprise other anti-viral agents such as, but not limited to, AZT (zidovudine, RETROVIR®, GlaxoSmithKline), 3TC (lamivudine, EPIVIR®, GlaxoSmithKline), AZT+3TC, (COMBIVIR®, GlaxoSmithKline), AZT+3TC+abacavir (TRIZIVIR®, GlaxoSmithKline), ddI (didanosine, VIDEX®, Bristol-Myers Squibb), ddC (zalcitabine, HIVID®, Hoffmann-La Roche), D4T (stavudine, ZERIT®, Bristol-Myers Squibb), abacavir (ZIAGEN®, GlaxoSmithKline), tenofovir (VIREAD®, Gilead Sciences), nevirapine (VIRAMUNE®, Boehringer Ingelheim), delavirdine (Pfizer), emtricitabine (EMTRIVA®, Gilead Sciences), efavirenz (SUSTIVA®, DuPont Pharmaceuticals), saquinavir (INVIRASE®, FORTOVASE®, Hoffmann-LaRoche), ritonavir (NORVIR®, Abbott Laboratories), indinavir (CRIXIVAN®, Merck and Company), nelfinavir (VIRACEPT®, Pfizer), amprenavir (AGENERASE®, GlaxoSmithKline), adefovir (PREVEON®, HEPSERA®, Gilead Sciences), atazanavir (Bristol-Myers Squibb), fosamprenavir (LEXIVA®, GlaxoSmithKline) and hydroxyurea (HYDREA®, Bristol-Meyers Squibb), or any other antiretroviral drugs or antibodies in combination with each other, or associated with a biologically based therapeutic, such as, for example, gp41-derived peptides enfuvirtide (FUZEON®, Roche and Trimeris) and T-1249, or soluble CD4, antibodies to CD4, and conjugates of CD4 or anti-CD4, or as additionally presented herein.

Additional suitable antiviral agents for optimal use with one of the compounds of Formulae I through XII of the present invention can include, but are not limited to, amphotericin B (FUNGIZONE®); Ampligen (mismatched RNA) developed by Hemispherx Biopharma; ; BETASERON® (β-interferon, Chiron); butylated hydroxytoluene; Carrosyn (polymannoacetate); Castanospermine; Contracan (stearic acid derivative); Creme Pharmatex (containing benzalkonium chloride); 5-unsubstituted derivative of zidovudine; penciclovir (DENAVIR® Novartis); famciclovir (FAMVIR® Novartis); acyclovir (ZOVIRAX® GlaxoSmithKline); cytofovir (VISTIDE® Gilead); ganciclovir (CYTOVENE®, Hoffman LaRoche); dextran sulfate; D-penicillamine (3-mercapto-D-valine); FOSCARNET® (trisodium phosphonoformate; AstraZeneca); fusidic acid; glycyrrhizin (a constituent of licorice root); HPA-23 (ammonium-21-tungsto-9-antimonate); ORNIDYL® (eflornithine; Aventis); nonoxynol; pentamidine isethionate (PENTAM-300); Peptide T (octapeptide sequence; ,Peninsula Laboratories); Phenytoin (Pfizer); INH or isoniazid; ribavirin (VIRAZOLE®, Valeant Pharmaceuticals); rifabutin, ansamycin (MYCOBUTIN® Pfizer); CD4-IgG2 (Progenics Pharmaceuticals) or other CD4-containing or CD4-based molecules; Trimetrexate (Medimmune); suramin and analogues thereof (Bayer); and WELLFERON® (α-interferon, GlaxoSmithKline).

Pharmaceutical compositions of the present invention can also further comprise immunomodulators. Suitable immunomodulators for optional use with a betulinic acid or betulin derivative of the present invention in accordance with the present invention can include, but are not limited to: ABPP (Bropririmine); Ampligen (mismatched RNA) Hemispherx Biopharma; anti-human interferon-α-antibody; ; ascorbic acid and derivatives thereof; interferon-β; Ciamexon; cyclosporin; cimetidine; CL-246,738; colony stimulating factors, including GM-CSF; dinitrochlorobenzene; HE2000 (Hollis-Eden Pharmaceuticals); inteferon-γ; glucan; hyperimmune gamma-globulin (Bayer); immuthiol (sodium diethylthiocarbamate); interleukin-1 (Hoffmann-LaRoche; Amgen), interleukin-2 (IL-2) (Chiron); isoprinosine (inosine pranobex); Krestin ; LC-9018 (Yakult); lentinan (Yamanouchi); LF-1695; methionine-enkephalin; Minophagen C; muramyl tripeptide, MTP-PE; naltrexone (Barr Laboratories); RNA immunomodulator; REMUNE® (Immune Response Corporation); RETICULOSE® (Advanced Viral Research Corporation); shosaikoto; ginseng; thymic humoral factor; Thymopentin; thymosin factor 5; thymosin 1 (ZADAXIN®, SciClone), thymostimulin, TNF (tumor necrosis factor, Genentech), and vitamin preparations.

Pharmaceutical compositions of the present invention can also further comprise anti-cancer therapeutic agents. Suitable anti-cancer therapeutic agents for optional use include an anti-cancer composition effective to inhibit neoplasia comprising a compound, or a pharmaceutically acceptable salt or prodrug of said anti-cancer agent, which can be used for combination therapy include, but are not limited to alkylating agents, such as busulfan, cis-platin, mitomycin C, and carboplatin antimitotic agents, such as colchicine, vinblastine, taxols, such as paclitaxel (TAXOL®, Bristol-Meyers Squibb) docetaxel (TAXOTERE®, Aventis), topo I inhibitors, such as camptothecin, irinotecan and topotecan (HYCAMTIN®, GlaxoSmithKline), topo II inhibitors, such as doxorubicin, daunorubicin and etoposides such as VP16; RNA/DNA antimetabolites, such as 5-azacytidine, 5-fluorouracil and methotrexate, DNA antimetabolites, such as 5-fluoro-2'-deoxyuridine, ara-C, hydroxyurea, thioguanine, and antibodies, such as trastuzumab (HERCEPTIN®, Genentech), and rituximab (RITUXAN®, Genentech and Biogen-Idec), melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen, alanosine, and combinations thereof.

The invention further provides methods for providing antibacterial therapeutics, anti-parasitic therapeutics, and anti-fungal therapeutics, for use in combination with the compounds of the invention and pharmaceutically-acceptable salts thereof. Examples of anti-bacterial therapeutics include compounds such as penicillins, ampicillin, amoxicillin, cyclacillin, epicillin, methicillin, nafcillin, oxacillin, cloxacillin, dicloxacillin, flucloxacillin, carbenicillin, cephalexin, cepharadine, cefadoxil, cefaclor, cefoxitin, cefotaxime, ceftizoxime, cefinenoxine, ceftriaxone, moxalactam, imipenem, clavulanate, timentin, sulbactam, erythromycin, neomycin, gentamycin, streptomycin, metronidazole, chloramphenicol, clindamycin, lincomycin, quinolones, rifampin, sulfonamides, bacitracin, polymyxin B, vancomycin, doxycycline, methacycline, minocycline, tetracycline, amphotericin B, cycloserine, ciprofloxacin, norfloxacin, isoniazid, ethambutol, and nalidixic acid, as well as derivatives and altered forms of each of these compounds.

Examples of anti-parasitic therapeutics include bithionol, diethylcarbamazine citrate, mebendazole, metrifonate, niclosamine, niridazole, oxamniquine and other quinine derivatives, piperazine citrate, praziquantel, pyrantel pamoate and thiabendazole, as well as derivatives and altered forms of each of these compounds.

Examples of anti-fungal therapeutics include amphotericin B, clotrimazole, econazole nitrate, flucytosine, griseofulvin, ketoconazole and miconazole, as well as derivatives and altered forms of each of these compounds. Anti-fungal compounds also include aculeacin A and papulocandin B.

The preferred animal subject of the present invention is a mammal. By the term "mammal" is meant an individual belonging to the class Mammalia. The invention is particularly useful in the treatment of human patients.

The term "treating" means the administering to subjects a compound of Formulae I through XII or a compound identified by one or more assays within the present invention, for purposes which can include prevention, amelioration, or cure of a retroviral-related pathology. Said compounds for treating a subject that are identified by one or more assays within the present inventions are identified as compounds which have the ability to disrupt Gag processing, described herein.

The term "inhibits the interaction" as used herein, means preventing, or reducing the rate of, direct or indirect association of one or more molecules, peptides, proteins, enzymes, or receptors; or preventing or reducing the normal activity of one or more molecules, peptides, proteins, enzymes or receptors.

Medicaments are considered to be provided "in combination" with one another if they are provided to the patient concurrently or if the time between the administration of each medicament is such as to permit an overlap of biological activity.

In one preferred embodiment, at least one compound of Formulae I through XII above comprises a single pharmaceutical composition.

Pharmaceutical compositions for administration according to the present invention can comprise at least one compound of Formulae I through XII above or compounds identified by one or more assays within the present invention. Said compounds for treating a subject that are identified by one or more assays within the present inventions are identified as compounds which have the ability to disrupt Gag processing, described herein. The compounds according to the present invention are further included in a pharmaceutically acceptable form optionally combined with a pharmaceutically acceptable carrier. These compositions can be administered by any means that achieve their intended purposes. Amounts and regimens for the administration of a compound of Formulae I through XII according to the present invention can be determined readily by those with ordinary skill in the clinical art of treating a retroviral pathology.

For example, administration can be by parenteral, such as subcutaneous, intravenous, intramuscular, intraperitoneal, transdermal, transmucosal, ocular, rectal, intravaginal, or buccal routes. Alternatively, or concurrently, administration can be by the oral route. The administration may be as an oral or nasal spray, or topically, such as powders, ointments, drops or a patch. The dosage administered depends upon the age, health and weight of the recipient, type of previous or concurrent treatment, if any, frequency of treatment, and the nature of the effect desired.

Compounds and methods of the invention are useful in additional ways. For example, such compounds may be used prophylatically, to minimize the risk of infection. In another embodiment, a compound may be used to minimize spread of the disease from an infected person.

The invention is also directed to novel methods of treating HIV in an infected individual. In one embodiment, the invention is particularly useful in stimulating an immune response in a person infected with HIV. For example, by allowing noninfectious virus to be released from infected cells, such infected cells continue to expose antigens and may be effectively targeted by the immune system or other therapies directed against such antigens. In another example, by continuing to permit the release of noninfectious virus, an infected individual continues to develop an immune response to said virus without suffering the deleterious effects of such a virus.

The invention is also useful in expanding the scope of treatment, and offers novel means of treating disease in patients in need thereof. In another embodiment, the invention may be practiced in a patient who does not respond to other therapy for reasons other than viral resistance. For example, conventional methods of treating HIV, as known in the art, are associated with deleterious side effects. In one embodiment, the methods and compositions of the invention are useful in treating a patient without a reduction in one or more deleterious side effects. In one embodiment the invention includes a method of treating a patient with a compound that does not have a particular side effect or has less of a particular side effect.

The bioavailability of drugs is also relevant in treatment. In an embodiment, the invention may be practiced such that compounds are more effectively absorbed into infected cells. In one embodiment the invention encompasses improved methods of delivering a drug to a cell infected with HIV.

Compositions within the scope of this invention include all compositions comprising at least one compound of Formulae I through XII above according to the present invention in an amount effective to achieve its intended purpose. While individual needs vary, determination of optimal ranges of effective amounts of each component is within the skill of the art. For example, a dose may comprise 0.0001 mg to 10 g/kg of body weight. Typical dosages comprise about 0.1 to about 100 mg/kg body weight. The preferred dosages comprise about 1 to about 100 mg/kg body weight of the active ingredient. More preferred dosages comprise about 5 to about 50 mg/kg body weight.

Administration of a compound of the present invention can also optionally include previous, concurrent, subsequent or adjunctive therapy using immune system boosters or immunomodulators. In addition to the pharmacologically active compounds, a pharmaceutical composition of the present invention can also contain suitable pharmaceutically acceptable carriers comprising excipients and auxiliaries which facilitate processing of the active compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from about 0.01 to 99 percent, preferably from about 20 to 75 percent of active compound(s), together with the excipient.

Pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture, and processing the mixture of granules, after adding suitable auxiliaries, if desired or necessary, to obtain tablets or dragee cores.

Suitable excipients are, e.g., fillers such as saccharide, for example, lactose or sucrose, mannitol or sorbitol; cellulose preparations and/or calcium phosphates, such as tricalcium phosphate or calcium hydrogen phosphate; as well as binders such as starch paste, using, for example, maize starch, wheat starch, rice starch, potato starch, gelatin, tragacanth, cellulose, methyl cellulose, hydroxypropylmethylcellulose, sodium carboxymethylcellulose, and/or polyvinyl pyrrolidone. If desired, disintegrating agents can be added such as the above-mentioned starches and also carboxymethyl starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions can be used, which can optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl cellulose phthalate are used. Dyestuffs or pigments can be added to the tablets or dragee coatings, for example, for identification or in order to characterize combinations of active compound doses.

Other pharmaceutical preparations which an be used orally include push-fit capsules made of gelatin, as well as soft, sealed capsules made of gelatin and a plasticizer such as glycerol or sorbitol. The push-fit capsules can contain the active compounds in the form of granules which can be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils or liquid paraffin. In addition, stabilizers can be added.

Possible pharmaceutical preparations which can be used rectally include, for example, suppositories which consist of a combination of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts. In addition, suspensions of the active compounds as appropriate oily injection suspensions can be administered. Suitable lipophilic solvents or vehicles include fatty oils, such as sesame oil, or synthetic fatty acid esters, such as ethyl oleate, triglycerides or glycol-400. Aqueous injection suspensions that can contain substances which increase the viscosity of the suspension include, for example, sodium carboxymethyl cellulose, sorbitol, and/or dextran. Optionally, the suspension can also contain stabilizers.

Liquid dosage forms for oral administration include pharmaceutically acceptable emulsions, solutions, suspensions, syrups, and elixirs. In addition to the active compounds, the liquid dosage forms may contain inert diluents commonly used in the art such as, for example, water or other solvents, solubilizing agents and emulsifiers such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils such as cottonseed, groundnut, corn, germ, olive, castor, and sesame oils, glycerol, tetrahydrofurfuryl alcohol, polyethylene glycols and fatty acid esters of sorbitan, and mixtures thereof.

Suspensions, in addition to the active compounds, may contain suspending agents as, for example, ethoxylated isostearyl alcohols, polyoxyethylene sorbitol and sorbitan esters, cellulose, microcrystalline cellulose, aluminum metahydroxide, bentonite, agar-agar, and tragacanth, and combinations thereof.

Pharmaceutical compositions for topical administration include formulations appropriate for administration to the skin, mucosa, surfaces of the lung or eye. Compositions may be prepared as a pressurized or non-pressurized dry powder, liquid or suspension. The active ingredients in non-pressurized powdered formulations may be admixed in a finely divided form in a pharmaceutically-acceptable inert carrier, including but not limited to mannitol, fructose, dextrose, sucrose, lactose, saccharin or other sugars or sweeteners.

The pressurized composition may contain a compressed gas, such as nitrogen, or a liquefied gas propellant. The propellant may also contain a surface-active ingredient, which may be a liquid or solid non-ionic or anionic agent. The anionic agent may be in the form of a sodium salt.

A formulation for use in the eye would comprise a pharmaceutically acceptable ophthalmic carrier, such as an ointment, oils, such as vegetable oils, or an encapsulating material. The regions of the eye to be treated include the corneal region, or internal regions such as the iris, lens, ciliary body, anterior chamber, posterior chamber, aqueous humor, vitreous humor, choroid or retina.

Compositions for rectal administration may be in the form of suppositories. Compositions for use in the vagina may be in the form of suppositories, creams, foams, or in-dwelling vaginal inserts.

The compositions may be administered in the form of liposomes. Liposomes may be made from phospholipids, phosphatidyl cholines (lecithins) administration. Indeed, all three types of formulation can be used simultaneously to achieve systemic administration of the active ingredient.

Suitable formulations for oral administration include hard or soft gelatin capsules, dragees, pills, tablets, including coated tablets, elixirs, suspensions, syrups or inhalations and controlled release forms thereof.

The compounds of Formula I or II above or compounds identified by one or more assays within the present invention and have the ability to disrupt Gag processing, can also be administered in the form of an implant when compounded with a biodegradable slow-release carrier. Alternatively, the compounds of the present invention can be formulated as a transdermal patch for continuous release of the active ingredient.

The following examples are illustrative only and are not intended to limit the scope of the invention as defined by the appended claims. It will be apparent to those skilled in the art that various modifications and variations can be made in the methods of the present invention without departing from the spirit and scope of the invention. Thus, it is intended that the present invention covers the modifications and variations of this invention provided they come within the scope of the appended claims and their equivalents.

EXAMPLES

Example 1

Anti-Viral Activity Against Primary HIV-1 Isolates

A robust virus inhibition assay was used to evaluate the anti-viral activity of DSB against primary HIV-1 isolates propagated in PMBC. Briefly, serial dilutions of DSB were made in medium into 96-well tissue culture plates. 25-250 $TCID_{50}$ of virus and $5\times10^5$ PHA-stimulated PBMCs were added to each well. On days 1, 3 and 5 post-infection, media was removed from each well and replaced with fresh media containing DSB at the appropriate concentration. On day 7 post-infection, culture supernatant was removed from each well for p24 detection of virus replication and 50% inhibitory concentrations ($IC_{50}$) were calculated by standard methods.

Table 5 shows the potent anti-viral activity of DSB against a panel of primary HIV-1 isolates. DSB exhibits levels of activity similar to approved drugs that were tested in parallel. Importantly, the activity of DSB was not restricted by co-receptor usage.

TABLE 5

Inhibitory activity ($IC_{50}$) of DSB and two approved drugs against a panel of primary Clade B HIV-1 isolates. Clinical HIV-1 isolates denoted by * were isolated at Panacos. All other virus isolates were obtained from the NIH AIDS Reference Repository.

| Virus Isolate # | Co-Receptor usage | $IC_{50}$ (nM) | | |
|---|---|---|---|---|
| | | DSB | AZT | Nevirapine |
| BZ167 | X4 | 4.0 | 2.2 | 31.2 |
| 92HT599 | X4 | 9.8 | 5.8 | 25.3 |
| US1 | R5 | 5.6 | 0.9 | 22.1 |
| 19101N* | R5 | 3.8 | 2.4 | 59.4 |
| 3401N* | R5/X4 | 12.0 | 17.5 | 32.1 |
| 92US723 | R5/X4 | 4.6 | 1.2 | 26.8 |
| 22101N* | R5/X4 | 2.6 | 0.9 | 4.9 |
| Mean | | 6.1 | 4.4 | 28.8 |

Note: R5 and X4 refer to the chemokine receptors CCR5 and CXCR4 respectively.

Toxicity of DSB was analyzed by incubating with PHA-stimulated PBMC for 7 days at a range of concentrations, then determining cell viability using the XTT method. The 50% cytotoxic concentration was >30 µM, corresponding to an in vitro therapeutic index of approximately 5000.

Example 2

Anti-Viral Activity of DSB against Drug Resistant HIV-1 Isolates

The activity of DSB was tested against a panel of HIV-1 isolates resistant to approved drugs. These viruses were obtained from the NIH AIDS Research and Reference Reagent Program. Assays were performed using virus propagated in PBMCs with a p24 endpoint (above), or using cell line targets (MT-2 cells) and a cell killing endpoint. The MT-2 assay format was as follows. Serial dilutions of DSB, or each approved drug, were prepared in 96 well plates. To each sample well was added media containing MT-2 cells at $3 \times 10^5$ cells/mL and virus inoculum at a concentration necessary to result in 80% killing of the cell targets at 5 days post-infection (PI). On day 5 post-infection, virus-induced cell killing was determined by the XTT method and the inhibitory activity of the compound was determined.

Table 6 shows the potent anti-viral activity of DSB against a panel of drug-resistant HIV-1 isolates. The results were not significantly different from those obtained with the panel of wild-type isolates (Table 5), demonstrating that DSB retains its activity against virus strains resistant to all of the major classes of approved drugs.

TABLE 6

Inhibitory activity (nM $IC_{50}$) of DSB against a panel of drug resistant HIV-1 isolates. Assays were done in fresh PBMC with a p24 endpoint except for the NNRTI-resistant isolates that were performed in MT-2 cells with a cell viability (XTT) endpoint.
*Fold Resistance.

| Virus Isolate # | Mutation(s) | Co-Receptor usage | $IC_{50}$(nM) | | | |
|---|---|---|---|---|---|---|
| | | | DSB | AZT | Nevirapine | Indinavir |
| | | | NRTI-resistant | | | |
| 1 | K70R T215Y/F | R5/X4 | 4.4 | 86.4 (54X)* | ND | 9.8 |
| 2 | K70R T215Y/F | R5/X4 | 4.2 | 63.4 (40X) | ND | 6.1 |
| | | | NNRTI-resistant | | | |
| 3 | Y181C | X4 | 1.0 | 5.1 | >3800 (>177X) | 2.5 |
| 4 | K103N Y181C | X4 | 1.3 | 2.0 | 2630 (122X) | 4.5 |
| | | | Protease-resistant | | | |
| 5 | V82A | X4 | 5.6 | 13.1 | ND | 39.7 (12X) |
| 6 | I84V | X4 | 5.5 | 14.4 | ND | 32.7 (10X) |
| 7 | L10R/M46I/ L63P/V82T/I 84V | X4 | 12.9 | 3.5 | ND | 72.5 (23X) |

Note: R5 and X4 refer to the chemokine receptors CCR5 and CXCR4 respectively.

Example 3

DSB Inhibits HIV-1 Replication at a Late Step in the Virus Life Cycle

To distinguish the inhibitory activity of DSB against early and late replication targets, a multinuclear activation of a galactosidase indicator (MAGI) assay was used. In this assay, the targets are HeLa cells stably expressing CD4, CXCR4, CCR5 and a reporter construct consisting of the—galactosidase gene (modified to localize to the nucleus) driven by a truncated HIV-1 LTR. Infection of these cells results in expression of Tat that drives activation of the β-galactosidase reporter gene. Expression of β-galactosidase in infected cells is detected using the chromogenic substrate X-gal. As shown in Table 7, the entry inhibitor T-20, the NRTI AZT and the NNRTI nevirapine caused significant reductions in β-galactosidase gene expression in HIV-1 infected MAGI cells due to their ability to disrupt early steps in viral replication that affect Tat protein expression. In contrast, the protease inhibitor indinavir targets a late step in virus replication (following Tat expression) and does not prevent β-galactosidase gene expression in this system. Similar results were obtained with DSB as with indinavir, indicating that DSB blocks virus replication at a time point following the completion of proviral DNA integration and synthesis of the viral transactivating protein (Table 7).

TABLE 7

Effect of DSB and inhibitors of entry (the gp41 peptide T-20), RT (AZT and Nevirapine) and protease (indinavir) on expression of b-galactosidase in HIV-1 infected MAGI cells. The DMSO control contained no drug.

| Inhibitor | DMSO | T-20 | AZT | Nevirapine | Indinavir | DSB |
|---|---|---|---|---|---|---|
| % Decrease (β-galactosidase expression) | 0 | 98 | 82 | 85 | 10 | 12 |

Kanamoto et al. (*Antimicrob. Agents Chemother., April;* 45(4):1225-30, (2002)) have also reported that DSB acts at a late step in HIV replication. However, they reported that the compound inhibits release of virus from chronically-infected cells. In contrast, our data using a variety of experimental systems indicate that DSB does not have a significant effect on virus release (e.g. Example 6).

Example 4

DSB does not Inhibit HIV-1 Protease Activity

It was previously determined that DSB had no effect on HIV-1 protease function using a cell-free fluorometric assay that characterized enzyme activity by following the cleavage of a synthetic peptide substrate. The results of these experiments indicated that at concentrations up to 50 μg/mL that DSB had no effect on protease function. As a result of the observation that DSB blocks virus replication at a late step, studies were also performed using a recombinant form of the Gag protein, which is a more relevant system than the synthetic peptide substrate used in the initial assays. The use of the recombinant Gag protein as substrate resulted in a similar experimental outcome. In these experiments DSB did not disrupt protease-mediated Gag protein processing at concentrations as high as 50 μg/mL. In contrast, as expected, the protease inhibitor indinavir blocked Gag protein processing at 5 μg/mL (FIG. 1).

Example 5

Figure 2:
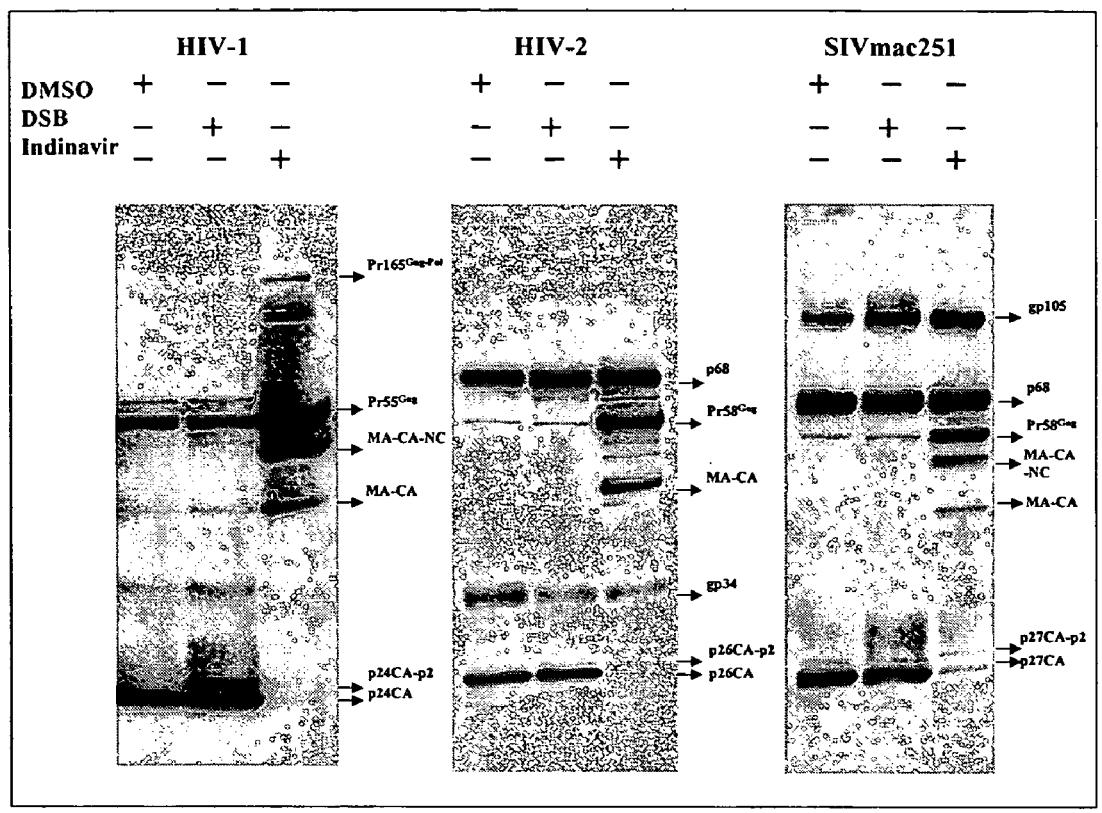
FIG. 2. Western blots of virion-associated Gag derived from chronically infected H9/HIV-1$_{IIIB}$, H9/HIV-2$_{ROD}$, and H9/SIVmac251 in the presence of DSB (1 µg/mL), indinavir (1 µg/mL) or control (DMSO). Gag proteins were visualized using HIV-Ig (HIV-1) or monkey anti-SIVmac251 serum (HIV-2 and SIV; NIH AIDS Research and Reference Reagent Program).

DSB Causes a Defect in the Final Step of Gag Processing (CA-SP1 Cleavage) that has been Associated with Viral Maturation Defects In order to better define DSB's mechanism of action, a detailed examination was undertaken of the virus produced from HIV-1-infected cell lines treated with DSB. Briefly, H9 cells chronically infected with the HIV-1$_{IIIB}$ isolate were treated with DSB at 1 μg/mL for a period of 48 hrs. Indinavir was used as a control. At the 48 hr time-point, spent media was removed and fresh media containing compound was added. At 24, 48 and 72 hrs post fresh compound addition, both cells and supernatant were recovered for analysis. The level of virus in the culture supernatant was determined and western blots were used to characterize viral protein production in both cell-associated and cell-free virus. As observed in previous experiments, DSB did not cause a significant reduction in the amount of virus produced by chronically infected H9 cells, however, there was a defect in Gag processing in both cell-associated and cell-free virus. This defect took the form of an additional band in the western blots corresponding to p25 (FIG. 2). This p25 band results from the incomplete processing of the capsid CA-SP1 precursor. DSB treatment of HIV-2 and SIV chronically infected cell lines exhibited normal Gag processing consistent with the observed lack of antiviral activity against these viruses. The Gag processing defect seen in the presence of DSB is completely distinct from that observed with the protease inhibitor indinavir (FIG. 2). As discussed above, mutations at the p25 to p24 cleavage site that prevent processing are associated with defects in viral maturation and infectivity (Wiegers K. et al., *J. Virol.* 72:2846-54 (1998)).

As previously discussed (C. T. Wild et al., *XIV Int. AIDS Conf.* Barcelona, Spain, Abstract MoPeA3030, (July 2002)), abnormal p25 to p24 processing is also seen in other maturation budding defects. These include mutations in the Gag late domain (PTAP) or defects in TSG-101 mediated viral assembly that disrupt budding (Garrus, J. E et al., *Cell,* 107:55-65, (2001); Demirov, D. G. et al., *J. Virology* 76:105-117, (2002)). However, these mutations cause inhibition of virus release, while DSB treatment does not have a significant effect on virus release. The morphology of these maturation/budding mutants is also quite distinct from that following DSB-treatment (see Example 6).

In addition, mutations that interfere with viral RNA dimerization and lead to the production of immature virus with defective core structures give a similar Gag processing phenotype (Liang, C. et al., *J. Virology,* 73:6147-6151, (1999)). However, in those cases RNA incorporation is inhibited and the morphology of particles released is distinct from those following DSB treatment (see Example 6).

Example 6

DSB Treatment Effects HIV-1 Maturation as Determined by Electron Microscopy (EM)

It has been demonstrated that mutations in HIV-1 Gag that disrupt p25 to p24 processing give rise to non-infectious viral particles characterized by an internal morphology distinct from normal virus (Wiegers K. et al., *J. Virol.* 72:2846-54

(1998)). To determine if virus generated in the presence of DSB exhibited this distinct morphology the following experiment was carried out.

Figure 3:
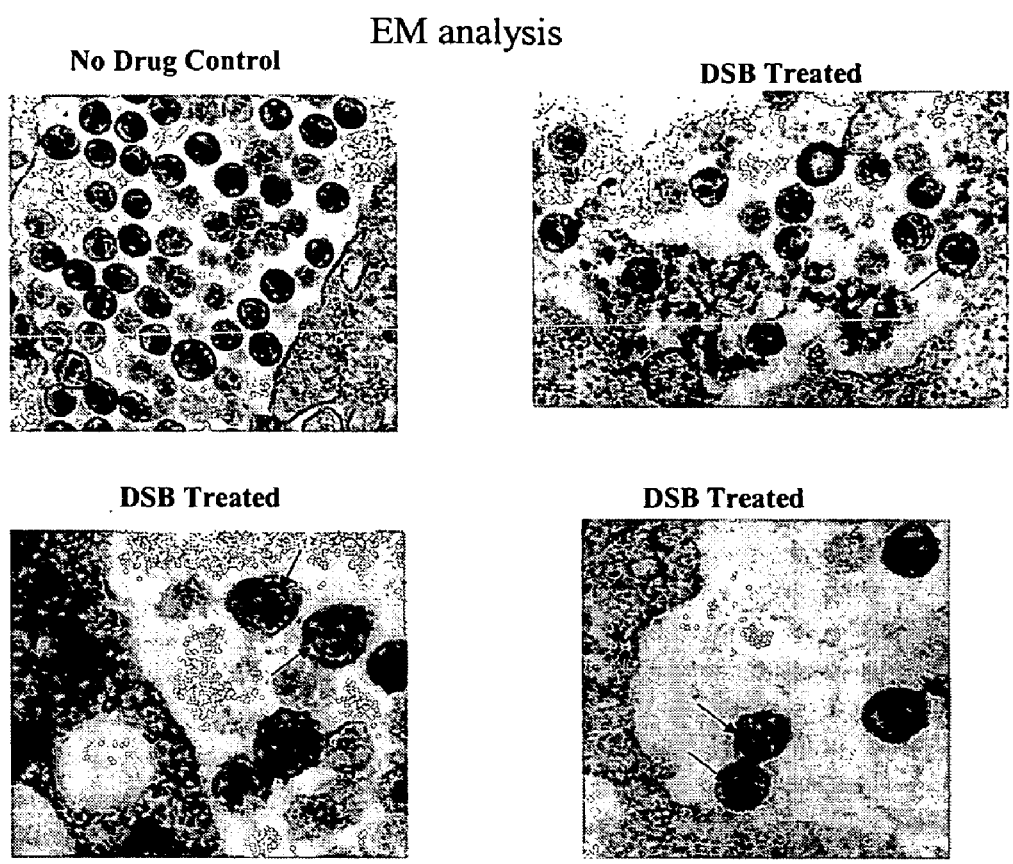
FIG. 3. EM analysis of DSB-treated HIV-1 infected cells. The EM data show two primary differences between DSB-treated and untreated samples. Virions generated in the presence of DSB are characterized by an absence of conical, mature cores. In these samples the cores are uniformly spherical and often acentric. Secondly, many virions display an electron dense layer inside the lipid bilayer but outside the core (indicated with arrows in the DSB-treated sample panels). In the DSB-treated samples no mature viral particles were observed.

HeLa cells were transfected with HIV-1 infectious molecular clone pNL4-3 and treated as described previously with DSB. Following treatment, DSB-treated infected cells were fixed in glutaraldehyde and analyzed by EM. The results of this analysis are shown in FIG. 3.

These results are consistent with a compound that disrupts p25 to p24 processing which generates non-infectious morphologically aberrant viral particles.

3O-(3',3'-dimethylsuccinyl) betulinic acid (DSB) is an example of a compound that disrupts p25 to p24 processing and potently inhibits HIV-1 replication. However, this compound does not inhibit PR activity, and its action is specific for the p25 to p24 processing step, not other steps in Gag processing. Furthermore, DSB treatment results in the aberrant HIV particle morphology described above.

Example 7

In vitro selection for HIV-1 isolates resistant to compounds that disrupt the processing of the viral Gag capsid (CA) protein from the CA-spacer peptide 1 protein precursor.

A series of experiments were performed to select for viruses resistant to inhibition by 3-O-(3',3'-dimethylsuccinyl) betulinic acid (DSB), an inhibitor HIV-1 maturation. For each experiment, either NL4-3 or RF virus isolate was used to infect two cell cultures. Following infection, one culture was maintained in growth medium containing DSB, while the other culture was maintained in parallel in growth medium lacking DSB.

In one experiment, H9 cells that had been infected with RF virus were maintained in the presence or absence of increasing concentrations of DSB (0.05-1.6 µg/ml). The cells were passaged every 2-3 days with the addition of fresh drug. Virus replication was monitored by p24 ELISA every 7 days. At that time, DSB-treated cultures with high levels of p24 were passaged by co-cultivation with fresh uninfected H9 cells at a 1:1 ratio of cells in the presence of 1× or 2× the original concentration of DSB. After 8 weeks of co-cultivation, cell-free virus was collected from the culture containing DSB at a concentration of 1.6 µg/ml and used to infect fresh H9 cells. Every 7 days, virus from cultures containing high levels of p24 was passaged by cell-free infection in the presence of 1× or 2× the original concentration of DSB. After 5 weeks of cell-free passaging, virus from the culture containing 3.2 µg/ml DSB was collected and used to infect MT-2 cells. Virus replication in the MT-2 cells, was monitored by observing syncytia formation microscopically. Every 1-3 days, the cells were washed to remove input virus, and fresh drug was added to the culture under selection. Every 3-4 days, following the emergence of extensive syncytia in the culture under selection, supernatant from each culture was collected and passed through a 0.45 µm filter to remove cell debris. This filtered virus supernatant was then used to infect fresh MT-2 cells in the presence or absence of fresh drug. After 4 rounds of cell-free infection (approximately 2 weeks in culture), with the concentration of drug at 3.2 µg/ml, virus stocks were collected and frozen for further analysis.

In a second experiment, a stock of virus derived from the molecular clone pNL4-3 ($5.7 \times 10^4$ TCID50) was used to infect MT-2 cells ($6 \times 10^6$ cells) and cultures were maintained in the presence or absence of PA-457DSB at a concentration of 1.6 µg/ml. Every 1-3 days, the cells were washed to remove input virus, and fresh drug was added to the culture under selection. Virus replication was monitored by observing syncytia formation microscopically. Every 3-7 days, following the emergence of extensive syncytia in the culture under selection, supernatant from each culture was collected and passed through a 0.45 µm filter to remove cell debris. This filtered virus supernatant was then used to infect fresh MT-2 cells in the presence or absence of fresh drug. After 5 rounds of cell-free infection, and every other round thereafter, the concentration of drug was doubled. After 10 rounds of cell-free infection (approximately 7 weeks in culture), when the concentration of drug reached 12.8 µg/ml, virus stocks were collected and frozen for further analysis.

Example 8

Characterization of HIV-1 isolates selected for resistance to compounds that disrupt the processing of the viral Gag capsid (CA) protein from the CA-spacer peptide 1 protein precursor.

Virus stocks derived as described above were further analyzed both phenotypically and genotypically to characterize the nature of their drug-resistance. The resistance of the viruses to 3-O-(3',3'-dimethylsuccinyl)-betulinic acid (DSB) was determined in virus replication assays. Briefly, the virus stocks were first titered in H9 cells by quantitating the levels of p24 (by ELISA) in cultures 8 days after infection with serial 4-fold dilutions of virus. Virus input was then normalized for a second assay in which each virus is cultured for 8 days in the presence of serial 4-fold dilutions of drug. The IC50 for each virus was determined as the dilution of drug that reduced the p24 endpoint level by 50% as compared to the no-drug control. In these assays, the two independently derived virus stocks resulted in $IC_{50}$ values greater than 2 µM for DSB, as compared to an $IC_{50}$ of 0.02 µM for virus that had been cultured in parallel in the absence of drug. In a subsequent series of experiments, the A364V mutation was engineered into the HIV-1 NL4-3 proviral DNA, which was subsequently transfected into HeLa cells. Resulting virus was collected and used to test the activity of DSB in a viral replication assay, as described above. In these assays, the DSB-resistant virus resulted in an $IC_{50}$ value of 0.1 µM whereas wild-type NL4-3 gave an $IC_{50}$ value of 0.01 µM.

To determine if the resistant viruses were able to escape the CA-SP1 cleavage defect caused by DSB in wild-type virus, stocks of each virus grown in either the presence or absence of drug were analyzed by Western blot. Virus was pelleted through a 20% sucrose cushion from filtered culture supernatants that were collected 60 hr post-infection and 18 hr after the cells had been washed and fresh drug added. The viruses were lysed, and the amount of each virus was normalized by quantitating p24 levels in each sample. Western blot analysis of the viral proteins in each sample demonstrated that the drug-resistant viruses did not contain the CA-SP1 product in the presence of DSB, confirming that these viruses were resistant to the effects of the drug on this cleavage event.

Finally, to identify the genetic determinants of DSB resistance, the entire Gag and PR coding regions of the viral genomes were amplified by high-fidelity RT-PCR for sequencing. The viral RNA was purified from each virus lysate prepared as described above and digested with DNase to remove any contaminating DNA. The RT-PCR products were then gel-purified to remove any non-specific PCR products. Finally, both strands of the resulting DNA fragments were sequenced using overlapping a series of primers. Two amino acid mutations were identified that are independently capable of conferring resistance to DSB, an alanine to valine substitution in the Gag polyprotein at residue 364 in the NL4-3 isolate and at residue 366 in the RF isolate. These are the first and the third residues, respectively, downstream of the CA-SP1 cleavage site (the N-terminus of SP1). Alanine is highly conserved at each of these positions throughout all HIV-1 clades in the database.

Having now fully described this invention, it will be understood to those of ordinary skill in the art that the same can be performed within a wide and equivalent range of conditions, formulations and other parameters without affecting the scope of the invention or any embodiment thereof. All patents, applications and publications cited herein are fully incorporated by reference in their entirety.

What is claimed is:

1. An isolated polypeptide comprising 10 amino acids downstream from the CA-SP1 cleavage site of HIV-1 Gag, wherein said polypeptide contains a substitution of Ala to Val at a position corresponding to residue 364 of HIV-1 Gag (residue 1 of SP1) as compared to the sequence of either the wild type strain NL4-3 or the wild type strain RF.

2. The isolated polypeptide of claim 1, which is encoded by an isolated polynucleotide which hybridizes under stringent conditions to the full length complement of SEQ ID NO: 5, 7, or 10.

3. An isolated polypeptide comprising 10 amino acids downstream from the CA-SP1 cleavage site of HIV-1 Gag, wherein said polypeptide contains a substitution of Ala to Val at a position corresponding to residue 366 of HIV-1 Gag (residue 3 of SP1) as compared to the sequence of either the wild type strain NL4-3 or the wild type strain RF.

4. An isolated polypeptide comprising 10 amino acids from either side of the CA-SP1 cleavage site of HIV-1 Gag, wherein said polypeptide contains a mutation selected from the group consisting of:

(a) a substitution of His to Tyr at a position corresponding to residue 358 of HIV-1 Gag as compared to the sequence of either the wild type strain NL4-3 or the wild type strain RF;

(b) a substitution of Leu to Phe at a position corresponding to residue 363 of HIV-1 Gag (the C-terminal residue of CA) as compared to the sequence of either the wild type strain NL4-3 or the wild type strain RF;

(c) a substitution of Leu to Met at a position corresponding to residue 363 of HIV-1 Gag (the C-terminal residue of CA) as compared to the sequence of either the wild type strain NL4-3 or the wild type strain RF; and (d) a deletion of the residue at a position corresponding to residue 370 of HIV-1 Gag (position 7 of SP1) as compared to the sequence of either the wild type strain NL4-3 or the wild type strain RF.

5. The isolated polypeptide of claim 4, which is encoded by an isolated polynucleotide which hybridizes under stringent conditions to the full length complement of SEQ ID NO: 5, 7, or 10.

6. The isolated polypeptide of claim 4, which is a chimeric or fusion protein.

7. The isolated polypeptide of claim 1, which is produced by a recombinant cell.

8. The isolated polypeptide of claim 1, which is produced by a recombinant HIV-1 virus.

9. The isolated polypeptide of claim 4, which is produced by a recombinant cell.

10. The isolated polypeptide of claim 4, which is produced by a recombinant HIV-1 virus.

11. The isolated polypeptide of claim 4, wherein said polypeptide contains a substitution of His to Tyr at a position corresponding to residue 358 of HIV-1 Gag as compared to the sequence of either the wild type strain NL4-3 or the wild type strain RF.

12. The isolated polypeptide of claim 4, wherein said polypeptide contains a substitution of Leu to Phe at a position corresponding to residue 363 of HIV-1 Gag (the C-terminal residue of CA) as compared to the sequence of either the wild type strain NL4-3 or the wild type strain RF.

13. The isolated polypeptide of claim 4, wherein said polypeptide contains a substitution of Leu to Met at a position corresponding to residue 363 of HIV-1 Gag (the C-terminal residue of CA) as compared to the sequence of either the wild type strain NL4-3 or the wild type strain RF.

14. The isolated polypeptide of claim 4, wherein said polypeptide contains a deletion of the residue at a position corresponding to residue 370 of HIV-1 Gag (position 7 of SP1) as compared to the sequence of either the wild type strain NL4-3 or the wild type strain RF.

15. The isolated polypeptide of claim 11, which is a chimeric or fusion protein.

16. The isolated polypeptide of claim 12, which is a chimeric or fusion protein.

17. The isolated polypeptide of claim 13, which is a chimeric or fusion protein.

18. The isolated polypeptide of claim 14, which is a chimeric or fusion protein.

19. An isolated polypeptide comprising 10 amino acids on either side of the CA-SP1 cleavage site of HIV-1 Gag, wherein said polypeptide contains a substitution of Ala to Val at a position corresponding to residue 366 of HIV-1 Gag (position 3 of SP1) as compared to the sequence of either the wild type strain NL4-3 or the wild type strain RF, and a Ser residue at a position corresponding to residue 357 of HIV-1 Gag as compared to the sequence of the wild type strain RF.

20. An isolated polypeptide comprising 10 amino acids on either side of the CA-SP1 cleavage site of HIV-1 Gag, wherein polypeptide contains a substitution of Ala to Val at a position corresponding to residue 366 of HIV-1 Gag (position 3 of SP1) as compared to the sequence of either the wild type strain NL4-3 or the wild type strain RF, and a substitution of Gly to Ser at a position corresponding to residue 357 of HIV-1 Gag as compared to the sequence of the wild type strain NL4-3.

21. The isolated polypeptide of claim 19, which is encoded by an isolated polynucleotide which hybridizes under stringent conditions to the full length complement of SEQ ID NO: 5, 7, or 10.

22. The isolated polypeptide of claim 19, which is a chimeric or fusion protein.

23. The isolated polypeptide of claim 19, which is produced by a recombinant cell.

24. The isolated polypeptide of claim 19, which is produced by a recombinant HIV-1 virus.

25. The isolated polypeptide of claim 20, which is encoded by an isolated polynucleotide which hybridizes under stringent conditions to the full length complement of SEQ ID NO: 5, 7, or 10.

26. The isolated polypeptide of claim 20, which is a chimeric or fusion protein.

27. The isolated polypeptide of claim 20, which is produced by a recombinant cell.

28. The isolated polypeptide of claim 20, which is produced by a recombinant HIV-1 virus.

29. An isolated polypeptide comprising a peptide consisting of (a) the SP1 region of HIV-1 Gag, or (b) 10 amino acids on either side of the CA-SP1 cleavage site of HIV-1 Gag; wherein said peptide contains a substitution of one amino acid or a deletion of one amino acid, wherein said substitution or said deletion results in a decrease in inhibition of processing of p25 by 3-O-(3',3'-dimethylsuccinyl) betulinic acid (DSB), wherein said polypeptide undergoes processing at the CA-SP1 cleavage site in the absence of DSB, and wherein a virus containing said substitution or said deletion is capable of efficient replication.

30. The isolated polypeptide of claim 29, which is encoded by an isolated polynucleotide which hybridizes under stringent conditions to the full length complement of SEQ ID NO: 5, 7, or 10.

31. The isolated polypeptide of claim 29, which is a chimeric or fusion protein.

32. The isolated polypeptide of claim 29, which is produced by a recombinant cell.

33. The isolated polypeptide of claim 29, which is produced by a recombinant HIV-1 virus.

34. The isolated peptide of claim 3, which is encoded by an isolated polynucleotide which hybridizes under stringent conditions to the full length complement of SEQ ID NO: 5, 7, or 10.

35. The isolated polypeptide of claim 3, which is a chimeric or fusion protein.

36. The isolated polypeptide of claim 3, which is produced by a recombinant cell.

37. The isolated polypeptide of claim 3, which is produced by a recombinant HIV-1 virus.

38. The isolated polypeptide of claim 1, which is a chimeric or fusion protein.

39. The isolated polypeptide of claim 29, which comprises a peptide consisting of (a).

40. The isolated polypeptide of claim 29, which comprises a peptide consisting of (b).

* * * * *

UNITED STATES PATENT AND TRADEMARK OFFICE
CERTIFICATE OF CORRECTION

| | | |
|---|---|---|
| PATENT NO. | : 7,537,765 B2 | Page 1 of 1 |
| APPLICATION NO. | : 10/851637 | |
| DATED | : May 26, 2009 | |
| INVENTOR(S) | : Salzwedel et al. | |

It is certified that error appears in the above-identified patent and that said Letters Patent is hereby corrected as shown below:

On the Cover page, (*) Notice:   Subject to any disclaimer, the term of this patent is extended or adjusted under 35 USC 154(b) by 311 days.

Delete the phrase "by 311 days" and insert -- by 440 days --.

Signed and Sealed this

Tenth Day of August, 2010

David J. Kappos
*Director of the United States Patent and Trademark Office*

```
                         SEQUENCE LISTING

<160> NUMBER OF SEQ ID NOS: 115

<210> SEQ ID NO 1
<211> LENGTH: 14
<212> TYPE: PRT
<213> ORGANISM: HIV-1
<220> FEATURE:
<221> NAME/KEY: MISC_FEATURE
<222> LOCATION: (1)..(1)
<223> OTHER INFORMATION: Xaa can be either Glycine or Serine
<220> FEATURE:
<221> NAME/KEY: MISC_FEATURE
<222> LOCATION: (6)..(6)
<223> OTHER INFORMATION: Xaa can be either Valine or Isoleucine

<400> SEQUENCE: 1

Xaa His Lys Ala Arg Xaa Leu Ala Glu Ala Met Ser Gln Val
1               5                  10

<210> SEQ ID NO 2
<211> LENGTH: 14
<212> TYPE: PRT
<213> ORGANISM: HIV-1 NL4-3

<400> SEQUENCE: 2

Gly His Lys Ala Arg Val Leu Val Glu Ala Met Ser Gln Val
1               5                  10

<210> SEQ ID NO 3
<211> LENGTH: 14
<212> TYPE: PRT
<213> ORGANISM: HIV-1 RF

<400> SEQUENCE: 3

Ser His Lys Ala Arg Ile Leu Ala Glu Val Met Ser Gln Val
1               5                  10

<210> SEQ ID NO 4
<211> LENGTH: 1823
<212> TYPE: DNA
<213> ORGANISM: HIV-1 NL4-3
<220> FEATURE:
<221> NAME/KEY: misc_feature
<222> LOCATION: (1365)..(1365)
<223> OTHER INFORMATION: N can be any nucleotide: a, t, g, c

<400> SEQUENCE: 4
atgggtgcga gagcgtcggt attaagcggg ggagaattag ataaatggga aaaaattcgg      60
ttaaggccag ggggaaagaa acaatataaa ctaaaacata tagtatgggc aagcagggag     120
ctagaacgat tcgcagttaa tcctggcctt ttagagacat cagaaggctg tagacaaata     180
ctgggacagc tacaaccatc ccttcagaca ggatcagaag aacttagatc attatataat     240
acaatagcag tcctctattg tgtgcatcaa aggatagatg taaaagacac caaggaagcc     300
ttagataaga tagaggaaga gcaaaacaaa agtaagaaaa aggcacagca agcagcagct     360
gacacaggaa acaacagcca ggtcagccaa aattacccta tagtgcagaa cctccagggg     420
caaatggtac atcaggccat atcacctaga actttaaatg catgggtaaa agtagtagaa     480
```

```
gagaaggctt tcagcccaga agtaataccc atgttttcag cattatcaga aggagccacc    540
ccacaagatt taaataccat gctaaacaca gtgggggggac atcaagcagc catgcaaatg   600
ttaaaagaga ccatcaatga ggaagctgca gaatgggata gattgcatcc agtgcatgca   660
gggcctattg caccaggcca gatgagagaa ccaaggggaa gtgacatagc aggaactact   720
agtacccttc aggaacaaat aggatggatg acacataatc cacctatccc agtaggagaa   780
atctataaaa gatggataat cctgggatta aataaaatag taagaatgta tagccctacc   840
agcattctgg acataagaca aggaccaaag gaacccttta gagactatgt agaccgattc   900
tataaaactc taagagccga gcaagcttca caagaggtaa aaaattggat gacagaaacc   960
ttgttggtcc aaaatgcgaa cccagattgt aagactattt taaaagcatt gggaccagga  1020
gcgacactag aagaaatgat gacagcatgt cagggagtgg ggggacccgg ccataaagca  1080
agagttttgg ttgaagcaat gagccaagta acaaatccag ctaccataat gatacagaaa  1140
ggcaatttta ggaaccaaag aaagactgtt aagtgtttca attgtggcaa agaagggcac  1200
atagccaaaa attgcagggc ccctaggaaa aagggctgtt ggaaatgtgg aaggaagga   1260 caccaaatga aagattgtac tgagagacag gctaattttt tagggaagat ctggccttcc  1320
cacaagggaa ggccagggaa ttttcttcag agcagaccag agccacagc cccaccagaa   1380 gagagcttca ggtttgggga agagacaaca actccctctc agaagcagga ccgatagac   1440 aaggaactgt atcctttagc ttccctcaga tcactctttg gcagcgaccc ctcgtcacaa  1500
taaagatagg gggcaatta aaggaagctc tattagatac aggagcagat gatacagtat  1560
tagaagaaat gaatttgcca ggaagatgga accaaaaat gataggggga attggaggtt   1620
ttatcaaagt aagacagtat gatcagatac tcatagaaat ctgcggacat aaagctatag  1680
gtacagtatt agtaggacct acacctgtca acataattgg aagaaatctg ttgactcaga  1740
ttggctgcac tttaaattt cccattagtc ctattgagac tgtaccagta aaattaaagc  1800
caggaatgga tggcccaaaa gtt                                            1823

<210> SEQ ID NO 5
<211> LENGTH: 1820
<212> TYPE: DNA
<213> ORGANISM: HIV-1 NL4-3

<400> SEQUENCE: 5
atgggtgcga gagcgtcggt attaagcggg ggagaattag ataaatggga aaaaattcgg    60
ttaaggccag ggggaaagaa acaatataaa ctaaaacata tagtatgggc aagcagggag   120
ctagaacgat tcgcagttaa tcctggcctt ttagagacat cagaaggctg tagacaaata   180
ctgggacagc tacaaccatc ccttcagaca ggatcagaag aacttagatc attatataat   240
acaatagcag tcctctattg tgtgcatcaa aggatagatg taaaagacac caaggaagcc   300
ttagataaga tagaggaaga gcaaaacaaa agtaagaaaa aggcacagca agcagcagct   360
gacacaggaa acaacagcca ggtcagccaa aattacccta gtgtcagaa cctccagggg   420 caaatggtac atcaggccat atcacctaga actttaaatg catgggtaaa agtagtagaa   480
gagaaggctt tcagcccaga agtaataccc atgttttcag cattatcaga aggagccacc   540
ccacaagatt taaataccat gctaaacaca gtgggggggac atcaagcagc catgcaaatg   600
ttaaaagaga ccatcaatga ggaagctgca gaatgggata gattgcatcc agtgcaggca   660
gggcctattg caccaggcca gatgagagaa ccaaggggaa gtgacatagc aggaactact   720
```

```
agtacccttc aggaacaaat aggatggatg acacataatc cacctatccc agtaggagaa      780
atctataaaa gatggataat cctgggatta aataaaatag taagaatgta tagccctacc      840
agcattctgg acataagaca aggaccaaag gaacccttta gagactatgt agaccgattc      900
tataaaactc taagagccga gcaagcttca caagaggtaa aaaattggat gacagaaacc      960
ttgttggtcc aaaatgcgaa cccagattgt aagactattt taaaagcatt gggaccagga     1020
gcgacactag aagaaatgat gacagcatgt cagggagtgg ggggacccgg ccataaagca     1080
agagttttgg ctgaagcaat gagccaagta acaaatccag ctaccataat gatacagaaa     1140
ggcaatttta ggaaccaaag aaagactgtt aagtgtttca attgtggcaa agaagggcac     1200
atagccaaaa attgcagggc ccctaggaaa aagggctgtt ggaaatgtgg aaaggaagga     1260
caccaaatga aagattgtac tgagagacag gctaattttt tagggaagat ctggccttcc     1320
cacaagggaa ggccagggaa ttttcttcag agcagaccag agccaacagc cccaccagaa     1380
gagagcttca ggtttgggga agagacaaca actccctctc agaagcagga gccgatagac     1440
aaggaactgt atcctttagc ttccctcaga tcactctttg gcagcgaccc ctcgtcacaa     1500
taaagatagg ggggcaatta aaggaagctc tattagatac aggagcagat gatacagtat     1560
tagaagaaat gaatttgcca ggaagatgga accaaaaat gataggggga attggaggtt     1620
ttatcaaagt aagacagtat gatcagatac tcatagaaat ctgcggacat aaagctatag     1680
gtacagtatt agtaggacct acacctgtca acataattgg aagaaatctg ttgactcaga     1740
ttggctgcac tttaaatttt cccattagtc ctattgagac tgtaccagta aaattaaagc     1800
caggaatgga tggcccaaag                                                 1820

<210> SEQ ID NO 6
<211> LENGTH: 1982
<212> TYPE: DNA
<213> ORGANISM: HIV-1 RF
<220> FEATURE:
<221> NAME/KEY: misc_feature
<222> LOCATION: (1961)..(1961)
<223> OTHER INFORMATION: n can be any nucleotide: a, t, g, c

<400> SEQUENCE: 6
atgggtgcga gagcgtcagt attaagcggc ggaaaattag acaaatggga aaaaattcgg       60
ttaaggccag ggggaaagaa aagatataag ttaaaacata atatatgggc aagcagggag      120
ctagaacgat tgctgtcaa tcctggcctt ttagagacag cagagggctg tagacaaata      180
ctgggacagc tacaaccagc ccttcagaca ggatcagaag aacttaaatc attatataat      240
gcagtagcaa ccctctattg tgtacatcaa aatatagagg taagagacac caaggaagct      300
ttagacaaga tagaggaaga gcaaaacaaa agtaagaaaa aagcacagca agcagcagct      360
gacacaggaa acggcagcca ggtcagccaa aattacccta gtgtgcagaa ccttcagggg      420
caaatggtac atcaagccat atcacctaga actttaaatg catgggtaaa agtagtagaa      480
gagaaggctt ttagcccaga agtaataccc atgttttcag cattatcaga aggagccacc      540
ccacaagatt taaacaccat gctaaacaca gtggggggac atcaagcagc catgcaaatg      600
ttaaaagaga ctatcaatga ggaagctgca gaatgggata gattgcatcc agtgcaagca      660
gggcctattg caccaggcca gatgagagaa ccaaggggaa gtgacatagc aggaaccact      720
agtacccttc aggaacaaat aggatggatg acaaataatc cacctatccc agtaggagaa      780
atctataaaa ggtggataat tctgggatta aataaaatag taagaatgta tagccccatc      840
agcattctgg acataagaca aggacctaag gaacccttta gagactatgt agaccggttc      900
```

```
tataaaactc taagagccga gcaagcttca caggatgtaa aaaattggat gacagaaacc   960
ttgctggtcc aaaatgcgaa cccagattgt aaaactattt taaaagcatt gggaccagca  1020
gctacactag aagaaatgat gacagcatgt cagggagtag ggggacccag ccataaagca  1080
agaattttgg ctgaagtaat gagccaagta acaaattcag ctaccataat gctgcagaaa  1140
ggtaatttta gggaccaaag aaaaattgtt aagtgtttca actgtggcaa agtagggcac  1200
atagccaaaa attgcagggc ccctaggaaa aagggctgtt ggaaatgtgg aaggaagga  1260
caccaaatga aagattgcac tactgaggga cgacaggcta ttttttagg gaaaatctgg  1320
ccttcccaca agggaaggcc agggaacttt cttcagagca gaccagagcc aacagcccca  1380
ccagaagaga gcttcaggtt tggggaagag acaactccct ctcagaagca ggagaagata  1440
gacaaggaac tgtatccttt agcttccctc aaatcactct ttggcaacga cccatcgtca  1500
cagtaaagat aggggggcaa ttaaaggaag ctctattaga tacaggagca gatgatacag  1560
tattagaaga aatgaatttg ccaggaaaat ggaaaccaaa aatgataggg ggaattggag  1620
gttttatcaa gtaaggcag tatgatcaaa tactcataga aatctgtgga cataaagcta  1680
taggtacagt attagtagga cctacacctg tcaacataat tggaagaaat ctgttgactc  1740
agattggttg cactttaaat tttcccatta gtcctattga aactatacca gtaaaattaa  1800
agccaggaat ggatggccca aaagttaaac aatggccatt gacagaggaa aaaataaaag  1860
cattgataga aatttgtaca gaatggaaa aggaaggaaa aatttcaaaa attgggcctg  1920
aaaatccata caatactcca gtatttgcca taaagaaaaa ngacagtact aaatggagaa  1980
aa                                                                1982

<210> SEQ ID NO 7
<211> LENGTH: 1904
<212> TYPE: DNA
<213> ORGANISM: HIV-1 RF

<400> SEQUENCE: 7
atgggtgcga gagcgtcagt attaagcggc ggaaaattag acaaatggga aaaaattcgg    60
ttaaggccag ggggaaagaa aagatataag ttaaaacata atatgggc aagcagggag   120
ctagaacgat tgctgtgtcaa tcctggcctt ttagagacag cagagggctg tagacaaata   180
ctgggacagc tacaaccagc ccttcagaca ggatcagaag aacttaaatc attatataat   240
gcagtagcaa ccctctattg tgtacatcaa aatatagagg taagagacac caaggaagct   300
ttagacaaga tagaggaaga gcaaaacaaa agtaagaaaa agcacagca agcagcagct   360
gacacaggaa acgcagcca ggtcagccaa aattacccta gtgcagaa ccttcagggg    420
caaatggtac atcaagccat atcacctaga actttaaatg catgggtaaa agtagtagaa   480
gagaaggctt ttagcccaga agtaataccc atgttttcag cattatcaga ggagccacc   540
ccacaagatt taaacaccat gctaaacaca gtggggggac atcaagcagc catgcaaatg   600
ttaaaagaga ctatcaatga ggaagctgca gaatgggata gattgcatcc agtgcaagca   660
gggcctattg caccaggcca gatgagagaa ccaaggggaa gtgacatagc aggaaccact   720
agtacccttc aggaacaaat aggatggatg acaataatc cacctatccc agtaggagaa   780
atctataaaa ggtggataat tctgggatta aataaaatag taagaatgta tagccccatc   840
agcattctgg acataagaca aggacctaag gaaccctta gagactatgt agaccggttc   900
tataaaactc taagagccga gcaagcttca caggatgtaa aaaattggat gacagaaacc   960
```

-continued

```
ttgctggtcc aaaatgcgaa cccagattgt aaaactattt taaaagcatt gggaccagca    1020
gctacactag aagaaatgat gacagcatgt cagggagtag ggggacccag ccataaagca    1080
agaattttgg ctgaagcaat gagccaagta acaaattcag ctaccataat gctgcagaaa    1140
ggtaatttta gggaccaaag aaaaattgtt aagtgtttca actgtggcaa agtagggcac    1200
atagccaaaa attgcagggc ccctaggaaa aagggctgtt ggaaatgtgg aaaggaagga    1260
caccaaatga aagattgcac tactgaggga cgacaggcta attttttagg gaaaatctgg    1320
ccttcccaca agggaaggcc agggaacttt cttcagagca gaccagagcc aacagcccca    1380
ccagaagaga gcttcaggtt tggggaagag acaactccct ctcagaagca ggagaagata    1440
gacaaggaac tgtatccttt agcttccctc aaatcactct ttggcaacga cccatcgtca    1500
cagtaaagat aggggggcaa ttaaaggaag ctctattaga tacaggagca gatgatacag    1560
tattagaaga aatgaatttg ccaggaaaat ggaaaccaaa aatgataggg ggaattggag    1620
gttttatcaa agtaaggcag tatgatcaaa tactcataga aatctgtgga cataaagcta    1680
taggtacagt attagtagga cctacacctg tcaacataat tggaagaaat ctgttgactc    1740
agattggttg cactttaaat tttcccatta gtcctattga aactatacca gtaaaattaa    1800
agccaggaat ggatggccca aaagttaaac aatggccatt gacagaggaa aaaataaaag    1860
cattgataga aatttgtaca gaaatggaaa aggaaggaaa aatt                    1904
```

<210> SEQ ID NO 8
<211> LENGTH: 42
<212> TYPE: DNA
<213> ORGANISM: Artificial Sequence
<220> FEATURE:
<223> OTHER INFORMATION: Region of the CA-SP1 cleavage site from
      DSB-sensitive HIV-1 isolates NL4-3

<400> SEQUENCE: 8

```
ggccataaag caagagtttt ggttgaagca atgagccaag ta                        42
```

<210> SEQ ID NO 9
<211> LENGTH: 42
<212> TYPE: DNA
<213> ORGANISM: Artificial Sequence
<220> FEATURE:
<223> OTHER INFORMATION: Region of the CA-SP1 cleavage site from
      DSB-sensitive HIV-1 isolates RF

<400> SEQUENCE: 9

```
agccataaag caagaatttt ggctgaagta atgagccaag ta                        42
```

<210> SEQ ID NO 10
<211> LENGTH: 42
<212> TYPE: DNA
<213> ORGANISM: Artificial Sequence
<220> FEATURE:
<223> OTHER INFORMATION: Region of the CA-SP1 cleavage site from
      DSB-sensitive HIV-1 isolates NL4-3

<400> SEQUENCE: 10

```
ggccataaag caagagtttt ggctgaagca atgagccaag ta                        42
```

<210> SEQ ID NO 11
<211> LENGTH: 64
<212> TYPE: PRT
<213> ORGANISM: HIV-1 RF

<400> SEQUENCE: 11

```
Lys Asn Trp Met Thr Glu Thr Phe Leu Val Gln Asn Ala Asn Pro Asp
1               5                   10                  15

Cys Lys Thr Ile Leu Lys Ala Leu Gly Pro Ala Ala Thr Leu Glu Glu
                20                  25                  30

Met Met Thr Ala Cys Gln Gly Val Gly Gly Pro Ser His Lys Ala Arg
                35                  40                  45

Ile Leu Ala Glu Ala Met Ser Gln Val Thr Asn Ser Ala Thr Ile Met
        50                  55                  60
```

<210> SEQ ID NO 12
<211> LENGTH: 42
<212> TYPE: DNA
<213> ORGANISM: Artificial Sequence
<220> FEATURE:
<223> OTHER INFORMATION: Region of the CA-SP1 cleavage site from
      DSB-sensitive HIV-1 isolates RF

<400> SEQUENCE: 12
agccataaag caagaatttt ggctgaagca atgagccaag ta                42

<210> SEQ ID NO 13
<211> LENGTH: 64
<212> TYPE: PRT
<213> ORGANISM: HIV-1 NL4-3

<400> SEQUENCE: 13

```
Lys Asn Trp Met Thr Glu Thr Leu Leu Val Gln Asn Ala Asn Pro Asp
1               5                   10                  15

Cys Lys Thr Ile Leu Lys Ala Leu Gly Pro Gly Ala Thr Leu Glu Glu
                20                  25                  30

Met Met Thr Ala Cys Gln Gly Val Gly Gly Pro Gly His Lys Ala Arg
                35                  40                  45

Val Leu Ala Glu Ala Met Ser Gln Val Thr Asn Pro Ala Thr Ile Met
        50                  55                  60
```

<210> SEQ ID NO 14
<211> LENGTH: 24
<212> TYPE: PRT
<213> ORGANISM: SIV mac239

<400> SEQUENCE: 14

```
Gly Gln Lys Ala Arg Leu Met Ala Glu Ala Leu Lys Glu Ala Leu Ala
1               5                   10                  15

Pro Val Pro Ile Pro Phe Ala Ala
                20
```

<210> SEQ ID NO 15
<211> LENGTH: 24
<212> TYPE: PRT
<213> ORGANISM: SIV DD

<400> SEQUENCE: 15

```
Gly Gln Lys Ala Arg Leu Met Ala Glu Ala Met Ser Gln Val Leu Ala
1               5                   10                  15

Pro Val Pro Ile Pro Phe Ala Ala
                20
```

<210> SEQ ID NO 16
<211> LENGTH: 42
<212> TYPE: DNA
<213> ORGANISM: HIV-1 NL4-3
<220> FEATURE:

```
<221> NAME/KEY: CDS
<222> LOCATION: (1)..(42)

<400> SEQUENCE: 16 ggc cat aaa gca aga gtt ttg gct gaa gca atg agc caa gta    42
Gly His Lys Ala Arg Val Leu Ala Glu Ala Met Ser Gln Val
1               5                   10

<210> SEQ ID NO 17
<211> LENGTH: 14
<212> TYPE: PRT
<213> ORGANISM: HIV-1 NL4-3

<400> SEQUENCE: 17

Gly His Lys Ala Arg Val Leu Ala Glu Ala Met Ser Gln Val
1               5                   10

<210> SEQ ID NO 18
<211> LENGTH: 9128
<212> TYPE: DNA
<213> ORGANISM: HIV-1 RF

<400> SEQUENCE: 18
```

| | | |
|---|---|---|
| gagctctctg gctagctagg gaacccactg cttaagcctc aataaagctt gccttgagtg | 60 |
| cttcaagtag tgtgtgcccg tctgttgtgt gactctggta actagagatc cctcagacct | 120 |
| ctttagtcag tgtggaaaat ctctagcagt ggcgcccgaa cagggaccag aaagcgaaag | 180 |
| tagaaccaga ggagatctct cgacgcagga ctcggcttgc tgaagcgcgc gcggcaagag | 240 |
| gcgaggggcg gcgaacggtg agtacgccga aaattttgac tagcggaggc tagaaggaga | 300 |
| gagatgggtg cgagagcgtc agtattaagc ggcggaaaat tagacaaatg gaaaaaatt | 360 |
| cggttaaggc caagggggaaa gaaaagatat aagttaaaac atatagtatg ggcaagcagg | 420 |
| gagctagaac gatttgctgt caatcctagc ctttttagaga cagcagaggg ctgtagacaa | 480 |
| atactgggac agctacaacc agcccttcag acaggatcag aagaacttaa atcattatat | 540 |
| aatgcagtag caaccctcta ttgtgtacat caaaatatag aggtaagaga caccaaggaa | 600 |
| gctttagaca agatagagga gagcaaaac aaaagtaaga aaaagcaca gcaagcagca | 660 |
| gctgacacag aaacggcag ccaggtcagc caaaattacc ctatagtgca gaaccttcag | 720 |
| gggcaaatgg tacatcaagc catatcacct agaactttaa atgcatgggt aaaagtagta | 780 |
| gaagagaagg cttttagccc agaagtaata cccatgtttt cagcattatc agaaggagcc | 840 |
| accccacaag atttaaacac catgctaaac acagtggggg gacatcaagc agccatgcaa | 900 |
| atgttaaaag agactatcaa tgaggaagct gcagaatggg atagattgca tccagtgcat | 960 |
| gcagggccta ttgcaccagg tcagatgaga gaaccaaggg gaagtgacat agcaggaacc | 1020 |
| actagtaccc ttcaggaaca aataggatgg atgacaaata atccacctat cccagtagga | 1080 |
| gaaatctata aaaggtggat aattctggga ttaaataaaa tagtaagaat gtatagccc | 1140 |
| atcagcattc tggacataag acaaggacct aaggaaccct ttagagacta tgtagaccgg | 1200 |
| ttctataaaa ctctaagagc cgagcaagct tcacaggatg taaaaaattg gatgacagaa | 1260 |
| accttcctgg tccaaaatgc gaacccagat tgtaaaacta ttttaaaagc attgggacca | 1320 |
| gcagctacac tagaagaaat gatgacagca tgtcagggag tagggggacc cagccataaa | 1380 |
| gcaagaattt tggctgaagc aatgagccaa gtaacaaatt cagctaccat aatgctgcag | 1440 |
| aaaggtaatt ttagggacca agaaaaaatt gttaagtgtt tcaactgtgg caaagtaggg | 1500 |
| cacatagcca aaaattgcag ggcccctagg aaaaagggct gttggaaatg tggaaaggaa | 1560 |

```
ggacaccaaa tgaaagattg cactaatgag ggacgacagg ctaatttttt agggaaaatc    1620
tggccttccc acaagggaag gccagggaac tttcttcaga gcagaccaga gccaacagcc    1680
ccaccagaag agagcttcag gtttggggaa gagacaactc cctctcagaa gcaggagaag    1740
atagacaagg aactgtatcc tttagcttcc ctcaaatcac tctttggcaa cgacccatcg    1800
tcacagtaaa gataggggggg caattaaagg aagctctatt agatacagga gcagatgata    1860
cagtattaga agaaatgaat ttgccaggaa aatggaaacc aaaaatgata gggggaattg    1920
gaggttttat caaagtgaga cagtatgatc aaatactcat agaaatctgt ggacataaag    1980
ctataggtac agtattagta ggacctacac ctgtcaacat aattggaaga aatctgttga    2040
ctcagattgg ttgcactttaa attttccca ttagtcctat tgaaactgta ccagtaaaat    2100
taaagccagg aatggatggc ccaaaagtta acaatggcc attgacagag gaaaaaataa    2160
aagcattggt agaaatttgt acagaaatgg aaaggaagg aaaaatttcc aaaattgggc    2220
ctgaaaatcc atacaatact ccagtatttg ccataaagaa aaaagacagt actaaatgga    2280
gaaaattagt agatttcaga gaacttaata agagaactca agacttctgg gaagttcagt    2340
taggaatacc acatcctgca gggttaaaaa agaagaaatc agtaacagta ttggatgtgg    2400
gtgatgcata ttttcagtt cccttagata aagagttcag gaagtatact gcatttacca    2460
tacctagtat aaacaatgaa acaccacgga ttagatatca gtacaatgtg cttccacaag    2520
ggtggaaagg atcaccagca atattccaaa gtagtgatgac aaaatctta gagcctttta    2580 aaaaacaaaa tccagaaata gttatctatc aatacatgga tgatttgtat gtaggatctg    2640
atttagaaat agggcagcat agaataaaaa tagaggaact gagagaacat ctgttaaagt    2700
gggggtttac cacaccggac aagaaacatc agaaagaacc tccatttctt tggatgggtt    2760
atgaactcca tcctgataaa tggacagtac agcctatagt gctgccagaa aaagacagct    2820
ggactgtcaa tgacatacag aagttagtgg gaaaattgaa ttgggcaagt cagatttatg    2880
cagggattaa agtaaagcaa ttatgtaaac tccttagggg aaccaaagca ctaacagaag    2940
tagtacaact aacaaaagaa gcagagctag aactggcaga aaatagggag attctaaaag    3000
aaccagtaca tggagtgtat tatgacccat caaaagactt aatagcagaa atacagaagc    3060
aggggcaagg ccaatggaca taccaaattt atcaagagcc atttaaaaac ctgaaaacag    3120
gaaagtatgc aagaatgagg ggtgcccaca ctaatgatgt aaaacaatta acagaggcag    3180
tacaaaaagt agccacagaa agcatagtaa tatgggggaaa gactcctaaa tttaaactac    3240
ccatacaaaa agaaacatgg gaggcatggt ggacagagta ttggcaagcc acctggattc    3300
ctgagtggga gtttgtcaat acccctccct tagtaaaatt gtggtaccag ttagaaaaag    3360
aacccataat aggagcagaa actttctatg tagatggggc agctaataga gagactaaat    3420
taggaaaagc aggatatgtt actgacagag gaagacaaaa agttgtctcc ctaactgaca    3480
caacaaatca gaagactgag ttacaagcaa ttcatctagc tttgcaggat tcgggattag    3540
aagtaaacat agtaacagac tcacaatatg cattgggaat cattcaagca caaccagata    3600
aaagtgaatc agagttagtc agtcagataa tagagcagtt aataaaaaag gaaaaggtct    3660
acctggcatg ggtaccagca cacaaaggga ttggaggaaa tgaacaagta gatgattag    3720 tcagtactgg aatcaggaaa gtactatttt tggatggaat agataaggcc caagatgaac    3780
atgagaaata tcacagtaat tggagagcaa tggctagtga ttttaacctg ccacctgtag    3840
tagcaaaaga aatagtagcc agctgtgata atgtcagct aaaaggagaa gccatgcatg    3900
```

```
gacaagtaga ttgtagtcca ggaatatggc aactagattg tacacatcta gaaggaaaaa    3960
ttatcctggt agcagttcat gtagccagtg gctatataga agcagaagtt attccagcag    4020
aaacaggaca ggaaacagca tactttatct taaaattagc aggaagatgg ccagtaaaag    4080
taatacatac agacaatggc agcaatttca ccagtactac agttaaggcc gcctgttggt    4140
gggcagggat caagcaggaa tttggcattc cctacaatcc ccaaagtcaa ggagtagtag    4200
aatctatgaa taaacaatta aagcaaatta taggacaggt aagagatcag gctgaacatc    4260
ttaagacagc agtacaaatg gcagtattca tccacaattt taaaagaaaa ggggggattg    4320
gggggtacag tgcagggaa agaatagtag acataatagc aacagacata caaactaaag    4380
aactacaaaa acaaattaca aaaattcaaa attttcgggt ttattacagg gacagcagag    4440
atccactttg gaaaggacac gcaaagcttc tctggaaagg tgaagggca gtagtaatac    4500 aagataatag tgacataaaa gtagtgccaa gaagaaaagc aaagatcatt agggattatg    4560
gaaaacagat ggcaggtgat gattgtgtgg caagtagaca ggatgaggat tagaacatgg    4620
aaaagtttag taaaacacca tatgtatatt tcaaggaaag ctaagggatg gttttataga    4680
catcactatg aaagcactca tccaagaata agttcagagg tacacatccc accagggga t    4740 gaaaggttgg taataacaac atattggggt ctgcatacag gagaaagaga ctggcatttg    4800 ggtcaggag tctccataga atggaggaaa aggagatata gcacacaagt agaccctgac    4860
ctagcagacc aactaattca cctgtactat tttgattgtt tttcagaatc tgctataaga    4920
aagccatcat taggacatat agttagtcct aggtgtgaat atcaagcagg acataacaag    4980
gtaggatctc tacagtacct ggcactagca gcattaacaa caccaaaaaa gataaagcca    5040
cctttgccta gtgttaagaa actgacagag gatagatgga acaagcccca gaagaccaag    5100
ggccacagag ggagccatac aatgaatgga cactagagct tttagaggag cttaagagtg    5160
aagctgtcag acattttcct aggctatggc tccatagctt aggacaacat atctatgaaa    5220
cttatgggga tacatgggca ggagtggaag ctataataag aattctgcaa caactgctgt    5280
ttattcattt cagaattggg tgtcaacata gcagaatagg cattactcga caaagaagag    5340
caagaaatgg agccagtaga tcctagacta gagccctgga agcatccagg aagtcagcct    5400
aagactgctt gtaacaattg ctattgtaaa aagtgttgct atcattgcca gtttgcttc    5460 ttaacaaaag gcttaggcat ctcctatggc aggaagaaga ggagacagcg acgaggacct    5520
cctcaaggca gtcagactca tcaagtctct ttatcaaagc agtaagtagt atatgtaatg    5580
caatctttag aaatattagc aatagtagca ttagtagtag cagcaatact agcaatagtt    5640
gtgtggacca tagttggcat agaaattagg aaaacattaa ggcaaaaaaa aaaatagaca    5700
ggttaattga tagaataaga gaaagagcag aagacagtgg caatgagagt gatggagatg    5760
aggaagaatt gtcagcactt gtggaaatgg ggcaccatgc tccttgggat gttgatgatc    5820
tgtagtgctg cagaggactt gtgggtcaca gtctattatg gggtacctgt gtggaaagaa    5880
gcaaccacca ctctattttg tgcatcagaa gctaaagcat ataaaacaga ggtacataat    5940
gtctgggcca acatgcttg tgtacctaca gaccccaacc cacaagaagt actattggaa    6000
aatgtgacag aaaattttaa catgtggaaa ataacatgg tagaacagat gcatgaggat    6060
ataatcagtt tatgggatca aagcctaaag ccatgtgtaa aattaacccc actctgtgtt    6120
actttaaatt gcactgatgc taacttgaat ggtactaatg tcactagtag tagcggggga    6180
acaatgatga gaacggaga aataaaaaac tgctcttttcc aagttaccac aagtagaaga    6240
gataagacgc agaaaaaata tgcacttttt tataaacttg atgtggtacc aatagagaag    6300
```

```
ggtaatatta gccctaagaa taatactagc aataatacta gctatggtaa ctatacattg    6360
atacattgta attcctcagt cattacacag gcctgtccaa aggtatcctt tgagccaatt    6420
cccatacatt attgcacccc ggctggtttt gcgattctaa agtgtaatga taagaagttc    6480
aatggaacag gaccatgtaa aaatgtcagc acagtacaat gtacacatgg aattaggcca    6540
gtagtgtcaa ctcaactgct gttaaatggc agtctagcag aagaagaggt agtaattaga    6600
tctgaaaatt tcacggacaa tgttaaaacc ataatagtac agctgaatgc atctgtacaa    6660
attaattgta caagacccaa caacaataca agaaaaagta taactaaggg accagggaga    6720
gtaatttatg caacaggaca aataatagga gatataagaa aagcacattg taaccttagt    6780
agagcacaat ggaataacac tttaaaacag gtagttacaa aattaagaga acaatttgac    6840
aataaaacaa tagtctttac gtcatcctca ggaggggacc cagaaattgt acttcacagt    6900
tttaattgtg gaggggaatt tttctactgt aatacaacac aactgtttaa tagtacttgg    6960
aatagtactg aagggtcaaa taacactgga ggaaatgaca caatcacact cccatgcaga    7020
ataaaacaaa ttgtaaacat gtggcaggaa gtaggaaaag caatgtatgc ccctcccatc    7080
agtggacaaa ttaaatgtat atcaaatatt acagggctac tattaacaag agatgggggt    7140
gaagatacaa ctaatactac agagatcttc agacttggag gaggaaatat gagggacaat    7200
tggagaagtg aattatataa atataaagtg gtaagaattg agccattagg agtggcaccc    7260
actagggcaa agagaagagt ggtgcaaaga gaaaaaagag cagtgggaac aataggagct    7320
atgttccttg ggttcttggg agcagcagga agcactatgg gcgcaggctc aataacgcta    7380
acggtacagg ccagacactt attgtctggt atagtgcaac agcaaaacaa tttgctgagg    7440
gctattgagg cgcaacagca tctgttgcaa ctcacggtct ggggcatcaa acagctccag    7500
gcaagagtcc tggctgtgga agataccta agggatcaac agctcctagg aatttgggga    7560
tgctctggaa aactcatttg caccactact gtgccttgga atgctagttg gagtaataaa    7620
tctctgaata tgatttggaa taacatgacc tggatgcagt gggaaagaga aattgacaat    7680
tacacaggca taatatacaa cttacttgaa gaatcgcaga accagcaaga aaagaatgaa    7740
caagaattat tggaattgga taaatgggca aatttgtgga attggtttga cataacacaa    7800
tggctgtggt atataagaat attcataatg atagtaggag gcttgtagg tctaaaaata    7860 gttttttctg tgctttctat agtgaataga gttaggcagg gatactcacc attatcattt    7920
cagacccacc tcccagcccc gaggggaccc gacaggcccg aaggaatcga aggagaaggt    7980
ggagagagag acagagacag atccggcggt gcagtgaatg gattcttgac acttatctgg    8040
gacgatctgt ggaccctgtg cagcttcagc taccaccgct tgagagactt actcttgata    8100
gtagtgagga ttgtggaact tctgggacgc aggggtggg aagccctcaa gtattggtgg    8160
aatctcctgc agtattggag tcaggagcta aagaatagtg ctgttagctt gcttaatacc    8220
acagcaatag cagtagctga agggacagat aggattatag aagtagcaca aagaattctt    8280
agagcttttc ttcacatacc tagaagaata agacagggct tagaaagggc tttgctgtaa    8340
aatgggtggc aagtggtcaa aaagtaagat gggtggatgg cctgctgtaa gggaaagaat    8400
gcaaaaagct gagccagcag cagatggggt gggagcagca tctcgagacc tggagaaaca    8460
tggaacaatc acaagtagca atacagcagc taataatgct gcttgcacct ggctagaagc    8520
acaagaggat gaggatgagg aggtgggttt tccagtcaga cctcaggtac ctttaaggcc    8580
tatgactttc aaggcagctg tagatcttag ccacttttta aagaaaaagg ggggactgga    8640
```

```
tgggctagtg ttctcccaga aaagacaaga tatccttgat ctgtgggttt accacacaca    8700
aggctacttc cctgactggc agaactacac accagggcca gggaccagat atccactgac    8760
ctttggatgg tgcttcaagc tagtaccagt tgagccagat aaggtagaag aggccactga    8820
aggagagaac aacagcttgt tacaccctat atgcctgcat gggatggatg acccagagaa    8880
agaagtgtta gtgtggaagt ttgacagccg cctcgcattt catcacgtcg cccgagagaa    8940
gcatccggag tactacaaag actgctgaca tcgagttttc tacaagggac tttccgctgg    9000
ggactttcca ggaggtgtg gcctgggcgg gactggggag tggcgagccc tcagatgctg    9060
catataagca gctgcttttt gcctgtactg ggtctctctg gttagaccag atctgagctt    9120
gggagctc                                                             9128
```

<210> SEQ ID NO 19
<211> LENGTH: 14824
<212> TYPE: DNA
<213> ORGANISM: HIV-1 NL4-3

<400> SEQUENCE: 19

```
tggaagggct aatttggtcc caaaaaagac aagagatcct tgatctgtgg atctaccaca      60
cacaaggcta cttccctgat tggcagaact acacaccagg gccagggatc agatatccac     120
tgacctttgg atggtgcttc aagttagtac cagttgaacc agagcaagta gaagaggcca     180
ataaggagaa gaacagcttg ttacacccta tgagccagca tgggatggag gacccggaga    240 gggagaagt attagtgtgg aagtttgaca gcctcctagc atttcgtcac atggcccgag     300
agctgcatcc ggagtactac aaagactgct gacatcgagc ttctacaag gactttccg     360 ctggggactt ccagggagg tgtggcctgg gcgggactgg ggagtggcga gccctcagat     420
gctacatata agcagctgct ttttgcctgt actgggtctc tctggttaga ccagatctga     480
gcctgggagc tctctggcta actagggaac ccactgctta agcctcaata aagcttgcct     540
tgagtgctca agtagtgtg tgcccgtctg ttgtgtgact ctggtaacta gagatccctc      600 agacccttt agtcagtgtg aaaatctct agcagtggcg cccgaacagg acttgaaag      660 cgaaagtaaa gccagaggag atctctcgac gcaggactcg gcttgctgaa gcgcgcacgg     720
caagaggcga gggcggcga ctggtgagta cgccaaaaat tttgactagc ggaggctaga     780
aggagagaga tgggtgcgag agcgtcggta ttaagcgggg gagaattaga taaatgggaa     840
aaaattcggt taaggccagg gggaaagaaa caatataaac taaaacatat agtatgggca     900
agcagggagc tagaacgatt cgcagttaat cctggccttt tagagacatc agaaggctgt     960
agacaaatac tgggacagct acaaccatcc cttcagacag gatcagaaga acttagatca    1020
ttatataata caatagcagt cctctattgt gtgcatcaaa ggatagatgt aaaagacacc    1080
aaggaagcct tagataagat agaggaagag caaaacaaaa gtaagaaaaa ggcacagcaa    1140
gcagcagctg acacaggaaa caacagccag gtcagccaaa attaccctat agtgcagaac    1200 ctccagggc aaatggtaca tcaggccata tcacctagaa ctttaaatgc atgggtaaaa    1260
gtagtagaag agaaggcttt cagcccagaa gtaataccca tgttttcagc attatcagaa    1320
ggagccaccc cacaagattt aaataccatg ctaaacacag tggggggaca tcaagcagcc    1380
atgcaaatgt taaaagagac catcaatgag gaagctgcag aatgggatag attgcatcca    1440
gtgcatgcag gcctattgc accaggccag atgagagaac caaggggaag tgacatagca    1500
ggaactacta gtacccttca ggaacaaata ggatggatga cacataatcc acctatccca    1560
gtaggagaaa tctataaaag atggataatc ctgggattaa ataaaatagt aagaatgtat    1620
```

```
agccctacca gcattctgga cataagacaa ggaccaaagg aacccttag agactatgta    1680 gaccgattct ataaaactct aagagccgag caagcttcac aagaggtaaa aaattggatg    1740
acagaaacct tgttggtcca aaatgcgaac ccagattgta agactatttt aaaagcattg    1800
ggaccaggag cgacactaga agaaatgatg acagcatgtc agggagtggg gggacccggc    1860
cataaagcaa gagttttggc tgaagcaatg agccaagtaa caaatccagc taccataatg    1920
atacagaaag gcaattttag gaaccaaaga aagactgtta agtgtttcaa ttgtggcaaa    1980
gaagggcaca tagccaaaaa ttgcagggcc cctaggaaaa agggctgttg gaaatgtgga    2040
aaggaaggac accaaatgaa agattgtact gagagacagg ctaattttt agggaagatc    2100 tggccttccc acaagggaag gccagggaat tttcttcaga gcagaccaga gccaacagcc    2160
ccaccagaag agagcttcag gtttgggaa gagacaacaa ctccctctca gaagcaggag    2220
ccgatagaca aggaactgta tcctttagct tccctcagat cactctttgg cagcgacccc    2280
tcgtcacaat aaagataggg gggcaattaa aggaagctct attagataca ggagcagatg    2340
atacagtatt agaagaaatg aatttgccag gaagatggaa accaaaaatg ataggggaa    2400 ttggaggttt tatcaaagta agacagtatg atcagatact catagaaatc tgcggacata    2460
aagctatagg tacagtatta gtaggaccta cacctgtcaa cataattgga agaaatctgt    2520
tgactcagat tggctgcact ttaaattttc ccattagtcc tattgagact gtaccagtaa    2580
aattaaagcc aggaatggat ggcccaaaag ttaacaatg gccattgaca gaagaaaaaa    2640
taaaagcatt agtagaaatt tgtacagaaa tggaaaagga aggaaaaatt tcaaaaattg    2700
ggcctgaaaa tccatacaat actccagtat ttgccataaa gaaaaagac agtactaaat    2760 ggagaaaatt agtagatttc agagaactta ataagagaac tcaagatttc tgggaagttc    2820
aattaggaat accacatcct gcagggttaa aacagaaaaa atcagtaaca gtactggatg    2880
tgggcgatgc atatttttca gttcccttag ataaagactt caggaagtat actgcattta    2940
ccatacctag tataaacaat gagacaccag ggattagata tcagtacaat gtgcttccac    3000
agggatggaa aggatcacca gcaatattcc agtgtagcat gacaaaaatc ttagagcctt    3060
ttagaaaaca aaatccagac atagtcatct atcaatacat ggatgatttg tatgtaggat    3120
ctgacttaga aatagggcag catagaacaa aaatagagga actgagacaa catctgttga    3180
ggtggggatt taccacacca gacaaaaaac atcagaaaga acctccattc ctttggatgg    3240
gttatgaact ccatcctgat aaatggacag tacagcctat agtgctgcca gaaaaggaca    3300
gctggactgt caatgacata cagaaattag tgggaaaatt gaattgggca agtcagattt    3360
atgcagggat taaagtaagg caattatgta aacttcttag gggaaccaaa gcactaacag    3420
aagtagtacc actaacagaa gaagcagagc tagaactggc agaaaacagg gagattctaa    3480
aagaaccggt acatggagtg tattatgacc catcaaaaga cttaatagca gaaatacaga    3540
agcaggggca aggccaatgg acatatcaaa tttatcaaga gccatttaaa aatctgaaaa    3600
caggaaaata tgcaagaatg aagggtgccc acactaatga tgtaaaacaa ttaacagagg    3660
cagtacaaaa aatagccaca gaaagcatag taatatgggg aaagactcct aaatttaaat    3720
tacccataca aaaggaaaca tgggaagcat ggtggacaga gtattggcaa gccacctgga    3780
ttcctgagtg ggagtttgtc aatacccctc ccttagtgaa gttatggtac cagttagaga    3840
aagaacccat aataggagca gaaacttct atgtagatgg ggcagccaat agggaaacta    3900
aattaggaaa agcaggatat gtaactgaca gaggaagaca aaaagttgtc cccctaacgg    3960
```

```
acacaacaaa tcagaagact gagttacaag caattcatct agctttgcag gattcgggat    4020
tagaagtaaa catagtgaca gactcacaat atgcattggg aatcattcaa gcacaaccag    4080
ataagagtga atcagagtta gtcagtcaaa taatagagca gttaataaaa aaggaaaaag    4140
tctacctggc atgggtacca gcacacaaag gaattggagg aaatgaacaa gtagatgggt    4200
tggtcagtgc tggaatcagg aaagtactat ttttagatgg aatagataag gcccaagaag    4260
aacatgagaa atatcacagt aattggagag caatggctag tgattttaac ctaccacctg    4320
tagtagcaaa agaaatagta gccagctgtg ataaatgtca gctaaaaggg gaagccatgc    4380
atggacaagt agactgtagc ccaggaatat ggcagctaga ttgtacacat ttagaaggaa    4440
aagttatctt ggtagcagtt catgtagcca gtggatatat agaagcagaa gtaattccag    4500
cagagacagg gcaagaaaca gcatacttcc tcttaaaatt agcaggaaga tggccagtaa    4560
aaacagtaca tacagacaat ggcagcaatt tcaccagtac tacagttaag gccgcctgtt    4620
ggtgggcggg gatcaagcag gaatttggca ttccctacaa tccccaaagt caaggagtaa    4680
tagaatctat gaataaagaa ttaaagaaaa ttataggaca ggtaagagat caggctgaac    4740
atcttaagac agcagtacaa atggcagtat tcatccacaa ttttaaaaga aaaggggggga    4800 ttggggggta cagtgcaggg gaaagaatag tagacataat agcaacagac atacaaacta    4860
aagaattaca aaaacaaatt acaaaaattc aaaattttcg ggtttattac agggacagca    4920
gagatccagt ttggaaagga ccagcaaagc tcctctggaa aggtgaaggg gcagtagtaa    4980
tacaagataa tagtgacata aaagtagtgc caagaagaaa agcaaagatc atcagggatt    5040
atggaaaaca gatggcaggt gatgattgtg tggcaagtag acaggatgag gattaacaca    5100
tggaaaagat tagtaaaaca ccatatgtat atttcaagga aagctaagga ctggttttat    5160
agacatcact atgaaagtac taatccaaaa ataagttcag aagtacacat cccactaggg    5220
gatgctaaat tagtaataac aacatattgg ggtctgcata caggagaaag agactggcat    5280
ttgggtcagg gagtctccat agaatggagg aaaaagagat atagcacaca agtagaccct    5340
gacctagcag accaactaat tcatctgcac tattttgatt gtttttcaga atctgctata    5400
agaaatacca tattaggacg tatagttagt cctaggtgtg aatatcaagc aggacataac    5460
aaggtaggat ctctacagta cttggcacta gcagcattaa taaaaccaaa acagataaag    5520
ccacctttgc ctagtgttag gaaactgaca gaggacagat ggaacaagcc ccagaagacc    5580
aagggccaca gagggagcca tacaatgaat ggacactaga gcttttagag gaacttaaga    5640
gtgaagctgt tagacatttt cctaggatat ggctccataa cttaggacaa catatctatg    5700
aaacttacgg ggatacttgg gcaggagtgg aagccataat aagaattctg caacaactgc    5760
tgtttatcca tttcagaatt gggtgtcgac atagcagaat aggcgttact cgacagagga    5820
gagcaagaaa tggagccagt agatcctaga ctagagccct ggaagcatcc aggaagtcag    5880
cctaaaactg cttgtaccaa ttgctattgt aaaaagtgtt gctttcattg ccaagtttgt    5940
ttcatgacaa aagccttagg catctcctat ggcaggaaga agcggagaca gcgacgaaga    6000
gctcatcaga acagtcagac tcatcaagct tctctatcaa gcagtaagt agtacatgta    6060 atgcaaccta taatagtagc aatagtagca ttagtagtag caataataat agcaatagtt    6120
gtgtggtcca tagtaatcat agaatatagg aaaatattaa gacaaagaaa atagacagg    6180 ttaattgata gactaataga aagagcagaa gacagtggca atgagagtga aggagaagta    6240
tcagcacttg tggagatggg ggtggaaatg gggcaccatg ctccttggga tattgatgat    6300
ctgtagtgct acagaaaaat tgtgggtcac agtctattat ggggtacctg tgtggaagga    6360
```

```
agcaaccacc actctatttt gtgcatcaga tgctaaagca tatgatacag aggtacataa    6420
tgtttgggcc acacatgcct gtgtacccac agaccccaac ccacaagaag tagtattggt    6480
aaatgtgaca gaaaatttta acatgtggaa aaatgacatg gtagaacaga tgcatgagga    6540
tataatcagt ttatgggatc aaagcctaaa gccatgtgta aaattaaccc cactctgtgt    6600
tagtttaaag tgcactgatt tgaagaatga tactaatacc aatagtagta gcgggagaat    6660
gataatggag aaaggagaga taaaaactg ctctttcaat atcagcacaa gcataagaga    6720
taaggtgcag aaagaatatg cattcttttta taaacttgat atagtaccaa tagataatac    6780
cagctatagg ttgataagtt gtaacacctc agtcattaca caggcctgtc caaaggtatc    6840
ctttgagcca attcccatac attattgtgc cccggctggt tttgcgattc taaaatgtaa    6900
taataagacg ttcaatggaa caggaccatg tacaaatgtc agcacagtac aatgtacaca    6960
tggaatcagg ccagtagtat caactcaact gctgttaaat ggcagtctag cagaagaaga    7020
tgtagtaatt agatctgcca atttcacaga caatgctaaa accataatag tacagctgaa    7080
cacatctgta gaattaattt gtacaagacc caacaacaat acaagaaaaa gtatccgtat    7140
ccagagggga ccagggagag catttgttac aataggaaaa ataggaaata tgagacaagc    7200
acattgtaac attagtagag caaaatggaa tgccactttta aaacagatag ctagcaaatt    7260
aagagaacaa tttggaaata taaaacaat aatctttaag caatcctcag gaggggaccc    7320
agaaattgta acgcacagtt ttaattgtgg aggggaattt ttctactgta attcaacaca    7380
actgtttaat agtacttggt ttaatagtac ttggagtact gaagggtcaa ataacactga    7440
aggaagtgac acaatcacac tcccatgcag aataaaacaa tttataaaca tgtggcagga    7500
agtaggaaaa gcaatgtatg cccctcccat cagtggacaa attagatgtt catcaaatat    7560
tactgggctg ctattaacaa gagatggtgg taataacaac aatgggtccg agatcttcag    7620
acctggagga ggcgatatga gggacaattg gagaagtgaa ttatataaat ataaagtagt    7680
aaaaattgaa ccattaggag tagcacccac caaggcaaag agaagagtgg tgcagagaga    7740
aaaaagagca gtgggaatag gagctttgtt ccttgggttc ttgggagcag caggaagcac    7800
tatgggctgc acgtcaatga cgctgacggt acaggccaga caattattgt ctgatatagt    7860
gcagcagcag aacaatttgc tgagggctat tgaggcgcaa cagcatctgt tgcaactcac    7920
agtctggggc atcaaacagc tccaggcaag aatcctggct gtggaaagat acctaaagga    7980
tcaacagctc ctggggattt ggggttgctc tggaaaactc atttgcacca ctgctgtgcc    8040
ttggaatgct agttggagta ataaatctct ggaacagatt tggaataaca tgacctggat    8100
ggagtgggac agagaaatta acaattacac aagcttaata cactccttaa ttgaagaatc    8160
gcaaaaccag caagaaaaga tgaacaaga attattggaa ttagataaat gggcaagttt    8220
gtggaattgg tttaacataa caaattggct gtggtatata aaattattca taatgatagt    8280
aggaggcttg gtaggtttaa gaatagtttt tgctgtactt tctatagtga atagagttag    8340
gcagggatat tcaccattat cgtttcagac ccacctccca atcccgaggg gacccgacag    8400
gcccgaagga atagaagaag aaggtggaga gagacaga acagatcca ttcgattagt    8460 gaacggatcc ttagcactta tctgggacga tctgcggagc ctgtgcctct tcagctacca    8520
ccgcttgaga gacttactct tgattgtaac gaggattgtg gaacttctgg gacgcagggg    8580
gtgggaagcc ctcaaatatt ggtggaatct cctacagtat tggagtcagg aactaaagaa    8640
tagtgctgtt aacttgctca atgccacagc catagcagta gctgagggga cagataggt    8700
```

```
tatagaagta ttacaagcag cttatagagc tattcgccac atacctagaa gaataagaca   8760
gggcttggaa aggattttgc tataagatgg gtggcaagtg gtcaaaaagt agtgtgattg   8820
gatggcctgc tgtaagggaa agaatgagac gagctgagcc agcagcagat ggggtgggag   8880
cagtatctcg agacctagaa aaacatggag caatcacaag tagcaataca gcagctaaca   8940
atgctgcttg tgcctggcta gaagcacaag aggaggaaga ggtgggtttt ccagtcacac   9000
ctcaggtacc tttaagacca atgacttaca aggcagctgt agatcttagc cacttttaa    9060 aagaaaaggg gggactggaa gggctaattc actcccaaag aagacaagat atccttgatc   9120
tgtggatcta ccacacacaa ggctacttcc ctgattggca gaactacaca ccagggccag   9180
gggtcagata tccactgacc tttggatggt gctacaagct agtaccagtt gagccagata   9240
aggtagaaga ggccaataaa ggagagaaca ccagcttgtt acaccctgtg agcctgcatg   9300
gaatggatga ccctgagaga gaagtgttag agtggaggtt tgacagccgc ctagcatttc   9360
atcacgtggc ccgagagctg catccggagt acttcaagaa ctgctgacat cgagcttgct   9420
acaagggact ttccgctggg gactttccag ggaggcgtgg cctgggcggg actggggagt   9480
ggcgagccct cagatgctgc atataagcag ctgcttttg cctgtactgg gtctctctgg    9540
ttagaccaga tctgagcctg ggagctctct ggctaactag ggaacccact gcttaagcct   9600
caataaagct tgccttgagt gcttcaagta gtgtgtgccc gtctgttgtg tgactctggt   9660
aactagagat ccctcagacc ctttagtca gtgtggaaaa tctctagcac ccaggaggta    9720
gaggttgcag tgagccaaga tcgcgccact gcattccagc ctgggcaaga aaacaagact   9780
gtctaaaata ataataataa gttaagggta ttaaatatat ttatacatgg aggtcataaa   9840
aatatatata tttgggctgg gcgcagtggc tcacacctgc gcccggccct ttgggaggcc   9900
gaggcaggtg gatcacctga gtttgggagt tccagaccag cctgaccaac atggagaaac   9960
cccttctctg tgtatttta gtagatttta ttttatgtgt atttattca caggtatttc    10020 tggaaaactg aaactgtttt tcctctactc tgataccaca agaatcatca gcacagagga   10080
agacttctgt gatcaaatgt ggtgggagag ggaggttttc accagcacat gagcagtcag   10140
ttctgccgca gactcggcgg gtgtccttcg gttcagttcc aacaccgcct gcctggagag   10200
aggtcagacc acagggtgag ggctcagtcc ccaagacata aacacccaag acataaacac   10260
ccaacaggtc caccccgcct gctgcccagg cagagccgat tcaccaagac gggaattagg   10320
atagagaaag agtaagtcac acagagccgg ctgtgcggga gaacggagtt ctattatgac   10380
tcaaatcagt ctccccaagc attcggggat cagagttttt aaggataact tagtgtgtag   10440
ggggccagtg agttggagat gaaagcgtag ggagtcgaag gtgtccttt gcgccgagtc     10500 agttcctggg tggggccac aagatcggat gagccagttt atcaatccgg gggtgccagc    10560
tgatccatgg agtgcagggt ctgcaaaata tctcaagcac tgattgatct taggttttac   10620
aatagtgatg ttaccccagg aacaatttgg ggaaggtcag aatcttgtag cctgtagctg   10680
catgactcct aaaccataat ttcttttttg ttttttttt tttattttg agacagggtc     10740 tcactctgtc acctaggctg gagtgcagtg gtgcaatcac agctcactgc agcctcaacg   10800
tcgtaagctc aagcgatcct cccacctcag cctgcctggt agctgagact acaagcgacg   10860
ccccagttaa ttttttgtatt tttggtagag cagcgtttt gccgtgtggc cctggctggt    10920
ctcgaactcc tgggctcaag tgatccagcc tcagcctccc aaagtgctgg gacaaccggg   10980
cccagtcact gcacctggcc ctaaaccata atttctaatc ttttggctaa tttgttagtc   11040
ctacaaaggc agtctagtcc ccagcaaaaa gggggtttgt ttcgggaaag ggctgttact   11100
```

```
gtctttgttt caaactataa actaagttcc tcctaaactt agttcggcct acacccagga    11160
atgaacaagg agagcttgga ggttagaagc acgatggaat tggttaggtc agatctcttt    11220
cactgtctga gttataattt tgcaatggtg gttcaaagac tgcccgcttc tgacaccagt    11280
cgctgcatta atgaatcggc caacgcgcgg ggagaggcgg tttgcgtatt gggcgctctt    11340
ccgcttcctc gctcactgac tcgctgcgct cggtcgttcg gctgcggcga gcggtatcag    11400
ctcactcaaa ggcggtaata cggttatcca cagaatcagg ggataacgca ggaaagaaca    11460
tgtgagcaaa aggccagcaa aaggccagga accgtaaaaa ggccgcgttg ctggcgtttt    11520
tccataggct ccgcccccct gacgagcatc acaaaaatcg acgctcaagt cagaggtggc    11580
gaaacccgac aggactataa agataccagg cgtttccccc tggaagctcc ctcgtgcgct    11640
ctcctgttcc gaccctgccg cttaccggat acctgtccgc ctttctccct tcgggaagcg    11700
tggcgctttc tcatagctca cgctgtaggt atctcagttc ggtgtaggtc gttcgctcca    11760
agctgggctg tgtgcacgaa ccccccgttc agcccgaccg ctgcgcctta tccggtaact    11820
atcgtcttga gtccaacccg gtaagacacg acttatcgcc actggcagca gccactggta    11880
acaggattag cagagcgagg tatgtaggcg gtgctacaga gttcttgaag tggtggccta    11940
actacggcta cactagaagg acagtatttg gtatctgcgc tctgctgaag ccagttacct    12000
tcggaaaaag agttggtagc tcttgatccg gcaaacaaac caccgctggt agcggtggtt    12060 ttttgtttg caagcagcag attacgcgca gaaaaaaagg atctcaagaa gatcctttga    12120
tcttttctac ggggtctgac gctcagtgga acgaaaactc acgttaaggg attttggtca    12180
tgagattatc aaaaaggatc ttcacctaga tccttttaaa ttaaaaatga agttttaaat    12240
caatctaaag tatatatgag taaacttggt ctgacagtta ccaatgctta atcagtgagg    12300
cacctatctc agcgatctgt ctatttcgtt catccatagt tgcctgactc cccgtcgtgt    12360
agataactac gatacgggag ggcttaccat ctggccccag tgctgcaatg ataccgcgag    12420
acccacgctc accggctcca gatttatcag caataaacca gccagccgga agggccgagc    12480
gcagaagtgg tcctgcaact ttatccgcct ccatccagtc tattaattgt tgccgggaag    12540
ctagagtaag tagttcgcca gttaatagtt tgcgcaacgt tgttgccatt gctacaggca    12600
tcgtggtgtc acgctcgtcg tttggtatgg cttcattcag ctccggttcc caacgatcaa    12660
ggcgagttac atgatccccc atgttgtgca aaaaagcggt tagctccttc ggtcctccga    12720
tcgttgtcag aagtaagttg gccgcagtgt tatcactcat ggttatggca gcactgcata    12780
attctcttac tgtcatgcca tccgtaagat gcttttctgt gactggtgag tactcaacca    12840
agtcattctg agaatagtgt atgcggcgac cgagttgctc ttgcccggcg tcaatacggg    12900
ataataccgc gccacatagc agaactttaa aagtgctcat cattggaaaa cgttcttcgg    12960
ggcgaaaact ctcaaggatc ttaccgctgt tgagatccag ttcgatgtaa cccactcgtg    13020
cacccaactg atcttcagca tcttttactt tcaccagcgt ttctgggtga gcaaaaacag    13080
gaaggcaaaa tgccgcaaaa aagggaataa gggcgacacg gaaatgttga atactcatac    13140
tcttcctttt tcaatattat tgaagcattt atcagggtta ttgtctcatg agcggataca    13200
tatttgaatg tatttagaaa aataaacaaa taggggttcc gcgcacattt ccccgaaaag    13260
tgccacctga cgtctaagaa accattatta tcatgacatt aacctataaa aataggcgta    13320
tcacgaggcc ctttcgtctc gcgcgtttcg gtgatgacgg tgaaaacctc tgacacatgc    13380
agctcccgga gacggtcaca gcttgtctgt aagcggatgc cgggagcaga caagcccgtc    13440
```

```
agggcgcgtc agcgggtgtt ggcgggtgtc ggggctggct taactatgcg gcatcagagc    13500
agattgtact gagagtgcac catatgcggt gtgaaatacc gcacagatgc gtaaggagaa    13560
aataccgcat caggcgccat cgccattca ggctgcgcaa ctgttgggaa gggcgatcgg      13620
tgcgggcctc ttcgctatta cgccagggga ggcagagatt gcagtaagct gagatcgcag    13680
cactgcactc cagcctgggc gacagagtaa gactctgtct caaaaataaa ataaataaat    13740
caatcagata ttccaatctt ttcctttatt tatttattta ttttctattt tggaaacaca    13800
gtccttcctt attccagaat tacacatata ttctattttt ctttatatgc tccagttttt    13860
tttagacctt cacctgaaat gtgtgtatac aaaatctagg ccagtccagc agagcctaaa    13920
ggtaaaaaat aaaataataa aaaataaata aaatctagct cactccttca catcaaaatg    13980
gagatacagc tgttagcatt aaataccaaa taacccatct tgtcctcaat aattttaagc    14040
gcctctctcc accacatcta actcctgtca aaggcatgtg ccccttccgg gcgctctgct    14100
gtgctgccaa ccaactggca tgtggactct gcagggtccc taactgccaa gccccacagt    14160
gtgccctgag gctgcccctt ccttctagcg gctgccccca ctcggctttg ctttccctag    14220
tttcagttac ttgcgttcag ccaaggtctg aaactaggtg cgcacagagc ggtaagactg    14280
cgagagaaag agaccagctt tacaggggggt ttatcacagt gcaccctgac agtcgtcagc    14340
ctcacagggg gtttatcaca ttgcaccctg acagtcgtca gcctcacagg gggtttatca    14400
cagtgcaccc ttacaatcat tccatttgat tcacaatttt tttagtctct actgtgccta    14460
acttgtaagt taaatttgat cagaggtgtg ttcccagagg ggaaaacagt atatacaggg    14520
ttcagtacta tcgcatttca ggcctccacc tgggtcttgg aatgtgtccc ccgagggggtg    14580 atgactacct cagttggatc tccacaggtc acagtgacac aagataacca agacacctcc    14640
caaggctacc acaatgggcc gccctccacg tgcacatggc cggaggaact gccatgtcgg    14700
aggtgcaagc acacctgcgc atcagagtcc ttggtgtgga ggggagggacc agcgcagctt    14760 ccagccatcc acctgatgaa cagaacctag ggaaagcccc agttctactt acaccaggaa    14820
aggc                                                                 14824
```

<210> SEQ ID NO 20
<211> LENGTH: 24
<212> TYPE: PRT
<213> ORGANISM: SIV DE

<400> SEQUENCE: 20

Gly Gln Lys Ala Arg Val Leu Ala Glu Ala Leu Lys Glu Ala Leu Ala
1               5                   10                  15

Pro Val Pro Ile Pro Phe Ala Ala
            20

<210> SEQ ID NO 21
<211> LENGTH: 63
<212> TYPE: PRT
<213> ORGANISM: Artificial Sequence
<220> FEATURE:
<223> OTHER INFORMATION: Used to inhibit the viral Gag p25 protein
      (CA-SP1)

<400> SEQUENCE: 21

Lys Asn Trp Met Thr Glu Thr Phe Leu Val Gln Asn Ala Asn Pro Asp
1               5                   10                  15

Cys Lys Thr Ile Leu Lys Ala Leu Gly Pro Ala Ala Thr Leu Glu Glu
            20                  25                  30

```
Met Met Thr Ala Cys Gln Gly Val Gly Gly Pro His Lys Ala Arg Ile
        35                  40                  45

Leu Ala Glu Ala Met Ser Gln Val Thr Asn Ser Ala Thr Ile Met
    50                  55                  60
```

<210> SEQ ID NO 22
<211> LENGTH: 64
<212> TYPE: PRT
<213> ORGANISM: Artificial Sequence
<220> FEATURE:
<223> OTHER INFORMATION: Used to inhibit the viral Gag p25 protein
      (CA-SP1)

<400> SEQUENCE: 22

```
Lys Asn Trp Met Thr Glu Thr Leu Leu Val Gln Asn Ala Asn Pro Asp
1               5                   10                  15

Cys Lys Thr Ile Leu Lys Ala Leu Gly Pro Gly Ala Thr Leu Glu Glu
                20                  25                  30

Met Met Thr Ala Cys Gln Gly Val Gly Gly Pro Gly His Lys Ala Arg
        35                  40                  45

Val Leu Ala Glu Ala Met Ser Gln Val Thr Asn Pro Ala Thr Ile Met
    50                  55                  60
```

<210> SEQ ID NO 23
<211> LENGTH: 30
<212> TYPE: PRT
<213> ORGANISM: Artificial Sequence
<220> FEATURE:
<223> OTHER INFORMATION: Used to inhibit the viral Gag p25 protein
      (CA-SP1)

<400> SEQUENCE: 23

```
Thr Ala Cys Gln Gly Val Gly Gly Pro Ser His Lys Ala Arg Ile Leu
1               5                   10                  15

Ala Glu Ala Met Ser Gln Val Thr Asn Ser Ala Thr Ile Met
            20                  25                  30
```

<210> SEQ ID NO 24
<211> LENGTH: 31
<212> TYPE: PRT
<213> ORGANISM: Artificial Sequence
<220> FEATURE:
<223> OTHER INFORMATION: Used to inhibit the viral Gag p25 protein
      (CA-SP1)

<400> SEQUENCE: 24

```
Met Thr Ala Cys Gln Gly Val Gly Gly Pro Gly His Lys Ala Arg Val
1               5                   10                  15

Leu Ala Glu Ala Met Ser Gln Val Thr Asn Pro Ala Thr Ile Met
            20                  25                  30
```

<210> SEQ ID NO 25
<211> LENGTH: 14
<212> TYPE: PRT
<213> ORGANISM: Artificial Sequence
<220> FEATURE:
<223> OTHER INFORMATION: Used to inhibit the viral Gag p25 protein
      (CA-SP1)

<400> SEQUENCE: 25

```
Ser His Lys Ala Arg Ile Leu Ala Glu Ala Met Ser Gln Val
1               5                   10
```

<210> SEQ ID NO 26

```
<211> LENGTH: 14
<212> TYPE: PRT
<213> ORGANISM: Artificial Sequence
<220> FEATURE:
<223> OTHER INFORMATION: Used to inhibit the viral Gag p25 protein
      (CA-SP1)

<400> SEQUENCE: 26

Gly His Lys Ala Arg Val Leu Ala Glu Ala Met Ser Gln Val
1               5                   10

<210> SEQ ID NO 27
<211> LENGTH: 24
<212> TYPE: PRT
<213> ORGANISM: SIV DM

<400> SEQUENCE: 27

Gly Gln Lys Ala Arg Val Leu Ala Glu Ala Met Ser Gln Val Leu Ala
1               5                   10                  15

Pro Val Pro Ile Pro Phe Ala Ala
            20

<210> SEQ ID NO 28
<211> LENGTH: 24
<212> TYPE: PRT
<213> ORGANISM: SIV DJ

<400> SEQUENCE: 28

Gly Gln Lys Ala Arg Val Met Ala Glu Ala Met Ser Gln Val Leu Ala
1               5                   10                  15

Pro Val Pro Ile Pro Phe Ala Ala
            20

<210> SEQ ID NO 29
<211> LENGTH: 15
<212> TYPE: PRT
<213> ORGANISM: FIV

<400> SEQUENCE: 29

Gly Tyr Lys Met Gln Leu Leu Ala Glu Ala Leu Thr Lys Val Gln
1               5                   10                  15

<210> SEQ ID NO 30
<211> LENGTH: 12
<212> TYPE: PRT
<213> ORGANISM: EIAV

<400> SEQUENCE: 30

Lys Gln Lys Met Met Leu Leu Ala Lys Ala Leu Gln
1               5                   10

<210> SEQ ID NO 31
<211> LENGTH: 32
<212> TYPE: PRT
<213> ORGANISM: BIV

<400> SEQUENCE: 31

Lys Ser Lys Met Gln Phe Leu Val Ala Ala Met Lys Glu Met Gly Ile
1               5                   10                  15

Gln Ser Pro Ile Pro Ala Val Leu Pro His Thr Pro Glu Ala Tyr Ala
            20                  25                  30

<210> SEQ ID NO 32
<211> LENGTH: 9
```

```
<212> TYPE: PRT
<213> ORGANISM: Artificial Sequence
<220> FEATURE:
<223> OTHER INFORMATION: HIV-1 CA-SP1 residues to be inserted into
      SIVmac239 backbone

<400> SEQUENCE: 32

Val Leu Ala Glu Ala Met Ser Gln Val
1               5

<210> SEQ ID NO 33
<211> LENGTH: 13
<212> TYPE: PRT
<213> ORGANISM: Artificial Sequence
<220> FEATURE:
<223> OTHER INFORMATION: Mutant SP1 region in HIV-1 NL4-3

<400> SEQUENCE: 33

Ala Ala Met Ser Gln Val Thr Asn Pro Ala Thr Ile Met
1               5                   10

<210> SEQ ID NO 34
<211> LENGTH: 13
<212> TYPE: PRT
<213> ORGANISM: Artificial Sequence
<220> FEATURE:
<223> OTHER INFORMATION: Mutant SP1 region in HIV-1 NL4-3

<400> SEQUENCE: 34

Ala Glu Met Ser Gln Val Thr Asn Pro Ala Thr Ile Met
1               5                   10

<210> SEQ ID NO 35
<211> LENGTH: 13
<212> TYPE: PRT
<213> ORGANISM: Artificial Sequence
<220> FEATURE:
<223> OTHER INFORMATION: Mutant SP1 region in HIV-1 NL4-3

<400> SEQUENCE: 35

Ala Glu Ala Ser Gln Val Thr Asn Pro Ala Thr Ile Met
1               5                   10

<210> SEQ ID NO 36
<211> LENGTH: 13
<212> TYPE: PRT
<213> ORGANISM: Artificial Sequence
<220> FEATURE:
<223> OTHER INFORMATION: Mutant SP1 region in HIV-1 NL4-3

<400> SEQUENCE: 36

Ala Glu Ala Met Gln Val Thr Asn Pro Ala Thr Ile Met
1               5                   10

<210> SEQ ID NO 37
<211> LENGTH: 24
<212> TYPE: DNA
<213> ORGANISM: Artificial Sequence
<220> FEATURE:
<223> OTHER INFORMATION: Sequence inserted into Gag SP1 domain

<400> SEQUENCE: 37
agccaaaact cttgctttat ggcc                                          24

<210> SEQ ID NO 38
<211> LENGTH: 28
<212> TYPE: DNA
```

<210> SEQ ID NO 39
<211> LENGTH: 24
<212> TYPE: DNA
<213> ORGANISM: Artificial Sequence
<220> FEATURE:
<223> OTHER INFORMATION: Sequence inserted into Gag SP1 domain

<400> SEQUENCE: 38
agtcagtgtg gaaaatctct agcagtgg          28

<210> SEQ ID NO 39
<211> LENGTH: 24
<212> TYPE: DNA
<213> ORGANISM: Artificial Sequence
<220> FEATURE:
<223> OTHER INFORMATION: Sequence inserted into Gag SP1 domain

<400> SEQUENCE: 39
gcaatgagcc aagtaacaaa tcca              24

<210> SEQ ID NO 40
<211> LENGTH: 31
<212> TYPE: DNA
<213> ORGANISM: Artificial Sequence
<220> FEATURE:
<223> OTHER INFORMATION: Sequence inserted into Gag SP1 domain

<400> SEQUENCE: 40
aggtatggta aatgcagtat acttcctgaa g       31

<210> SEQ ID NO 41
<211> LENGTH: 27
<212> TYPE: DNA
<213> ORGANISM: Artificial Sequence
<220> FEATURE:
<223> OTHER INFORMATION: Sequence inserted into Gag SP1 domain

<400> SEQUENCE: 41
ttcagccaaa actcttgctt tatggcc           27

<210> SEQ ID NO 42
<211> LENGTH: 23
<212> TYPE: DNA
<213> ORGANISM: Artificial Sequence
<220> FEATURE:
<223> OTHER INFORMATION: Sequence inserted into Gag SP1 domain

<400> SEQUENCE: 42
atgagccaag taacaaatcc agc                23

<210> SEQ ID NO 43
<211> LENGTH: 21
<212> TYPE: DNA
<213> ORGANISM: Artificial Sequence
<220> FEATURE:
<223> OTHER INFORMATION: Sequence inserted into Gag SP1 domain

<400> SEQUENCE: 43
tgcttcagcc aaaactcttg c                  21

<210> SEQ ID NO 44
<211> LENGTH: 21
<212> TYPE: DNA
<213> ORGANISM: Artificial Sequence
<220> FEATURE:
<223> OTHER INFORMATION: Sequence inserted into Gag SP1 domain

<400> SEQUENCE: 44
agccaagtaa caaatccagc t                  21

```
<210> SEQ ID NO 45
<211> LENGTH: 24
<212> TYPE: DNA
<213> ORGANISM: Artificial Sequence
<220> FEATURE:
<223> OTHER INFORMATION: Sequence inserted into Gag SP1 domain

<400> SEQUENCE: 45
cattgcttca gccaaaactc ttgc                                          24

<210> SEQ ID NO 46
<211> LENGTH: 22
<212> TYPE: DNA
<213> ORGANISM: Artificial Sequence
<220> FEATURE:
<223> OTHER INFORMATION: Sequence inserted into Gag SP1 domain

<400> SEQUENCE: 46
caagtaacaa atccagctac ca                                            22

<210> SEQ ID NO 47
<211> LENGTH: 25
<212> TYPE: DNA
<213> ORGANISM: Artificial Sequence
<220> FEATURE:
<223> OTHER INFORMATION: Sequence inserted into Gag SP1 domain

<400> SEQUENCE: 47
gctcattgct tcagccaaaa ctctt                                         25

<210> SEQ ID NO 48
<211> LENGTH: 22
<212> TYPE: DNA
<213> ORGANISM: Artificial Sequence
<220> FEATURE:
<223> OTHER INFORMATION: Sequence inserted into Gag SP1 domain

<400> SEQUENCE: 48
gtaacaaatc cagctaccat aa                                            22

<210> SEQ ID NO 49
<211> LENGTH: 25
<212> TYPE: DNA
<213> ORGANISM: Artificial Sequence
<220> FEATURE:
<223> OTHER INFORMATION: Sequence inserted into Gag SP1 domain

<400> SEQUENCE: 49
acaaatccag ctaccataat gatac                                         25

<210> SEQ ID NO 50
<211> LENGTH: 26
<212> TYPE: DNA
<213> ORGANISM: Artificial Sequence
<220> FEATURE:
<223> OTHER INFORMATION: Sequence inserted into Gag SP1 domain

<400> SEQUENCE: 50
ttggctcatt gcttcagcca aaactc                                        26

<210> SEQ ID NO 51
<211> LENGTH: 24
<212> TYPE: DNA
<213> ORGANISM: Artificial Sequence
<220> FEATURE:
```

```
<223> OTHER INFORMATION: Sequence inserted into Gag SP1 domain

<400> SEQUENCE: 51
tacttggctc attgcttcag ccaa                                              24

<210> SEQ ID NO 52
<211> LENGTH: 24
<212> TYPE: DNA
<213> ORGANISM: Artificial Sequence
<220> FEATURE:
<223> OTHER INFORMATION: Sequence inserted into Gag SP1 domain

<400> SEQUENCE: 52
aatccagcta ccataatgat acag                                              24

<210> SEQ ID NO 53
<211> LENGTH: 21
<212> TYPE: DNA
<213> ORGANISM: Artificial Sequence
<220> FEATURE:
<223> OTHER INFORMATION: Sequence inserted into Gag SP1 domain

<400> SEQUENCE: 53
tgttacttgg ctcattgctt c                                                 21

<210> SEQ ID NO 54
<211> LENGTH: 24
<212> TYPE: DNA
<213> ORGANISM: Artificial Sequence
<220> FEATURE:
<223> OTHER INFORMATION: Sequence inserted into Gag SP1 domain

<400> SEQUENCE: 54
ccagctacca taatgataca gaaa                                              24

<210> SEQ ID NO 55
<211> LENGTH: 24
<212> TYPE: DNA
<213> ORGANISM: Artificial Sequence
<220> FEATURE:
<223> OTHER INFORMATION: Sequence inserted into Gag SP1 domain

<400> SEQUENCE: 55
atttgttact tggctcattg cttc                                              24

<210> SEQ ID NO 56
<211> LENGTH: 26
<212> TYPE: DNA
<213> ORGANISM: Artificial Sequence
<220> FEATURE:
<223> OTHER INFORMATION: Sequence inserted into Gag SP1 domain

<400> SEQUENCE: 56
gctaccataa tgatacagaa aggcaa                                            26

<210> SEQ ID NO 57
<211> LENGTH: 24
<212> TYPE: DNA
<213> ORGANISM: Artificial Sequence
<220> FEATURE:
<223> OTHER INFORMATION: Sequence inserted into Gag SP1 domain

<400> SEQUENCE: 57
tggatttgtt acttggctca ttgc                                              24
```

<210> SEQ ID NO 58
<211> LENGTH: 21
<212> TYPE: DNA
<213> ORGANISM: Artificial Sequence
<220> FEATURE:
<223> OTHER INFORMATION: Sequence inserted into Gag SP1 domain

<400> SEQUENCE: 58
accataatga tacagaaagg c                                              21

<210> SEQ ID NO 59
<211> LENGTH: 22
<212> TYPE: DNA
<213> ORGANISM: Artificial Sequence
<220> FEATURE:
<223> OTHER INFORMATION: Sequence inserted into Gag SP1 domain

<400> SEQUENCE: 59
agctggattt gttacttggc tc                                             22

<210> SEQ ID NO 60
<211> LENGTH: 27
<212> TYPE: DNA
<213> ORGANISM: Artificial Sequence
<220> FEATURE:
<223> OTHER INFORMATION: Sequence inserted into Gag SP1 domain

<400> SEQUENCE: 60
ataatgatac agaaaggcaa ttttagg                                        27

<210> SEQ ID NO 61
<211> LENGTH: 21
<212> TYPE: DNA
<213> ORGANISM: Artificial Sequence
<220> FEATURE:
<223> OTHER INFORMATION: Sequence inserted into Gag SP1 domain

<400> SEQUENCE: 61
ggtagctgga tttgttactt g                                              21

<210> SEQ ID NO 62
<211> LENGTH: 28
<212> TYPE: DNA
<213> ORGANISM: Artificial Sequence
<220> FEATURE:
<223> OTHER INFORMATION: Sequence inserted into Gag SP1 domain

<400> SEQUENCE: 62
atgatacaga aaggcaattt taggaacc                                       28

<210> SEQ ID NO 63
<211> LENGTH: 21
<212> TYPE: DNA
<213> ORGANISM: Artificial Sequence
<220> FEATURE:
<223> OTHER INFORMATION: Sequence inserted into Gag SP1 domain

<400> SEQUENCE: 63
tatggtagct ggatttgtta c                                              21

<210> SEQ ID NO 64
<211> LENGTH: 21
<212> TYPE: DNA
<213> ORGANISM: Artificial Sequence
<220> FEATURE:
<223> OTHER INFORMATION: Sequence inserted into Gag SP1 domain

```
<400> SEQUENCE: 64
atacagaaag gcaattttag g                                            21

<210> SEQ ID NO 65
<211> LENGTH: 19
<212> TYPE: DNA
<213> ORGANISM: Artificial Sequence
<220> FEATURE:
<223> OTHER INFORMATION: Sequence inserted into Gag SP1 domain

<400> SEQUENCE: 65
ccacctatcc cagtaggag                                               19

<210> SEQ ID NO 66
<211> LENGTH: 20
<212> TYPE: DNA
<213> ORGANISM: Artificial Sequence
<220> FEATURE:
<223> OTHER INFORMATION: Sequence inserted into Gag SP1 domain

<400> SEQUENCE: 66
ggcacagcaa gcagcagctg                                              20

<210> SEQ ID NO 67
<211> LENGTH: 29
<212> TYPE: DNA
<213> ORGANISM: Artificial Sequence
<220> FEATURE:
<223> OTHER INFORMATION: Sequence inserted into Gag SP1 domain

<400> SEQUENCE: 67
gtagaccaac agcaccatct agcggcaga                                    29

<210> SEQ ID NO 68
<211> LENGTH: 28
<212> TYPE: DNA
<213> ORGANISM: Artificial Sequence
<220> FEATURE:
<223> OTHER INFORMATION: Sequence inserted into Gag SP1 domain

<400> SEQUENCE: 68
ggtaaagtaa aggcagtgta ctgcctaa                                     28

<210> SEQ ID NO 69
<211> LENGTH: 37
<212> TYPE: DNA
<213> ORGANISM: Artificial Sequence
<220> FEATURE:
<223> OTHER INFORMATION: Sequence inserted into Gag SP1 domain

<400> SEQUENCE: 69
cactggtgcg aggacctgac tcatggcttc tgccatt                           37

<210> SEQ ID NO 70
<211> LENGTH: 37
<212> TYPE: DNA
<213> ORGANISM: Artificial Sequence
<220> FEATURE:
<223> OTHER INFORMATION: Sequence inserted into Gag SP1 domain

<400> SEQUENCE: 70
aatggcagaa gccatgagtc aggtcctcgc accagtg                           37

<210> SEQ ID NO 71
<211> LENGTH: 28
```

```
<212> TYPE: DNA
<213> ORGANISM: Artificial Sequence
<220> FEATURE:
<223> OTHER INFORMATION: Sequence inserted into Gag SP1 domain

<400> SEQUENCE: 71
ggcttctgcc agtactctag ccttctgt                                            28

<210> SEQ ID NO 72
<211> LENGTH: 28
<212> TYPE: DNA
<213> ORGANISM: Artificial Sequence
<220> FEATURE:
<223> OTHER INFORMATION: Sequence inserted into Gag SP1 domain

<400> SEQUENCE: 72
acagaaggct agagtactgg cagaagcc                                            28

<210> SEQ ID NO 73
<211> LENGTH: 28
<212> TYPE: DNA
<213> ORGANISM: Artificial Sequence
<220> FEATURE:
<223> OTHER INFORMATION: Sequence inserted into Gag SP1 domain

<400> SEQUENCE: 73
ggcttctgcc agtactctag ccttctgt                                            28

<210> SEQ ID NO 74
<211> LENGTH: 28
<212> TYPE: DNA
<213> ORGANISM: Artificial Sequence
<220> FEATURE:
<223> OTHER INFORMATION: Sequence inserted into Gag SP1 domain

<400> SEQUENCE: 74
acagaaggct agagtactgg cagaagcc                                            28

<210> SEQ ID NO 75
<211> LENGTH: 25
<212> TYPE: DNA
<213> ORGANISM: Artificial Sequence
<220> FEATURE:
<223> OTHER INFORMATION: Sequence inserted into Gag SP1 domain

<400> SEQUENCE: 75
atccaactgg ggttgcaaaa atgtg                                               25

<210> SEQ ID NO 76
<211> LENGTH: 25
<212> TYPE: PRT
<213> ORGANISM: HIV-1

<400> SEQUENCE: 76

Gly His Lys Ala Arg Val Leu Ala Glu Ala Met Ser Gln Val Thr Asn
 1               5                  10                  15

Pro Ala Thr Ile Met Ile Gln Lys Gly
            20                  25

<210> SEQ ID NO 77
<211> LENGTH: 19
<212> TYPE: PRT
<213> ORGANISM: FIV

<400> SEQUENCE: 77
```

-continued

Gly Tyr Lys Met Gln Leu Leu Ala Glu Ala Leu Thr Lys Val Gln Val
1 5 10 15

Val Gln Ser

<210> SEQ ID NO 78
<211> LENGTH: 16
<212> TYPE: PRT
<213> ORGANISM: EIAV

<400> SEQUENCE: 78

Lys Gln Lys Met Met Leu Leu Ala Lys Ala Leu Gln Thr Gly Leu Ala
1 5 10 15

<210> SEQ ID NO 79
<211> LENGTH: 36
<212> TYPE: PRT
<213> ORGANISM: BIV

<400> SEQUENCE: 79

Lys Ser Lys Met Gln Phe Leu Val Ala Ala Met Lys Glu Met Gly Ile
1 5 10 15

Gln Ser Pro Ile Pro Ala Val Leu Pro His Thr Pro Glu Ala Tyr Ala
20 25 30

Ser Gln Thr Ser
35

<210> SEQ ID NO 80
<211> LENGTH: 14
<212> TYPE: PRT
<213> ORGANISM: Artificial Sequence
<220> FEATURE:
<223> OTHER INFORMATION: HIV-1 CA-SP1 sequence used for replacement

<400> SEQUENCE: 80

Gly His Lys Ala Arg Val Leu Ala Glu Ala Met Ser Gln Val
1 5 10

<210> SEQ ID NO 81
<211> LENGTH: 9
<212> TYPE: PRT
<213> ORGANISM: Artificial Sequence
<220> FEATURE:
<223> OTHER INFORMATION: haemagglutinin epitope HA

<400> SEQUENCE: 81

Tyr Pro Tyr Asp Val Pro Asp Tyr Ala
1 5

<210> SEQ ID NO 82
<211> LENGTH: 6
<212> TYPE: PRT
<213> ORGANISM: Artificial Sequence
<220> FEATURE:
<223> OTHER INFORMATION: Bluetongue virus epitope VP7

<400> SEQUENCE: 82

Gln Tyr Pro Ala Leu Thr
1 5

<210> SEQ ID NO 83
<211> LENGTH: 8
<212> TYPE: PRT
<213> ORGANISM: Artificial Sequence
<220> FEATURE:
<223> OTHER INFORMATION: Flag epitope

```
<400> SEQUENCE: 83

Asp Tyr Lys Asp Asp Asp Asp Lys
1               5

<210> SEQ ID NO 84
<211> LENGTH: 11
<212> TYPE: PRT
<213> ORGANISM: Artificial Sequence
<220> FEATURE:
<223> OTHER INFORMATION: VSV-G epitope

<400> SEQUENCE: 84

Tyr Thr Asp Ile Glu Met Asn Arg Leu Gly Lys
1               5                   10

<210> SEQ ID NO 85
<211> LENGTH: 13
<212> TYPE: PRT
<213> ORGANISM: Artificial Sequence
<220> FEATURE:
<223> OTHER INFORMATION: Mutant SP1 region in HIV-1 NL4-3

<400> SEQUENCE: 85

Ala Glu Ala Met Ser Val Thr Asn Pro Ala Thr Ile Met
1               5                   10

<210> SEQ ID NO 86
<211> LENGTH: 13
<212> TYPE: PRT
<213> ORGANISM: Artificial Sequence
<220> FEATURE:
<223> OTHER INFORMATION: Mutant SP1 region in HIV-1 NL4-3

<400> SEQUENCE: 86

Ala Glu Ala Met Ser Gln Thr Asn Pro Ala Thr Ile Met
1               5                   10

<210> SEQ ID NO 87
<211> LENGTH: 13
<212> TYPE: PRT
<213> ORGANISM: Artificial Sequence
<220> FEATURE:
<223> OTHER INFORMATION: Mutant SP1 region in HIV-1 NL4-3

<400> SEQUENCE: 87

Ala Glu Ala Met Ser Gln Val Asn Pro Ala Thr Ile Met
1               5                   10

<210> SEQ ID NO 88
<211> LENGTH: 13
<212> TYPE: PRT
<213> ORGANISM: Artificial Sequence
<220> FEATURE:
<223> OTHER INFORMATION: Mutant SP1 region in HIV-1 NL4-3

<400> SEQUENCE: 88

Ala Glu Ala Met Ser Gln Val Thr Pro Ala Thr Ile Met
1               5                   10

<210> SEQ ID NO 89
<211> LENGTH: 13
<212> TYPE: PRT
<213> ORGANISM: Artificial Sequence
<220> FEATURE:
<223> OTHER INFORMATION: Mutant SP1 region in HIV-1 NL4-3
```

```
<400> SEQUENCE: 89

Ala Glu Ala Met Ser Gln Val Thr Asn Ala Thr Ile Met
1               5                   10

<210> SEQ ID NO 90
<211> LENGTH: 1530
<212> TYPE: DNA
<213> ORGANISM: SIV DM

<400> SEQUENCE: 90
atgggcgtga gaaactccgt cttgtcaggg aagaaagcag atgaattaga aaaaattagg      60
ctacgaccca acggaaagaa aaagtacatg ttgaagcatg tagtatgggc agcaaatgaa    120
ttagatagat ttggattagc agaaagcctg ttggagaaca agaaggatg tcaaaaaata     180 ctttcggtct tagctccatt agtgccaaca ggctcagaaa atttaaaaag cctttataat    240
actgtctgcg tcatctggtg cattcacgca gaagagaaat gaaacacac tgaggaagca    300 aaacagatag tgcagagaca cctagtggtg gaaacaggaa caacagaaac tatgccaaaa    360
acaagtagac caacagcacc atctagcggc agaggaggaa attacccagt acaacaaata    420
ggtggtaact atgtccacct gccattaagc ccgagaacat aaatgcctg ggtaaaattg     480 atagaggaaa agaaatttgg agcagaagta gtgccaggat tcaggcact gtcagaaggt     540 tgcacccct atgacattaa tcagatgtta aattgtgtgg agaccatca agcggctatg      600 cagattatca gagatattat aaacgaggag gctgcagatt gggacttgca gcacccacaa    660
ccagctccac aacaaggaca acttaggag ccgtcaggat cagatattgc aggaacaact     720
agttcagtag atgaacaaat ccagtggatg tacagacaac agaacccccat accagtaggc    780 aacatttaca ggagatggat ccaactgggg ttgcaaaaat gtgtcagaat gtataaccca    840
acaaacattc tagatgtaaa acaagggcca aaagagccat tcagagcta tgtagacagg    900 ttctacaaaa gtttaagagc agaacagaca gatgcagcag taaagaattg gatgactcaa    960
acactgctga ttcaaaatgc taacccagat gcaagctag tgctgaaggg gctgggtgtg     1020
aatcccaccc tagaagaaat gctgacggct tgtcaaggag taggggggcc gggacagaag    1080
gctagagtat tggcagaagc catgagtcag gtcctcgcac cagtgccaat cctttttgca    1140
gcagcccaac agaggggacc aagaaagcca attaagtgtt ggaattgtgg aaagaggga    1200 cactctgcaa ggcaatgcag agccccaaga agacagggat gctggaaatg tggaaaaatg    1260
gaccatgtta tggccaaatg cccagacaga caggcgggtt ttttaggcct tggtccatgg    1320
ggaaagaagc cccgcaattt ccccatggct caagtgcatc aggggctgat gccaactgct    1380
cccccagagg acccagctgt ggatctgcta agaactaca tgcagttggg caagcagcag    1440
agagaaaagc agagagaaag cagagagaag ccttacaagg aggtgacaga ggatttgctg    1500
cacctcaatt ctctctttgg aggagaccag                                     1530

<210> SEQ ID NO 91
<211> LENGTH: 67
<212> TYPE: PRT
<213> ORGANISM: SIV DM

<400> SEQUENCE: 91

Lys Asn Trp Met Thr Gln Thr Leu Leu Ile Gln Asn Ala Asn Pro Asp
1               5                   10                  15

Cys Lys Leu Val Leu Lys Gly Leu Gly Val Asn Pro Thr Leu Glu Glu
            20                  25                  30
```

-continued

```
Met Leu Thr Ala Cys Gln Gly Val Gly Gly Pro Gly Gln Lys Ala Arg
         35                  40                  45

Val Leu Ala Glu Ala Met Ser Gln Val Leu Ala Pro Val Pro Ile Pro
     50                  55                  60

Phe Ala Ala
 65

<210> SEQ ID NO 92
<211> LENGTH: 1530
<212> TYPE: DNA
<213> ORGANISM: Artificial Sequence
<220> FEATURE:
<223> OTHER INFORMATION: GAG gene of SIV Chimera with Q358 changed to
      H358

<400> SEQUENCE: 92
atgggcgtga gaaactccgt cttgtcaggg aagaaagcag atgaattaga aaaaattagg      60
ctacgaccca cggaaagaa aaagtacatg ttgaagcatg tagtatgggc agcaaatgaa     120
ttagatagat ttggattagc agaaagcctg ttggagaaca agaaggatg tcaaaaaata     180 ctttcggtct tagctccatt agtgccaaca ggctcagaaa atttaaaaag ccttatataat    240 actgtctgcg tcatctggtg cattcacgca gaagagaaag tgaaacacac tgaggaagca    300
aaacagatag tgcagagaca cctagtggtg aaacaggaa caacgaaac tatgccaaaa     360 acaagtagac aacagcacc atctagcggc agaggaggaa attacccagt acaacaaata    420
ggtggtaact atgtccacct gccattaagc ccgagaacat aaatgcctg gtaaaattg      480 atagaggaaa agaaatttgg agcagaagta gtgccaggat tcaggcact gtcagaaggt     540 tgcaccccct atgacattaa tcagatgtta aattgtgtgg gagaccatca agcggctatg    600
cagattatca gagatattat aaacgaggag gctgcagatt gggacttgca gcacccacaa    660
ccagctccac aacaaggaca acttaggggag ccgtcaggat cagatattgc aggaacaact   720
agttcagtag atgaacaaat ccagtggatg tacagacaac agaacccat accagtaggc   780 aacatttaca gagatggat ccaactgggg ttgcaaaaat gtgtcagaat gtataaccca     840
acaaacattc tagatgtaaa acaagggcca aaagagccat ttcagagcta tgtagacagg    900
ttctacaaaa gtttaagagc agaacagaca atgcagcag taagaattg gatgactcaa     960 acactgctga ttcaaaatgc taacccagat tgcaagctag tgctgaaggg gctgggtgtg    1020
aatcccaccc tagaagaaat gctgacggct tgtcaaggag tagggggggcc gggacataag   1080 gctagagtat tggcagaagc catgagtcag gtcctcgcac cagtgccaat ccctttttgca   1140 gcagcccaac agaggggacc aagaaagcca attaagtgtt ggaattgtgg gaaaggggga     1200
cactctgcaa ggcaatgcag agcccccaaga gacagggat gctggaaatg tggaaaaaatg   1260 gaccatgtta tggccaaatg cccagacaga caggcgggtt ttttaggcct tggtccatgg    1320
ggaagaaagc cccgcaattt ccccatggct caagtgcatc aggggctgat gccaactgct    1380
cccccagagg acccagctgt ggatctgcta aagaactaca tgcagttggg caagcagcag    1440
agagaaaagc agagagaaag cagagagaag ccttacaagg aggtgacaga ggatttgctg    1500
cacctcaatt ctctctttgg aggagaccag                                      1530

<210> SEQ ID NO 93
<211> LENGTH: 67
<212> TYPE: PRT
<213> ORGANISM: Artificial Sequence
<220> FEATURE:
<223> OTHER INFORMATION: GAG gene of SIV Chimera with Q358 changed to
```

H358

<400> SEQUENCE: 93

| Lys | Asn | Trp | Met | Thr | Gln | Thr | Leu | Leu | Ile | Gln | Asn | Ala | Asn | Pro | Asp |
|---|---|---|---|---|---|---|---|---|---|---|---|---|---|---|---|
| 1 | | | | 5 | | | | | 10 | | | | | 15 | |

| Cys | Lys | Leu | Val | Leu | Lys | Gly | Leu | Gly | Val | Asn | Pro | Thr | Leu | Glu | Glu |
|---|---|---|---|---|---|---|---|---|---|---|---|---|---|---|---|
| | | | 20 | | | | | 25 | | | | | 30 | | |

| Met | Leu | Thr | Ala | Cys | Gln | Gly | Val | Gly | Pro | Gly | His | Lys | Ala | Arg |
|---|---|---|---|---|---|---|---|---|---|---|---|---|---|---|
| | | 35 | | | | | 40 | | | | | 45 | | |

| Val | Leu | Ala | Glu | Ala | Met | Ser | Gln | Val | Leu | Ala | Pro | Val | Pro | Ile | Pro |
|---|---|---|---|---|---|---|---|---|---|---|---|---|---|---|---|
| | 50 | | | | | 55 | | | | | 60 | | | | |

Phe Ala Ala
65

<210> SEQ ID NO 94
<211> LENGTH: 1353
<212> TYPE: DNA
<213> ORGANISM: FIV

<400> SEQUENCE: 94

| atggggaatg gacagggggcg agattggaaa atggccatta agagatgtag taatgttgct | 60 |
|---|---|
| gtaggagtag gggggaagag taaaaaattt ggagaaggga atttcagatg ggccattaga | 120 |
| atggctaatg tatctacagg acgagaacct ggtgatatac agagactttt agatcaacta | 180 |
| aggttggtta tttgcgattt acaagaaaga agagaaaaat ttggatctag caaagaaatt | 240 |
| gatatggcaa ttgtgacatt aaaagtcttt gcggtagcag acttttaaa tatgacggtg | 300 |
| tctactgctg ctgcagctga aaatatgtat tctcaaatgg gattagacac taggccatct | 360 |
| atgaagaag caggtggaaa agaggaaggc cctccacagg catatcctat tcaaacagta | 420 |
| aatggagtac cacaatatgt agcacttgac ccaaaaatgg tgtccatttt tatggaaaag | 480 |
| gcaagagaag gactaggagg tgaggaagtt caactatggt ttactgcctt ctctgcaaat | 540 |
| ttaacaccta ctgacatggc cacattaata atggccgcac agggtgcgc tgcagataaa | 600 |
| gaaatattgg atgaaagctt aaagcaactg acagcagaat atgatcgcac acatcccct | 660 |
| gatgctccca gaccattacc ctatttact gcagcagaaa ttatgggtat aggattaact | 720 |
| caagaacaac aagcagaagc aagatttgca ccagctagga tgcagtgtag agcatggtat | 780 |
| ctcgaggcat taggaaaatt ggctgccata aaagctaagt ctcctcgagc tgtgcagtta | 840 |
| agacaaggag ctaaggaaga ttattcatcc tttatagaca gattgtttgc ccaaatagat | 900 |
| caagaacaaa atacagctga agttaagtta tatttaaaac agtcattgag catagctaat | 960 |
| gctaatgcag actgtaaaaa ggcaatgagc caccttaagc cagaaagtac cctagaagaa | 1020 |
| aagttgagag cttgtcaaga aataggctca ccaggccata agcaagagt tttggctgaa | 1080 |
| gcaatgagcc aagtacaagt agtgcaatca aaaggatcag gaccagtgtg ttttaattgt | 1140 |
| aaaaaaccag acatctagc aagacaatgt agagaagtga aaaatgtaa taatgtggaa | 1200 |
| aaacctggtc atgtagctgc caaatgttgg caaggaaata gaaagaattc gggaaactgg | 1260 |
| aaggcgggggc gagctgcagc cccagtgaat caaatgcagc aagcagtaat gccatctgca | 1320 |
| cctccaatgg aggagaaact attggattta taa | 1353 |

<210> SEQ ID NO 95

<400> SEQUENCE: 95

000

<210> SEQ ID NO 96
<211> LENGTH: 1467
<212> TYPE: DNA
<213> ORGANISM: EIAV

<400> SEQUENCE: 96

```
atgggagacc ctttgacatg gagcaaggcg ctcaagaagt tagagaaggt gacggtacaa      60
gggtctcaga aattaactac tggtaactgt aattgggcgc taagtctagt agacttattt     120
catgatacca actttgtaaa agaaaaggac tggcagctga gggatgtcat tccattgctg     180
gaagatgtaa ctcagacgct gtcaggacaa gaaagagagg cctttgaaag aacatggtgg     240
gcaatttctg ctgtaaagat gggcctccag attaataatg tagtagatgg aaaggcatca     300
ttccagctcc taagagcgaa atatgaaaag aagactgcta ataaaagca gtctgagccc      360
tctgaagaat atccaatcat gatagatggg ctggaaaaca gaaattttag acctctaaca     420
cctagaggat atactacttg ggtgaatacc atacagacaa atggtctatt aaatgaagct     480
agtcaaaact tatttgggat attatcagta gactgtactt ctgaagaaat gaatgcattt     540
ttggatgtgg tacctggcca ggcaggacaa aagcagatat tacttgatgc aattgataag     600
atagcagatg attgggataa tagacatcca ttaccgaatg ctccactggt ggcaccacca     660
caagggccta ttcccatgac agcaaggttt attagaggtt taggagtacc tagagaaaga     720
cagatggagc ctgctttga tcagtttagg cagacatata gacaatggat aatagaagcc     780
atgtcagaag gcatcaaagt gatgattgga aaacctaaag ctcaaaatat taggcaagga     840
gctaaggaac cttacccaga atttgtagac agactattat cccaaataaa agtgagggga     900
catccacaag agatttcaaa attcttgact gatacactga ctattcagaa cgcaaatgag     960
gaatgtagaa atgctatgag acatttaaga ccagaggata cattagaaga gaaaatgtat    1020
gcttgcagag acattggaac tacaggccat aaagcaagag ttttggctga gcaatgagc    1080
caagtaactg gtcttgcggg cccatttaaa ggtggagcct tgaaaggagg gccactaaag    1140
gcagcacaaa catgttataa ctgtgggaag ccaggacatt tatctagtca atgtagagca    1200
cctaaagtct gttttaaatg taaacagcct ggacatttct caaagcaatg cagaagtgtt    1260
ccaaaaaacg ggaagcaagg ggctcaaggg aggcccaga acaaactttt cccgatacaa    1320
cagaagagtc agcacaacaa atctgttgta caagagactc ctcagactca aaatctgtac    1380
ccagatctga gcgaaataaa aaaggaatac aatgtcaagg agaaggatca agtagaggat    1440
ctcaacctgg acagttttgtg ggagtaa                                        1467
```

<210> SEQ ID NO 97

<400> SEQUENCE: 97

000

<210> SEQ ID NO 98
<211> LENGTH: 1431
<212> TYPE: DNA
<213> ORGANISM: BIV

<400> SEQUENCE: 98

```
atgaagagaa gggagttaga aaagaagctt cgtaaggtta gggtgacacc ccaacaggat      60
aaatattata ctatagggaa tcttcaatgg gccattagaa tgataaatct aatggggatc     120
aaatgtgtgt gtgacgagga gtgctcggca gcagaggtag ccccttatcat aacccaattt     180
```

```
tcagctttag acttagaaaa ttctcctatc agaggtaagg aggaggtggc cataaaaaat    240
actctgaagg ttttctggtc cctgctggcg gggtacaaac cagagagtac agaaacggcc    300
ctaggatatt gggaggcctt tacatataga gaaagggagg ccagagctga taaggaaggc    360
gaaattaaga gtatttaccc ttccctaaca cagaacacac agaataagaa gcagacatcg    420
aatcagacaa acactcaatc attaccagct atcactactc aagatggtac tcctaggttt    480
gatcctgacc tcatgaagca gcttaagatc tggtcagacg ccactgaaag aaatggggtt    540
gaccttcatg cagtgaatat attaggggtc attacagcaa acctagtaca ggaagaaatt    600
aaactcctct tgaatagtac acccaagtgg agattagatg tacaacttat agaatcaaaa    660
gtaagagaga agaaaatgc ccacagaacg tggaaacagc atcatccaga gcccccaaaa    720
acagatgaaa tcatcggtaa ggggcttagt tctgctgaac aagccaccct gatctcagta    780
gaatgcagag aaactttcag acagtgggtg ctgcaggcag ctatggaggt ggcacaggca    840
aaacatgcta ccccaggtcc catcaacatt catcagggac ccaaggagcc gtacacagac    900
tttataaata gattagtggc agcccttgaa ggtatggcgg ctccagaaac cacaaaagaa    960
tacttactcc aacatctatc tattgatcat gccaatgaag actgccagtc tattctaaga   1020
cctttgggac ccaacacccc aatggagaaa aaattagaag catgtagggt agtgggatct   1080
cagggccata agcaagagt tttggctgaa gcaatgagcc aagtagggat ccaatcacca   1140
attccagcag tcttgcctca cacaccagaa gcatatgcct cccaaacctc agggcccgag   1200
gatggtagga gatgttacgg atgtgggaag acaggacatt tgaagaggaa ttgtaaacag   1260
caaaaatgct accattgtgg caaacctggc caccaagcaa gaaactgcag gtcaaaaaac   1320
gggaagtgct cctctgcccc ttatgggcag aggagccaac cacagaacaa ttttcaccag   1380
agcaacatga gttctgtgac cccatctgca cccctctta tattagatta g              1431
```

```
<210> SEQ ID NO 99
<211> LENGTH: 10
<212> TYPE: DNA
<213> ORGANISM: Abudefduf declivifrons

<400> SEQUENCE: 99
aaaaaaaaaa                                                             10

<210> SEQ ID NO 100
<211> LENGTH: 13
<212> TYPE: PRT
<213> ORGANISM: Artificial Sequence
<220> FEATURE:
<223> OTHER INFORMATION: Mutant SP1 region in HIV-1 NL4-3

<400> SEQUENCE: 100

Ala Glu Ala Met Ser Gln Val Thr Asn Pro Thr Ile Met
1               5                   10

<210> SEQ ID NO 101
<211> LENGTH: 13
<212> TYPE: PRT
<213> ORGANISM: Artificial Sequence
<220> FEATURE:
<223> OTHER INFORMATION: Mutant SP1 region in HIV-1 NL4-3

<400> SEQUENCE: 101

Ala Glu Ala Met Ser Gln Val Thr Asn Pro Ala Ile Met
1               5                   10
```

```
<210> SEQ ID NO 102
<211> LENGTH: 13
<212> TYPE: PRT
<213> ORGANISM: Artificial Sequence
<220> FEATURE:
<223> OTHER INFORMATION: Mutant SP1 region in HIV-1 NL4-3

<400> SEQUENCE: 102

Ala Glu Ala Met Ser Gln Val Thr Asn Pro Ala Thr Met
1               5                   10

<210> SEQ ID NO 103
<211> LENGTH: 13
<212> TYPE: PRT
<213> ORGANISM: Artificial Sequence
<220> FEATURE:
<223> OTHER INFORMATION: Mutant SP1 region in HIV-1 NL4-3

<400> SEQUENCE: 103

Ala Glu Ala Met Ser Gln Val Thr Asn Pro Ala Thr Ile
1               5                   10

<210> SEQ ID NO 104
<211> LENGTH: 20
<212> TYPE: PRT
<213> ORGANISM: Artificial Sequence
<220> FEATURE:
<223> OTHER INFORMATION: CA-SP1 in HIV-1 NL4-3 with HA epitope

<400> SEQUENCE: 104

Ala Glu Ala Met Ser Gln Val Thr Tyr Pro Tyr Asp Val Pro Asp Tyr
1               5                   10                  15

Ala Thr Ile Met
            20

<210> SEQ ID NO 105
<211> LENGTH: 19
<212> TYPE: PRT
<213> ORGANISM: Artificial Sequence
<220> FEATURE:
<223> OTHER INFORMATION: CA-SP1 in HIV-1 NL4-3 with HA epitope

<400> SEQUENCE: 105

Ala Glu Ala Met Ser Gln Val Thr Tyr Pro Tyr Asp Val Pro Asp Tyr
1               5                   10                  15

Ala Ile Met

<210> SEQ ID NO 106
<211> LENGTH: 19
<212> TYPE: PRT
<213> ORGANISM: Artificial Sequence
<220> FEATURE:
<223> OTHER INFORMATION: CA-SP1 in HIV-1 NL4-3 with HA epitope

<400> SEQUENCE: 106

Ala Glu Ala Met Ser Gln Val Tyr Pro Tyr Asp Val Pro Asp Tyr Ala
1               5                   10                  15

Thr Ile Met

<210> SEQ ID NO 107
<211> LENGTH: 18
<212> TYPE: PRT
<213> ORGANISM: Artificial Sequence
<220> FEATURE:
<223> OTHER INFORMATION: CA-SP1 in HIV-1 NL4-3 with HA epitope
```

```
<400> SEQUENCE: 107

Ala Glu Ala Met Ser Gln Val Tyr Pro Tyr Asp Val Pro Asp Tyr Ala
1               5                   10                  15

Ile Met

<210> SEQ ID NO 108
<211> LENGTH: 15
<212> TYPE: PRT
<213> ORGANISM: Artificial Sequence
<220> FEATURE:
<223> OTHER INFORMATION: CA-SP1 in HIV-1 NL4-3 with blue-tongue virus
      VP7 epitope

<400> SEQUENCE: 108

Ala Glu Ala Met Ser Gln Val Gln Tyr Pro Ala Leu Thr Ile Met
1               5                   10                  15

<210> SEQ ID NO 109
<211> LENGTH: 17
<212> TYPE: PRT
<213> ORGANISM: Artificial Sequence
<220> FEATURE:
<223> OTHER INFORMATION: CA-SP1 in HIV-1 NL4-3 with blue-tongue virus
      VP7 epitope

<400> SEQUENCE: 109

Ala Glu Ala Met Ser Gln Val Gln Tyr Pro Ala Leu Thr Ala Thr Ile
1               5                   10                  15

Met

<210> SEQ ID NO 110
<211> LENGTH: 17
<212> TYPE: PRT
<213> ORGANISM: Artificial Sequence
<220> FEATURE:
<223> OTHER INFORMATION: CA-SP1 in HIV-1 NL4-3 with alpha-tubulin
      epitope

<400> SEQUENCE: 110

Ala Glu Ala Met Ser Gln Val Thr Asn Pro Glu Glu Phe Ala Thr Ile
1               5                   10                  15

Met

<210> SEQ ID NO 111
<211> LENGTH: 18
<212> TYPE: PRT
<213> ORGANISM: Artificial Sequence
<220> FEATURE:
<223> OTHER INFORMATION: CA-SP1 in HIV-1 NL4-3 with alpha-tubulin
      epitope

<400> SEQUENCE: 111

Ala Glu Ala Met Ser Gln Val Thr Glu Glu Phe Glu Glu Phe Ala Thr
1               5                   10                  15

Ile Met

<210> SEQ ID NO 112
<211> LENGTH: 20
<212> TYPE: PRT
<213> ORGANISM: Artificial Sequence
<220> FEATURE:
<223> OTHER INFORMATION: CA-SP1 in HIV-1 NL4-3 with flag epitope

<400> SEQUENCE: 112
```

```
Ala Glu Ala Met Ser Gln Val Thr Asp Tyr Lys Asp Asp Asp Lys
1               5                   10                  15

Ala Thr Ile Met
            20

<210> SEQ ID NO 113
<211> LENGTH: 18
<212> TYPE: PRT
<213> ORGANISM: Artificial Sequence
<220> FEATURE:
<223> OTHER INFORMATION: CA-SP1 in HIV-1 NL4-3 with flag epitope

<400> SEQUENCE: 113

Ala Glu Ala Met Ser Gln Val Thr Asp Tyr Lys Asp Asp Asp Lys
1               5                   10                  15

Ile Met

<210> SEQ ID NO 114
<211> LENGTH: 22
<212> TYPE: PRT
<213> ORGANISM: Artificial Sequence
<220> FEATURE:
<223> OTHER INFORMATION: CA-SP1 in HIV-1 NL4-3 with flag epitope

<400> SEQUENCE: 114

Ala Glu Ala Met Ser Gln Val Thr Asn Pro Ala Thr Ile Asp Tyr Lys
1               5                   10                  15

Asp Asp Asp Asp Ile Met
            20

<210> SEQ ID NO 115
<211> LENGTH: 23
<212> TYPE: PRT
<213> ORGANISM: Artificial Sequence
<220> FEATURE:
<223> OTHER INFORMATION: CA-SP1 in HIV-1 NL4-3 with VSV-G-tag construct

<400> SEQUENCE: 115

Ala Glu Ala Met Ser Gln Val Thr Tyr Thr Asp Ile Glu Met Asn Arg
1               5                   10                  15

Leu Gly Lys Ala Thr Ile Met
            20
```